United States Patent
Soros et al.

(10) Patent No.: US 11,345,757 B2
(45) Date of Patent: May 31, 2022

(54) ANTI-CD39 ANTIBODIES

(71) Applicant: Trishula Therapeutics, Inc., South San Francisco, CA (US)

(72) Inventors: Vanessa Soros, San Francisco, CA (US); Maria Kovalenko, Portola Valley, CA (US); John Corbin, Oakland, CA (US); Courtney Beers, San Francisco, CA (US); Paul Fredrick Widboom, Hanover, NH (US); Joseph Robert Warfield, White River Junction, VT (US)

(73) Assignee: Trishula Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/635,526

(22) PCT Filed: Jul. 30, 2018

(86) PCT No.: PCT/US2018/044449
§ 371 (c)(1),
(2) Date: Jan. 30, 2020

(87) PCT Pub. No.: WO2019/027935
PCT Pub. Date: Feb. 7, 2019

(65) Prior Publication Data
US 2021/0009708 A1   Jan. 14, 2021

Related U.S. Application Data

(60) Provisional application No. 62/539,527, filed on Jul. 31, 2017.

(51) Int. Cl.
| | |
|---|---|
| *C07K 16/28* | (2006.01) |
| *C12N 15/11* | (2006.01) |
| *C12N 15/63* | (2006.01) |
| *A61K 39/395* | (2006.01) |
| *G01N 33/566* | (2006.01) |
| *A61P 37/04* | (2006.01) |
| *A61K 45/06* | (2006.01) |
| *A61K 39/00* | (2006.01) |

(52) U.S. Cl.
CPC ...... *C07K 16/2896* (2013.01); *A61K 39/3955* (2013.01); *A61P 37/04* (2018.01); *C12N 15/11* (2013.01); *C12N 15/63* (2013.01); *G01N 33/566* (2013.01); *A61K 39/39541* (2013.01); *A61K 45/06* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/74* (2013.01); *C07K 2317/76* (2013.01); *C07K 2317/77* (2013.01); *C07K 2317/92* (2013.01); *G01N 2333/70596* (2013.01); *G01N 2500/04* (2013.01)

(58) Field of Classification Search
CPC .................. C07K 16/2896; A61K 39/3955
See application file for complete search history.

(56) References Cited

U.S. PATENT DOCUMENTS

| | | |
|---|---|---|
| 6,335,013 B1 | 1/2002 | Ford et al. |
| 6,350,447 B1 | 2/2002 | Chadwick et al. |
| 6,387,645 B1 | 5/2002 | Ford et al. |
| 6,447,771 B1 | 9/2002 | Ford et al. |
| 6,476,211 B1 | 11/2002 | Ford et al. |
| 6,759,214 B1 | 7/2004 | Chadwick et al. |
| 6,780,410 B1 | 8/2004 | Chadwick et al. |
| 6,780,977 B1 | 8/2004 | Chadwick et al. |
| 6,787,328 B1 | 9/2004 | Chadwick et al. |
| 6,828,423 B1 | 12/2004 | Chadwick et al. |
| 6,858,207 B2 | 2/2005 | Ford et al. |
| 6,899,875 B1 | 5/2005 | Chadwick et al. |
| 10,662,253 B2 | 5/2020 | Levy et al. |
| 10,738,128 B2 | 8/2020 | Chappel et al. |
| 10,793,637 B2 | 10/2020 | Chappel et al. |
| 2003/0040094 A1 | 2/2003 | Beaudoin et al. |
| 2005/0037382 A1 | 2/2005 | Robson et al. |
| 2005/0158280 A1 | 7/2005 | Robson et al. |
| 2010/0303828 A1 | 12/2010 | Levy et al. |
| 2011/0020329 A1 | 1/2011 | King et al. |
| 2011/0229476 A1 | 9/2011 | Liu et al. |
| 2011/0318339 A1 | 12/2011 | Smider et al. |
| 2013/0273062 A1 | 10/2013 | Bensussan et al. |
| 2017/0165366 A1 | 6/2017 | Hicklin et al. |
| 2017/0335007 A1 | 11/2017 | Chen |
| 2018/0140724 A1 | 5/2018 | Deng et al. |
| 2018/0186827 A1 | 7/2018 | Billedequ et al. |

(Continued)

FOREIGN PATENT DOCUMENTS

| | | |
|---|---|---|
| EP | 805871 B1 | 11/1999 |
| EP | 2654789 B1 | 5/2018 |

(Continued)

OTHER PUBLICATIONS

Zhang, H., "The role of NK cells and CD39 in the immunological control of tumor metastases", Oncoimmunology, 2019, vol. 8, No. 6., p. e1593809-1-e1593809-11.

(Continued)

*Primary Examiner* — Zachary C Howard
(74) *Attorney, Agent, or Firm* — K&L Gates LLP

(57) ABSTRACT

Provided herein are antibodies that selectively bind to CD39 and its isoforms and homologs, and compositions comprising the antibodies. Also provided are methods of using the antibodies, such as therapeutic and diagnostic methods.

7 Claims, 32 Drawing Sheets

Specification includes a Sequence Listing.

(56) References Cited

U.S. PATENT DOCUMENTS

| | | |
|---|---|---|
| 2019/0071514 A1 | 3/2019 | Gauthier et al. |
| 2019/0153113 A1 | 5/2019 | Bastid et al. |
| 2019/0218304 A1 | 7/2019 | Chanteux et al. |
| 2019/0218308 A1 | 7/2019 | Chanteux et al. |
| 2019/0389961 A1 | 12/2019 | Chanteux et al. |
| 2020/0399394 A1 | 12/2020 | Chappel et al. |
| 2021/0032367 A1 | 2/2021 | Levy et al. |
| 2021/0095041 A1 | 4/2021 | Chappel et al. |

FOREIGN PATENT DOCUMENTS

| | | |
|---|---|---|
| WO | 2003052121 A1 | 6/2003 |
| WO | 2006111986 A1 | 10/2006 |
| WO | 2009095478 A1 | 8/2009 |
| WO | 2012085132 A1 | 6/2012 |
| WO | 2016073845 A1 | 5/2016 |
| WO | 2016081748 A2 | 5/2016 |
| WO | 2017064043 A1 | 4/2017 |
| WO | 2017089334 A1 | 6/2017 |
| WO | 2017/157948 A1 | 9/2017 |
| WO | 2017191300 A1 | 11/2017 |
| WO | 2018065552 A1 | 4/2018 |
| WO | 2018167267 A1 | 9/2018 |
| WO | 2019027935 A1 | 2/2019 |
| WO | 2019178269 A1 | 9/2019 |
| WO | 2019178269 A2 | 9/2019 |
| WO | 2021030251 A1 | 2/2021 |
| WO | 2021037037 A1 | 3/2021 |
| WO | 2021056610 A1 | 4/2021 |

OTHER PUBLICATIONS

Abhishek S. Kashyap et al: "Antisense oligonucleotide targeting CD39 improves anti-tumor T cell immunity", Journal for Immunotherapy of Cancer, vol. 7, No. 1, Mar. 12, 2019, XP055662772, DOI: 10.1186/s40425-019-0545-9 the whole document.
Opposition to European Patent No. EP2654789B filed by AbbVie, Inc.
Opposition to European Patent No. EP2654789B filed by Boult Wade Tennant LLP.
Opposition to European Patent No. EP 2654789B filed by D Young & Co LLP.
Opposition to European Patent No. EP 2654789B filed by Tizona Therapeutics, Inc.
Patentees Response to Oppositions of Abbvie, Inc., Tizona Therapeutics, D Young & Co. LLP and Boult WAde Tennant LLP.
Opposition to European Patent No. EP 3153526 B1 filed by Boult Wade Tennant LLP.
Opposition to European Patent No. EP 3153526 B1 filed by AbbVie Inc.
Opposition to European Patent No. EP 3153526 B1 filed by Trishula Therapeutics, Inc.
Opposition to European Patent No. EP 3153526 B1 filed by Surface Oncology, Inc.
Farkona, S. et al., Cancer immunotherapy: the beginning of the end of cancer? BMC Med, May 5, 2016, vol. 14, pp. 73: 1-18 p. 4 right col. third para., p. 7-13.
Exhibit 1—In Vivo Proof of Concept in Ramos Tumor-Bearing Scid Mice Treated With the Anti-CD39 Antibody BY40.
Exhibit 2—Assessment of CD39 Expression in Tumoral Cells of Ovarian, Lung, Thyroid, Kidneyk, Testis Cancer and Lymphoma Patients (D5).
Exhibit 3—CD39 Expression in Cancer Cells is Associated With Decreased Survival Probability.
Whiteside, T.L., "Disarming suppressor cells to improve immunotherapy", Cancer Immunol Immunother (2012), 61 (2): 283-288.
Hausler et al., poster"CD39 wird von humanen Ovarialkarzinomzellinien exprimiert und hemmt die immunologishe Tumorabwehr" (date: unknown).
Hausler et al., Congress Abstract: "CD39 wird in vivo und in vitro von Ovarialkarzinomzellen exprimiert und inhibiert die lytische Aktivitiit von NK-Zellen", Geburtshilfe Frauenheilkunde (alleged date: 2009), 69: P106.
Geburtshilfe und Frauenheilkunde. v. 69, No. 5 (May 2009) General Collection W1 GE103 Jun. 23, 2009 13:05:26.
Zhang, B., "CD73: a novel target for cancer immunotherapy", Cancer Research (Aug. 3, 2010), 70(16): 6407-641.
Gouttefangeas, et al., Abstract T17: "Biochemical analysis and epitope mapping of mAb defining CD39", Leucocyte Typing V, White Cell Differentiation Antigens, Proceedings of the 5th International Workshop (1995).
Official Letter dated Jan. 27, 2017.
CrossRef (D7a).
UniProt KB accession No. P49961 "Ectonucleoside triphosphate diphosphohydrolase 1" Jun. 7, 2017, [online] [Retrieved Nov. 18, 2018]. Retrieved from the Internet.
Sun et al., "CD39/ENTPD1 expression by CD4+Foxp3+ regulatory T cells promotes hepatic metastatic tumor growth in mice", Gastroenterology. Sep. 2010;139(3):1030-40. doi: 10.1053/j.gastro.2010.05.007. Epub 201 O Jun. 25.
Rowe et al., "Monoclonal antibodies to Epstein-Barr virus-induced, transformation-associated cell surface antigens: binding patterns and effect upon virus-specific Tcell cytotoxicity", Int J Cancer Apr. 15, 1982;29(4 ):373-81.
Mielke et al., "Histomorphologic and Immunophenotypic Spectrum of Primary Gastro-Intestinal B-Cell Lymphomas", Int Jour Cancer 47:334-343, 1991.
Mandapathil et al., "Isolation of functional human regulatory T cells (Treg) from the peripheral blood based on the CD39 expression", J Immunol Methods. Jul. 31, 2009 ;346(1-2):55-63. Doi: 10.1016/j.jim.2009.05.004. Epub May 18, 2009.
Rawstrom et al., "Chronic Lymphocytic Leukaemia (CLL) and CLL-Type Monoclonal B-Cell Lymphocytosis (MBL) Show Differential Expression of Molecules Involved in Lymphoid Tissue Homing", Cytometry Part B (Clinical Cytometry) 78B (Suppl. 1 ):S42-S46, 2010.
Loos et al., "Quantitation of CD39 gene expression in pancreatic tissue by real-time polymerase chain reaction", Methods Mal Biol., 576:351-62. Doi: 10.1007/978-1-59745-54549, 2010.
Ling et al., "A phenotypic study of cells from Burkitt lymphoma and EBV-B-lymphoblastoid lines and their relationship to cells in normal lymphoid tissues", Int J Cancer. Jan. 15, 1989,43(1 ): 112-8.
Kittel et al., "Localization of NTPDase1/CD39 in normal and transformed human pancreas", J Histochem Cytochem. Apr. 2002;50(4):549-56.
International Search Report for PCT Application PCT/US18/044449 dated Dec. 4, 2018, 6 pages.
International Search Report and Written Opinion for PCT Application PCT/EP2011/073659 dated Feb. 24, 2012, 10 pages.
Hilchey et al., "Human follicular lymphoma CD39+-infiltrating T cells contribute to adenosine-mediated T cell hyporesponsiveness", J Immunol. Nov. 15, 2009;183(10):6157-66. Doi: 10.4049/jimmunol.0900475. Epub Oct. 28, 2009.
European Office Action for European Patent Application EP11801741.7 dated Dec. 11, 2015, 6 pages.
Davi et al., "Burkitt-like lymphomas in AIDS patients: characterization within a series of 103 human immunodeficiency virus-associated non-Hodgkin's lymphomas. Burkitt's Lymphoma Study Group", J Clin Oncol. Dec. 1998; 16 (12):3788-95.
Damle et al., B-cell chronic lymphocytic leukemia cells express a surface membrane phenotype of activated, antigen-experienced B lymphocytes, Blood, Jun. 1 ;99(11 ):4087-93, 2002.
Certified U.S. Appl. No. 61/426,041, Priority Document of EP Patent No. EP Patent No. 2 654 789.
Beyer et al., "CD4+ CD25highFOXP3+ Regulatory T Cells in peripheral Blood are primarilv of Effector Memory Phenotype" Journal of Clinical Oncology, Doi: 10.1200/JC0.2007.
Bending, M.M., "Humanization of Rodent Monoclonal Antibodies by CDR Grafting", Methods: A Companion to Methods in Enzymology, 1995; 8:83-93, 1993.
Pascalis, "Grafting of "abbreviated" Complementarity-Determining Regions Containing Specificity-Determining Residues Essential for

(56) References Cited

OTHER PUBLICATIONS

Ligand Contact to Engineer a Less Immunogenic Humanized Monoclonal Antibody", (The Journal of Immunology (2002) 169: 3076-3084) (Year: 2002).
Vajdos, "Comprehensive Functional Maps of the Antigen-binding Site of an Anti-ErbB2 Antibody Obtained with Shotgun Scanning Mutagenesis", J Mol. Biol. (2002) 320: 415-428, 2002.
Portolano, et al., "Lack of Promiscuity in Autoantigen-Specific H and L Chain Combinations as Revealed by Human H and L Chain Roulette", The Journal of Immunology, vol. 150, No. 3, p. 880-887, 1993.
Soderlind, et al., "Complementarity-determining region (CDR) implantation: a theme of recombination", immunotechnology, vol. 4, p. 279-285, 1999.
Rudikoff et al., "single amino acid substitution altering antigen-binding specificity", Proc Natl Acad Sci USA 79: 1979-1983, 1982.
Paul, et al, Chapter 9, Fundamental Immunology, 3rd Edition, 1993, pp. 292-295).
Beiboer, et al., "Guided Selection of a Pan Carcinoma Specific Antibody Reveals Similar Binding Characteristics yet Structural Divergence Between the Original Murine Antibody and Its Human Equivalent", J. Mol. Biol. (2000) 296:833-849).
Maccallum, et al., "Antibody-antigen Interactions: Contact Analysis and Binding Site Topography", J. Mol. Biol., 262, 732-745, 1996.
Klimka, et al., "Human anti-CD30 recombinant antibodies by guided phage antibody selection using cell panning", British Journal of Cancer (2000) 83: 252-260.
Declaration of Armand Bensussan, dated Feb. 21, 2015.
Declaration of Armand Bensussan, dated Jan. 24, 2020.
Declaration of Dr. Silvia Deaglio, dated Jan. 24, 2020.
Exhibit 2—Declaration of Dr. Cecile Bonnafafous, dated Jun. 2018.
Exhibit B—*Homos sapiens* ENTPD1 (CD39) Cellular Expression (online source: Expression Atlas).
"CD39 (BU61): sc-65262", Santa Cruz Biotechnology, Inc.
Wu, Y, et al., RanBPM associates with CD39 and odulates ecto-nucleotidase activity, Biochem, J. (2006) 396, 23-30.
Appendix A—Inhibition of AMP generation by anti-CD39 antibodies.
Sade-Feldman Moshe et al., "Defining T 1,18,19, Cell States Associated with Response to 21 Checkpoint Immunotherapy in Melanoma", Cell, Els Ev I Er, Amsterdam, NL, vol. 175, No. 4, Nov. 1, 2018 (Nov. 1, 2018), p. 998, XP085522260, ISSN: 0092-8674, DOI: 10.1016/J.CELL.2018.10.038 the whole document.
Anonymous: "TTX-030 Single Agent and in Combination With Immunotherapy or Chemotherapy for Patients With Advanced Cancers—Full Text View—ClinicalTrials.gov".
Mar. 21, 2019 (Mar. 21, 2019), XP055700883, Retrieved from the Internet: URL:https://clinicaltrials.gov/ct2/show/NCT03884556?term=NCT03884556&draw=2&rank=I [retrieved on Jun. 4, 2020] the whole document.
Ivan Perrot et al: "Blocking Antibodies Targeting the CD39/CD73 Immunosuppressive Pathway Unleash Immune Responses in Combination Cancer Therapies", Cell Reports, vol. 27, No. 8, May 21, 2019, pp. 2411-2425.
Moller, S., et al., "Monitoring the expression of purinoceptors and nucleotide-metabolizing ecto-enzymes with antibodies directed against proteins in native conformation.", Purinergic Signalling Sep. 2007, vol. 3, No. 4, Sep. 2007, pp. 359-366.
Dwyer et al., "CD39 and control of cellular immune responses", Purinergic Signalling, vol. 3, Feb. 6, 2007, pp. 171-180.
Deaglio S., et al., "Adenosine generation catalyzed by CD39 and CD73 expressed on regulatory T cells mediates immune suppression", Journal of Experimental Medicine, vol. 204, No. 6, Jun. 2007, pp. 1257-1265.
Shevach, EM et al., "The lifestyle of naturally occurring CD4(+)CD25(+)Foxp3(+) regulatory T cells", Mmunological Reviews, vol. 212, Aug. 2006, pp. 60-73.
Schetinger, MR C, et al., "NTPDase and 5'- nucleotidase activities in physiological and disease conditions: New perspectives for human health", Biofactors, vol. 31, No. 2, 2007, pp. 77-98.

Hausler, et al., "CD39 wird van humanen varialkarzinomzelllinien exprimiert und hemmt die immunologische Tumorabwehr /Abstract/", Thieme E-Journals—Geburtshilfe Frauenheilkunde, 2008 Retrieved from the Internet:URL:https://www.thiemeconnect.de/products/ejournals/abstract/10.1055/s-0028-1 089305.
Hoskin, DW, et al., "Inhibition of T cell and natural killer cell function by adenosine and its contribution to immune evasion by tumor cells (Review)", International Journal of Oncology, vol. 32, 2008, pp. 527-535.
Hausler et al., Congress Abstract: "CD39 wird von humanen ovarialkarzinomzellinien exprimiert und hemmt die immunologishe Tumorabwehr", Geburtsiiilfe Frauenheilkd, 68: SI-S194 (also referred as 68: PO_Onko_04_33).
Pages of the physical paper publication of Hausler et al., Congress Abstract: "CD39 wird von humanen varialkarzinomzellinien exprimiert und hemmt die immunologishe Tumorabwehr", Geburtsilfe Frauenheilkd, 68: SI-5194 (also referred as 68: PO_Onko_04_33) obtained from the United States National Library of Medicine, Bethesda, Maryland including the library date and time stamp "Oct. 1, 2008 11 :54:02" on the front page of the abstracts supplement.
Product datasheet for the anti-CD39 antibody A1, "Purified anti-human CD39 Antibody", BioLegend Version: 3 Revision Date: Feb. 10, 2017.
Knowles, AE, et al., (1999) Inhibition of an ecto-ATPdiphosphohydrolase by azide. Eur J Biochem 262, 349-357.
Borsellino, G, et al., Expression of ectonucleotidase CD39 by Foxp3+ Treg cells: hydrolysis of extracellular ATP and immune suppression, Blood, 2007; 110: 1225-32.
Sitkovsky, et al., "Adenosine AZA receptor antagonists: blockade of adenosinergic effects and T regulatory cells", British Journal of Pharmacology (2008), 153: S457-S464.
Beyer, et al., "Regulatory T Cells in Cancer", The American Society of Hematology, Blood, Aug. 1, 2006, vol. 108, No. 3, 804-811.
Curiel, T.J., "Tregs and rethinking cancer immunotherapy", J. Clin. Invest 117:1167-1174 (2007).
Knutson, et al., The Journal of Immunology, 2006, 177: 84-91.
Fecci, et al., Clin Cancer Res 2006:12(14), pp. 4294—Jul. 15, 2006.
Colombo, et al., Nature Reviews Cancer, vol. 7, Nov. 2007, 881-887.
Wang, et al., Current Opinion in Immunology, Feb. 15, 2007, 19:217-223.
Vieweg et al., Clin Can Res 2007;13(2 Suppl), pp. 727s-732s, Jan. 15, 2007.
Shi et al., "Prevalence of the Mercurial-Sensitive EctoATPase in Human Small Cell Lung Carcinoma: Characterization and Partial Purification", Archives of Biochemistry and Biophysics (1994), 315(1): 77-184.
Dzhandzhugazyan, et al., Ecto-ATP diphosphohydrolase / CD39 is overexpressed in differentiated human melanomas, FEBS Letters (1998), 430(3): 227-230.
Pulte et al., "CD39 activity correlates with stage and inhibits platelet reactivity in chronic lymphocytic leukemia", Journal of Translational Medicine (2007), 5(23): 1-10.
Declaration of Francisco J. Quintana, PhD., Jun. 18, 2021.
Declaration of Dr. Nathalie Bonnefoy under 37 C.F.R. 1.132—2016.
Blay, J., et al., "The extracellular fluid of solid carcinomas contains immunosuppressive concentrations of adenosine", Cancer Res., 57, 2602-2605, Jul. 1, 1997.
Huang, S., et al., "Role of A2a Extracellular Adenosine Receptor-Mediated Signaling in Adenosine-Mediated Inhibition of T-Cell Activation and Expansion" Blood, vol. 90, No. 4 (Aug. 15), 1997; pp. 1600-1610.
Spychala, J., Tumor-promoting functions of adenosine, Pharmacology & Therapeutics 87 (2000), 161-173.
Gershon, R.K., et al., "Infectious Immunological Tolerance", Immunology, (1971) 21, 903-914.
Brown, J.A. et al., "Blockade of Programmed Death-1 Ligands on Dendritic Cells Enhances T Cell Activation and Cytokine Production" J Immunol., 2003, 1257-1266.
Ohta A. et al., "A2A adenosine receptor protects tumors from antitumor T cells", PNAS, 2006, vol. 103(35), 13132-13137.

(56) References Cited

OTHER PUBLICATIONS

Curiel, T et al., "Specific recruitment of regulatory T cells in ovarian carcinoma fosters immune privilege and predicts reduced survival", Nature Medicine, vol. 10(9), (2004), 42-49.
Jackson, S.W. et al., "Disordered purinergic signaling inhibits pathological angiogenesis in cd39/Entpd1-null mice", American Journal of Pathology, vol. 171, No. 4, Oct. 2007 p. 1395-1404.
Hodi, F.S. et al., "Biologic activity of cytotoxic T lymphocyte-associated antigen 4 antibody blockade in previously vaccinated metastatic melanoma and ovarian carcinoma patients", PNAS, 2003, vol. 100(8) 4712-4717.
Kansas, G.S. et al., "Expression, distribution, and biochemistry of human CD39. Role in activation-associated homotypic adhesion of lymphocytes" J Immunol. 1991; 146:2235-2244.
Gouttefangeas, C. et al., "Biochemical analysis and epitope mapping of mAb defining CD39" p. 383-385 Schlossman, S.F. et al., Editors. Leucocyte Typing V. New York: Oxford, published in 1995.
Gouttefangeas, C. et al., "The CD39 molecule defines distinct cytotoxic subsets within alloactivated human CDS-positive cells" Eur J. Immunol., 1992. 22: 2681-2685.
Bensussan, A. et al., "Detection of membrane-bound HLA-G translated products with a specific monoclonal antibody" Proc Natl Acad Sci USA, vol. 92, pp. 10292-10296, Oct. 1995.
Hausler, S.F.M. et al., "Anti-CD39 and anti-CD73 antibodies A1 and 7G2 improve targeted therapy in ovarian cancer by blocking adenosine-dependent immune evasion" Am J Transl Res, 2014;6(2):129-139.
Goettel, J.A. et al., "AHR Activation Is Protective against Colitis Driven by T Cells in Humanized Mice" Cell Rep, 2016, 17, 1318-1329.
Communication Sep. 25, 2018 Comm, from Exam. Division and Annex—D26 Surface Oncology.
Reply to Comm. Mar. 26, 2019 Reply to the Comm, from the Exam. Div.—D27 Surface Oncology.
Claim amendment—Mar. 26, 2019 Claim Amend. with Ann. Aux. Claim Set 2—D28 Surface Oncology.
Written submission—Jan. 30, 2020 Writ.Subm. in Prep, for Oral Proc.—D29 Surface Oncology.
Written submission—Feb. 28, 2020 Writ. Subm. in prep, for oral proc.—D30 Surface Oncology.
Summons to Attend Oral Proceedings—Jul. 15, 2019 Summ. to Attend Oral Proc, and Annex—D31 Surface Oncology.
Observations by third party—May 10, 2019 Observations by Third Party—D32 Surface Oncology.
Preliminary Opinion—Nov. 12, 2019 Prel. Opinion in Oppo, to EP 2654789—D33 Surface Oncology.
Robson, S.C., et al., "The E-NTPDase family of ectonucleotidases: Structure function relationships and pathophysiological significance", Purinergic Signalling (2006) 2:409-430.
Appendix A filed by Proprietor with response to USPTO Feb. 20, 2015—Exhibit A from USPPTO file D8 Boult Wade Tenannt.
Szczepanski et al., "Mechanisms of suppression used by regulatory T cells in patients newly diagnosed with acute myeloid leukemia" Blood, vol. 112, No. 11, 2008 pp. 1-7.
Applicant's letter to USPTO Jan. 26, 2017—Applicant's letter to USPTO Jan. 26, 2017 D16 Boult Wade Tennant Submission With Request for Cotinued Examination and Information Disclosure Statement.
Fredholm, BB., "Adenosine, an endogenous distress signal, modulates tissue damage and repair", Cell Death and Differentiation (2007) 14, 1315-1323.
Kobie, J.J., et al., T Regulatory and Primed Uncommitted CD4 T Cells Express CD73, Which Supresses Effector CD4 T Cells by Converting 5'-Adenosine Monophosphate to Adenosine, J Immunol 2006; 177:6780-6786.
Kaczmarek, E., et al., "Identification and Characterization of CD39/Vascular ATP Diphosphohydrolase", The Journal of Biological Chemistry, vol. 271, No. 51, Dec. 20, pp. 33116-33122, 1996.
Spatola, B.N., et al., "Fully human anti-CD39 antibody potently inhibits ATPase Activity in Cancer Cells via uncompetitive allosteric mechanism", MASS 12(1); e1838036 (2020).
Patentee's response to USPTO of Aug. 18, 2015 (D26 Trishula).
Aiello, A., et al., "Expression of Differentiation and Adhesion Molecules in Sporadic Burkitt's Lymphoma", Hematological Oncology, 8(4): 229-238 (1990).
Wang, T.F, et al., "CD39 Is an Ecto-(Ca2+,Mg2+)-apyrase", J Bioll Chem. 271(17):9898-9901 (1996).
Marcus, A.J., et al., "The endothelial Cell Ecto-AdPase Responsible for Inhibition of Platelet Function is CD39" J Clin Invest. 99(6): 1351-1360 (1997).
Declaration of Achim K. Moesta, Ph D Jun. 22, 2021.
Knowles, A.F., et al., "The Common Occurrence of ATP Diphosphohydrolase in Mammalian Plasma Membranes", Biochim Biophys Acta 26; 731(1): 88-96 (1983).
Xian-Yan Li, et al.. "Targeting CD39 in Cancer Reveals an Extracellular ATP- and Inflammasome-Driven Tumor Immunity", Cancer Discov.9(12): 1754-1773 (2019).
Moesta, A.K., et al., "Targeting CD39 in cancer", Nat Rev Immunol 20(12: 739-755 (2020).
Declaration of Dr. Nathalie Bonnefoy, dated Jan. 23, 2017 (7 pages).
Dr. Nathalie Bonnefoy's CV.
Exhibit A Human CD39 Protein.
Exhibit B Munkonda, M.N. "Characterization of a Monoclonal antibody as the first specific inhibitor of human NTP diphosphohydrolase-3", FEBS Journal 276 (2009) 479-496.
Kunzli, B., et al., "Upregulation of CD39/NTPDases and P2 receptors in human pancreatic disease", Am J Physiol Gastrointest Liver Physiol (2007), 292: G223-G230.
Hausler, et al., "Ectonucleotidases CD39 and CD73 on OvCA cells are potent adenosine-generating enzymes responsible for adenosine receptor 2A-dependent suppression of T cell function and NK cell cytotoxicity" Cancer Immunol Immunother (Jun. 3, 2011) 60:1405-1418.
Mandapathil et al., "Increased Ectonucleotidase Expression and Activity in Regulatory T Cells of Patients with Head and Neck Cancer", Clin. Cancer Res. (2009), 15 (20):6348-6357.
Meyer, C., et al.: Abstract "Expression of CD39 and CD73 as means of evading anti-tumor immune responses in lung cancer", J Immunol (Apr. 2010), 184 (100.7).
Clayton, A., et al.: "Cancer exosomes express CD39 and CD73, which suppress T Cells through adenosine production". Journal of Immunology (Jul. 2011), 187 (2): 676-683.
Hou, T.J.,, "Comparison of multiple comparison methods for identifying differential gene expression in simulated and real papillary thyroid cancer microarray data", presented to the Faculty of the University of Texas School of Public Health (Aug. 2009).
Hausler et al., Congress Abstract: "Ovarialkarzinomzellen unterdrucken antitumorale Immunantworten durch extrazelluliire Generierung von Adenosin via CD39 und CD73 ", Geburtshilfe Frauenheilkd (alleged date: 2009), 69: A042.
Fujarewicz, K., et al., "A multi-gene approach to differentiate papillary thyroid carcinoma from benign lesions: gene selection using support vector machines with bootstrapping", Endocrine-Related Cancer (2007), 14: 809-826.
Traverso, P., et al., Abstract 365 "Analysis of Regulatory T cells in patients affected by renal cell carcinoma", The Journal of Urology (May 30, 2010), 183 (4), Supplement: e144-e145.
Schueiz, A.N,, et al., "Molecular classification of renal tumors by gene expression profiling", Journal of Molecular Diagnostics (2005),7 (2): 206-218.
Whiteside, T.L. et al. "The role of the adenosinergic pathway in immunosuppression mediated by human regulatory T cells (Treg)" Current Medicinal Chemistry (2011), 18(34): 5217-5223.
Jin, D., et al: "CD73 on tumor cells impairs antitumor T-cell responses: a novel mechanism of tumor-induced immune suppression", Cancer Research (Mar. 2010), 70 (6): 2245-2255.
Bastid, J., et al: "Inhibition of CD39 enzymatic function at the surface of tumor cells alleviates their immunosuppressive Activity", Cancer Immunology Research (2014), 3 (3): 254-265.

(56) References Cited

OTHER PUBLICATIONS

Sun, X., et al., "CD39/ENTPDJ expression by CD4+Foxp3+ regulatory Tcells promotes hepatic metastatic tumor growth in mice", Gastroenterology (Jun. 25, 2010), 139: 1030-1040.

Stagg, J. et al., "Extracellular adenosine triphosphate and adenosine in cancer", Oncogene (Jul. 26, 2010), 29: 5346-5358.

Kondo, et al., "Expression of CD73 and its ecto-5'-nucleotidase activity are elevated in papillary thyroid carcinomas", Histopathology (2006), 48: 612-614.

Buffon, A., et al., "NTPDase and 5' ecto- nucleotidase expression profiles and the pattern of extracellular ATP metabolism in the Walker 256 tumor", Biochimica et Biophysica Acta (2007), 1770: 1259-1265.

Mandapathil, M., et al., "Targeting human inducible regulatory T cells (Tr 1) in patients with cancer: blocking of adenosine-prostaglandin E2 cooperation", Expert Opin Biol Ther (Sep. 2011), 11(9): 1203-1214.

Rawstron, A,C., et al., "Chronic lymphocytic leukaemia (CLL) and CLL-type monoclonal B-cell lymphocytosis (MEL) show differential expression of molecules involved in lymphoid tissue homing", Cytometry Part B (Clinical Cytometry) (Dec. 14, 2010), 78B: S42-S46.

Kishore, B.K., et al., "Expression of NTPDaseI and NTPDase2 in murine kidney: relevance to regulation of P2 receptor signaling", Am J Physiol Renal Physiol (2005), 288: F1032-F1043.

Hausler, S., et al., Ovarian Carcinoma Cells Suppress Anti-tumoral Immune responses by extracellular generation of adenosine via CD39 and CD73.

U.S. Appl. No. 61/426,041.

Bastid, et al., "ENTPDJ/CD39 is a promising therapeutic target in oncology", Oncogene (2013), 32(14): 1743-1751.

Buffon et al., "NTPDase and 5' ecto-nucleotidase expression profiles and the pattern of extracellular ATP metabolism in the Walker 256 tumor", Biochimica Et Biophysica Acta, (2007), 1770: 1259-1265.

Biological deposit receipt for CNCM I-3889.
Biological deposit receipt for CNCM I-4171.
Official Letter dated Dec. 11, 2015.
Response dated Jun. 16, 2016.
Internet Archive Wayback machine (D7a).
CrossRef (D8a).
Internet Archive Wayback machine (D25a).
CrossRef (D25a).

FIG. 1

| Clone ID | $K_D$ (M) | kon ($M^{-1}s^{-1}$) | koff ($s^{-1}$) | Clone ID | $K_D$ (M) | kon ($M^{-1}s^{-1}$) | koff ($s^{-1}$) |
|---|---|---|---|---|---|---|---|
| 27535 | PF | PF | PF | 29872 | 1.13E-08 | 1.75E+05 | 2.02E-03 |
| 27536 | 1.14E-07 | 6.59E+04 | 7.51E-03 | 31393 | 6.72E-10 | 2.98E+05 | 2.00E-04 |
| 27549 | 4.05E-08 | 1.93E+04 | 7.82E-04 | 31414 | 1.01E-08 | 4.31E+05 | 4.37E-03 |
| 27550 | 1.43E-07 | 4.44E+05 | 6.33E-02 | 31415 | 1.63E-08 | 2.27E+05 | 3.71E-03 |
| 27568 | 1.73E-07 | 2.72E+05 | 4.70E-02 | 31418 | 1.30E-08 | 3.14E+05 | 4.06E-03 |
| 27571 | 1.64E-08 | 6.39E+05 | 1.05E-02 | 31421 | 1.88E-08 | 2.81E+05 | 5.26E-03 |
| 27575 | PF | PF | PF | 31429 | 2.39E-08 | 4.73E+05 | 1.13E-02 |
| 27577 | 4.09E-07 | 8.93E+05 | 3.65E-01 | 31430 | 1.01E-08 | 3.26E+05 | 3.28E-03 |
| 27579 | 1.67E-07 | 9.55E+05 | 1.60E-01 | 31431 | 1.60E-08 | 1.73E+05 | 2.76E-03 |
| 27587 | 3.37E-08 | 2.11E+05 | 7.11E-03 | 31432 | 1.07E-09 | 2.68E+05 | 2.86E-04 |
| 27588 | 5.49E-08 | 1.17E+05 | 6.44E-03 | 31436 | 9.24E-10 | 2.63E+05 | 2.43E-04 |
| 27589 | 1.91E-07 | 2.02E+05 | 3.85E-02 | 31437 | 5.58E-10 | 3.82E+05 | 2.13E-04 |
| 27590 | 1.31E-07 | 1.76E+05 | 2.30E-02 | 31861 | 1.16E-09 | 2.46E+05 | 2.86E-04 |
| 27596 | 3.11E-08 | 1.72E+06 | 5.33E-02 | 31873 | 9.22E-10 | 3.11E+05 | 2.86E-04 |
| 27597 | 3.35E-07 | 2.73E+05 | 9.14E-02 | 31891 | 1.34E-09 | 4.53E+05 | 6.09E-04 |
| 28337 | 1.27E-08 | 1.43E+05 | 1.80E-03 | 31895 | 1.81E-09 | 4.63E+05 | 8.39E-04 |
| 28347 | 9.05E-09 | 9.01E+05 | 8.15E-03 | 31896 | 9.05E-09 | 9.01E+05 | 8.15E-03 |
| 29851 | 1.23E-09 | 3.13E+05 | 3.85E-04 | 31901 | 1.28E-10 | 1.03E+06 | 1.32E-04 |
| 29852 | 2.66E-10 | 5.03E+05 | 1.34E-04 | 31905 | 7.31E-11 | 1.52E+06 | 1.11E-04 |
| 29857 | 7.60E-10 | 3.02E+05 | 2.29E-04 | 31915 | 8.11E-10 | 3.53E+05 | 2.86E-04 |
| 29871 | 2.44E-07 | 2.73E+05 | 6.66E-02 | A1 | 1.92E-09 | 1.66E+05 | 3.18E-04 |

| Clone Name | Human CD39 Inhibition Assay Cell Titer Glo Average Response (RLU) |
|---|---|
| 27536 | 7489 |
| 27549 | 16867 |
| 27550 | 5574 |
| 27568 | 5727 |
| 27571 | 6823 |
| 27575 | 2598 |
| 27577 | 3596 |
| 27579 | 6471 |
| 27587 | 8733 |
| 27588 | 11166 |
| 27589 | 6580 |
| 27590 | 5680 |
| 27596 | 3929 |
| 27597 | 8889 |
| Isotype Control | 375 |

B.

| Clone Name | Human CD39 Inhibition Assay Cell Titer Glo Average Response (RLU) |
|---|---|
| 28337 | 9399 |
| 28347 | 9083 |
| 27535 | 4890 |
| Isotype Control | 857 |

| Clone Name | Human CD39 Inhibition Assay Cell Titer Glo Average Response (RLU) |
|---|---|
| 28337 | 11708 |
| 27549 | 15648 |
| 28347 | 11182 |
| 29851 | 11554 |
| 29852 | 11980 |
| 29857 | 11637 |
| 27571 | 8543 |
| 27579 | 8878 |
| 29871 | 8708 |
| 29872 | 8372 |
| BY40va | 415 |
| no IgG | 979 |

D.

| Clone Name | Human CD39 Inhibition Assay Cell Titer Glo Average Response (RLU) |
|---|---|
| 27571 | 10885 |
| 31393 | 12105 |
| 27579 | 8035 |
| 29872 | 8368 |
| 31414 | 10254 |
| 31415 | 10289 |
| 31418 | 9447 |
| 31421 | 7263 |
| 31429 | 11441 |
| 31430 | 8380 |
| 31431 | 9993 |
| 28347 | 13306 |
| 31436 | 14157 |
| 31437 | 13509 |
| 31393 | 12105 |
| Isotype Control | 38 |

E.

| Clone Name | Human CD39 Inhibition Assay Cell Titer Glo Average Response (RLU) |
|---|---|
| 27571 | 14303 |
| 31861 | 17866 |
| 31873 | 16045 |
| 27579 | 6575 |
| 31414 | 11375 |
| 31891 | 13470 |
| 31895 | 12828 |
| 28347 | 18736 |
| 31432 | 18610 |
| 31896 | 11911 |
| 31901 | 14798 |
| 31905 | 20329 |
| 31915 | 15694 |
| Isotype Control | 44 |
| BY40va | 11 |

FIG. 2F

| Clone Number | Cell Binding (FOB) | | Clone Number | Cell Binding (FOB) | |
|---|---|---|---|---|---|
| | hCD39-CHO | cCD39-CHO | | hCD39-CHO | cCD39-CHO |
| 27535 | 301 | 738 | 31393 | 1064 | 2955 |
| 27536 | 89 | 113 | 31414 | 1236 | 3568 |
| 27549 | 822 | 566 | 31415 | 1168 | 3365 |
| 27550 | 2,033 | 2870 | 31418 | 1077 | 3183 |
| 27568 | 267 | 260 | 31421 | 1075 | 3053 |
| 27571 | 1,405 | 1607 | 31429 | 1291 | 3800 |
| 27575 | 2 | 128 | 31430 | 1222 | 3573 |
| 27577 | 390 | 339 | 31431 | 1235 | 3533 |
| 27579 | 1,953 | 2667 | 31432 | 1167 | 5697 |
| 27587 | 1,450 | 1403 | 31436 | 1317 | 3568 |
| 27588 | 10 | 14 | 31437 | 1292 | 3643 |
| 27589 | 311 | 531 | 31861 | 1432 | 5477 |
| 27590 | 33 | 44 | 31873 | 1321 | 5083 |
| 27596 | 252 | 257 | 31891 | 1026 | 4651 |
| 27597 | 799 | 908 | 31895 | 1042 | 4493 |
| 28337 | 4 | 17 | 31896 | 1042 | 4539 |
| 28347 | 1,020 | 1340 | 31901 | 1113 | 4662 |
| 29851 | 129 | 398 | 31905 | 1077 | 4937 |
| 29852 | 337 | 1418 | 31915 | 1087 | 4578 |
| 29857 | 224 | 1145 | A1 | 796-2191 | 2426-3054 |
| 29871 | 451 | 3350 | BY40va | 1292 | 3867 |
| 29872 | 1454 | 4191 | Isotype Control | 1 | 1 |

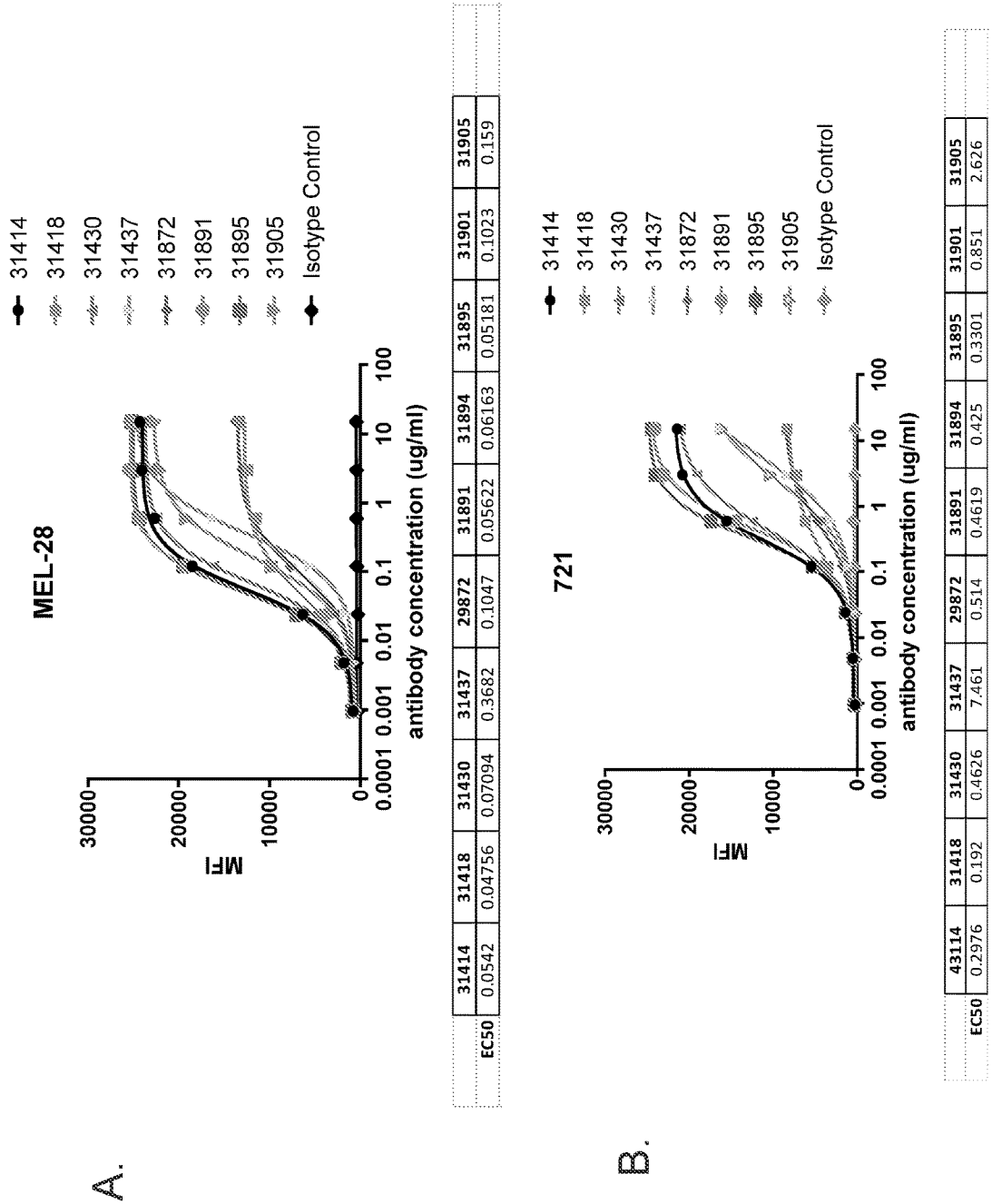

FIG. 14B
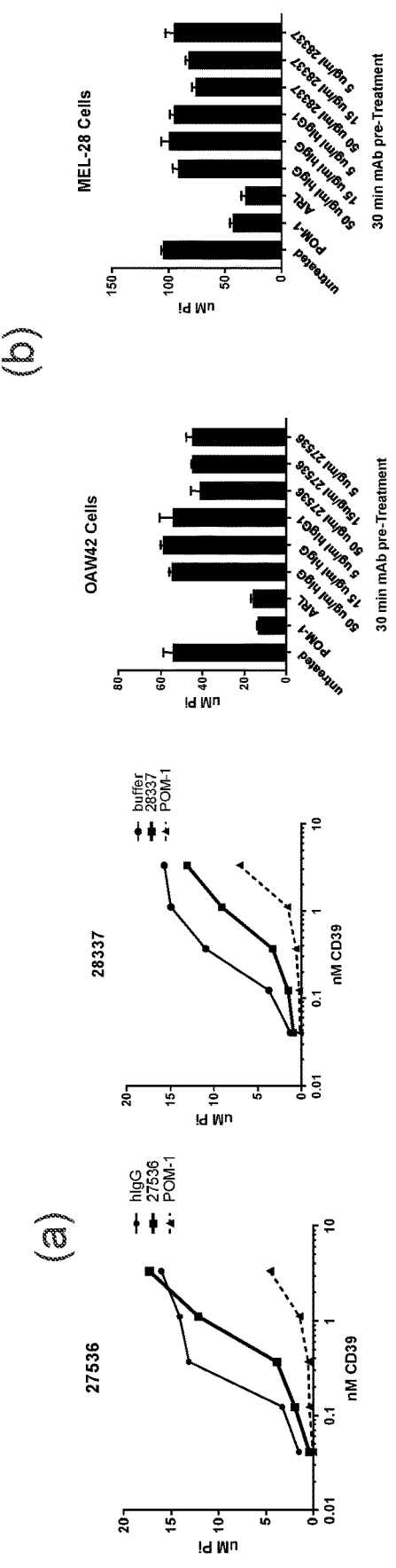
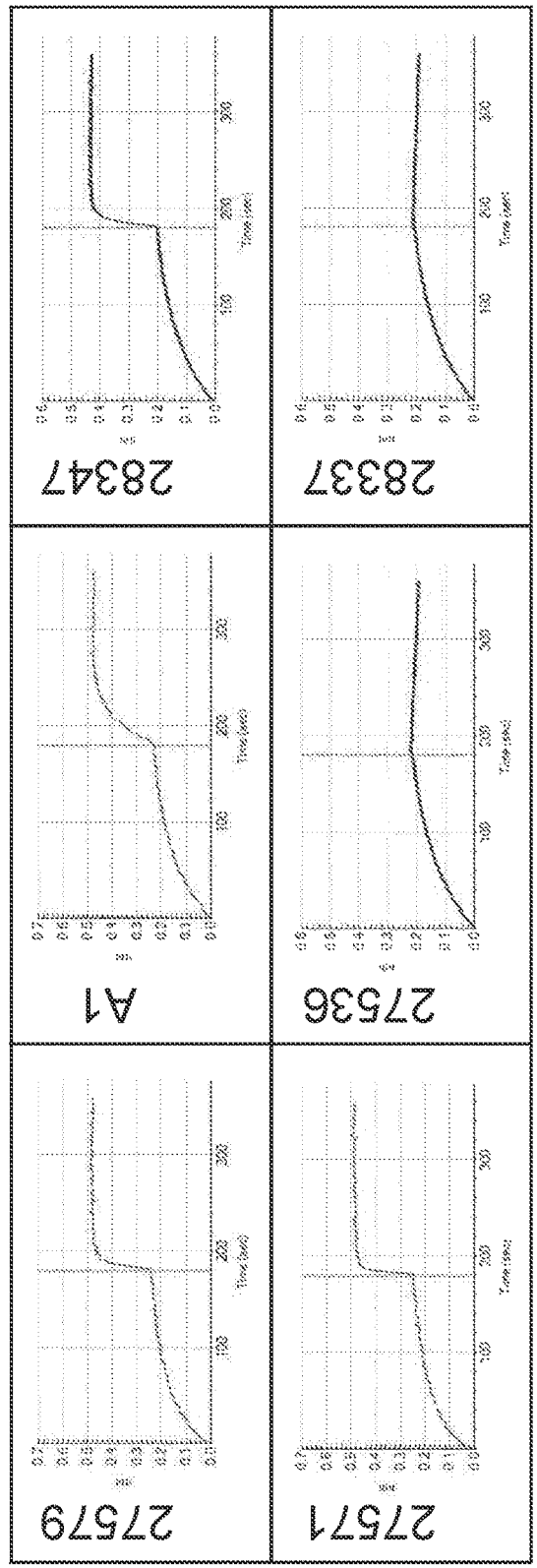

Table 1.

| Chimera # | FASTA Residue Number from Species of Origin in Chimera | | | Mouse amino acid sequence[4] | mAb binding to human-mouse CD39 chimeras | | | | | |
|---|---|---|---|---|---|---|---|---|---|---|
| | Human[1] | Mouse[2] | Human[3] | | 31895 31414 31418 | 31873 | 31801 31905 | BY40v9 | 9-8B | A1 498403[#] |
| 1 | M1-E110 | L111-Q123 | T124-V510 | $L_{111}$STELIPTSKHHQ | yes | yes | yes | yes | yes | yes |
| 2 | M1-E142 | Q143-S158 | Y159-V510 | $Q_{143}$SADEVLAAVSTSLKS | NO | NO | yes | yes | yes | yes |
| 3 | M1-G187 | R188-K204 | Q206-V510 | $R_{188}$FTQESWLSLISDSQK | yes | yes | NO | yes | yes | yes |
| 4 | M1-S274 | G274-V277 | L278-V510 | $G_{278}$GV | yes | yes | yes | yes | yes | NO |
| 5 | M1-E306 | K306-E322 | Q324-V510 | $K_{306}$KLPFDQFRIQGTGDYE | yes | yes | yes | yes | yes | yes |
| 6 | M1-M367 | D367-I378 | S378-V510 | $D_{367}$FFKKVAKNSVI | yes | yes | yes | yes | yes | yes |
| 7 | M1-C390 | S392-S404 | V404-V510 | $S_{392}$KSWEETKTSYPS | yes | yes | yes | yes | yes | yes |
| 8 | M1-H428 | N428-N447 | A448-V510 | $N_{428}$FTDSSWEQIHFMGKIK DSN | yes | yes | yes | yes | yes | yes |

FIG. 14E

Table 2.

| Chimera # | FASTA Residue Number from Species of Origin in Chimera Human | FASTA Residue Number from Species of Origin in Chimera Mouse | FASTA Residue Number from Species of Origin in Chimera Human | Mouse and Human amino acid sequences* | mAb binding to human-mouse CD39 chimeras 31895 31414 31418 | mAb binding to human-mouse CD39 chimeras 31873 | mAb binding to human-mouse CD39 chimeras 31901 31905 | mAb binding to human-mouse CD39 chimeras BY40v9 | mAb binding to human-mouse CD39 chimeras 9-8B |
|---|---|---|---|---|---|---|---|---|---|
| 2 | M1-E142 | Q143-S158 | Y159-V510 | $Q_{143}$SADEVLAAVSTSLKS | NO | NO | NO | yes | yes |
| 9 | M1-E142 Y159-V510 | Q143-L149 A151-S158 | D150 | $Q_{143}$SADEVLDAVSTSLKS | YES | NO | NO | yes | yes |
| 10 | M1-E142 Y159-V510 | Q143-V152 R154-S158 | E153 | $Q_{143}$SADEVLAAVETSLKS | YES | NO | NO | yes | yes |
| WT | M1-V510 | | | $V_{95}$QKVNEIGI $E_{143}$LADRVLDVVERSKSN | yes | yes | yes | yes | yes |
| 11 | M1-V98 E100-V510 | D99 | | $V_{95}$QKVDEIGI | yes | yes | yes | yes | yes |
| 12 | M1-E153 S155-V510 | T154 | | $E_{143}$LADRVLDVVETSKSN | yes | yes | yes | yes | yes |
| 13 | M1-V98 E100-E153 S155-V510 | D99 T154 | | $V_{95}$QKVDEIGI $E_{143}$LADRVLDVVETSKSN | yes | NO | NO | yes | yes |
| 14 | M1-V152 S155-V510 | S153 T154 | | $E_{143}$LADRVLDVVSTSKSN | yes | NO | NO | yes | yes |

FIG. 14E (Cont.)

FIG. 20
A. 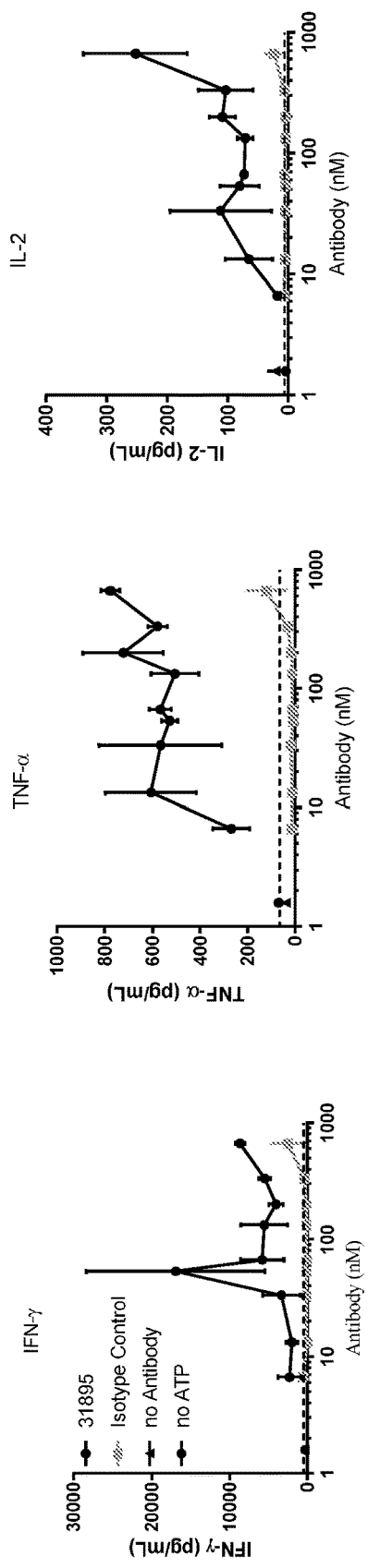
B. 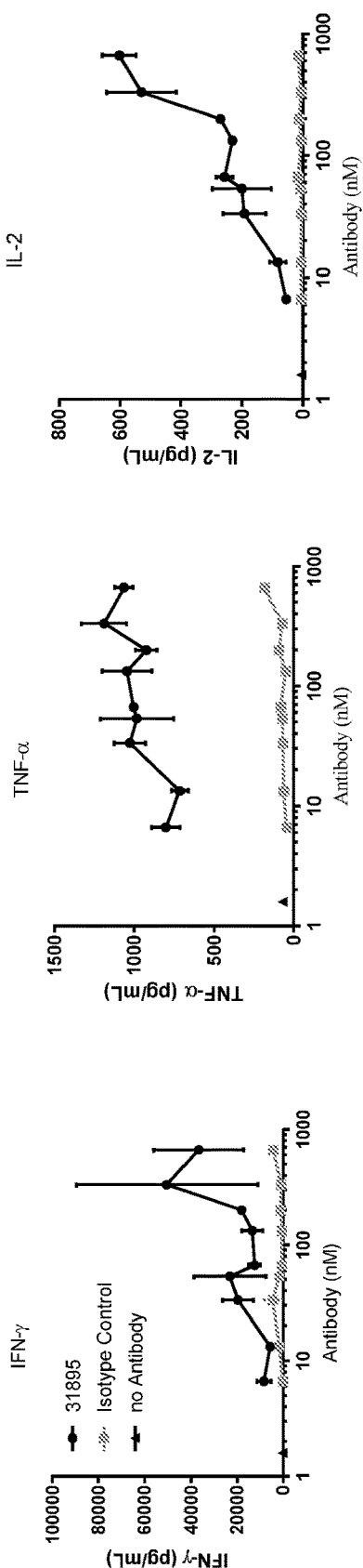

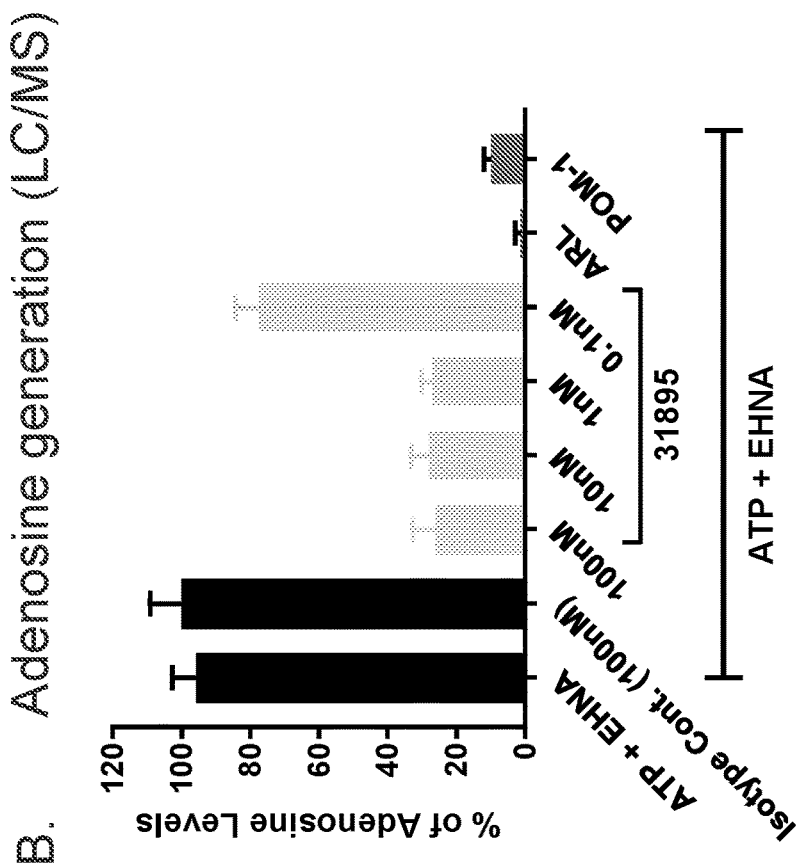
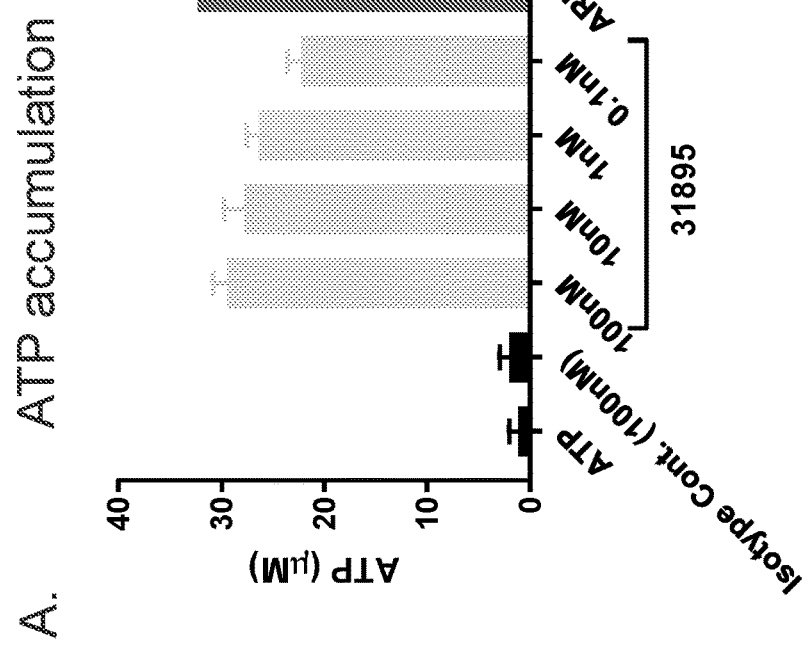
FIG. 22

ANTI-CD39 ANTIBODIES

RELATED APPLICATION

This application is the U.S. National Stage of International Application No. PCT/US2018/044449, filed Jul. 30, 2018, which claims priority to U.S. provisional application No. 62/539,527, filed Jul. 31, 2017, each of which is incorporated by reference herein in its entirety, including any drawings.

FIELD

Provided herein are antibodies with binding specificity for CD39 and compositions comprising the antibodies, including pharmaceutical compositions, diagnostic compositions and kits. Also provided are methods of using anti-CD39 antibodies for therapeutic and diagnostic purposes.

BACKGROUND

CD39 is an integral membrane protein that phosphohydrolyzes ATP to yield ADP and AMP. Human CD39 is a 510-amino acid protein with seven potential N-linked glycosylation sites, 11 cysteine residues, and two transmembrane regions. Structurally, it is characterized by two transmembrane domains, a small cytoplasmic domain comprising the $NH_2$— and COOH-terminal segments, and a large extracellular hydrophobic domain consisting of five highly conserved domains, known as apyrase conserved regions (ACR) 1-5, which are pivotal for the catabolic activity of the enzyme. CD39 becomes catalytically active upon its localization on the cell surface, and its glycosylation is important for protein folding, membrane targeting, and enzyme activity.

CD39 is constitutively expressed in spleen, thymus, lung, and placenta and in these tissues it is associated primarily with endothelial cells and immune cell populations, such as B cells, natural killer (NK) cells, dendritic cells, Langerhans cells, monocytes, macrophages, mesangial cells, neutrophils, and regulatory T cells (Tregs). Given that CD39, along with other enzymes, degrades ATP, ADP, and AMP to adenosine, CD39 can be viewed as an immunological switch that shifts ATP-driven pro-inflammatory immune cell activity toward an anti-inflammatory state mediated by adenosine.

Within a neoplastic milieu, cancer and immune cells can closely interact to generate an immunosuppressive environment by releasing immunomodulatory factors, which support neoplastic growth. The expression of CD39 is increased in many solid tumors (for example, colorectal cancer, head and neck cancer, pancreatic cancer (Kunzli et al., *Am J Physiol,* 2006, 292: 223-230), bladder cancer, brain cancer, breast cancer, gastric cancer, hepatocellular carcinoma, lung cancer, non-small cell lung cancer (Li et al., *Oncoimmunology,* 2017, 6: 6), chronic lymphocytic leukemia (Pulte et al., *Clin Lymphoma Myeloma Leuk,* 2011, 11(4): 367-372) and lymphoma, melanoma (Dzhandzhugazyan et al., *FEBS Letters,* 1998, 430: 227-230), ovarian cancer, and prostate cancer, among others) suggesting this enzyme is involved in the development and progression of malignancies. Modulators of CD39 may provide potential therapies for these types of cancers.

Interactions between tumor cells and their microenvironment are important for tumorigenesis. CD39 can participate in tumor immunoescape by inhibiting the activation, clonal expansion, and homing of tumor-specific T cells, impairing tumor cell killing by effector T lymphocytes. In addition to these immunoregulatory roles, CD39 can contribute directly to the modulation of cancer cell growth, differentiation, invasion, migration, metastasis, and angiogenesis. CD39 is important for both the initiation of angiogenesis and the progression of neovascularization. CD39 on vasculature mediates the angiogenic process in mouse models of melanoma, lung, and liver malignancy.

Modulators of CD39 activity may also provide potential therapeutics for the treatment of CD39 conditions including, but not limited to, autoimmune diseases and infections. In particular, modulators of CD39 activity may provide potential therapeutics for diseases such as, for example, without limitation, Celiac disease (Cook et al., *American Academy of Allergy, Asthma & Immunology,* 2017, Article in Press), colitis (Longhi et al., *JCI Insight.* 2017, 2(9)), thrombotic disease (Marcus et al., *Journal of Pharmacology and Experimental Therapeutics,* 2003, 305, 1: 9-16), HIV infection (zur Wiesch et al., *Journal of Virology,* 2011, February: 1287-1297), HBV infection, HCV infection, and inflammatory bowel disease (Friedman et al. *PNAS,* 2009, 106, 39: 16788-16793) and Crohn's disease (Bai et al., *J Immunol,* 2014, 3366-3377).

SUMMARY

Provided herein are antibodies that selectively bind CD39. In some embodiments, the antibodies bind human CD39. In some embodiments, the antibodies also bind homologs of human CD39.

In some embodiments, the antibodies comprise at least one CDR sequence defined by a consensus sequence provided in this disclosure. In some embodiments, the antibodies comprise an illustrative CDR, $V_H$, or $V_L$ sequence provided in this disclosure, heavy chain or light chain provided in the disclosure, or a variant thereof. In some aspects, the variant is a variant with one or more conservative amino acid substitutions.

Also provided are compositions and kits comprising the antibodies. In some embodiments, the compositions are pharmaceutical compositions. Any suitable pharmaceutical composition may be used. In some embodiments, the pharmaceutical composition is a composition for parenteral administration.

This disclosure also provides methods of using the anti-CD39 antibodies provided herein. In some embodiments, the method is a method of treatment. In some embodiments, the method is a diagnostic method. In some embodiments, the method is an analytical method. In some embodiments, the method is a method of purifying and/or quantifying CD39.

In some embodiments, the antibodies are used to treat a disease or condition. In some aspects, the disease or condition is selected from a cancer, autoimmune disease, and infection.

BRIEF DESCRIPTION OF THE DRAWINGS

FIG. 1 provides a table showing monovalent affinity of anti-huCD39 antibodies to recombinant human CD39 extracellular domain. The table provides binding kinetics of anti-CD39 antibodies interacting with soluble recombinant human CD39 (ENTDP1) extracellular domain (ECD) by biolayer interferometry (ForteBio Octet). Anti-CD39 antibodies were captured on an anti-human Fc sensor and exposed to recombinant human CD39 ECD at concentration ranging from 10-300 nanomolar. The kinetic data was globally fit with a simple 1:1 Langmuir binding model to yield on-rate (kon) and off-rate (koff) values. The equilibrium dissociation constants ($K_D$) were calculated from the kon and koff values.

FIGS. 2 A-E show inhibition of enzymatic catabolism of ATP and ADP to Pi by human CD39 extracellular domain (ECD). Recombinant human CD39 at a final concentration of either 10 nanomolar (A-D) or 5 nanomolar (E) was incubated with anti-CD39 IgGs at a final concentration of either 1 micromolar (A-D) or 0.25 micromolar (E) in 25 mM Tris, 5 mM $CaCl_2$, pH 7.5 at room temperature for 2 hours. ATP (500 micromolar) was added to the reaction and incubated at 37° C. for 60 minutes. Residual ATP levels in the reaction were measured using the CellTiter-Glo assay. Data values are the average of two replicates.

FIG. 2 F shows antibodies that bind to CHO cells expressing human or cyno CD39.

FIG. 3 shows evaluation of antibody binding to MEL-28 (A) and 721 (B) cells. Anti-CD39 antibodies (each antibody clone number indicated in the figure) were titrated from 15 to 0.001 µg/ml. $EC_{50}$s were calculated using GraphPad Prism Software. The figure represents three independent experiments.

FIG. 4A shows the results when anti-CD39 antibodies were compared to the non-specific small molecule inhibitors POM-1 and ARL. Inhibition is determined by decreased phosphate release (Pi). Data is representative of at least 10 independent experiments. Anti-CD39 antibodies (each antibody clone number is indicated in the figure) were titrated from 15 to 0.001 µg/ml. IC50 values were calculated using GraphPad Prism Software, as can be seen in FIG. 4B. Three independent experiments were performed.

FIG. 5A shows evaluation of ATP levels after incubating MEL-28 cells with a dose titration of anti-CD39 antibodies that inhibit enzymatic activity. FIG. 5B provides IC50 values calculated using GrapPad Prism. At least three independent experiments were performed.

FIG. 6A shows anti-CD39 antibodies (each number represents a unique clone indicated in the figure) were titrated from 100 nM to 0.000610 nM. FIG. 6B provide IC50 values calculated using GraphPad Prism Software. Three independent experiments are represented.

In FIG. 7A, anti-CD39 antibodies were titrated on purified B cells from healthy donor and detected with anti-human IgG-PE secondary antibody. EC50 was calculated using GrapPad Prism software. In FIG. 7B, anti-CD39 antibodies were titrated on cyno PBMCs and detected using a-human IgG PE secondary antibody. B cells were gated using FlowJo software and $EC_{50}$s were calculated using GraphPad Prism.

FIGS. 14 A-G provides examples of antibodies. FIG. 14B provides examples of antibodies that have limited ability to inhibit the ATPase activity of both soluble recombinant and cellular CD39 and bin separately from other cellular CD39 inhibitors. FIG. 14E provides examples of inhibitory antibodies that make distinct contacts with CD39. FIG. 14E has two tables, Table 1 and Table 2. Table 1 provides examples of inhibitory antibodies that make distinct contacts with CD39. Table 2 provides examples of inhibitory antibodies that bind critical yet distinct contacts residues with CD39.

FIG. 20 shows anti-CD39 antibody increases stimulated PBMC secretion of INF-γ, TNF-α and IL-2.

FIG. 22 shows CD39 inhibition leads to accumulation of ATP and blocks generation of adenosine.

DETAILED DESCRIPTION

1. Definitions

Figure 4:
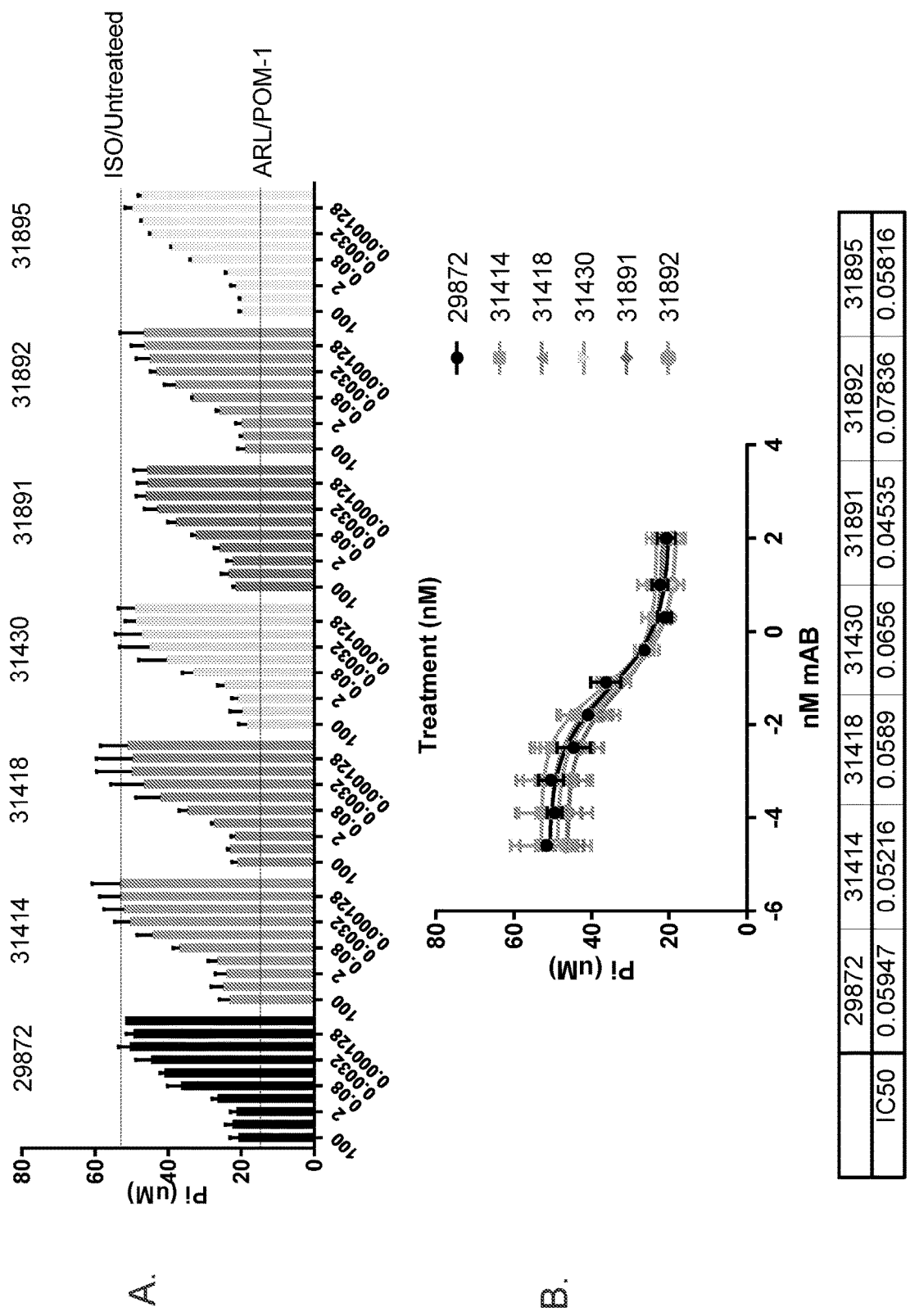
FIG. 4 provides evaluation of antibody driven inhibition of ATP hydrolysis of CD39 on MEL-28 cells in a short term ATP assay.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value±10%, ±5%, or ±1%. In certain embodiments, the term "about" indicates the designated value one standard deviation of that value.

The term "combinations thereof" includes every possible combination of elements to which the term refers.

The terms "CD39" and "CD39 antigen" and "Cluster of Differentiation 39" are used interchangeably herein. CD39 is also known as ectonucleoside triphosphate diphosphohydrolase-1 (gene: ENTPDJ; protein: NTPDase1. CD39 has also been referred to as ATPDase and SPG64. Each of the terms set forth may be used interchangeably. Unless specified otherwise, the terms include any variants, isoforms and species homologs of human CD39 that are naturally expressed by cells, or that are expressed by cells transfected with a CD39 gene. In some embodiments, CD39 proteins include murine CD39. In some embodiments, CD39 proteins include cynomolgus CD39.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "CD39 antibody," "anti-CD39 antibody," "CD39 Ab," "CD39-specific antibody" or "anti-CD39 Ab" is an antibody, as described herein, which binds specifically to the antigen CD39. In some embodiments, the antibody binds the extracellular domain of CD39.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes. FIG. 1 provides a comparison of the Kabat and Chothia numbering schemes for CDR-H1. See Martin (2010), supra.

Unless otherwise specified, the numbering scheme used for identification of a particular CDR herein is the Kabat/Chothia numbering scheme. Where the residues encompassed by these two numbering schemes diverge, the numbering scheme is specified as either Kabat or Chothia.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by papain digestion of a full-length antibody.

"F(ab')$_2$" fragments contain two Fab' fragments joined, near the hinge region, by disulfide bonds. F(ab')$_2$ fragments may be generated, for example, by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety. "scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is provided as a solution comprising at least 85%, 90%, 95%, 98%, 99% to 100% by weight of an antibody, the remainder of the weight comprising the weight of other solutes dissolved in the solvent.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$) Affinity can be measured by common methods known in the art, including those described herein Affinity can be determined, for example, using surface plasmon resonance (SPR) technology, such as a Biacore instrument.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "$k_d$" (sec$^{-1}$), as used herein, refers to the dissociation rate constant of a particular antibody-antigen interaction. This value is also referred to as the kaf value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$.

The term "KA" (M$^{-1}$), as used herein, refers to the association equilibrium constant of a particular antibody-antigen interaction. $K_A = k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen Affinity matured antibodies may be produced using a variety of methods known in the art. For example, Marks et al. (*Bio/Technology,* 1992, 10:779-783, incorporated by reference in its entirety) describes affinity maturation by V$_H$ and V$_L$ domain shuffling Random mutagenesis of CDR and/or framework residues is described by, for example, Barbas et al. (*Proc. Nat. Acad. Sci. USA.,* 1994, 91:3809-3813); Schier et al., *Gene,* 1995, 169:147-155; Yelton et al., J. Immunol., 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen (e.g., CD39). In one exemplary assay, CD39 is coated on a plate and allowed to bind a first antibody, after which a second, labeled antibody is added. If the presence of the first antibody reduces binding of the second antibody, then the antibodies compete. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to CD39 variants with different point-mutations.

Percent "identity" between a polypeptide sequence and a reference sequence is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGA-LIGN (DNASTAR), CLUSTALW, or CLUSTAL OMEGA software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the following groups of amino acids are considered conservative substitutions for one another.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

| | |
|---|---|
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |
| Small Residues | A, C, D, G, N, P, S, T, and V |
| Very Small Residues | A, G, and S |
| Residues Involved in Turn Formation | A, C, D, E, G, H, K, Q, R, S, P, and T |
| Flexible Residues | Q, T, K, S, G, P, D, F, and R |

| | |
|---|---|
| Group 1 | A, S, and T |
| Group 2 | D and E |
| Group 3 | N and Q |

-continued

| | |
|---|---|
| Group 4 | R and K |
| Group 5 | I, L, and M |
| Group 6 | F, Y, and W |

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, N.Y. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of an antibody or composition that when administered to a subject is effective to treat a disease or disorder.

As used herein, the term "subject" means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has cancer, an autoimmune disease or condition, and/or an infection that can be treated with an antibody provided herein. In some embodiments, the subject is a human that is suspected to have cancer, an autoimmune disease or condition, and/or an infection.

2. Antibodies

Provided herein are antibodies that selectively bind human CD39, as well as the nucleic acids that encode the antibodies. In some aspects, the antibody selectively binds to the extracellular domain of human CD39.

In some embodiments, the antibody binds to homologs of human CD39. In some aspects, the antibody binds to a homolog of human CD39 from a species selected from monkeys, mice, dogs, cats, rats, cows, horses, goats, and sheep. In some aspects, the homolog is a cynomolgus monkey homolog. In some aspects, the homolog is a murine homolog.

In some embodiments, the antibody has one or more CDRs having particular lengths, in terms of the number of amino acid residues. In some embodiments, the Chothia CDR-H1 of the antibody is 6, 7, 8, or 9 residues in length. In some embodiments, the Kabat CDR-H1 of the antibody is 4, 5, 6, or 7 residues in length. In some embodiments, the Chothia CDR-H2 of the antibody is 5, 6, or 7 residues in length. In some embodiments, the Kabat CDR-H2 of the antibody is 15, 16, 17, or 18 residues in length. In some embodiments, the Kabat/Chothia CDR-H3 of the antibody is 5, 6, 7, 8, 9, 10, 11, or 12 residues in length.

In some aspects, the Kabat/Chothia CDR-L1 of the antibody is 9, 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, 10, 11, or 12 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

In some aspects, the antibody inhibits conversion by CD39 of ATP to ADP and/or ADP to AMP. In some aspects, the antibody decreases the levels of phosphate, ADP, AMP, and/or adenosine and/or increases the levels of ATP.

In some embodiments, the antibody increases proliferation of stimulated CD4⁻ and CD8⁺ T cells. In some embodiments, the antibody increases stimulated PBMC secretion of INF-γ, TNF-α, IL-2, and/or IL-1β.

In some embodiments, the antibody increases a T effector cell function. In some embodiments, the antibody decreases the number of regulatory T cells in tissues or in circulation. In some embodiments, the antibody suppresses a regulatory or T cell activity. In some embodiments, the antibody increase B cell function. In some embodiments, the antibody increases antigen presenting cell function. In some embodiments, the antibody decreases or prevents activation of phospho antigen specific T cells selected from MAIT cells and gamma delta T cells.

In some aspects, the decrease is about or less than a 10% decrease, about or less than a 20% decrease, about or less than a 30% decrease, about or less than a 40% decrease, about or less than a 50% decrease, about or less than a 60% decrease, about or less than a 70% decrease, about or less than an 80% decrease, about or less than a 90% decrease, or about a complete decrease. In some aspects, the increase is about or greater than a 10% increase, about or greater than a 20% increase, about or greater than a 30% increase, about or greater than a 40% increase, about or greater than a 50% increase, about or greater than a 60% increase, about or greater than a 70% increase, about or greater than an 80% increase, about or greater than a 90% increase, or a complete increase.

Given that CD39 degrades ATP and ADP to adenosine, CD39 can be viewed as an immunological switch that shifts ATP-driven pro-inflammatory immune cell activity toward an anti-inflammatory state mediated by adenosine. CD39 has a role in regulating the function of several immune cell types, including lymphocytes, neutrophils, monocytes/macrophages, dendritic cells, and endothelial cells and shifting the switch can have a significant impact on disease. For example, the generation of adenosine via CD39 is recognized as a major mechanism of regulatory T cell (Treg) immunosuppressive function.

The antibodies provided herein may be useful for the treatment of a variety of diseases and conditions, including cancers, autoimmune diseases, and infections. In some embodiments, the antibody inhibits CD39 function on tumor cells. In some embodiments, the antibody inhibits angiogenesis.

The frequency of CD39$^+$ Tregs and the expression on the cell surface is increased in some human cancers, and the importance of CD39$^+$ Tregs in promoting tumor growth and metastasis has been demonstrated using several in vivo models. Immunohistochemical staining of normal and tumor tissues has revealed that CD39 expression is significantly higher in several types of human cancer than in normal tissues. In cancer specimens, CD39 is expressed by infiltrating lymphocytes, the tumor stroma, and/or tumor cells. CD39 in cancer cells displays ATPase activity and generates adenosine. CD39$^+$ cancer cells inhibited the proliferation of CD4 and CD8 T cells and the generation of cytotoxic effector CD8 T cells (CTL) in a CD39– and adenosine-dependent manner.

2.1. CDR-H3 Sequences

In some embodiments, the antibody comprises a CDR-H3 sequence comprising, consisting of, or consisting essentially of a sequence selected from SEQ ID NOs: 82-109. In some aspects, the antibody comprises a CDR-H3 sequence comprising, consisting of, or consisting essentially of SEQ ID NO: 82. In some aspects, the antibody comprises a CDR-H3 sequence comprising, consisting of, or consisting essentially of SEQ ID NO: 83. In some aspects, the antibody comprises a CDR-H3 sequence comprising, consisting of, or consisting essentially of SEQ ID NO: 84. In some aspects, the antibody comprises a CDR-H3 sequence comprising, consisting of, or consisting essentially of SEQ ID NO: 85. In some aspects, the antibody comprises a CDR-H3 sequence comprising, consisting of, or consisting essentially of SEQ ID NO: 86. In some aspects, the antibody comprises a CDR-H3 sequence comprising, consisting of, or consisting essentially of SEQ ID NO: 87. In some aspects, the antibody comprises a CDR-H3 sequence comprising, consisting of, or consisting essentially of SEQ ID NO: 88. In some aspects, the antibody comprises a CDR-H3 sequence comprising, consisting of, or consisting essentially of SEQ ID NO: 89. In some aspects, the antibody comprises a CDR-H3 sequence comprising, consisting of, or consisting essentially of SEQ ID NO: 90. In some aspects, the antibody comprises a CDR-H3 sequence comprising, consisting of, or consisting essentially of SEQ ID NO: 91. In some aspects, the antibody comprises a CDR-H3 sequence comprising, consisting of, or consisting essentially of SEQ ID NO: 92. In some aspects, the antibody comprises a CDR-H3 sequence comprising, consisting of, or consisting essentially of SEQ ID NO: 93. In some aspects, the antibody comprises a CDR-H3 sequence comprising, consisting of, or consisting essentially of SEQ ID NO: 94. In some aspects, the antibody comprises a CDR-H3 sequence comprising, consisting of, or consisting essentially of SEQ ID NO: 95. In some aspects, the antibody comprises a CDR-H3 sequence comprising, consisting of, or consisting essentially of SEQ ID NO: 96. In some aspects, the antibody comprises a CDR-H3 sequence comprising, consisting of, or consisting essentially of SEQ ID NO: 97. In some aspects, the antibody comprises a CDR-H3 sequence comprising, consisting of, or consisting essentially of SEQ ID NO: 98. In some aspects, the antibody comprises a CDR-H3 sequence comprising, consisting of, or consisting essentially of SEQ ID NO: 99. In some aspects, the antibody comprises a CDR-H3 sequence comprising, consisting of, or consisting essentially of SEQ ID NO: 100. In some aspects, the antibody comprises a CDR-H3 sequence comprising, consisting of, or consisting essentially of SEQ ID NO: 101. In some aspects, the antibody comprises a CDR-H3 sequence comprising, consisting of, or consisting essentially of SEQ ID NO: 102. In some aspects, the antibody comprises a CDR-H3 sequence comprising, consisting of, or consisting essentially of SEQ ID NO: 103. In some aspects, the antibody comprises a CDR-H3 sequence comprising, consisting of, or consisting essentially of SEQ ID NO: 104. In some aspects, the antibody comprises a CDR-H3 sequence comprising, consisting of, or consisting essentially of SEQ ID NO: 105. In some aspects, the antibody comprises a CDR-H3 sequence comprising, consisting of, or consisting essentially of SEQ ID NO: 106. In some aspects, the antibody comprises a CDR-H3 sequence comprising, consisting of, or consisting essentially of SEQ ID NO: 107. In some aspects, the antibody comprises a CDR-H3 sequence comprising, consisting of, or consisting essentially of SEQ ID NO: 108. In some aspects, the antibody comprises a CDR-H3 sequence comprising, consisting of, or consisting essentially of SEQ ID NO: 109.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

2.2. $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H3

In some embodiments, the antibody comprises a $V_H$ sequence comprising a Kabat CDR-H3 sequence comprising, consisting of, or consisting essentially of a sequence selected from SEQ ID NOs: 82-109. In some aspects, the antibody comprises a $V_H$ sequence comprising a Kabat CDR-H3 sequence comprising, consisting of, or consisting essentially of SEQ ID NO: 82. In some aspects, the antibody comprises a $V_H$ sequence comprising a Kabat CDR-H3 sequence comprising, consisting of, or consisting essentially of SEQ ID NO: 83. In some aspects, the antibody comprises a $V_H$ sequence comprising a Kabat CDR-H3 sequence comprising, consisting of, or consisting essentially of SEQ ID NO: 84. In some aspects, the antibody comprises a $V_H$ sequence comprising a Kabat CDR-H3 sequence comprising, consisting of, or consisting essentially of SEQ ID NO: 85. In some aspects, the antibody comprises a $V_H$ sequence comprising a Kabat CDR-H3 sequence comprising, consisting of, or consisting essentially of SEQ ID NO: 86. In some aspects, the antibody comprises a $V_H$ sequence comprising a Kabat CDR-H3 sequence comprising, consisting of, or consisting essentially of SEQ ID NO: 87. In some aspects, the antibody comprises a $V_H$ sequence comprising a Kabat CDR-H3 sequence comprising, consisting of, or consisting essentially of SEQ ID NO: 88. In some aspects, the antibody comprises a $V_H$ sequence comprising a Kabat CDR-H3 sequence comprising, consisting of, or consisting essentially of SEQ ID NO: 89. In some aspects, the antibody comprises a Vu sequence comprising a Kabat CDR-H3 sequence comprising, consisting of, or consisting essentially of SEQ ID NO: 90. In some aspects, the antibody comprises a $V_H$ sequence comprising a Kabat CDR-H3 sequence comprising, consisting of, or consisting essentially of SEQ ID NO: 91. In some aspects, the antibody comprises a $V_H$ sequence comprising a Kabat CDR-H3 sequence comprising, consisting of, or consisting essentially of SEQ ID NO: 92. In some aspects, the antibody comprises a $V_H$ sequence comprising a Kabat CDR-H3 sequence comprising, consisting of, or consisting essentially of SEQ ID NO: 93. In some aspects, the antibody comprises a $V_H$ sequence comprising a Kabat CDR-H3 sequence comprising, consisting of, or consisting essentially of SEQ ID NO: 94. In some aspects, the antibody comprises a $V_H$ sequence comprising a Kabat CDR-H3 sequence comprising, consisting of, or consisting essentially of SEQ ID NO: 95. In some aspects, the antibody comprises a $V_H$ sequence comprising a Kabat CDR-H3 sequence comprising, consisting of, or consisting essentially of SEQ ID NO: 96. In some aspects, the antibody comprises a $V_H$ sequence comprising a Kabat CDR-H3 sequence comprising, consisting of, or consisting essentially of SEQ ID NO: 97. In some aspects, the antibody comprises a $V_H$ sequence comprising a Kabat CDR-H3 sequence comprising, consisting of, or consisting essentially of SEQ ID NO: 98. In some aspects, the antibody comprises a $V_H$ sequence comprising a Kabat CDR-H3 sequence comprising, consisting of, or consisting essentially of SEQ ID NO: 99. In some aspects, the antibody comprises a $V_H$ sequence comprising a Kabat CDR-H3 sequence comprising, consisting of, or consisting essentially of SEQ ID NO: 100. In some aspects, the antibody comprises a $V_H$ sequence comprising a Kabat CDR-H3 sequence comprising, consisting of, or consisting essentially of SEQ ID NO: 101. In some aspects, the antibody comprises a $V_H$ sequence comprising a Kabat CDR-H3 sequence comprising, consisting of, or consisting essentially of SEQ ID NO: 102. In some aspects, the antibody comprises a $V_H$ sequence comprising a Kabat CDR-H3 sequence comprising, consisting of, or consisting essentially of SEQ ID NO: 103. In some aspects, the antibody comprises a $V_H$ sequence comprising a Kabat CDR-H3 sequence comprising, consisting of, or consisting essentially of SEQ ID NO: 104. In some aspects, the antibody comprises a $V_H$ sequence comprising a Kabat CDR-H3 sequence comprising, consisting of, or consisting essentially of SEQ ID NO: 105. In some aspects, the antibody comprises a $V_H$ sequence comprising a Kabat CDR-H3 sequence comprising, consisting of, or consisting essentially of SEQ ID NO: 106. In some aspects, the antibody comprises a $V_H$ sequence comprising a Kabat CDR-H3 sequence comprising, consisting of, or consisting essentially of SEQ ID NO: 107. In some aspects, the antibody comprises a $V_H$ sequence comprising a Kabat CDR-H3 sequence comprising, consisting of, or consisting essentially of SEQ ID NO: 108. In some aspects, the antibody comprises a $V_H$ sequence comprising a Kabat CDR-H3 sequence comprising, consisting of, or consisting essentially of SEQ ID NO: 109.

2.2.1.2. Kabat CDR-H2

In some embodiments, the antibody comprises a $V_H$ sequence comprising a Kabat CDR-H2 sequence comprising, consisting of, or consisting essentially of a sequence selected from SEQ ID NOs: 63-81. In some aspects, the antibody comprises a $V_H$ sequence comprising a Kabat CDR-H2 sequence comprising, consisting of, or consisting essentially of SEQ ID NO: 63. In some aspects, the antibody comprises a $V_H$ sequence comprising a Kabat CDR-H2 sequence comprising, consisting of, or consisting essentially of SEQ ID NO: 64. In some aspects, the antibody comprises a $V_H$ sequence comprising a Kabat CDR-H2 sequence comprising, consisting of, or consisting essentially of SEQ ID NO: 65. In some aspects, the antibody comprises a $V_H$ sequence comprising a Kabat CDR-H2 sequence comprising, consisting of, or consisting essentially of SEQ ID NO: 66. In some aspects, the antibody comprises a $V_H$ sequence comprising a Kabat CDR-H2 sequence comprising, consisting of, or consisting essentially of SEQ ID NO: 67. In some aspects, the antibody comprises a $V_H$ sequence comprising a Kabat CDR-H2 sequence comprising, consisting of, or consisting essentially of SEQ ID NO: 68. In some aspects, the antibody comprises a $V_H$ sequence comprising a Kabat CDR-H2 sequence comprising, consisting of, or consisting essentially of SEQ ID NO: 69. In some aspects, the antibody comprises a $V_H$ sequence comprising a Kabat CDR-H2 sequence comprising, consisting of, or consisting essentially of SEQ ID NO: 70. In some aspects, the antibody comprises a $V_H$ sequence comprising a Kabat CDR-H2 sequence comprising, consisting of, or consisting essentially of SEQ ID NO: 71. In some aspects, the antibody comprises a $V_H$ sequence comprising a Kabat CDR-H2 sequence comprising, consisting of, or consisting essentially of SEQ ID NO: 72. In some aspects, the antibody comprises a $V_H$ sequence comprising a Kabat CDR-H2 sequence comprising, consisting of, or consisting essentially of SEQ ID NO: 73. In some aspects, the antibody comprises a $V_H$ sequence comprising a Kabat CDR-H2 sequence comprising, consisting of, or consisting essentially of SEQ ID NO: 74. In some aspects, the antibody comprises a $V_H$ sequence comprising a Kabat CDR-H2 sequence comprising, consisting of, or consisting essentially of SEQ ID NO: 75. In some aspects, the antibody comprises a $V_H$ sequence comprising a Kabat CDR-H2 sequence comprising, consisting of, or consisting essentially of SEQ ID NO: 76. In some aspects, the antibody comprises a $V_H$ sequence comprising a Kabat CDR-H2 sequence comprising, consisting of, or consisting essentially of SEQ ID NO: 77. In some aspects, the antibody comprises a $V_H$ sequence comprising a Kabat CDR-H2 sequence comprising, consisting of, or consisting essentially of SEQ ID NO: 78. In some aspects, the antibody comprises a $V_H$ sequence comprising a Kabat CDR-H2 sequence comprising, consisting of, or consisting essentially of SEQ ID NO: 79. In some aspects, the antibody comprises a $V_H$ sequence comprising a Kabat CDR-H2 sequence comprising, consisting of, or consisting essentially of SEQ ID NO: 80. In some aspects, the antibody comprises a $V_H$ sequence comprising a Kabat CDR-H2 sequence comprising, consisting of, or consisting essentially of SEQ ID NO: 81.

2.2.1.3. Kabat CDR-H1

In some embodiments, the antibody comprises a $V_H$ sequence comprising a Kabat CDR-H1 sequence comprising, consisting of, or consisting essentially of a sequence selected from SEQ ID NOs: 25-45. In some aspects, the antibody comprises a $V_H$ sequence comprising a Kabat CDR-H1 sequence comprising, consisting of, or consisting essentially of SEQ ID NO: 25. In some aspects, the antibody comprises a $V_H$ sequence comprising a Kabat CDR-H1 sequence comprising, consisting of, or consisting essentially of SEQ ID NO: 26. In some aspects, the antibody comprises a $V_H$ sequence comprising a Kabat CDR-H1 sequence comprising, consisting of, or consisting essentially of SEQ ID NO: 27. In some aspects, the antibody comprises a $V_H$ sequence comprising a Kabat CDR-H1 sequence comprising, consisting of, or consisting essentially of SEQ ID NO: 28. In some aspects, the antibody comprises a $V_H$ sequence comprising a Kabat CDR-H1 sequence comprising, consisting of, or consisting essentially of SEQ ID NO: 29. In some aspects, the antibody comprises a $V_H$ sequence comprising a Kabat CDR-H1 sequence comprising, consisting of, or consisting essentially of SEQ ID NO: 30. In some aspects, the antibody comprises a $V_H$ sequence comprising a Kabat CDR-H1 sequence comprising, consisting of, or consisting essentially of SEQ ID NO: 31. In some aspects, the antibody comprises a $V_H$ sequence comprising a Kabat CDR-H1 sequence comprising, consisting of, or consisting essentially of SEQ ID NO: 32. In some aspects, the antibody comprises a $V_H$ sequence comprising a Kabat CDR-H1 sequence comprising, consisting of, or consisting essentially of SEQ ID NO: 33. In some aspects, the antibody comprises a $V_H$ sequence comprising a Kabat CDR-H1 sequence comprising, consisting of, or consisting essentially of SEQ ID NO: 34. In some aspects, the antibody comprises a $V_H$ sequence comprising a Kabat CDR-H1 sequence comprising, consisting of, or consisting essentially of SEQ ID NO: 35. In some aspects, the antibody comprises a $V_H$ sequence comprising a Kabat CDR-H1 sequence comprising, consisting of, or consisting essentially of SEQ ID NO: 36. In some aspects, the antibody comprises a $V_H$ sequence comprising a Kabat CDR-H1 sequence comprising, consisting of, or consisting essentially of SEQ ID NO: 37. In some aspects, the antibody comprises a $V_H$ sequence comprising a Kabat CDR-H1 sequence comprising, consisting of, or consisting essentially of SEQ ID NO: 38. In some aspects, the antibody comprises a $V_H$ sequence comprising a Kabat CDR-H1 sequence comprising, consisting of, or consisting essentially of SEQ ID NO: 39. In some aspects, the antibody comprises a $V_H$ sequence comprising a Kabat CDR-H1 sequence comprising, consisting of, or consisting essentially of SEQ ID NO: 40. In some aspects, the antibody comprises a $V_H$ sequence comprising a Kabat CDR-H1 sequence comprising, consisting of, or consisting essentially of SEQ ID NO: 41. In some aspects, the antibody comprises a $V_H$ sequence comprising a Kabat CDR-H1 sequence comprising, consisting of, or consisting essentially of SEQ ID NO: 42. In some aspects, the antibody comprises a $V_H$ sequence comprising a Kabat CDR-H1 sequence comprising, consisting of, or consisting essentially of SEQ ID NO: 43. In some aspects, the antibody comprises a $V_H$ sequence comprising a Kabat CDR-H1 sequence comprising, consisting of, or consisting essentially of SEQ ID NO: 44. In some aspects, the antibody comprises a Vu sequence comprising a Kabat CDR-H1 sequence comprising, consisting of, or consisting essentially of SEQ ID NO: 45.

2.2.1.4. Kabat CDR-H3+ Kabat CDR-H2

In some embodiments, the antibody comprises a $V_H$ sequence comprising a Kabat CDR-H3 sequence comprising, consisting of, or consisting essentially of a sequence selected from SEQ ID NOs: 82-109, and a Kabat CDR-H2 sequence comprising, consisting of, or consisting essentially of a sequence selected from SEQ ID NOs: 63-81. In some aspects, the Kabat CDR-H3 sequence and the Kabat CDR-H2 sequence are both from a single illustrative Vu sequence provided in this disclosure. For example, in some aspects, the Kabat CDR-H3 and Kabat CDR-H2 are both from a single illustrative Vu sequence selected from SEQ ID NOs: 179-218.

2.2.1.5. Kabat CDR-H3+ Kabat CDR-H1

In some embodiments, the antibody comprises a $V_H$ sequence comprising a Kabat CDR-H3 sequence comprising, consisting of, or consisting essentially of a sequence selected from SEQ ID NOs: 82-109, and a Kabat CDR-H1 sequence comprising, consisting of, or consisting essentially of a sequence selected from SEQ ID NOs: 25-45. In some aspects, the Kabat CDR-H3 sequence and the Kabat CDR-H1 sequence are both from a single illustrative $V_H$ sequence provided in this disclosure. For example, in some aspects, the Kabat CDR-H3 and Kabat CDR-H1 are both from a single illustrative $V_H$ sequence selected from SEQ ID NOs: 179-218.

2.2.1.6. Kabat CDR-H1+ Kabat CDR-112

In some embodiments, the antibody comprises a $V_H$ sequence comprising a Kabat CDR-H1 sequence comprising, consisting of, or consisting essentially of a sequence selected from SEQ ID NOs: 25-45 and a Kabat CDR-H2 sequence comprising, consisting of, or consisting essentially of a sequence selected from SEQ ID NOs: 63-81. In some aspects, the Kabat CDR-H1 sequence and the Kabat CDR-H2 sequence are both from a single illustrative $V_H$ sequence provided in this disclosure. For example, in some aspects, the Kabat CDR-H1 and Kabat CDR-H2 are both from a single illustrative $V_H$ sequence selected from SEQ ID NOs: 179-218.

2.2.1.7. Kabat CDR-H1+ Kabat CDR-H2+ Kabat CDR-H3

In some embodiments, the antibody comprises a $V_H$ sequence comprising a Kabat CDR-H1 sequence comprising, consisting of, or consisting essentially of a sequence selected from SEQ ID NOs: 25-45, a Kabat CDR-H2 sequence comprising, consisting of, or consisting essentially of a sequence selected from SEQ ID NOs: 63-81, and a Kabat CDR-H3 sequence comprising, consisting of, or consisting essentially of a sequence selected from SEQ ID NOs: 82-109. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 179-218.

In some aspects, the antibody comprises a $V_H$ sequence comprising a Kabat CDR-H1 sequence comprising SEQ ID NO: 25, a Kabat CDR-H2 sequence comprising SEQ ID NO: 63, and a Kabat CDR-H3 sequence comprising SEQ ID NO: 82. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 83. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 84. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 85. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 86. In some aspects, the antibody comprises a $V_H$ sequence comprising a Kabat CDR-H1 sequence comprising SEQ ID NO: 25, a Kabat CDR-H2 sequence comprising SEQ ID NO: 66, and a Kabat CDR-H3 sequence comprising SEQ ID NO: 82. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 82. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 82. In some aspects, the antibody comprises a $V_H$ sequence comprising a Kabat CDR-H1 sequence comprising SEQ ID NO: 28, a Kabat CDR-H2 sequence comprising SEQ ID NO: 67, and a Kabat CDR-H3 sequence comprising SEQ ID NO: 82. In some aspects, the antibody comprises a $V_H$ sequence comprising a Kabat CDR-H1 sequence comprising SEQ ID NO: 29, a Kabat CDR-H2 sequence comprising SEQ ID NO: 68, and a Kabat CDR-H3 sequence comprising SEQ ID NO: 82. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 82. In some aspects, the antibody comprises a $V_H$ sequence comprising a Kabat CDR-H1 sequence comprising SEQ ID NO: 30, a Kabat CDR-H2 sequence comprising SEQ ID NO: 69, and a Kabat CDR-H3 sequence comprising SEQ ID NO: 87. In some aspects, the antibody comprises a $V_H$ sequence comprising a Kabat CDR-H1 sequence comprising SEQ ID NO: 31, a Kabat CDR-H2 sequence comprising SEQ ID NO: 70, and a Kabat CDR-H3 sequence comprising SEQ ID NO: 88. In some aspects, the antibody comprises a $V_H$ sequence comprising a Kabat CDR-H1 sequence comprising SEQ ID NO: 32, a Kabat CDR-H2 sequence comprising SEQ ID NO: 71, and a Kabat CDR-H3 sequence comprising SEQ ID NO: 89. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 90. In some aspects, the antibody comprises a $V_H$ sequence comprising a Kabat CDR-H1 sequence comprising SEQ ID NO: 34, a Kabat CDR-H2 sequence comprising SEQ ID NO: 72, and a Kabat CDR-H3 sequence comprising SEQ ID NO: 91. In some aspects, the antibody comprises a $V_H$ sequence comprising a Kabat CDR-H1 sequence comprising SEQ ID NO: 30, a Kabat CDR-H2 sequence comprising SEQ ID NO: 71, and a Kabat CDR-H3 sequence comprising SEQ ID NO: 92. In some aspects, the antibody comprises a $V_H$ sequence comprising a Kabat CDR-H1 sequence comprising SEQ ID NO: 35, a Kabat CDR-H2 sequence comprising SEQ ID NO: 70, and a Kabat CDR-H3 sequence comprising SEQ ID NO: 93. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 92. In some aspects, the antibody comprises a $V_H$ sequence comprising a Kabat CDR-H1 sequence comprising SEQ ID NO: 36, a Kabat CDR-H2 sequence comprising SEQ ID NO: 72, and a Kabat CDR-H3 sequence comprising SEQ ID NO: 87. In some aspects, the antibody comprises a $V_H$ sequence comprising a Kabat CDR-H1 sequence comprising SEQ ID NO: 30, a Kabat CDR-H2 sequence comprising SEQ ID NO: 73, and a Kabat CDR-H3 sequence comprising SEQ ID NO: 87. In some aspects, the antibody comprises a $V_H$ sequence comprising a Kabat CDR-H1 sequence comprising SEQ ID NO: 37, a Kabat CDR-H2 sequence comprising SEQ ID NO: 74, and a Kabat CDR-H3 sequence comprising SEQ ID NO: 87. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 94. In some aspects, the antibody comprises a $V_H$ sequence comprising a Kabat CDR-H1 sequence comprising SEQ ID NO: 39, a Kabat CDR-H2 sequence comprising SEQ ID NO: 76, and a Kabat CDR-H3 sequence comprising SEQ ID NO: 95. In some aspects, the antibody comprises a $V_H$ sequence comprising a Kabat CDR-H1 sequence comprising SEQ ID NO: 40, a Kabat CDR-H2 sequence comprising SEQ ID NO: 76, and a Kabat CDR-H3 sequence comprising SEQ ID NO: 96. In some aspects, the antibody comprises a $V_H$ sequence comprising a Kabat CDR-H1 sequence comprising SEQ ID NO: 39, a Kabat CDR-H2 sequence comprising SEQ ID NO: 76, and a Kabat CDR-H3 sequence comprising SEQ ID NO: 94. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 97. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 98. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 99. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 100. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 101. In some aspects, the antibody comprises a $V_H$ sequence comprising a Kabat CDR-H1 sequence comprising SEQ ID NO: 42, a Kabat CDR-H2 sequence comprising SEQ ID NO: 78, and a Kabat CDR-H3 sequence comprising SEQ ID NO: 102. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 103. In some aspects, the antibody comprises a $V_H$ sequence comprising a Kabat CDR-H1 sequence comprising SEQ ID NO: 43, a Kabat CDR-H2 sequence comprising SEQ ID NO: 79, and a Kabat CDR-H3 sequence comprising SEQ ID NO: 104. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 103. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 106. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 107. In some aspects, the antibody comprises a $V_H$ sequence comprising a Kabat CDR-H1 sequence comprising SEQ ID NO: 44, a Kabat CDR-H2 sequence comprising SEQ ID NO: 80, and a Kabat CDR-H3 sequence comprising SEQ ID NO: 108. In some aspects, the antibody comprises a $V_H$ sequence comprising a Kabat CDR-H1 sequence comprising SEQ ID NO: 45, a Kabat CDR-H2 sequence comprising SEQ ID NO: 81, and a Kabat CDR-H3 sequence comprising SEQ ID NO: 109.

In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 83. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 84. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 85. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 86. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 84. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 86. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 83. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 86. In some aspects, the antibody comprises a $V_H$ sequence comprising a Kabat CDR-H1 sequence comprising SEQ ID NO: 30, a Kabat CDR-H2 sequence comprising SEQ ID NO: 71, and a Kabat CDR-H3 sequence comprising SEQ ID NO: 93. In some aspects, the antibody comprises a $V_H$ sequence comprising a Kabat CDR-H1 sequence comprising SEQ ID NO: 30, a Kabat CDR-H2 sequence comprising SEQ ID NO: 73, and a Kabat CDR-H3 sequence comprising SEQ ID NO: 87. In some aspects, the antibody comprises a $V_H$ sequence comprising a Kabat CDR-H1 sequence comprising SEQ ID NO: 30, a Kabat CDR-H2 sequence comprising SEQ ID NO: 72, and a Kabat CDR-H3 sequence comprising SEQ ID NO: 87. In some aspects, the antibody comprises a $V_H$ sequence comprising a Kabat CDR-H1 sequence comprising SEQ ID NO: 30, a Kabat CDR-H2 sequence comprising SEQ ID NO: 70, and a Kabat CDR-H3 sequence comprising SEQ ID NO: 87. In some aspects, the antibody comprises a $V_H$ sequence comprising a Kabat CDR-H1 sequence comprising SEQ ID NO: 31, a Kabat CDR-H2 sequence comprising SEQ ID NO: 70, and a Kabat CDR-H3 sequence comprising SEQ ID NO: 87. In some aspects, the antibody comprises a $V_H$ sequence comprising a Kabat CDR-H1 sequence comprising SEQ ID NO: 31, a Kabat CDR-H2 sequence comprising SEQ ID NO: 71, and a Kabat CDR-H3 sequence comprising SEQ ID NO: 87. In some aspects, the antibody comprises a $V_H$ sequence comprising a Kabat CDR-H1 sequence comprising SEQ ID NO: 32, a Kabat CDR-H2 sequence comprising SEQ ID NO: 71, and a Kabat CDR-H3 sequence comprising SEQ ID NO: 87. In some aspects, the antibody comprises a $V_H$ sequence comprising a Kabat CDR-H1 sequence comprising SEQ ID NO: 33, a Kabat CDR-H2 sequence comprising SEQ ID NO: 71, and a Kabat CDR-H3 sequence comprising SEQ ID NO: 87. In some aspects, the antibody comprises a $V_H$ sequence comprising a Kabat CDR-H1 sequence comprising SEQ ID NO: 33, a Kabat CDR-H2 sequence comprising SEQ ID NO: 72, and a Kabat CDR-H3 sequence comprising SEQ ID NO: 87. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 87. In some aspects, the antibody comprises a $V_H$ sequence comprising a Kabat CDR-H1 sequence comprising SEQ ID NO: 33, a Kabat CDR-H2 sequence comprising SEQ ID NO: 71, and a Kabat CDR-H3 sequence comprising SEQ ID NO: 93. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 93. In some aspects, the antibody comprises a $V_H$ sequence comprising a Kabat CDR-H1 sequence comprising SEQ ID NO: 34, a Kabat CDR-H2 sequence comprising SEQ ID NO: 72, and a Kabat CDR-H3 sequence comprising SEQ ID NO: 87. In some aspects, the antibody comprises a $V_H$ sequence comprising a Kabat CDR-H1 sequence comprising SEQ ID NO: 30, a Kabat CDR-H2 sequence comprising SEQ ID NO: 71, and a Kabat CDR-H3 sequence comprising SEQ ID NO: 87. In some aspects, the antibody comprises a $V_H$ sequence comprising a Kabat CDR-H1 sequence comprising SEQ ID NO: 35, a Kabat CDR-H2 sequence comprising SEQ ID NO: 70, and a Kabat CDR-H3 sequence comprising SEQ ID NO: 87. In some aspects, the antibody comprises a $V_H$ sequence comprising a Kabat CDR-H1 sequence comprising SEQ ID NO: 35, a Kabat CDR-H2 sequence comprising SEQ ID NO: 70, and a Kabat CDR-H3 sequence comprising SEQ ID NO: 90. In some aspects, the antibody comprises a $V_H$ sequence comprising a Kabat CDR-H1 sequence comprising SEQ ID NO: 30, a Kabat CDR-H2 sequence comprising SEQ ID NO: 70, and a Kabat CDR-H3 sequence comprising SEQ ID NO: 87. In some aspects, the antibody comprises a $V_H$ sequence comprising a Kabat CDR-H1 sequence comprising SEQ ID NO: 39, a Kabat CDR-H2 sequence comprising SEQ ID NO: 76, and a Kabat CDR-H3 sequence comprising SEQ ID NO: 94.

2.2.1.8. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-113 sequence comprises, consists of, or consists essentially of a sequence having at least 70%, 75%, 80%, 85%, 90%, or 95% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, or 95% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, or 95% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.2. Vu Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chothia CDR-H3

In some embodiments, the antibody comprises a $V_H$ sequence comprising a Chothia CDR-H3 sequence comprising, consisting of, or consisting essentially of a sequence selected from SEQ ID NOs: 82-109. In some aspects, the antibody comprises a $V_H$ sequence comprising a Chothia CDR-H3 sequence comprising, consisting of, or consisting essentially of SEQ ID NO: 82. In some aspects, the antibody comprises a $V_H$ sequence comprising a Chothia CDR-H3 sequence comprising, consisting of, or consisting essentially of SEQ ID NO: 83. In some aspects, the antibody comprises a $V_H$ sequence comprising a Chothia CDR-H3 sequence comprising, consisting of, or consisting essentially of SEQ ID NO: 84. In some aspects, the antibody comprises a $V_H$ sequence comprising a Chothia CDR-H3 sequence comprising, consisting of, or consisting essentially of SEQ ID NO: 85. In some aspects, the antibody comprises a $V_H$ sequence comprising a Chothia CDR-H3 sequence comprising, consisting of, or consisting essentially of SEQ ID NO: 86. In some aspects, the antibody comprises a $V_H$ sequence comprising a Chothia CDR-H3 sequence comprising, consisting of, or consisting essentially of SEQ ID NO: 87. In some aspects, the antibody comprises a $V_H$ sequence comprising a Chothia CDR-H3 sequence comprising, consisting of, or consisting essentially of SEQ ID NO: 88. In some aspects, the antibody comprises a $V_H$ sequence comprising a Chothia CDR-H3 sequence comprising, consisting of, or consisting essentially of SEQ ID NO: 89. In some aspects, the antibody comprises a $V_H$ sequence comprising a Chothia CDR-H3 sequence comprising, consisting of, or consisting essentially of SEQ ID NO: 90. In some aspects, the antibody comprises a $V_H$ sequence comprising a Chothia CDR-H3 sequence comprising, consisting of, or consisting essentially of SEQ ID NO: 91. In some aspects, the antibody comprises a $V_H$ sequence comprising a Chothia CDR-H3 sequence comprising, consisting of, or consisting essentially of SEQ ID NO: 92. In some aspects, the antibody comprises a $V_H$ sequence comprising a Chothia CDR-H3 sequence comprising, consisting of, or consisting essentially of SEQ ID NO: 93. In some aspects, the antibody comprises a $V_H$ sequence comprising a Chothia CDR-H3 sequence comprising, consisting of, or consisting essentially of SEQ ID NO: 94. In some aspects, the antibody comprises a $V_H$ sequence comprising a Chothia CDR-H3 sequence comprising, consisting of, or consisting essentially of SEQ ID NO: 95. In some aspects, the antibody comprises a $V_H$ sequence comprising a Chothia CDR-H3 sequence comprising, consisting of, or consisting essentially of SEQ ID NO: 96. In some aspects, the antibody comprises a $V_H$ sequence comprising a Chothia CDR-H3 sequence comprising, consisting of, or consisting essentially of SEQ ID NO: 97. In some aspects, the antibody comprises a $V_H$ sequence comprising a Chothia CDR-H3 sequence comprising, consisting of, or consisting essentially of SEQ ID NO: 98. In some aspects, the antibody comprises a $V_H$ sequence comprising a Chothia CDR-H3 sequence comprising, consisting of, or consisting essentially of SEQ ID NO: 99. In some aspects, the antibody comprises a $V_H$ sequence comprising a Chothia CDR-H3 sequence comprising, consisting of, or consisting essentially of SEQ ID NO: 100. In some aspects, the antibody comprises a $V_H$ sequence comprising a Chothia CDR-H3 sequence comprising, consisting of, or consisting essentially of SEQ ID NO: 101. In some aspects, the antibody comprises a $V_H$ sequence comprising a Chothia CDR-H3 sequence comprising, consisting of, or consisting essentially of SEQ ID NO: 102. In some aspects, the antibody comprises a $V_H$ sequence comprising a Chothia CDR-H3 sequence comprising, consisting of, or consisting essentially of SEQ ID NO: 103. In some aspects, the antibody comprises a $V_H$ sequence comprising a Chothia CDR-H3 sequence comprising, consisting of, or consisting essentially of SEQ ID NO: 104. In some aspects, the antibody comprises a $V_H$ sequence comprising a Chothia CDR-H3 sequence comprising, consisting of, or consisting essentially of SEQ ID NO: 105. In some aspects, the antibody comprises a $V_H$ sequence comprising a Chothia CDR-H3 sequence comprising, consisting of, or consisting essentially of SEQ ID NO: 106. In some aspects, the antibody comprises a $V_H$ sequence comprising a Chothia CDR-H3 sequence comprising, consisting of, or consisting essentially of SEQ ID NO: 107. In some aspects, the antibody comprises a $V_H$ sequence comprising a Chothia CDR-H3 sequence comprising, consisting of, or consisting essentially of SEQ ID NO: 108. In some aspects, the antibody comprises a $V_H$ sequence comprising a Chothia CDR-H3 sequence comprising, consisting of, or consisting essentially of SEQ ID NO: 109.

2.2.2.2. Chothia CDR-H2

In some embodiments, the antibody comprises a $V_H$ sequence comprising a Chothia CDR-H2 sequence comprising, consisting of, or consisting essentially of a sequence selected from SEQ ID NOs: 46-62. In some aspects, the antibody comprises a $V_H$ sequence comprising a Chothia CDR-H2 sequence comprising, consisting of, or consisting essentially of SEQ ID NO: 46. In some aspects, the antibody comprises a $V_H$ sequence comprising a Chothia CDR-H2 sequence comprising, consisting of, or consisting essentially of SEQ ID NO: 47. In some aspects, the antibody comprises a $V_H$ sequence comprising a Chothia CDR-H2 sequence comprising, consisting of, or consisting essentially of SEQ ID NO: 48. In some aspects, the antibody comprises a $V_H$ sequence comprising a Chothia CDR-H2 sequence comprising, consisting of, or consisting essentially of SEQ ID NO: 49. In some aspects, the antibody comprises a $V_H$ sequence comprising a Chothia CDR-H2 sequence comprising, consisting of, or consisting essentially of SEQ ID NO: 50. In some aspects, the antibody comprises a $V_H$ sequence comprising a Chothia CDR-H2 sequence comprising, consisting of, or consisting essentially of SEQ ID NO: 51. In some aspects, the antibody comprises a $V_H$ sequence comprising a Chothia CDR-H2 sequence comprising, consisting of, or consisting essentially of SEQ ID NO: 52. In some aspects, the antibody comprises a $V_H$ sequence comprising a Chothia CDR-H2 sequence comprising, consisting of, or consisting essentially of SEQ ID NO: 53. In some aspects, the antibody comprises a $V_H$ sequence comprising a Chothia CDR-H2 sequence comprising, consisting of, or consisting essentially of SEQ ID NO: 54. In some aspects, the antibody comprises a $V_H$ sequence comprising a Chothia CDR-H2 sequence comprising, consisting of, or consisting essentially of SEQ ID NO: 55. In some aspects, the antibody comprises a $V_H$ sequence comprising a Chothia CDR-H2 sequence comprising, consisting of, or consisting essentially of SEQ ID NO: 56. In some aspects, the antibody comprises a $V_H$ sequence comprising a Chothia CDR-H2 sequence comprising, consisting of, or consisting essentially of SEQ ID NO: 57. In some aspects, the antibody comprises a $V_H$ sequence comprising a Chothia CDR-H2 sequence comprising, consisting of, or consisting essentially of SEQ ID NO: 58. In some aspects, the antibody comprises a $V_H$ sequence comprising a Chothia CDR-H2 sequence comprising, consisting of, or consisting essentially of SEQ ID NO: 59. In some aspects, the antibody comprises a $V_H$ sequence comprising a Chothia CDR-H2 sequence comprising, consisting of, or consisting essentially of SEQ ID NO: 60. In some aspects, the antibody comprises a $V_H$ sequence comprising a Chothia CDR-H2 sequence comprising, consisting of, or consisting essentially of SEQ ID NO: 61. In some aspects, the antibody comprises a $V_H$ sequence comprising a Chothia CDR-H2 sequence comprising, consisting of, or consisting essentially of SEQ ID NO: 62.

2.2.2.3. Chothia CDR-H1

In some embodiments, the antibody comprises a $V_H$ sequence comprising a Chothia CDR-H1 sequence comprising, consisting of, or consisting essentially of a sequence selected from SEQ ID NOs: 1-24. In some aspects, the antibody comprises a $V_H$ sequence comprising a Chothia CDR-H1 sequence comprising, consisting of, or consisting essentially of SEQ ID NO: 1. In some aspects, the antibody comprises a $V_H$ sequence comprising a Chothia CDR-H1 sequence comprising, consisting of, or consisting essentially of SEQ ID NO: 2. In some aspects, the antibody comprises a $V_H$ sequence comprising a Chothia CDR-H1 sequence comprising, consisting of, or consisting essentially of SEQ ID NO: 3. In some aspects, the antibody comprises a $V_H$ sequence comprising a Chothia CDR-H1 sequence comprising, consisting of, or consisting essentially of SEQ ID NO: 4. In some aspects, the antibody comprises a $V_H$ sequence comprising a Chothia CDR-H1 sequence comprising, consisting of, or consisting essentially of SEQ ID NO: 5. In some aspects, the antibody comprises a $V_H$ sequence comprising a Chothia CDR-H1 sequence comprising, consisting of, or consisting essentially of SEQ ID NO: 6. In some aspects, the antibody comprises a $V_H$ sequence comprising a Chothia CDR-H1 sequence comprising, consisting of, or consisting essentially of SEQ ID NO: 7. In some aspects, the antibody comprises a $V_H$ sequence comprising a Chothia CDR-H1 sequence comprising, consisting of, or consisting essentially of SEQ ID NO: 8. In some aspects, the antibody comprises a $V_H$ sequence comprising a Chothia CDR-H1 sequence comprising, consisting of, or consisting essentially of SEQ ID NO: 9. In some aspects, the antibody comprises a $V_H$ sequence comprising a Chothia CDR-H1 sequence comprising, consisting of, or consisting essentially of SEQ ID NO: 10. In some aspects, the antibody comprises a $V_H$ sequence comprising a Chothia CDR-H1 sequence comprising, consisting of, or consisting essentially of SEQ ID NO: 11. In some aspects, the antibody comprises a $V_H$ sequence comprising a Chothia CDR-H1 sequence comprising, consisting of, or consisting essentially of SEQ ID NO: 12. In some aspects, the antibody comprises a $V_H$ sequence comprising a Chothia CDR-H1 sequence comprising, consisting of, or consisting essentially of SEQ ID NO: 13. In some aspects, the antibody comprises a $V_H$ sequence comprising a Chothia CDR-H1 sequence comprising, consisting of, or consisting essentially of SEQ ID NO: 14. In some aspects, the antibody comprises a $V_H$ sequence comprising a Chothia CDR-H1 sequence comprising, consisting of, or consisting essentially of SEQ ID NO: 15. In some aspects, the antibody comprises a $V_H$ sequence comprising a Chothia CDR-H1 sequence comprising, consisting of, or consisting essentially of SEQ ID NO: 16. In some aspects, the antibody comprises a $V_H$ sequence comprising a Chothia CDR-H1 sequence comprising, consisting of, or consisting essentially of SEQ ID NO: 17. In some aspects, the antibody comprises a $V_H$ sequence comprising a Chothia CDR-H1 sequence comprising, consisting of, or consisting essentially of SEQ ID NO: 18. In some aspects, the antibody comprises a $V_H$ sequence comprising a Chothia CDR-H1 sequence comprising, consisting of, or consisting essentially of SEQ ID NO: 19. In some aspects, the antibody comprises a $V_H$ sequence comprising a Chothia CDR-H1 sequence comprising, consisting of, or consisting essentially of SEQ ID NO: 20. In some aspects, the antibody comprises a $V_H$ sequence comprising a Chothia CDR-H1 sequence comprising, consisting of, or consisting essentially of SEQ ID NO: 21. In some aspects, the antibody comprises a $V_H$ sequence comprising a Chothia CDR-H1 sequence comprising, consisting of, or consisting essentially of SEQ ID NO: 22. In some aspects, the antibody comprises a $V_H$ sequence comprising a Chothia CDR-H1 sequence comprising, consisting of, or consisting essentially of SEQ ID NO: 23. In some aspects, the antibody comprises a V$_H$ sequence comprising a Chothia CDR-H1 sequence comprising, consisting of, or consisting essentially of SEQ ID NO: 24.

2.2.2.4. Chothia CDR-H3+ Chothia CDR-H2

In some embodiments, the antibody comprises a V$_H$ sequence comprising a Chothia CDR-H3 sequence comprising, consisting of, or consisting essentially of a sequence selected from SEQ ID NOs: 82-109, and a Chothia CDR-H2 sequence comprising, consisting of, or consisting essentially of a sequence selected from SEQ ID NOs: 46-62. In some aspects, the Chothia CDR-H3 sequence and the Chothia CDR-H2 sequence are both from a single illustrative V$_H$ sequence provided in this disclosure. For example, in some aspects, the Chothia CDR-H3 and Chothia CDR-H2 are both from a single illustrative V$_H$ sequence selected from SEQ ID NOs: 179-218.

2.2.2.5. Chothia CDR-H3+ Chothia CDR-H1

In some embodiments, the antibody comprises a V$_H$ sequence comprising a Chothia CDR-H3 sequence comprising, consisting of, or consisting essentially of a sequence selected from SEQ ID NOs: 82-109, and a Chothia CDR-H1 sequence comprising, consisting of, or consisting essentially of a sequence selected from SEQ ID NOs: 1-24. In some aspects, the Chothia CDR-H3 sequence and the Chothia CDR-H1 sequence are both from a single illustrative V$_H$ sequence provided in this disclosure. For example, in some aspects, the Chothia CDR-H3 and Chothia CDR-H1 are both from a single illustrative V$_H$ sequence selected from SEQ ID NOs: 179-218.

2.2.2.6. Chothia CDR-H1+ Chothia CDR-H2

In some embodiments, the antibody comprises a V$_H$ sequence comprising a Chothia CDR-H1 sequence comprising, consisting of, or consisting essentially of a sequence selected from SEQ ID NOs: 1-24 and a Chothia CDR-H2 sequence comprising, consisting of, or consisting essentially of a sequence selected from SEQ ID NOs: 46-62. In some aspects, the Chothia CDR-H1 sequence and the Chothia CDR-H2 sequence are both from a single illustrative V$_H$ sequence provided in this disclosure. For example, in some aspects, the Chothia CDR-H1 and Chothia CDR-H2 are both from a single illustrative V$_H$ sequence selected from SEQ ID NOs: 179-218.

2.2.2.7. Chothia CDR-H1+ Chothia CDR-112+ Chothia CDR-113

In some embodiments, the antibody comprises a V$_H$ sequence comprising a Chothia CDR-H1 sequence comprising, consisting of, or consisting essentially of a sequence selected from SEQ ID NOs: 1-24, a Chothia CDR-H2 sequence comprising, consisting of, or consisting essentially of a sequence selected from SEQ ID NOs: 46-62, and a Chothia CDR-H3 sequence comprising, consisting of, or consisting essentially of a sequence selected from SEQ ID NOs: 82-109. In some aspects, the Chothia CDR-H1 sequence, Chothia CDR-H2 sequence, and Chothia CDR-H3 sequence are all from a single illustrative V$_H$ sequence provided in this disclosure. For example, in some aspects, the Chothia CDR-H1, Chothia CDR-H2, and Chothia CDR-H3 are all from a single illustrative V$_H$ sequence selected from SEQ ID NOs: 179-218.

In some embodiments, the antibody comprises a V$_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 82. In some embodiments, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 83. In some embodiments, the antibody comprises a V$_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 84. In some embodiments, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 85. In some embodiments, the antibody comprises a V$_H$ sequence comprising a Chothia CDR-H1 sequence comprising SEQ ID NO: 3, a Chothia CDR-H2 sequence comprising SEQ ID NO: 47, and a Chothia CDR-H3 sequence comprising SEQ ID NO: 86. In some embodiments, the antibody comprises a V$_H$ sequence comprising a Chothia CDR-H1 sequence comprising SEQ ID NO: 4, a Chothia CDR-H2 sequence comprising SEQ ID NO: 46, and a Chothia CDR-H3 sequence comprising SEQ ID NO: 82. In some embodiments, the antibody comprises a V$_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 82. In some embodiments, the antibody comprises a V$_H$ sequence comprising a Chothia CDR-H1 sequence comprising SEQ ID NO: 5, a Chothia CDR-H2 sequence comprising SEQ ID NO: 49, and a Chothia CDR-H3 sequence comprising SEQ ID NO: 82. In some embodiments, the antibody comprises a V$_H$ sequence comprising a Chothia CDR-H1 sequence comprising SEQ ID NO: 6, a Chothia CDR-H2 sequence comprising SEQ ID NO: 50, and a Chothia CDR-H3 sequence comprising SEQ ID NO: 82. In some embodiments, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 82. In some embodiments, the antibody comprises a V$_H$ sequence comprising a Chothia CDR-H1 sequence comprising SEQ ID NO: 7, a Chothia CDR-H2 sequence comprising SEQ ID NO: 51, and a Chothia CDR-H3 sequence comprising SEQ ID NO: 87. In some embodiments, the antibody comprises a V$_H$ sequence comprising a Chothia CDR-H1 sequence comprising SEQ ID NO: 8, a Chothia CDR-H2 sequence comprising SEQ ID NO: 52, and a Chothia CDR-H3 sequence comprising SEQ ID NO: 88. In some embodiments, the antibody comprises a V$_H$ sequence comprising a Chothia CDR-H1 sequence comprising SEQ ID NO: 9, a Chothia CDR-H2 sequence comprising SEQ ID NO: 53, and a Chothia CDR-H3 sequence comprising SEQ ID NO: 89. In some embodiments, the antibody comprises a V$_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 90. In some embodiments, the antibody comprises a V$_H$ sequence comprising a Chothia CDR-H1 sequence comprising SEQ ID NO: 11, a Chothia CDR-H2 sequence comprising SEQ ID NO: 54, and a Chothia CDR-H3 sequence comprising SEQ ID NO: 91. In some embodiments, the antibody comprises a V$_H$ sequence comprising a Chothia CDR-H1 sequence comprising SEQ ID NO: 12, a Chothia CDR-H2 sequence comprising SEQ ID NO: 53, and a Chothia CDR-H3 sequence comprising SEQ ID NO: 92. In some embodiments, the antibody comprises a V$_H$ sequence comprising a Chothia CDR-H1 sequence comprising SEQ ID NO: 13, a Chothia CDR-H2 sequence comprising SEQ ID NO: 52, and a Chothia CDR-H3 sequence comprising SEQ ID NO: 93. In some embodiments, the antibody comprises a $V_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 92. In some embodiments, the antibody comprises a $V_H$ sequence comprising a Chothia CDR-H1 sequence comprising SEQ ID NO: 14, a Chothia CDR-H2 sequence comprising SEQ ID NO: 54, and a Chothia CDR-H3 sequence comprising SEQ ID NO: 87. In some embodiments, the antibody comprises a $V_H$ sequence comprising a Chothia CDR-H1 sequence comprising SEQ ID NO: 15, a Chothia CDR-H2 sequence comprising SEQ ID NO: 55, and a Chothia CDR-H3 sequence comprising SEQ ID NO: 87. In some embodiments, the antibody comprises a $V_H$ sequence comprising a Chothia CDR-H1 sequence comprising SEQ ID NO: 16, a Chothia CDR-H2 sequence comprising SEQ ID NO: 56, and a Chothia CDR-H3 sequence comprising SEQ ID NO: 87. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 94. In some embodiments, the antibody comprises a $V_H$ sequence comprising a Chothia CDR-H1 sequence comprising SEQ ID NO: 18, a Chothia CDR-H2 sequence comprising SEQ ID NO: 57, and a Chothia CDR-H3 sequence comprising SEQ ID NO: 95. In some embodiments, the antibody comprises a $V_H$ sequence comprising a Chothia CDR-H1 sequence comprising SEQ ID NO: 19, a Chothia CDR-H2 sequence comprising SEQ ID NO: 57, and a Chothia CDR-H3 sequence comprising SEQ ID NO: 96. In some embodiments, the antibody comprises a $V_H$ sequence comprising a Chothia CDR-H1 sequence comprising SEQ ID NO: 21, a Chothia CDR-H2 sequence comprising SEQ ID NO: 57, and a Chothia CDR-H3 sequence comprising SEQ ID NO: 94. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 97. In some embodiments, the antibody comprises a $V_H$ sequence comprising a Chothia CDR-H1 sequence comprising SEQ ID NO: 22, a Chothia CDR-H2 sequence comprising SEQ ID NO: 51, and a Chothia CDR-H3 sequence comprising SEQ ID NO: 98. In some embodiments, the antibody comprises a $V_H$ sequence comprising a Chothia CDR-H1 sequence comprising SEQ ID NO: 22, a Chothia CDR-H2 sequence comprising SEQ ID NO: 51, and a Chothia CDR-H3 sequence comprising SEQ ID NO: 99. In some embodiments, the antibody comprises a $V_H$ sequence comprising a Chothia CDR-H1 sequence comprising SEQ ID NO: 22, a Chothia CDR-H2 sequence comprising SEQ ID NO: 51, and a Chothia CDR-H3 sequence comprising SEQ ID NO: 100. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 101. In some embodiments, the antibody comprises a $V_H$ sequence comprising a Chothia CDR-H1 sequence comprising SEQ ID NO: 17, a Chothia CDR-H2 sequence comprising SEQ ID NO: 59, and a Chothia CDR-H3 sequence comprising SEQ ID NO: 102. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 103. In some embodiments, the antibody comprises a $V_H$ sequence comprising a Chothia CDR-H1 sequence comprising SEQ ID NO: 23, a Chothia CDR-H2 sequence comprising SEQ ID NO: 60, and a Chothia CDR-H3 sequence comprising SEQ ID NO: 104. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 105. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 106. In some embodiments, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 107. In some embodiments, the antibody comprises a $V_H$ sequence comprising a Chothia CDR-H1 sequence comprising SEQ ID NO: 17, a Chothia CDR-H2 sequence comprising SEQ ID NO: 61, and a Chothia CDR-H3 sequence comprising SEQ ID NO: 108. In some embodiments, the antibody comprises a $V_H$ sequence comprising a Chothia CDR-H1 sequence comprising SEQ ID NO: 17, a Chothia CDR-H2 sequence comprising SEQ ID NO: 62, and a Chothia CDR-H3 sequence comprising SEQ ID NO: 109.

In some embodiments, the antibody comprises a $V_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 83. In some embodiments, the antibody comprises a $V_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 84. In some embodiments, the antibody comprises a $V_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 85. In some embodiments, the antibody comprises a VII sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 86. In some embodiments, the antibody comprises a $V_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 84. In some embodiments, the antibody comprises a $V_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 86. In some embodiments, the antibody comprises a $V_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 83. In some embodiments, the antibody comprises a VII sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 86. In some embodiments, the antibody comprises a $V_H$ sequence comprising a Chothia CDR-H1 sequence comprising SEQ ID NO: 10, a Chothia CDR-H2 sequence comprising SEQ ID NO: 53, and a Chothia CDR-H3 sequence comprising SEQ ID NO: 93. In some embodiments, the antibody comprises a $V_H$ sequence comprising a Chothia CDR-H1 sequence comprising SEQ ID NO: 10, a Chothia CDR-H2 sequence comprising SEQ ID NO: 55, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 54, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 87. In some embodiments, the antibody comprises a $V_H$ sequence comprising a Chothia CDR-H1 sequence comprising SEQ ID NO: 8, a Chothia CDR-H2 sequence comprising SEQ ID NO: 52, and a Chothia CDR-H3 sequence comprising SEQ ID NO: 87. In some embodiments, the antibody comprises a $V_H$ sequence comprising a Chothia CDR-H1 sequence comprising SEQ ID NO: 8, a Chothia CDR-H2 sequence comprising SEQ ID NO: 53, and a Chothia CDR-H3 sequence comprising SEQ ID NO: 87. In some embodiments, the antibody comprises a $V_H$ sequence comprising a Chothia CDR-H1 sequence comprising SEQ ID NO: 9, a Chothia CDR-H2 sequence comprising SEQ ID NO: 53, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 53, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 54, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 87. In some embodiments, the antibody comprises a $V_H$ sequence comprising a Chothia CDR-H1 sequence comprising SEQ ID NO: 10, a Chothia CDR-H2 sequence comprising SEQ ID NO: 53, and a Chothia CDR-H3 sequence comprising SEQ ID NO: 93. In some embodiments, the antibody comprises a $V_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 93. In some embodiments, the antibody comprises a $V_H$ sequence comprising a Chothia CDR-H1 sequence comprising SEQ ID NO: 11, a Chothia CDR-H2 sequence comprising SEQ ID NO: 54, and a Chothia CDR-H3 sequence comprising SEQ ID NO: 87. In some embodiments, the antibody comprises a $V_H$ sequence comprising a Chothia CDR-H1 sequence comprising SEQ ID NO: 12, a Chothia CDR-H2 sequence comprising SEQ ID NO: 53, and a Chothia CDR-H3 sequence comprising SEQ ID NO: 87. In some embodiments, the antibody comprises a $V_H$ sequence comprising a Chothia CDR-H1 sequence comprising SEQ ID NO: 13, a Chothia CDR-H2 sequence comprising SEQ ID NO: 52, and a Chothia CDR-H3 sequence comprising SEQ ID NO: 87. In some embodiments, the antibody comprises a $V_H$ sequence comprising a Chothia CDR-H1 sequence comprising SEQ ID NO: 13, a Chothia CDR-H2 sequence comprising SEQ ID NO: 52, and a Chothia CDR-H3 sequence comprising SEQ ID NO: 90. In some embodiments, the antibody comprises a $V_H$ sequence comprising a Chothia CDR-H1 sequence comprising SEQ ID NO: 15, a Chothia CDR-H2 sequence comprising SEQ ID NO: 52, and a Chothia CDR-H3 sequence comprising SEQ ID NO: 87. In some embodiments, the antibody comprises a $V_H$ sequence comprising a Chothia CDR-H1 sequence comprising SEQ ID NO: 18, a Chothia CDR-H2 sequence comprising SEQ ID NO: 57, and a Chothia CDR-H3 sequence comprising SEQ ID NO: 94.

2.2.2.8. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, or 95% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, or 95% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, or 95% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.3. $V_H$ Sequences

In some embodiments, the antibody comprises a $V_H$ sequence comprising, consisting of, or consisting essentially of a sequence selected from SEQ ID NOs: 179-218. In some aspects, the antibody comprises a $V_H$ sequence comprising, consisting of, or consisting essentially of SEQ ID NO: 179. In some aspects, the antibody comprises a $V_H$ sequence comprising, consisting of, or consisting essentially of SEQ ID NO: 180. In some aspects, the antibody comprises a $V_H$ sequence comprising, consisting of, or consisting essentially of SEQ ID NO: 181. In some aspects, the antibody comprises a $V_H$ sequence comprising, consisting of, or consisting essentially of SEQ ID NO: 182. In some aspects, the antibody comprises a $V_H$ sequence comprising, consisting of, or consisting essentially of SEQ ID NO: 183. In some aspects, the antibody comprises a $V_H$ sequence comprising, consisting of, or consisting essentially of SEQ ID NO: 184. In some aspects, the antibody comprises a $V_H$ sequence comprising, consisting of, or consisting essentially of SEQ ID NO: 185. In some aspects, the antibody comprises a $V_H$ sequence comprising, consisting of, or consisting essentially of SEQ ID NO: 186. In some aspects, the antibody comprises a $V_H$ sequence comprising, consisting of, or consisting essentially of SEQ ID NO: 187. In some aspects, the antibody comprises a $V_H$ sequence comprising, consisting of, or consisting essentially of SEQ ID NO: 188. In some aspects, the antibody comprises a $V_H$ sequence comprising, consisting of, or consisting essentially of SEQ ID NO: 189. In some aspects, the antibody comprises a $V_H$ sequence comprising, consisting of, or consisting essentially of SEQ ID NO: 190. In some aspects, the antibody comprises a $V_H$ sequence comprising, consisting of, or consisting essentially of SEQ ID NO: 191. In some aspects, the antibody comprises a $V_H$ sequence comprising, consisting of, or consisting essentially of SEQ ID NO: 192. In some aspects, the antibody comprises a $V_H$ sequence comprising, consisting of, or consisting essentially of SEQ ID NO: 193. In some aspects, the antibody comprises a $V_H$ sequence comprising, consisting of, or consisting essentially of SEQ ID NO: 194. In some aspects, the antibody comprises a $V_H$ sequence comprising, consisting of, or consisting essentially of SEQ ID NO: 195. In some aspects, the antibody comprises a $V_H$ sequence comprising, consisting of, or consisting essentially of SEQ ID NO: 196. In some aspects, the antibody comprises a $V_H$ sequence comprising, consisting of, or consisting essentially of SEQ ID NO: 197. In some aspects, the antibody comprises a $V_H$ sequence comprising, consisting of, or consisting essentially of SEQ ID NO: 198. In some aspects, the antibody comprises a $V_H$ sequence comprising, consisting of, or consisting essentially of SEQ ID NO: 199. In some aspects, the antibody comprises a $V_H$ sequence comprising, consisting of, or consisting essentially of SEQ ID NO: 200. In some aspects, the antibody comprises a $V_H$ sequence comprising, consisting of, or consisting essentially of SEQ ID NO: 201. In some aspects, the antibody comprises a $V_H$ sequence comprising, consisting of, or consisting essentially of SEQ ID NO: 202. In some aspects, the antibody comprises a $V_H$ sequence comprising, consisting of, or consisting essentially of SEQ ID NO: 203. In some aspects, the antibody comprises a $V_H$ sequence comprising, consisting of, or consisting essentially of SEQ ID NO: 204. In some aspects, the antibody comprises a $V_H$ sequence comprising, consisting of, or consisting essentially of SEQ ID NO: 205. In some aspects, the antibody comprises a $V_H$ sequence comprising, consisting of, or consisting essentially of SEQ ID NO: 206. In some aspects, the antibody comprises a $V_H$ sequence comprising, consisting of, or consisting essentially of SEQ ID NO: 207. In some aspects, the antibody comprises a $V_H$ sequence comprising, consisting of, or consisting essentially of SEQ ID NO: 208. In some aspects, the antibody comprises a $V_H$ sequence comprising, consisting of, or consisting essentially of SEQ ID NO: 209. In some aspects, the antibody comprises a $V_H$ sequence comprising, consisting of, or consisting essentially of SEQ ID NO: 210. In some aspects, the antibody comprises a $V_H$ sequence comprising, consisting of, or consisting essentially of SEQ ID NO: 211. In some aspects, the antibody comprises a $V_H$ sequence comprising, consisting of, or consisting essentially of SEQ ID NO: 212. In some aspects, the antibody comprises a $V_H$ sequence comprising, consisting of, or consisting essentially of SEQ ID NO: 213. In some aspects, the antibody comprises a $V_H$ sequence comprising, consisting of, or consisting essentially of SEQ ID NO: 214. In some aspects, the antibody comprises a $V_H$ sequence comprising, consisting of, or consisting essentially of SEQ ID NO: 215. In some aspects, the antibody comprises a $V_H$ sequence comprising, consisting of, or consisting essentially of SEQ ID NO: 216. In some aspects, the antibody comprises a $V_H$ sequence comprising, consisting of, or consisting essentially of SEQ ID NO: 217. In some aspects, the antibody comprises a $V_H$ sequence comprising, consisting of, or consisting essentially of SEQ ID NO: 218.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.4. CDR-L3 Sequences

In some embodiments, the antibody comprises a CDR-L3 sequence comprising, consisting of, or consisting essentially of a sequence selected from SEQ ID NOs: 141-166. In some aspects, the antibody comprises a CDR-L3 sequence comprising, consisting of, or consisting essentially of SEQ ID NO: 141. In some aspects, the antibody comprises a CDR-L3 sequence comprising, consisting of, or consisting essentially of SEQ ID NO: 142. In some aspects, the antibody comprises a CDR-L3 sequence comprising, consisting of, or consisting essentially of SEQ ID NO: 143. In some aspects, the antibody comprises a CDR-L3 sequence comprising, consisting of, or consisting essentially of SEQ ID NO: 144. In some aspects, the antibody comprises a CDR-L3 sequence comprising, consisting of, or consisting essentially of SEQ ID NO: 145. In some aspects, the antibody comprises a CDR-L3 sequence comprising, consisting of, or consisting essentially of SEQ ID NO: 146. In some aspects, the antibody comprises a CDR-L3 sequence comprising, consisting of, or consisting essentially of SEQ ID NO: 147. In some aspects, the antibody comprises a CDR-L3 sequence comprising, consisting of, or consisting essentially of SEQ ID NO: 148. In some aspects, the antibody comprises a CDR-L3 sequence comprising, consisting of, or consisting essentially of SEQ ID NO: 149. In some aspects, the antibody comprises a CDR-L3 sequence comprising, consisting of, or consisting essentially of SEQ ID NO: 150. In some aspects, the antibody comprises a CDR-L3 sequence comprising, consisting of, or consisting essentially of SEQ ID NO: 151. In some aspects, the antibody comprises a CDR-L3 sequence comprising, consisting of, or consisting essentially of SEQ ID NO: 152. In some aspects, the antibody comprises a CDR-L3 sequence comprising, consisting of, or consisting essentially of SEQ ID NO: 153. In some aspects, the antibody comprises a CDR-L3 sequence comprising, consisting of, or consisting essentially of SEQ ID NO: 154. In some aspects, the antibody comprises a CDR-L3 sequence comprising, consisting of, or consisting essentially of SEQ ID NO: 155. In some aspects, the antibody comprises a CDR-L3 sequence comprising, consisting of, or consisting essentially of SEQ ID NO: 156. In some aspects, the antibody comprises a CDR-L3 sequence comprising, consisting of, or consisting essentially of SEQ ID NO: 157. In some aspects, the antibody comprises a CDR-L3 sequence comprising, consisting of, or consisting essentially of SEQ ID NO: 158. In some aspects, the antibody comprises a CDR-L3 sequence comprising, consisting of, or consisting essentially of SEQ ID NO: 159. In some aspects, the antibody comprises a CDR-L3 sequence comprising, consisting of, or consisting essentially of SEQ ID NO: 160. In some aspects, the antibody comprises a CDR-L3 sequence comprising, consisting of, or consisting essentially of SEQ ID NO: 161. In some aspects, the antibody comprises a CDR-L3 sequence comprising, consisting of, or consisting essentially of SEQ ID NO: 162. In some aspects, the antibody comprises a CDR-L3 sequence comprising, consisting of, or consisting essentially of SEQ ID NO: 163. In some aspects, the antibody comprises a CDR-L3 sequence comprising, consisting of, or consisting essentially of SEQ ID NO: 164. In some aspects, the antibody comprises a CDR-L3 sequence comprising, consisting of, or consisting essentially of SEQ ID NO: 165. In some aspects, the antibody comprises a CDR-L3 sequence comprising, consisting of, or consisting essentially of SEQ ID NO: 166.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.5. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.5.1. CDR-L3

In some embodiments, the antibody comprises a $V_L$ sequence comprising a CDR-L3 sequence comprising, consisting of, or consisting essentially of a sequence selected from SEQ ID NOs: 141-166. In some aspects, the antibody comprises a $V_L$ sequence comprising a CDR-L3 sequence comprising, consisting of, or consisting essentially of SEQ ID NO: 141. In some aspects, the antibody comprises a $V_L$ sequence comprising a CDR-L3 sequence comprising, consisting of, or consisting essentially of SEQ ID NO: 142. In some aspects, the antibody comprises a $V_L$ sequence comprising a CDR-L3 sequence comprising, consisting of, or consisting essentially of SEQ ID NO: 143. In some aspects, the antibody comprises a $V_L$ sequence comprising a CDR-L3 sequence comprising, consisting of, or consisting essentially of SEQ ID NO: 144. In some aspects, the antibody comprises a $V_L$ sequence comprising a CDR-L3 sequence comprising, consisting of, or consisting essentially of SEQ ID NO: 145. In some aspects, the antibody comprises a $V_L$ sequence comprising a CDR-L3 sequence comprising, consisting of, or consisting essentially of SEQ ID NO: 146. In some aspects, the antibody comprises a $V_L$ sequence comprising a CDR-L3 sequence comprising, consisting of, or consisting essentially of SEQ ID NO: 147. In some aspects, the antibody comprises a $V_L$ sequence comprising a CDR-L3 sequence comprising, consisting of, or consisting essentially of SEQ ID NO: 148. In some aspects, the antibody comprises a $V_L$ sequence comprising a CDR-L3 sequence comprising, consisting of, or consisting essentially of SEQ ID NO: 149. In some aspects, the antibody comprises a $V_L$ sequence comprising a CDR-L3 sequence comprising, consisting of, or consisting essentially of SEQ ID NO: 150. In some aspects, the antibody comprises a $V_L$ sequence comprising a CDR-L3 sequence comprising, consisting of, or consisting essentially of SEQ ID NO: 151. In some aspects, the antibody comprises a $V_L$ sequence comprising a CDR-L3 sequence comprising, consisting of, or consisting essentially of SEQ ID NO: 152. In some aspects, the antibody comprises a $V_L$ sequence comprising a CDR-L3 sequence comprising, consisting of, or consisting essentially of SEQ ID NO: 153. In some aspects, the antibody comprises a $V_L$ sequence comprising a CDR-L3 sequence comprising, consisting of, or consisting essentially of SEQ ID NO: 154. In some aspects, the antibody comprises a $V_L$ sequence comprising a CDR-L3 sequence comprising, consisting of, or consisting essentially of SEQ ID NO: 155. In some aspects, the antibody comprises a $V_L$ sequence comprising a CDR-L3 sequence comprising, consisting of, or consisting essentially of SEQ ID NO: 156. In some aspects, the antibody comprises a $V_L$ sequence comprising a CDR-L3 sequence comprising, consisting of, or consisting essentially of SEQ ID NO: 157. In some aspects, the antibody comprises a $V_L$ sequence comprising a CDR-L3 sequence comprising, consisting of, or consisting essentially of SEQ ID NO: 158. In some aspects, the antibody comprises a $V_L$ sequence comprising a CDR-L3 sequence comprising, consisting of, or consisting essentially of SEQ ID NO: 159. In some aspects, the antibody comprises a $V_L$ sequence comprising a CDR-L3 sequence comprising, consisting of, or consisting essentially of SEQ ID NO: 160. In some aspects, the antibody comprises a $V_L$ sequence comprising a CDR-L3 sequence comprising, consisting of, or consisting essentially of SEQ ID NO: 161. In some aspects, the antibody comprises a $V_L$ sequence comprising a CDR-L3 sequence comprising, consisting of, or consisting essentially of SEQ ID NO: 162. In some aspects, the antibody comprises a $V_L$ sequence comprising a CDR-L3 sequence comprising, consisting of, or consisting essentially of SEQ ID NO: 163. In some aspects, the antibody comprises a $V_L$ sequence comprising a CDR-L3 sequence comprising, consisting of, or consisting essentially of SEQ ID NO: 164. In some aspects, the antibody comprises a $V_L$ sequence comprising a CDR-L3 sequence comprising, consisting of, or consisting essentially of SEQ ID NO: 165. In some aspects, the antibody comprises a $V_L$ sequence comprising a CDR-L3 sequence comprising, consisting of, or consisting essentially of SEQ ID NO: 166.

2.5.2. CDR-L2

In some embodiments, the antibody comprises a $V_L$ sequence comprising a CDR-L2 sequence comprising, consisting of, or consisting essentially of a sequence selected from SEQ ID NOs: 125-140. In some aspects, the antibody comprises a $V_L$ sequence comprising a CDR-L2 sequence comprising, consisting of, or consisting essentially of SEQ ID NO: 125. In some aspects, the antibody comprises a $V_L$ sequence comprising a CDR-L2 sequence comprising, consisting of, or consisting essentially of SEQ ID NO: 126. In some aspects, the antibody comprises a $V_L$ sequence comprising a CDR-L2 sequence comprising, consisting of, or consisting essentially of SEQ ID NO: 127. In some aspects, the antibody comprises a $V_L$ sequence comprising a CDR-L2 sequence comprising, consisting of, or consisting essentially of SEQ ID NO: 128. In some aspects, the antibody comprises a $V_L$ sequence comprising a CDR-L2 sequence comprising, consisting of, or consisting essentially of SEQ ID NO: 129. In some aspects, the antibody comprises a $V_L$ sequence comprising a CDR-L2 sequence comprising, consisting of, or consisting essentially of SEQ ID NO: 130. In some aspects, the antibody comprises a $V_L$ sequence comprising a CDR-L2 sequence comprising, consisting of, or consisting essentially of SEQ ID NO: 131. In some aspects, the antibody comprises a $V_L$ sequence comprising a CDR-L2 sequence comprising, consisting of, or consisting essentially of SEQ ID NO: 132. In some aspects, the antibody comprises a $V_L$ sequence comprising a CDR-L2 sequence comprising, consisting of, or consisting essentially of SEQ ID NO: 133. In some aspects, the antibody comprises a $V_L$ sequence comprising a CDR-L2 sequence comprising, consisting of, or consisting essentially of SEQ ID NO: 134. In some aspects, the antibody comprises a $V_L$ sequence comprising a CDR-L2 sequence comprising, consisting of, or consisting essentially of SEQ ID NO: 135. In some aspects, the antibody comprises a $V_L$ sequence comprising a CDR-L2 sequence comprising, consisting of, or consisting essentially of SEQ ID NO: 136. In some aspects, the antibody comprises a $V_L$ sequence comprising a CDR-L2 sequence comprising, consisting of, or consisting essentially of SEQ ID NO: 137. In some aspects, the antibody comprises a $V_L$ sequence comprising a CDR-L2 sequence comprising, consisting of, or consisting essentially of SEQ ID NO: 138. In some aspects, the antibody comprises a $V_L$ sequence comprising a CDR-L2 sequence comprising, consisting of, or consisting essentially of SEQ ID NO: 139. In some aspects, the antibody comprises a $V_L$ sequence comprising a CDR-L2 sequence comprising, consisting of, or consisting essentially of SEQ ID NO: 140.

2.5.3. CDR-L1

In some embodiments, the antibody comprises a $V_L$ sequence comprising a CDR-L1 sequence comprising, consisting of, or consisting essentially of a sequence selected from SEQ ID NOs: 110-124. In some aspects, the antibody comprises a $V_L$ sequence comprising a CDR-L1 sequence comprising, consisting of, or consisting essentially of SEQ ID NO: 110. In some aspects, the antibody comprises a $V_L$ sequence comprising a CDR-L1 sequence comprising, consisting of, or consisting essentially of SEQ ID NO: 111. In some aspects, the antibody comprises a $V_L$ sequence comprising a CDR-L1 sequence comprising, consisting of, or consisting essentially of SEQ ID NO: 112. In some aspects, the antibody comprises a $V_L$ sequence comprising a CDR-L1 sequence comprising, consisting of, or consisting essentially of SEQ ID NO: 113. In some aspects, the antibody comprises a $V_L$ sequence comprising a CDR-L1 sequence comprising, consisting of, or consisting essentially of SEQ ID NO: 114. In some aspects, the antibody comprises a $V_L$ sequence comprising a CDR-L1 sequence comprising, consisting of, or consisting essentially of SEQ ID NO: 115. In some aspects, the antibody comprises a $V_L$ sequence comprising a CDR-L1 sequence comprising, consisting of, or consisting essentially of SEQ ID NO: 116. In some aspects, the antibody comprises a $V_L$ sequence comprising a CDR-L1 sequence comprising, consisting of, or consisting essentially of SEQ ID NO: 117. In some aspects, the antibody comprises a $V_L$ sequence comprising a CDR-L1 sequence comprising, consisting of, or consisting essentially of SEQ ID NO: 118. In some aspects, the antibody comprises a $V_L$ sequence comprising a CDR-L1 sequence comprising, consisting of, or consisting essentially of SEQ ID NO: 119. In some aspects, the antibody comprises a $V_L$ sequence comprising a CDR-L1 sequence comprising, consisting of, or consisting essentially of SEQ ID NO: 120. In some aspects, the antibody comprises a $V_L$ sequence comprising a CDR-L1 sequence comprising, consisting of, or consisting essentially of SEQ ID NO: 121. In some aspects, the antibody comprises a $V_L$ sequence comprising a CDR-L1 sequence comprising, consisting of, or consisting essentially of SEQ ID NO: 122. In some aspects, the antibody comprises a $V_L$ sequence comprising a CDR-L1 sequence comprising, consisting of, or consisting essentially of SEQ ID NO: 123. In some aspects, the antibody comprises a $V_L$ sequence comprising a CDR-L1 sequence comprising, consisting of, or consisting essentially of SEQ ID NO: 124.

2.5.4. CDR-L3+ CDR-L2

In some embodiments, the antibody comprises a $V_L$ sequence comprising a CDR-L3 sequence comprising, consisting of, or consisting essentially of a sequence selected from SEQ ID NOs: 141-166 and a CDR-L2 sequence comprising, consisting of, or consisting essentially of a sequence selected from SEQ ID NOs: 125-140. In some aspects, the CDR-L3 sequence and the CDR-L2 sequence are both from a single illustrative $V_L$ sequence provided in this disclosure. For example, in some aspects, the CDR-L3 and CDR-L2 are both from a single illustrative $V_L$ sequence selected from SEQ ID NOs: 219-248.

2.5.5. CDR-L3+ CDR-L1

In some embodiments, the antibody comprises a $V_L$ sequence comprising a CDR-L3 sequence comprising, consisting of, or consisting essentially of a sequence selected from SEQ ID NOs: 141-166 and a CDR-L1 sequence comprising, consisting of, or consisting essentially of a sequence selected from SEQ ID NOs: 110-124. In some aspects, the CDR-L3 sequence and the CDR-L1 sequence are both from a single illustrative $V_L$ sequence provided in this disclosure. For example, in some aspects, the CDR-L3 and CDR-L1 are both from a single illustrative $V_L$ sequence selected from SEQ ID NOs: 219-248.

2.5.6. CDR-L1+ CDR-L2

In some embodiments, the antibody comprises a $V_L$ sequence comprising a CDR-L1 sequence comprising, consisting of, or consisting essentially of a sequence selected from SEQ ID NOs: 110-124 and a CDR-L2 sequence comprising, consisting of, or consisting essentially of a sequence selected from SEQ ID NOs: 125-140. In some aspects, the CDR-L1 sequence and the CDR-L2 sequence are both from a single illustrative $V_L$ sequence provided in this disclosure. For example, in some aspects, the CDR-L1 and CDR-L2 are both from a single illustrative $V_L$ sequence selected from SEQ ID NOs: 219-248.

2.5.7. CDR-L1+ CDR-L2+ CDR-L3

In some embodiments, the antibody comprises a $V_L$ sequence comprising a CDR-L1 sequence comprising, consisting of, or consisting essentially of a sequence selected from SEQ ID NOs: 110-124, a CDR-L2 sequence comprising, consisting of, or consisting essentially of a sequence selected from SEQ ID NOs: 125-140, and a CDR-L3 sequence comprising, consisting of, or consisting essentially of a sequence selected from SEQ ID NOs: 141-166. In some aspects, the CDR-L1 sequence, CDR-L2 sequence, and CDR-L3 sequence are all from a single illustrative $V_L$ sequence provided in this disclosure. For example, in some aspects, the CDR-L1, CDR-L2, and CDR-L3 are all from a single illustrative $V_L$ sequence selected from SEQ ID NOs: 219-248.

In some aspects, the antibody comprises a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a VL sequence comprising a CDR-L1 sequence comprising SEQ ID NO: 111, a CDR-L2 sequence comprising SEQ ID NO: 126, and a CDR-L3 sequence comprising SEQ ID NO: 142. In some aspects, the antibody comprises a VL sequence comprising a CDR-L1 sequence comprising SEQ ID NO: 110, a CDR-L2 sequence comprising SEQ ID NO: 127, and a CDR-L3 sequence comprising sequence selected from SEQ ID NO: 142. In some aspects, the antibody comprises a VL sequence comprising a CDR-L1 sequence comprising SEQ ID NO: 110, a CDR-L2 sequence comprising SEQ ID NO: 125, and a CDR-L3 sequence comprising SEQ ID NO: 143. In some aspects, the antibody comprises a VL sequence comprising a CDR-L1 sequence comprising SEQ ID NO: 112, a CDR-L2 sequence comprising SEQ ID NO: 128, and a CDR-L3 sequence comprising SEQ ID NO: 144. In some aspects, the antibody comprises a VL sequence comprising a CDR-L1 sequence comprising SEQ ID NO: 111, a CDR-L2 sequence comprising SEQ ID NO: 126, and a CDR-L3 sequence comprising SEQ ID NO: 145. In some aspects, the antibody comprises a VL sequence comprising a CDR-L1 sequence comprising SEQ ID NO: 113, a CDR-L2 sequence comprising SEQ ID NO: 129, and a CDR-L3 sequence comprising SEQ ID NO: 146. In some aspects, the antibody comprises a VL sequence comprising a CDR-L1 sequence comprising SEQ ID NO: 114, a CDR-L2 sequence comprising SEQ ID NO: 130, and a CDR-L3 sequence comprising SEQ ID NO: 147. In some aspects, the antibody comprises a VL sequence comprising a CDR-L1 sequence comprising SEQ ID NO: 115, a CDR-L2 sequence comprising SEQ ID NO: 131, and a CDR-L3 sequence comprising SEQ ID NO: 148. In some aspects, the antibody comprises a VL sequence comprising a CDR-L1 sequence comprising SEQ ID NO: 115, a CDR-L2 sequence comprising SEQ ID NO: 131, and a CDR-L3 sequence comprising SEQ ID NO: 148. In some aspects, the antibody comprises a VL sequence comprising a CDR-L1 sequence comprising SEQ ID NO: 116, a CDR-L2 sequence comprising SEQ ID NO: 131, and a CDR-L3 sequence comprising SEQ ID NO: 149. In some aspects, the antibody comprises a VL sequence comprising a CDR-L1 sequence comprising SEQ ID NO: 115, a CDR-L2 sequence comprising SEQ ID NO: 131, and a CDR-L3 sequence comprising SEQ ID NO: 148. In some aspects, the antibody comprises a VL sequence comprising a CDR-L1 sequence comprising SEQ ID NO: 115, a CDR-L2 sequence comprising SEQ ID NO: 132, and a CDR-L3 sequence comprising SEQ ID NO: 149. In some aspects, the antibody comprises a VL sequence comprising a CDR-L1 sequence comprising SEQ ID NO: 117, a CDR-L2 sequence comprising SEQ ID NO: 133, and a CDR-L3 sequence comprising SEQ ID NO: 150. In some aspects, the antibody comprises a VL sequence comprising a CDR-L1 sequence comprising SEQ ID NO: 115, a CDR-L2 sequence comprising SEQ ID NO: 134, and a CDR-L3 sequence comprising SEQ ID NO: 148. In some aspects, the antibody comprises a VL sequence comprising a CDR-L1 sequence comprising SEQ ID NO: 118, a CDR-L2 sequence comprising SEQ ID NO: 135, and a CDR-L3 sequence comprising SEQ ID NO: 151. In some aspects, the antibody comprises a VL sequence comprising a CDR-L1 sequence comprising SEQ ID NO: 118, a CDR-L2 sequence comprising SEQ ID NO: 135, and a CDR-L3 sequence comprising SEQ ID NO: 152. In some aspects, the antibody comprises a VL sequence comprising a CDR-L1 sequence comprising SEQ ID NO: 118, a CDR-L2 sequence comprising SEQ ID NO: 136, and a CDR-L3 sequence comprising SEQ ID NO: 152. In some aspects, the antibody comprises a VL sequence comprising a CDR-L1 sequence comprising SEQ ID NO: 115, a CDR-L2 sequence comprising SEQ ID NO: 131, and a CDR-L3 sequence comprising SEQ ID NO: 153. In some aspects, the antibody comprises a VL sequence comprising a CDR-L1 sequence comprising SEQ ID NO: 119, a CDR-L2 sequence comprising SEQ ID NO: 131, and a CDR-L3 sequence comprising SEQ ID NO: 154. In some aspects, the antibody comprises a VL sequence comprising a CDR-L1 sequence comprising SEQ ID NO: 120, a CDR-L2 sequence comprising SEQ ID NO: 137, and a CDR-L3 sequence comprising SEQ ID NO: 155. In some aspects, the antibody comprises a VL sequence comprising a CDR-L1 sequence comprising SEQ ID NO: 121, a CDR-L2 sequence comprising SEQ ID NO: 138, and a CDR-L3 sequence comprising SEQ ID NO: 156. In some aspects, the antibody comprises a VL sequence comprising a CDR-L1 sequence comprising SEQ ID NO: 121, a CDR-L2 sequence comprising SEQ ID NO: 138, and a CDR-L3 sequence comprising SEQ ID NO: 157. In some aspects, the antibody comprises a VL sequence comprising a CDR-L1 sequence comprising SEQ ID NO: 122, a CDR-L2 sequence comprising SEQ ID NO: 138, and a CDR-L3 sequence comprising SEQ ID NO: 158. In some aspects, the antibody comprises a VL sequence comprising a CDR-L1 sequence comprising SEQ ID NO: 121, a CDR-L2 sequence comprising SEQ ID NO: 138, and a CDR-L3 sequence comprising SEQ ID NO: 159. In some aspects, the antibody comprises a VL sequence comprising a CDR-L1 sequence comprising SEQ ID NO: 118, a CDR-L2 sequence comprising SEQ ID NO: 135, and a CDR-L3 sequence comprising SEQ ID NO: 160. In some aspects, the antibody comprises a VL sequence comprising a CDR-L1 sequence comprising SEQ ID NO: 121, a CDR-L2 sequence comprising SEQ ID NO: 139, and a CDR-L3 sequence comprising SEQ ID NO: 161. In some aspects, the antibody comprises a VL sequence comprising a CDR-L1 sequence comprising SEQ ID NO: 123, a CDR-L2 sequence comprising SEQ ID NO: 140, and a CDR-L3 sequence comprising SEQ ID NO: 162. In some aspects, the antibody comprises a VL sequence comprising a CDR-L1 sequence comprising SEQ ID NO: 121, a CDR-L2 sequence comprising SEQ ID NO: 138, and a CDR-L3 sequence comprising SEQ ID NO: 163. In some aspects, the antibody comprises a VL sequence comprising a CDR-L1 sequence comprising SEQ ID NO: 121, a CDR-L2 sequence comprising SEQ ID NO: 139, and a CDR-L3 sequence comprising SEQ ID NO: 164. In some aspects, the antibody comprises a VL sequence comprising a CDR-L1 sequence comprising SEQ ID NO: 120, a CDR-L2 sequence comprising SEQ ID NO: 137, and a CDR-L3 sequence comprising SEQ ID NO: 165. In some aspects, the antibody comprises a VL sequence comprising a CDR-L1 sequence comprising SEQ ID NO: 124, a CDR-L2 sequence comprising SEQ ID NO: 125, and a CDR-L3 sequence comprising SEQ ID NO: 166.

In some aspects, the antibody comprises a VL sequence comprising a CDR-L1 sequence comprising SEQ ID NO: 110, a CDR-L2 sequence comprising SEQ ID NO: 128, and a CDR-L3 sequence SEQ ID NO: 144. In some aspects, the antibody comprises a VL sequence comprising a CDR-L1 sequence comprising SEQ ID NO: 110, a CDR-L2 sequence comprising SEQ ID NO: 125, and a CDR-L3 sequence comprising SEQ ID NO: 144. In some aspects, the antibody comprises a VL sequence comprising a CDR-L1 sequence comprising SEQ ID NO: 110, a CDR-L2 sequence comprising SEQ ID NO: 126, and a CDR-L3 sequence comprising sequence selected from SEQ ID NO: 144. In some aspects, the antibody comprises a VL sequence comprising a CDR- L1 sequence comprising SEQ ID NO: 116, a CDR-L2 sequence comprising SEQ ID NO: 131, and a CDR-L3 sequence comprising SEQ ID NO: 150. In some aspects, the antibody comprises a VL sequence comprising a CDR-L1 sequence comprising SEQ ID NO: 117, a CDR-L2 sequence comprising SEQ ID NO: 134, and a CDR-L3 sequence comprising SEQ ID NO: 150.

2.5.8. Variants of $V_L$ Sequences Comprising Illustrative CDR-Ls

In some embodiments, the $V_L$ sequences provided herein comprise a variant of an illustrative CDR-L3, CDR-L2, and/or CDR-L1 sequence provided in this disclosure.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, or 95% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, or 95% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

2.6. $V_L$ Sequences

In some embodiments, the antibody comprises a $V_L$ sequence comprising, consisting of, or consisting essentially of a sequence selected from SEQ ID NOs: 219-248. In some aspects, the antibody comprises a $V_L$ sequence comprising, consisting of, or consisting essentially of SEQ ID NO: 219. In some aspects, the antibody comprises a $V_L$ sequence comprising, consisting of, or consisting essentially of SEQ ID NO: 220. In some aspects, the antibody comprises a $V_L$ sequence comprising, consisting of, or consisting essentially of SEQ ID NO: 221. In some aspects, the antibody comprises a $V_L$ sequence comprising, consisting of, or consisting essentially of SEQ ID NO: 222. In some aspects, the antibody comprises a $V_L$ sequence comprising, consisting of, or consisting essentially of SEQ ID NO: 223. In some aspects, the antibody comprises a $V_L$ sequence comprising, consisting of, or consisting essentially of SEQ ID NO: 224. In some aspects, the antibody comprises a $V_L$ sequence comprising, consisting of, or consisting essentially of SEQ ID NO: 225. In some aspects, the antibody comprises a $V_L$ sequence comprising, consisting of, or consisting essentially of SEQ ID NO: 226. In some aspects, the antibody comprises a $V_L$ sequence comprising, consisting of, or consisting essentially of SEQ ID NO: 227. In some aspects, the antibody comprises a $V_L$ sequence comprising, consisting of, or consisting essentially of SEQ ID NO: 228. In some aspects, the antibody comprises a $V_L$ sequence comprising, consisting of, or consisting essentially of SEQ ID NO: 229. In some aspects, the antibody comprises a $V_L$ sequence comprising, consisting of, or consisting essentially of SEQ ID NO: 230. In some aspects, the antibody comprises a $V_L$ sequence comprising, consisting of, or consisting essentially of SEQ ID NO: 231. In some aspects, the antibody comprises a $V_L$ sequence comprising, consisting of, or consisting essentially of SEQ ID NO: 232. In some aspects, the antibody comprises a $V_L$ sequence comprising, consisting of, or consisting essentially of SEQ ID NO: 233. In some aspects, the antibody comprises a $V_L$ sequence comprising, consisting of, or consisting essentially of SEQ ID NO: 234. In some aspects, the antibody comprises a $V_L$ sequence comprising, consisting of, or consisting essentially of SEQ ID NO: 235. In some aspects, the antibody comprises a $V_L$ sequence comprising, consisting of, or consisting essentially of SEQ ID NO: 236. In some aspects, the antibody comprises a $V_L$ sequence comprising, consisting of, or consisting essentially of SEQ ID NO: 237. In some aspects, the antibody comprises a $V_L$ sequence comprising, consisting of, or consisting essentially of SEQ ID NO: 238. In some aspects, the antibody comprises a $V_L$ sequence comprising, consisting of, or consisting essentially of SEQ ID NO: 239. In some aspects, the antibody comprises a $V_L$ sequence comprising, consisting of, or consisting essentially of SEQ ID NO: 240. In some aspects, the antibody comprises a $V_L$ sequence comprising, consisting of, or consisting essentially of SEQ ID NO: 241. In some aspects, the antibody comprises a $V_L$ sequence comprising, consisting of, or consisting essentially of SEQ ID NO: 242. In some aspects, the antibody comprises a $V_L$ sequence comprising, consisting of, or consisting essentially of SEQ ID NO: 243. In some aspects, the antibody comprises a $V_L$ sequence comprising, consisting of, or consisting essentially of SEQ ID NO: 244. In some aspects, the antibody comprises a $V_L$ sequence comprising, consisting of, or consisting essentially of SEQ ID NO: 245. In some aspects, the antibody comprises a $V_L$ sequence comprising, consisting of, or consisting essentially of SEQ ID NO: 246. In some aspects, the antibody comprises a $V_L$ sequence comprising, consisting of, or consisting essentially of SEQ ID NO: 247. In some aspects, the antibody comprises a $V_L$ sequence comprising, consisting of, or consisting essentially of SEQ ID NO: 248.

2.6.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7. Pairs 2.7.1. CDR-H3-CDR-L3 Pairs

In some embodiments, the antibody comprises a CDR-H3 sequence and a CDR-L3 sequence. In some aspects, the CDR-H3 sequence is part of a $V_H$ and the CDR-L3 sequence is part of a $V_L$.

In some aspects, the CDR-H3 sequence is a CDR-H3 sequence comprising, consisting of, or consisting essentially of SEQ ID NOs: 82-109, and the CDR-L3 sequence is a CDR-L3 sequence comprising, consisting of, or consisting essentially of SEQ ID NOs: 141-166.

In some aspects, the CDR-H3 sequence is SEQ ID NO: 82 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 83 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 84 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 85 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 86 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 87 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 88 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 89 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 90 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 91 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 92 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 93 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 94 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 95 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 96 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 97 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 98 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 99 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 100 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 101 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 102 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 103 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 104 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 105 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 106 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 107 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 108 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

In some aspects, the CDR-H3 sequence is SEQ ID NO: 109 and the CDR-L3 sequence is selected from SEQ ID NOs: 141-166. In some aspects, the CDR-L3 sequence is SEQ ID NO: 141. In some aspects, the CDR-L3 sequence is SEQ ID NO: 142. In some aspects, the CDR-L3 sequence is SEQ ID NO: 143. In some aspects, the CDR-L3 sequence is SEQ ID NO: 144. In some aspects, the CDR-L3 sequence is SEQ ID NO: 145. In some aspects, the CDR-L3 sequence is SEQ ID NO: 146. In some aspects, the CDR-L3 sequence is SEQ ID NO: 147. In some aspects, the CDR-L3 sequence is SEQ ID NO: 148. In some aspects, the CDR-L3 sequence is SEQ ID NO: 149. In some aspects, the CDR-L3 sequence is SEQ ID NO: 150. In some aspects, the CDR-L3 sequence is SEQ ID NO: 151. In some aspects, the CDR-L3 sequence is SEQ ID NO: 152. In some aspects, the CDR-L3 sequence is SEQ ID NO: 153. In some aspects, the CDR-L3 sequence is SEQ ID NO: 154. In some aspects, the CDR-L3 sequence is SEQ ID NO: 155. In some aspects, the CDR-L3 sequence is SEQ ID NO: 156. In some aspects, the CDR-L3 sequence is SEQ ID NO: 157. In some aspects, the CDR-L3 sequence is SEQ ID NO: 158. In some aspects, the CDR-L3 sequence is SEQ ID NO: 159. In some aspects, the CDR-L3 sequence is SEQ ID NO: 160. In some aspects, the CDR-L3 sequence is SEQ ID NO: 161. In some aspects, the CDR-L3 sequence is SEQ ID NO: 162. In some aspects, the CDR-L3 sequence is SEQ ID NO: 163. In some aspects, the CDR-L3 sequence is SEQ ID NO: 164. In some aspects, the CDR-L3 sequence is SEQ ID NO: 165. In some aspects, the CDR-L3 sequence is SEQ ID NO: 166.

2.7.1.1. Variants of CDR-H3– CDR-L3 Pairs

In some embodiments, the CDR-H3– CDR-L3 pairs provided herein comprise a variant of an illustrative CDR-H3 and/or CDR-L1 sequence provided in this disclosure.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, or 95% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, or 95% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

2.7.2. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 179-218 and the $V_L$ sequence is a $V_L$ sequence comprising, consisting of, or consisting essentially of SEQ ID NOs: 219-248.

In some aspects, the $V_H$ sequence is SEQ ID NO: 179 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 180 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 181 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 182 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 183 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 184 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 185 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 186 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 187 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 188 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 189 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 190 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 191 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 192 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 193 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 194 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 195 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 196 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 197 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 198 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 199 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 200 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 201 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 202 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 203 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 204 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 205 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 206 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 207 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 208 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 209 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 210 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the V_L sequence is SEQ ID NO: 235. In some aspects, the V_L sequence is SEQ ID NO: 236. In some aspects, the V_L sequence is SEQ ID NO: 237. In some aspects, the V_L sequence is SEQ ID NO: 238. In some aspects, the V_L sequence is SEQ ID NO: 239. In some aspects, the V_L sequence is SEQ ID NO: 240. In some aspects, the V_L sequence is SEQ ID NO: 241. In some aspects, the V_L sequence is SEQ ID NO: 242. In some aspects, the V_L sequence is SEQ ID NO: 243. In some aspects, the V_L sequence is SEQ ID NO: 244. In some aspects, the V_L sequence is SEQ ID NO: 245. In some aspects, the V_L sequence is SEQ ID NO: 246. In some aspects, the V_L sequence is SEQ ID NO: 247. In some aspects, the V_L sequence is SEQ ID NO: 248.

In some aspects, the V_H sequence is SEQ ID NO: 211 and the V_L sequence is selected from SEQ ID NOs: 219-248. In some aspects, the V_L sequence is SEQ ID NO: 219. In some aspects, the V_L sequence is SEQ ID NO: 220. In some aspects, the V_L sequence is SEQ ID NO: 221. In some aspects, the V_L sequence is SEQ ID NO: 222. In some aspects, the V_L sequence is SEQ ID NO: 223. In some aspects, the V_L sequence is SEQ ID NO: 224. In some aspects, the V_L sequence is SEQ ID NO: 225. In some aspects, the V_L sequence is SEQ ID NO: 226. In some aspects, the V_L sequence is SEQ ID NO: 227. In some aspects, the V_L sequence is SEQ ID NO: 228. In some aspects, the V_L sequence is SEQ ID NO: 229. In some aspects, the V_L sequence is SEQ ID NO: 230. In some aspects, the V_L sequence is SEQ ID NO: 231. In some aspects, the V_L sequence is SEQ ID NO: 232. In some aspects, the V_L sequence is SEQ ID NO: 233. In some aspects, the V_L sequence is SEQ ID NO: 234. In some aspects, the V_L sequence is SEQ ID NO: 235. In some aspects, the V_L sequence is SEQ ID NO: 236. In some aspects, the V_L sequence is SEQ ID NO: 237. In some aspects, the V_L sequence is SEQ ID NO: 238. In some aspects, the V_L sequence is SEQ ID NO: 239. In some aspects, the V_L sequence is SEQ ID NO: 240. In some aspects, the V_L sequence is SEQ ID NO: 241. In some aspects, the V_L sequence is SEQ ID NO: 242. In some aspects, the V_L sequence is SEQ ID NO: 243. In some aspects, the V_L sequence is SEQ ID NO: 244. In some aspects, the V_L sequence is SEQ ID NO: 245. In some aspects, the V_L sequence is SEQ ID NO: 246. In some aspects, the V_L sequence is SEQ ID NO: 247. In some aspects, the V_L sequence is SEQ ID NO: 248.

In some aspects, the V_H sequence is SEQ ID NO: 212 and the V_L sequence is selected from SEQ ID NOs: 219-248. In some aspects, the V_L sequence is SEQ ID NO: 219. In some aspects, the V_L sequence is SEQ ID NO: 220. In some aspects, the V_L sequence is SEQ ID NO: 221. In some aspects, the V_L sequence is SEQ ID NO: 222. In some aspects, the V_L sequence is SEQ ID NO: 223. In some aspects, the V_L sequence is SEQ ID NO: 224. In some aspects, the V_L sequence is SEQ ID NO: 225. In some aspects, the V_L sequence is SEQ ID NO: 226. In some aspects, the V_L sequence is SEQ ID NO: 227. In some aspects, the V_L sequence is SEQ ID NO: 228. In some aspects, the V_L sequence is SEQ ID NO: 229. In some aspects, the V_L sequence is SEQ ID NO: 230. In some aspects, the V_L sequence is SEQ ID NO: 231. In some aspects, the V_L sequence is SEQ ID NO: 232. In some aspects, the V_L sequence is SEQ ID NO: 233. In some aspects, the V_L sequence is SEQ ID NO: 234. In some aspects, the V_L sequence is SEQ ID NO: 235. In some aspects, the V_L sequence is SEQ ID NO: 236. In some aspects, the V_L sequence is SEQ ID NO: 237. In some aspects, the V_L sequence is SEQ ID NO: 238. In some aspects, the V_L sequence is SEQ ID NO: 239. In some aspects, the V_L sequence is SEQ ID NO: 240. In some aspects, the V_L sequence is SEQ ID NO: 241. In some aspects, the V_L sequence is SEQ ID NO: 242. In some aspects, the V_L sequence is SEQ ID NO: 243. In some aspects, the V_L sequence is SEQ ID NO: 244. In some aspects, the V_L sequence is SEQ ID NO: 245. In some aspects, the V_L sequence is SEQ ID NO: 246. In some aspects, the V_L sequence is SEQ ID NO: 247. In some aspects, the V_L sequence is SEQ ID NO: 248.

In some aspects, the V_H sequence is SEQ ID NO: 213 and the V_L sequence is selected from SEQ ID NOs: 219-248. In some aspects, the V_L sequence is SEQ ID NO: 219. In some aspects, the V_L sequence is SEQ ID NO: 220. In some aspects, the V_L sequence is SEQ ID NO: 221. In some aspects, the V_L sequence is SEQ ID NO: 222. In some aspects, the V_L sequence is SEQ ID NO: 223. In some aspects, the V_L sequence is SEQ ID NO: 224. In some aspects, the V_L sequence is SEQ ID NO: 225. In some aspects, the V_L sequence is SEQ ID NO: 226. In some aspects, the V_L sequence is SEQ ID NO: 227. In some aspects, the V_L sequence is SEQ ID NO: 228. In some aspects, the V_L sequence is SEQ ID NO: 229. In some aspects, the V_L sequence is SEQ ID NO: 230. In some aspects, the V_L sequence is SEQ ID NO: 231. In some aspects, the V_L sequence is SEQ ID NO: 232. In some aspects, the V_L sequence is SEQ ID NO: 233. In some aspects, the V_L sequence is SEQ ID NO: 234. In some aspects, the V_L sequence is SEQ ID NO: 235. In some aspects, the V_L sequence is SEQ ID NO: 236. In some aspects, the V_L sequence is SEQ ID NO: 237. In some aspects, the V_L sequence is SEQ ID NO: 238. In some aspects, the V_L sequence is SEQ ID NO: 239. In some aspects, the V_L sequence is SEQ ID NO: 240. In some aspects, the V_L sequence is SEQ ID NO: 241. In some aspects, the V_L sequence is SEQ ID NO: 242. In some aspects, the V_L sequence is SEQ ID NO: 243. In some aspects, the V_L sequence is SEQ ID NO: 244. In some aspects, the V_L sequence is SEQ ID NO: 245. In some aspects, the V_L sequence is SEQ ID NO: 246. In some aspects, the V_L sequence is SEQ ID NO: 247. In some aspects, the V_L sequence is SEQ ID NO: 248.

In some aspects, the V_H sequence is SEQ ID NO: 214 and the V_L sequence is selected from SEQ ID NOs: 219-248. In some aspects, the V_L sequence is SEQ ID NO: 219. In some aspects, the V_L sequence is SEQ ID NO: 220. In some aspects, the V_L sequence is SEQ ID NO: 221. In some aspects, the V_L sequence is SEQ ID NO: 222. In some aspects, the V_L sequence is SEQ ID NO: 223. In some aspects, the V_L sequence is SEQ ID NO: 224. In some aspects, the V_L sequence is SEQ ID NO: 225. In some aspects, the V_L sequence is SEQ ID NO: 226. In some aspects, the V_L sequence is SEQ ID NO: 227. In some aspects, the V_L sequence is SEQ ID NO: 228. In some aspects, the V_L sequence is SEQ ID NO: 229. In some aspects, the V_L sequence is SEQ ID NO: 230. In some aspects, the V_L sequence is SEQ ID NO: 231. In some aspects, the V_L sequence is SEQ ID NO: 232. In some aspects, the V_L sequence is SEQ ID NO: 233. In some aspects, the V_L sequence is SEQ ID NO: 234. In some aspects, the V_L sequence is SEQ ID NO: 235. In some aspects, the V_L sequence is SEQ ID NO: 236. In some aspects, the V_L sequence is SEQ ID NO: 237. In some aspects, the V_L sequence is SEQ ID NO: 238. In some aspects, the V_L sequence is SEQ ID NO: 239. In some aspects, the V_L sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 215 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 216 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 217 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the $V_L$ sequence is SEQ ID NO: 247. In some aspects, the $V_L$ sequence is SEQ ID NO: 248.

In some aspects, the $V_H$ sequence is SEQ ID NO: 218 and the $V_L$ sequence is selected from SEQ ID NOs: 219-248. In some aspects, the $V_L$ sequence is SEQ ID NO: 219. In some aspects, the $V_L$ sequence is SEQ ID NO: 220. In some aspects, the $V_L$ sequence is SEQ ID NO: 221. In some aspects, the $V_L$ sequence is SEQ ID NO: 222. In some aspects, the $V_L$ sequence is SEQ ID NO: 223. In some aspects, the $V_L$ sequence is SEQ ID NO: 224. In some aspects, the $V_L$ sequence is SEQ ID NO: 225. In some aspects, the $V_L$ sequence is SEQ ID NO: 226. In some aspects, the $V_L$ sequence is SEQ ID NO: 227. In some aspects, the $V_L$ sequence is SEQ ID NO: 228. In some aspects, the $V_L$ sequence is SEQ ID NO: 229. In some aspects, the $V_L$ sequence is SEQ ID NO: 230. In some aspects, the $V_L$ sequence is SEQ ID NO: 231. In some aspects, the $V_L$ sequence is SEQ ID NO: 232. In some aspects, the $V_L$ sequence is SEQ ID NO: 233. In some aspects, the $V_L$ sequence is SEQ ID NO: 234. In some aspects, the $V_L$ sequence is SEQ ID NO: 235. In some aspects, the $V_L$ sequence is SEQ ID NO: 236. In some aspects, the $V_L$ sequence is SEQ ID NO: 237. In some aspects, the $V_L$ sequence is SEQ ID NO: 238. In some aspects, the $V_L$ sequence is SEQ ID NO: 239. In some aspects, the $V_L$ sequence is SEQ ID NO: 240. In some aspects, the $V_L$ sequence is SEQ ID NO: 241. In some aspects, the $V_L$ sequence is SEQ ID NO: 242. In some aspects, the $V_L$ sequence is SEQ ID NO: 243. In some aspects, the $V_L$ sequence is SEQ ID NO: 244. In some aspects, the $V_L$ sequence is SEQ ID NO: 245. In some aspects, the $V_L$ sequence is SEQ ID NO: 246. In some aspects, the V_L sequence is SEQ ID NO: 247. In some aspects, the V_L sequence is SEQ ID NO: 248.

2.7.3. CDR-H1+ CDR-H2+ CDR-H3+ CDR-L1+ CDR-L2+ CDR-L3

In some aspects, the antibody comprises a $V_H$ sequence comprising a Kabat CDR-H1 sequence comprising SEQ ID NO: 25, a Kabat CDR-H2 sequence comprising SEQ ID NO: 63, and a Kabat CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 83 and a VL sequence comprising a CDR-L1 sequence comprising SEQ ID NO: 111, a CDR-L2 sequence comprising SEQ ID NO: 126, and a CDR-L3 sequence SEQ ID NO: 142. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 84 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 85 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 86 and a VL sequence comprising a CDR-L1 sequence comprising SEQ ID NO: 110, a CDR-L2 sequence comprising SEQ ID NO: 127, and a CDR-L3 sequence SEQ ID NO: 142. In some aspects, the antibody comprises a $V_H$ sequence comprising a Kabat CDR-H1 sequence comprising SEQ ID NO: 25, a Kabat CDR-H2 sequence comprising SEQ ID NO: 66, and a Kabat CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 143. In some aspects, the antibody comprises a $V_H$ sequence comprising a Kabat CDR-H1 sequence comprising SEQ ID NO: 26, a Kabat CDR-H2 sequence comprising SEQ ID NO: 65, and a Kabat CDR-H3 sequence comprising SEQ ID NO: 82 and a VL sequence comprising a CDR-L1 sequence comprising SEQ ID NO: 112, a CDR-L2 sequence comprising SEQ ID NO: 128, and a CDR-L3 sequence SEQ ID NO: 144. In some aspects, the antibody comprises a $V_H$ sequence comprising a Kabat CDR-H1 sequence comprising SEQ ID NO: 27, a Kabat CDR-H2 sequence comprising SEQ ID NO: 65, and a Kabat CDR-H3 sequence comprising SEQ ID NO: 82 and a VL sequence comprising a CDR-L1 sequence comprising SEQ ID NO: 111, a CDR-L2 sequence comprising SEQ ID NO: 126, and a CDR-L3 sequence SEQ ID NO: 145. In some aspects, the antibody comprises a $V_H$ sequence comprising a Kabat CDR-H1 sequence comprising SEQ ID NO: 28, a Kabat CDR-H2 sequence comprising SEQ ID NO: 67, and a Kabat CDR-H3 sequence comprising SEQ ID NO: 82 and a VL sequence comprising a CDR-L1 sequence comprising SEQ ID NO: 113, a CDR-L2 sequence comprising SEQ ID NO: 129, and a CDR-L3 sequence SEQ ID NO: 146. In some aspects, the antibody comprises a $V_H$ sequence comprising a Kabat CDR-H1 sequence comprising SEQ ID NO: 29, a Kabat CDR-H2 sequence comprising SEQ ID NO: 68, and a Kabat CDR-H3 sequence comprising SEQ ID NO: 82 and a VL sequence comprising a CDR-L1 sequence comprising SEQ ID NO: 114, a CDR-L2 sequence comprising SEQ ID NO: 130, and a CDR-L3 sequence SEQ ID NO: 147. In some aspects, the antibody comprises a $V_H$ sequence comprising a Kabat CDR-H1 sequence comprising SEQ ID NO: 26, a Kabat CDR-H2 sequence comprising SEQ ID NO: 64, and a Kabat CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a $V_H$ sequence comprising a Kabat CDR-H1 sequence comprising SEQ ID NO: 30, a Kabat CDR-H2 sequence comprising SEQ ID NO: 69, and a Kabat CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 31, a Kabat CDR-H2 sequence comprising SEQ ID NO: 70, and a Kabat CDR-H3 sequence comprising SEQ ID NO: 88 and a VL sequence comprising a CDR-L1 sequence comprising SEQ ID NO: 116, a CDR-L2 sequence comprising SEQ ID NO: 131, and a CDR-L3 sequence SEQ ID NO: 149. In some aspects, the antibody comprises a $V_H$ sequence comprising a Kabat CDR-H1 sequence comprising SEQ ID NO: 32, a Kabat CDR-H2 sequence comprising SEQ ID NO: 71, and a Kabat CDR-H3 sequence comprising SEQ ID NO: 89 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 90 and a VL sequence comprising a CDR-L1 sequence comprising SEQ ID NO: 115, a CDR-L2 sequence comprising SEQ ID NO: 132, and a CDR-L3 sequence SEQ ID NO: 149. In some aspects, the antibody comprises a $V_H$ sequence comprising a Kabat CDR-H1 sequence comprising SEQ ID NO: 34, a Kabat CDR-H2 sequence comprising SEQ ID NO: 72, and a Kabat CDR-H3 sequence comprising SEQ ID NO: 91 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 30, a Kabat CDR-H2 sequence comprising SEQ ID NO: 71, and a Kabat CDR-H3 sequence comprising SEQ ID NO: 92 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 35, a Kabat CDR-H2 sequence comprising SEQ ID NO: 70, and a Kabat CDR-H3 sequence comprising SEQ ID NO: 93 and a $V_L$ sequence comprising a CDR-L1 sequence comprising SEQ ID NO: 117, a CDR-L2 sequence comprising SEQ ID NO: 133, and a CDR-L3 sequence SEQ ID NO: 150. In some aspects, the antibody comprises a $V_H$ sequence comprising a Kabat CDR-H1 sequence comprising SEQ ID NO: 33, a Kabat CDR-H2 sequence comprising SEQ ID NO: 70, and a Kabat CDR-H3 sequence comprising SEQ ID NO: 92 and a $V_L$ sequence comprising a CDR-L1 sequence comprising SEQ ID NO: 115, a CDR-L2 sequence comprising SEQ ID NO: 134, and a CDR-L3 sequence SEQ ID NO: 148. In some aspects, the antibody comprises a $V_H$ sequence comprising a Kabat CDR-H1 sequence comprising SEQ ID NO: 36, a Kabat CDR-H2 sequence comprising SEQ ID NO: 72, and a Kabat CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 30, a Kabat CDR-H2 sequence comprising SEQ ID NO: 73, and a Kabat CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 37, a Kabat CDR-H2 sequence comprising SEQ ID NO: 74, and a Kabat CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 94 and a VL sequence comprising a CDR-L1 sequence comprising SEQ ID NO: 118, a CDR-L2 sequence comprising SEQ ID NO: 135, and a CDR-L3 sequence SEQ ID NO: 151. In some aspects, the antibody comprises a $V_H$ sequence comprising a Kabat CDR-H1 sequence comprising SEQ ID NO: 39, a Kabat CDR-H2 sequence comprising SEQ ID NO: 76, and a Kabat CDR-H3 sequence comprising SEQ ID NO: 95 and a VL sequence comprising a CDR-L1 sequence comprising SEQ ID NO: 118, a CDR-L2 sequence comprising SEQ ID NO: 135, and a CDR-L3 sequence SEQ ID NO: 152. In some aspects, the antibody comprises a $V_H$ sequence comprising a Kabat CDR-H1 sequence comprising SEQ ID NO: 40, a Kabat CDR-H2 sequence comprising SEQ ID NO: 76, and a Kabat CDR-H3 sequence comprising SEQ ID NO: 96 and a VL sequence comprising a CDR-L1 sequence comprising SEQ ID NO: 118, a CDR-L2 sequence comprising SEQ ID NO: 136, and a CDR-L3 sequence SEQ ID NO: 152. In some aspects, the antibody comprises a $V_H$ sequence comprising a Kabat CDR-H1 sequence comprising SEQ ID NO: 39, a Kabat CDR-H2 sequence comprising SEQ ID NO: 76, and a Kabat CDR-H3 sequence comprising SEQ ID NO: 94 and a VL sequence comprising a CDR-L1 sequence comprising SEQ ID NO: 118, a CDR-L2 sequence comprising SEQ ID NO: 135, and a CDR-L3 sequence SEQ ID NO: 152. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 97 and a VL sequence comprising a CDR-L1 sequence comprising SEQ ID NO: 115, a CDR-L2 sequence comprising SEQ ID NO: 131, and a CDR-L3 sequence SEQ ID NO: 153. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 98 and a VL sequence comprising a CDR-L1 sequence comprising SEQ ID NO: 119, a CDR-L2 sequence comprising SEQ ID NO: 131, and a CDR-L3 sequence SEQ ID NO: 154. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 99 and a VL sequence comprising a CDR-L1 sequence comprising SEQ ID NO: 120, a CDR-L2 sequence comprising SEQ ID NO: 137, and a CDR-L3 sequence SEQ ID NO: 155. In some aspects, the antibody comprises a $V_H$ sequence comprising a Kabat CDR-H1 sequence comprising SEQ ID NO: 41, a Kabat CDR-H2 sequence comprising SEQ ID NO: 69, and a Kabat CDR-H3 sequence comprising SEQ ID NO: 100 and a VL sequence comprising a CDR-L1 sequence comprising SEQ ID NO: 121, a CDR-L2 sequence comprising SEQ ID NO: 138, and a CDR-L3 sequence SEQ ID NO: 156. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 101 and a VL sequence comprising a CDR-L1 sequence comprising SEQ ID NO: 121, a CDR-L2 sequence comprising SEQ ID NO: 138, and a CDR-L3 sequence SEQ ID NO: 157. In some aspects, the antibody comprises a $V_H$ sequence comprising a Kabat CDR-H1 sequence comprising SEQ ID NO: 42, a Kabat CDR-H2 sequence comprising SEQ ID NO: 78, and a Kabat CDR-H3 sequence comprising SEQ ID NO: 102 and a VL sequence comprising a CDR-L1 sequence comprising SEQ ID NO: 122, a CDR-L2 sequence comprising SEQ ID NO: 138, and a CDR-L3 sequence SEQ ID NO: 158. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 103 and a VL sequence comprising a CDR-L1 sequence comprising SEQ ID NO: 121, a CDR-L2 sequence comprising SEQ ID NO: 138, and a CDR-L3 sequence SEQ ID NO: 159. In some aspects, the antibody comprises a $V_H$ sequence comprising a Kabat CDR-H1 sequence comprising SEQ ID NO: 43, a Kabat CDR-H2 sequence comprising SEQ ID NO: 79, and a Kabat CDR-H3 sequence comprising SEQ ID NO: 104 and a VL sequence comprising a CDR-L1 sequence comprising SEQ ID NO: 118, a CDR-L2 sequence comprising SEQ ID NO: 135, and a CDR-L3 sequence SEQ ID NO: 160. In some aspects, the antibody comprises a $V_H$ sequence comprising a Kabat CDR-H1 sequence comprising SEQ ID NO: 38, a Kabat CDR-H2 sequence comprising SEQ ID NO: 75, and a Kabat CDR-H3 sequence comprising SEQ ID NO: 103 and a VL sequence comprising a CDR-L1 sequence comprising SEQ ID NO: 121, a CDR-L2 sequence comprising SEQ ID NO: 139, and a CDR-L3 sequence SEQ ID NO: 161. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 105 and a VL sequence comprising a CDR-L1 sequence comprising SEQ ID NO: 123, a CDR-L2 sequence comprising SEQ ID NO: 140, and a CDR-L3 sequence SEQ ID NO: 162. In some aspects, the antibody comprises a $V_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 106 and a VL sequence comprising a CDR-L1 sequence comprising SEQ ID NO: 121, a CDR-L2 sequence comprising SEQ ID NO: 138, and a CDR-L3 sequence SEQ ID NO: 163. In some aspects, the antibody comprises a V$_H$ sequence comprising a Kabat CDR-H1 sequence comprising SEQ ID NO: 38, a Kabat CDR-H2 sequence comprising SEQ ID NO: 69, and a Kabat CDR-H3 sequence comprising SEQ ID NO: 107 and a VL sequence comprising a CDR-L1 sequence comprising SEQ ID NO: 121, a CDR-L2 sequence comprising SEQ ID NO: 139, and a CDR-L3 sequence SEQ ID NO: 164. In some aspects, the antibody comprises a V$_H$ sequence comprising a Kabat CDR-H1 sequence comprising SEQ ID NO: 44, a Kabat CDR-H2 sequence comprising SEQ ID NO: 80, and a Kabat CDR-H3 sequence comprising SEQ ID NO: 108 and a VL sequence comprising a CDR-L1 sequence comprising SEQ ID NO: 120, a CDR-L2 sequence comprising SEQ ID NO: 137, and a CDR-L3 sequence SEQ ID NO: 165. In some aspects, the antibody comprises a V$_H$ sequence comprising a Kabat CDR-H1 sequence comprising SEQ ID NO: 45, a Kabat CDR-H2 sequence comprising SEQ ID NO: 81, and a Kabat CDR-H3 sequence comprising SEQ ID NO: 109 and a VL sequence comprising a CDR-L1 sequence comprising SEQ ID NO: 124, a CDR-L2 sequence comprising SEQ ID NO: 125, and a CDR-L3 sequence SEQ ID NO: 166.

In some aspects, the antibody comprises a V$_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 83 and a V$_L$ sequence comprising a CDR-L1 sequence comprising SEQ ID NO: 111, a CDR-L2 sequence comprising SEQ ID NO: 126, and a CDR-L3 sequence SEQ ID NO: 142. In some aspects, the antibody comprises a V$_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 84 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 85 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a V$_H$ sequence comprising a Chothia CDR-H1 sequence comprising SEQ ID NO: 3, a Chothia CDR-H2 sequence comprising SEQ ID NO: 47, and a Chothia CDR-H3 sequence comprising SEQ ID NO: 86 and a VL sequence comprising a CDR-L1 sequence comprising SEQ ID NO: 110, a CDR-L2 sequence comprising SEQ ID NO: 127, and a CDR-L3 sequence SEQ ID NO: 142. In some aspects, the antibody comprises a V$_H$ sequence comprising a Chothia CDR-H1 sequence comprising SEQ ID NO: 4, a Chothia CDR-H2 sequence comprising SEQ ID NO: 46, and a Chothia CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a V$_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 143. In some aspects, the antibody comprises a V$_H$ sequence comprising a Chothia CDR-H1 sequence comprising SEQ ID NO: 2, a Chothia CDR-H2 sequence comprising SEQ ID NO: 46, and a Chothia CDR-H3 sequence comprising SEQ ID NO: 82 and a VL sequence comprising a CDR-L1 sequence comprising SEQ ID NO: 112, a CDR-L2 sequence comprising SEQ ID NO: 128, and a CDR-L3 sequence SEQ ID NO: 144. In some aspects, the antibody comprises a V$_H$ sequence comprising a Chothia CDR-H1 sequence comprising SEQ ID NO: 1, a Chothia CDR-H2 sequence comprising SEQ ID NO: 46, and a Chothia CDR-H3 sequence comprising SEQ ID NO: 82 and a VL sequence comprising a CDR-L1 sequence comprising SEQ ID NO: 111, a CDR-L2 sequence comprising SEQ ID NO: 126, and a CDR-L3 sequence SEQ ID NO: 145. In some aspects, the antibody comprises a V$_H$ sequence comprising a Chothia CDR-H1 sequence comprising SEQ ID NO: 5, a Chothia CDR-H2 sequence comprising SEQ ID NO: 49, and a Chothia CDR-H3 sequence comprising SEQ ID NO: 82 and a VL sequence comprising a CDR-L1 sequence comprising SEQ ID NO: 113, a CDR-L2 sequence comprising SEQ ID NO: 129, and a CDR-L3 sequence SEQ ID NO: 146. In some aspects, the antibody comprises a V$_H$ sequence comprising a Chothia CDR-H1 sequence comprising SEQ ID NO: 6, a Chothia CDR-H2 sequence comprising SEQ ID NO: 50, and a Chothia CDR-H3 sequence comprising SEQ ID NO: 82 and a VL sequence comprising a CDR-L1 sequence comprising SEQ ID NO: 114, a CDR-L2 sequence comprising SEQ ID NO: 130, and a CDR-L3 sequence SEQ ID NO: 147. In some aspects, the antibody comprises a V$_H$ sequence comprising a Chothia CDR-H1 sequence comprising SEQ ID NO: 2, a Chothia CDR-H2 sequence comprising SEQ ID NO: 47, and a Chothia CDR-H3 sequence comprising SEQ ID NO: 82 and a VL sequence comprising a CDR-L1 sequence comprising SEQ ID NO: 110, a CDR-L2 sequence comprising SEQ ID NO: 125, and a CDR-L3 sequence SEQ ID NO: 141. In some aspects, the antibody comprises a V$_H$ sequence comprising a Chothia CDR-H1 sequence comprising SEQ ID NO: 7, a Chothia CDR-H2 sequence comprising SEQ ID NO: 51, and a Chothia CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a V$_H$ sequence comprising a Chothia CDR-H1 sequence comprising SEQ ID NO: 8, a Chothia CDR-H2 sequence comprising SEQ ID NO: 52, and a Chothia CDR-H3 sequence comprising SEQ ID NO: 88 and a VL sequence comprising a CDR-L1 sequence comprising SEQ ID NO: 116, a CDR-L2 sequence comprising SEQ ID NO: 131, and a CDR-L3 sequence SEQ ID NO: 149. In some aspects, the antibody comprises a V$_H$ sequence comprising a Chothia CDR-H1 sequence comprising SEQ ID NO: 9, a Chothia CDR-H2 sequence comprising SEQ ID NO: 53, and a Chothia CDR-H3 sequence comprising SEQ ID NO: 89 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a V$_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 90 and a VL sequence comprising a CDR-L1 sequence comprising SEQ ID NO: 115, a CDR-L2 sequence comprising SEQ ID NO: 132, and a CDR-L3 sequence SEQ ID NO: 149. In some aspects, the antibody comprises a $V_H$ sequence comprising a Chothia CDR-H1 sequence comprising SEQ ID NO: 11, a Chothia CDR-H2 sequence comprising SEQ ID NO: 54, and a Chothia CDR-H3 sequence comprising SEQ ID NO: 91 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Chothia CDR-H1 sequence comprising SEQ ID NO: 12, a Chothia CDR-H2 sequence comprising SEQ ID NO: 53, and a Chothia CDR-H3 sequence comprising SEQ ID NO: 92 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Chothia CDR-H1 sequence comprising SEQ ID NO: 13, a Chothia CDR-H2 sequence comprising SEQ ID NO: 52, and a Chothia CDR-113 sequence comprising SEQ ID NO: 93 and a VL sequence comprising a CDR-L1 sequence comprising SEQ ID NO: 117, a CDR-L2 sequence comprising SEQ ID NO: 133, and a CDR-L3 sequence SEQ ID NO: 150. In some aspects, the antibody comprises a $V_H$ sequence comprising a Chothia CDR-H1 sequence comprising SEQ ID NO: 10, a Chothia CDR-H2 sequence comprising SEQ ID NO: 52, and a Chothia CDR-H3 sequence comprising SEQ ID NO: 92 and a VL sequence comprising a CDR-L1 sequence comprising SEQ ID NO: 115, a CDR-L2 sequence comprising SEQ ID NO: 134, and a CDR-L3 sequence SEQ ID NO: 148. In some aspects, the antibody comprises a $V_H$ sequence comprising a Chothia CDR-H1 sequence comprising SEQ ID NO: 14, a Chothia CDR-H2 sequence comprising SEQ ID NO: 54, and a Chothia CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Chothia CDR-H1 sequence comprising SEQ ID NO: 15, a Chothia CDR-H2 sequence comprising SEQ ID NO: 55, and a Chothia CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Chothia CDR-H1 sequence comprising SEQ ID NO: 16, a Chothia CDR-H2 sequence comprising SEQ ID NO: 56, and a Chothia CDR-H3 sequence comprising SEQ ID NO: 87 and a VL sequence comprising a CDR-L1 sequence comprising SEQ ID NO: 115, a CDR-L2 sequence comprising SEQ ID NO: 131, and a CDR-L3 sequence SEQ ID NO: 148. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 94 and a VL sequence comprising a CDR-L1 sequence comprising SEQ ID NO: 118, a CDR-L2 sequence comprising SEQ ID NO: 135, and a CDR-L3 sequence SEQ ID NO: 151. In some aspects, the antibody comprises a $V_H$ sequence comprising a Chothia CDR-H1 sequence comprising SEQ ID NO: 18, a Chothia CDR-H2 sequence comprising SEQ ID NO: 57, and a Chothia CDR-H3 sequence comprising SEQ ID NO: 95 and a VL sequence comprising a CDR-L1 sequence comprising SEQ ID NO: 118, a CDR-L2 sequence comprising SEQ ID NO: 135 and a CDR-L3 sequence SEQ ID NO: 152. In some aspects, the antibody comprises a $V_H$ sequence comprising a Chothia CDR-H1 sequence comprising SEQ ID NO: 19, a Chothia CDR-H2 sequence comprising SEQ ID NO: 57, and a Chothia CDR-H3 sequence comprising SEQ ID NO: 96 and a $V_L$ sequence comprising a CDR-L1 sequence comprising SEQ ID NO: 118, a CDR-L2 sequence comprising SEQ ID NO: 136, and a CDR-L3 sequence SEQ ID NO: 152. In some aspects, the antibody comprises a $V_H$ sequence comprising a Chothia CDR-H1 sequence comprising SEQ ID NO: 21, a Chothia CDR-H2 sequence comprising SEQ ID NO: 57, and a Chothia CDR-H3 sequence comprising SEQ ID NO: 94 and a VL sequence comprising a CDR-L1 sequence comprising SEQ ID NO: 118, a CDR-L2 sequence comprising SEQ ID NO: 135, and a CDR-L3 sequence comprising SEQ ID NO: 152. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 97 and a VL sequence comprising a CDR-L1 sequence comprising SEQ ID NO: 115, a CDR-L2 sequence comprising SEQ ID NO: 131, and a CDR-L3 sequence SEQ ID NO: 153. In some aspects, the antibody comprises a $V_H$ sequence comprising a Chothia CDR-H1 sequence comprising SEQ ID NO: 22, a Chothia CDR-H2 sequence comprising SEQ ID NO: 52, and a Chothia CDR-H3 sequence comprising SEQ ID NO: 98 and a VL sequence comprising a CDR-L1 sequence comprising SEQ ID NO: 119, a CDR-L2 sequence comprising SEQ ID NO: 131, and a CDR-L3 sequence SEQ ID NO: 154. In some aspects, the antibody comprises a $V_H$ sequence comprising a Chothia CDR-H1 sequence comprising SEQ ID NO: 22, a Chothia CDR-H2 sequence comprising SEQ ID NO: 51, and a Chothia CDR-H3 sequence comprising SEQ ID NO: 99 and a VL sequence comprising a CDR-L1 sequence comprising SEQ ID NO: 120, a CDR-L2 sequence comprising SEQ ID NO: 137, and a CDR-L3 sequence SEQ ID NO: 155. In some aspects, the antibody comprises a $V_H$ sequence comprising a Chothia CDR-H1 sequence comprising SEQ ID NO: 22, a Chothia CDR-H2 sequence comprising SEQ ID NO: 51, and a Chothia CDR-H3 sequence comprising SEQ ID NO: 100 and a VL sequence comprising a CDR-L1 sequence comprising SEQ ID NO: 121, a CDR-L2 sequence comprising SEQ ID NO: 138, and a CDR-L3 sequence SEQ ID NO: 156. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 101 and a VL sequence comprising a CDR-L1 sequence comprising SEQ ID NO: 121, a CDR-L2 sequence comprising SEQ ID NO: 138, and a CDR-L3 sequence SEQ ID NO: 157. In some aspects, the antibody comprises a $V_H$ sequence comprising a Chothia CDR-H1 sequence comprising SEQ ID NO: 17, a Chothia CDR-H2 sequence comprising SEQ ID NO: 59, and a Chothia CDR-H3 sequence comprising SEQ ID NO: 102 and a VL sequence comprising a CDR-L1 sequence comprising SEQ ID NO: 122, a CDR-L2 sequence comprising SEQ ID NO: 138, and a CDR-L3 sequence SEQ ID NO: 158. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 103 and a VL sequence comprising a CDR-L1 sequence comprising SEQ ID NO: 121, a CDR-L2 sequence comprising SEQ ID NO: 138, and a CDR-L3 sequence SEQ ID NO: 159. In some aspects, the antibody comprises a $V_H$ sequence comprising a Chothia CDR-H1 sequence comprising SEQ ID NO: 23, a Chothia CDR-H2 sequence comprising SEQ ID NO: 60, and a Chothia CDR-H3 sequence comprising SEQ ID NO: 104 and a VL sequence comprising a CDR-L1 sequence comprising SEQ ID NO: 118, a CDR-L2 sequence comprising SEQ ID NO: 135, and a CDR-L3 sequence SEQ ID NO: 160. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 103 and a VL sequence comprising a CDR-L1 sequence comprising SEQ ID NO: 121, a CDR-L2 sequence comprising SEQ ID NO: 139, and a CDR-L3 sequence SEQ ID NO: 161. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 105 and a VL sequence comprising a CDR-L1 sequence comprising SEQ ID NO: 123, a CDR-L2 sequence comprising SEQ ID NO: 140, and a CDR-L3 sequence SEQ ID NO: 162. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 106 and a VL sequence comprising a CDR-L1 sequence comprising SEQ ID NO: 121, a CDR-L2 sequence comprising SEQ ID NO: 138, and a CDR-L3 sequence SEQ ID NO: 163. In some aspects, the antibody comprises a $V_H$ sequence comprising a Chothia CDR-H1 sequence comprising SEQ ID NO: 17, a Chothia CDR-H2 sequence comprising SEQ ID NO: 51, and a Chothia CDR-H3 sequence comprising SEQ ID NO: 107 and a VL sequence comprising a CDR-L1 sequence comprising SEQ ID NO: 121, a CDR-L2 sequence comprising SEQ ID NO: 139, and a CDR-L3 sequence SEQ ID NO: 164. In some aspects, the antibody comprises a $V_H$ sequence comprising a Chothia CDR-H1 sequence comprising SEQ ID NO: 17, a Chothia CDR-H2 sequence comprising SEQ ID NO: 61, and a Chothia CDR-H3 sequence comprising SEQ ID NO: 108 and a VL sequence comprising a CDR-L1 sequence comprising SEQ ID NO: 120, a CDR-L2 sequence comprising SEQ ID NO: 137, and a CDR-L3 sequence SEQ ID NO: 165. In some aspects, the antibody comprises a $V_H$ sequence comprising a Chothia CDR-H1 sequence comprising SEQ ID NO: 17, a Chothia CDR-H2 sequence comprising SEQ ID NO: 62, and a Chothia CDR-H3 sequence comprising SEQ ID NO: 109 and a VL sequence comprising a CDR-L1 sequence comprising SEQ ID NO: 124, a CDR-L2 sequence comprising SEQ ID NO: 125, and a CDR-L3 sequence SEQ ID NO: 166.

2.7.3.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.1% identity with any of the illustrative $V_H$ sequences provided in this disclosure.

In some embodiments, the $V_H$ sequence comprises, consists of, or consists essentially of any of the illustrative $V_H$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.05% identity with any of the illustrative $V_L$ sequences provided in this disclosure.

In some embodiments, the $V_L$ sequence comprises, consists of, or consists essentially of any of the illustrative $V_L$ sequences provided in this disclosure, 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7.4 HC+LC

In some embodiments, the antibody comprises or consists of one or more heavy chains consisting of an HC sequence and one or more light chains consisting of an LC sequence. In some embodiments, the antibody comprises or consists of two identical heavy chains consisting of an HC sequence and two identical light chains consisting of an LC sequence.

In some embodiments, the HC sequence is an HC sequence comprising, consisting of, or consisting essentially of SEQ ID NO: 255, SEQ ID NO: 257, SEQ ID NO: 259, SEQ ID NO: 261, SEQ ID NO: 263, SEQ ID NO: 265, SEQ ID NO: 267, SEQ ID NO: 269, SEQ ID NO: 271, SEQ ID NO: 273, SEQ ID NO: 275, SEQ ID NO: 277, SEQ ID NO: 279, SEQ ID NO: 281, SEQ ID NO: 283, SEQ ID NO: 285, SEQ ID NO: 287, SEQ ID NO: 289, SEQ ID NO: 291, SEQ ID NO: 293, SEQ ID NO: 295, or SEQ ID NO: 297 and the LC sequence is a LC sequence comprising, consisting of, or consisting essentially of SEQ ID NO: 256, SEQ ID NO: 258, SEQ ID NO: 260, SEQ ID NO: 262, SEQ ID NO: 264, SEQ ID NO: 266, SEQ ID NO: 268, SEQ ID NO: 270, SEQ ID NO: 272, SEQ ID NO: 274, SEQ ID NO: 276, SEQ ID NO: 278, SEQ ID NO: 280, SEQ ID NO: 282, SEQ ID NO: 284, SEQ ID NO: 286, SEQ ID NO: 288, SEQ ID NO: 290, SEQ ID NO: 292, SEQ ID NO: 294, SEQ ID NO: 296, or SEQ ID NO: 298. In some embodiments, the HC sequence is an HC sequence consisting of SEQ ID NO: 255, SEQ ID NO: 257, SEQ ID NO: 259, SEQ ID NO: 261, SEQ ID NO: 263, SEQ ID NO: 265, SEQ ID NO: 267, SEQ ID NO: 269, SEQ ID NO: 271, SEQ ID NO: 273, SEQ ID NO: 275, SEQ ID NO: 277, SEQ ID NO: 279, SEQ ID NO: 281, SEQ ID NO: 283, SEQ ID NO: 285, SEQ ID NO: 287, SEQ ID NO: 289, SEQ ID NO: 291, SEQ ID NO: 293, SEQ ID NO: 295, or SEQ ID NO: 297 and the LC sequence is an LC sequence consisting of SEQ ID NO: 256, SEQ ID NO: 258, SEQ ID NO: 260, SEQ ID NO: 262, SEQ ID NO: 264, SEQ ID NO: 266, SEQ ID NO: 268, SEQ ID NO: 270, SEQ ID NO: 272, SEQ ID NO: 274, SEQ ID NO: 276, SEQ ID NO: 278, SEQ ID NO: 280, SEQ ID NO: 282, SEQ ID NO: 284, SEQ ID NO: 286, SEQ ID NO: 288, SEQ ID NO: 290, SEQ ID NO: 292, SEQ ID NO: 294, SEQ ID NO: 296, or SEQ ID NO: 298.

In some embodiments, the HC sequence is an HC sequence consisting of SEQ ID NO: 255 and the LC sequence is an LC sequence consisting of SEQ ID NO: 256.

In some embodiments, the HC sequence is an HC sequence consisting of SEQ ID NO: 257 and the LC sequence is an LC sequence consisting of SEQ ID NO: 258. In some embodiments, the HC sequence is an HC sequence consisting of SEQ ID NO: 259 and the LC sequence is an LC sequence consisting of SEQ ID NO: 260. In some embodiments, the HC sequence is an HC sequence consisting of SEQ ID NO: 261 and the LC sequence is an LC sequence consisting of SEQ ID NO: 262. In some embodiments, the HC sequence is an HC sequence consisting of SEQ ID NO: 263 and the LC sequence is an LC sequence consisting of SEQ ID NO: 264. In some embodiments, the HC sequence is an HC sequence consisting of SEQ ID NO: 265 and the LC sequence is an LC sequence consisting of SEQ ID NO: 266. In some embodiments, the HC sequence is an HC sequence consisting of SEQ ID NO: 267 and the LC sequence is an LC sequence consisting of SEQ ID NO: 268. In some embodiments, the HC sequence is an HC sequence consisting of SEQ ID NO: 269 and the LC sequence is an LC sequence consisting of SEQ ID NO: 270. In some embodiments, the HC sequence is an HC sequence consisting of SEQ ID NO: 271 and the LC sequence is an LC sequence consisting of SEQ ID NO: 272. In some embodiments, the HC sequence is an HC sequence consisting of SEQ ID NO: 273 and the LC sequence is an LC sequence consisting of SEQ ID NO: 274. In some embodiments, the HC sequence is an HC sequence consisting of SEQ ID NO: 275 and the LC sequence is an LC sequence consisting of SEQ ID NO: 276. In some embodiments, the HC sequence is an HC sequence consisting of SEQ ID NO: 277 and the LC sequence is an LC sequence consisting of SEQ ID NO: 278. In some embodiments, the HC sequence is an HC sequence consisting of SEQ ID NO: 279 and the LC sequence is an LC sequence consisting of SEQ ID NO: 280. In some embodiments, the HC sequence is an HC sequence consisting of SEQ ID NO: 281 and the LC sequence is an LC sequence consisting of SEQ ID NO: 282. In some embodiments, the HC sequence is an HC sequence consisting of SEQ ID NO: 283 and the LC sequence is an LC sequence consisting of SEQ ID NO: 284. In some embodiments, the HC sequence is an HC sequence consisting of SEQ ID NO: 285 and the LC sequence is an LC sequence consisting of SEQ ID NO: 286. In some embodiments, the HC sequence is an HC sequence consisting of SEQ ID NO: 287 and the LC sequence is an LC sequence consisting of SEQ ID NO: 288. In some embodiments, the HC sequence is an HC sequence consisting of SEQ ID NO: 289 and the LC sequence is an LC sequence consisting of SEQ ID NO: 290. In some embodiments, the HC sequence is an HC sequence consisting of SEQ ID NO: 291 and the LC sequence is an LC sequence consisting of SEQ ID NO: 292. In some embodiments, the HC sequence is an HC sequence consisting of SEQ ID NO: 293 and the LC sequence is an LC sequence consisting of SEQ ID NO: 294. In some embodiments, the HC sequence is an HC sequence consisting of SEQ ID NO: 295 and the LC sequence is an LC sequence consisting of SEQ ID NO: 296. In some embodiments, the HC sequence is an HC sequence consisting of SEQ ID NO: 297 and the LC sequence is an LC sequence consisting of SEQ ID NO: 298.

2.8. Consensus Sequences

In some embodiments, provided herein are anti-CD39 antibodies comprising one or more sequences defined by consensus sequences. Each consensus sequence is based, at least in part, on one or more alignments of two or more useful anti-CD39 CDR sequences provided in this disclosure. Based on such alignments, a person of skill in the art would recognize that different amino acid residues may be useful in certain positions of the CDRs. Accordingly, each consensus sequence encompasses two or more useful anti-CD39 CDR sequences.

2.8.1. CDR-H3 Consensus Sequences

In some embodiments, the antibody comprises a CDR-H3 sequence defined by the consensus sequence G-K-R-E-G-G-T-E-Y-L-R-$y_{12}$ (SEQ ID NOS: 82-86), where $y_{12}$ is H, K, S, N, or V.

In some aspects, $y_{12}$ is H. In some aspects, $y_{12}$ is K. In some aspects, $y_{12}$ is S. In some aspects, $y_{12}$ is N. In some aspects, $y_{12}$ is V.

In some embodiments, the antibody comprises a CDR-H3 sequence defined by the consensus sequence E-S-G-$\Phi_4$-Y-R-D-H-R-L-$\Phi_{11}$-V (SEQ ID NOS: 94-96), where $\Phi_4$ is G or T and $\Phi_{11}$ is D or G.

In some aspects, $\Phi_4$ is G when $\Phi_{11}$ is D or G. In some aspects, $\Phi_{11}$ is D when $\Phi_4$ is G or T.

In some aspects, $\Phi_4$ is G and $\Phi_{11}$ is D. In some aspects, $\Phi_4$ is T and $\Phi_{11}$ is D. In some aspects, $\Phi_4$ is G and $\Phi_{11}$ is G.

In some embodiments, the antibody comprises a CDR-H3 sequence defined by the consensus sequence G-G-A-K-Y-A-$\vartheta_7$-$\vartheta_8$-$\vartheta_9$-G-M-D-V (SEQ ID NOS: 87-93), where $\vartheta_7$ is S, V, G, or R; $\vartheta_8$ is T, Q, K, G, or R; and $\vartheta_9$ is Y, H, L, or W.

In some aspects, $\vartheta_7$ is S when $\vartheta_8$ is T, Q, or K and $\vartheta_9$ is Y, H, L, or W. In some aspects, $\vartheta_8$ is T when $\vartheta_7$ is S or R and $\vartheta_9$ is Y or H. In some aspects, $\vartheta_9$ is Y when $\vartheta_7$ is S, V, G, or R and $\vartheta_8$ is T, G, or R.

In some aspects, $\vartheta_7$ is S when $\vartheta_8$ is T and $\vartheta_9$ is Y. In some aspects, $\vartheta_7$ is S when $\vartheta_8$ is T and $\vartheta_9$ is H. In some aspects, $\vartheta_7$ is S when $\vartheta_8$ is Q and $\vartheta_9$ is L. In some aspects, $\vartheta_7$ is S when $\vartheta_8$ is K and $\vartheta_9$ is W. In some aspects, $\vartheta_7$ is V when $\vartheta_8$ is G and $\vartheta_9$ is Y. In some aspects, $\vartheta_7$ is G when $\vartheta_8$ is R and $\vartheta_9$ is Y. In some aspects, $\vartheta_7$ is R when $\vartheta_8$ is T and $\vartheta_9$ is Y.

2.8.2. Chothia CDR-H2 Consensus Sequences

In some embodiments, the antibody comprises a Chothia CDR-H2 sequence defined by the consensus sequence N-P-$\varepsilon_5$-$\varepsilon_6$-G-S-T (SEQ ID NOS: 46-48), where $\varepsilon_5$ is L, R, or S and $\varepsilon_6$ is G or V.

In some aspects, when $\varepsilon_5$ is S, $\varepsilon_6$ is G or V. In some aspects, when $\varepsilon_5$ is G, $\varepsilon_6$ is S, L, or R.

In some aspects, when $\varepsilon_5$ is L, $\varepsilon_6$ is G. In some aspects, when $\varepsilon_5$ is S, $\varepsilon_6$ is G. In some aspects, when $\varepsilon_5$ is S, $\varepsilon_6$ is V. In some aspects, when $\varepsilon_5$ is R, $\varepsilon_6$ is G.

In some embodiments, the antibody comprises a Chothia CDR-H2 sequence defined by the consensus sequence $\alpha_3$-$\alpha_4$-$\alpha_5$-$\alpha_6$-G-T-A (SEQ ID NOS: 51-54), where $\alpha_3$ is I or L or is absent; $\alpha_4$ is P or is absent; and $\alpha_5$ is I, G, or R; and $\alpha_6$ is A, F, or G.

In some aspects, when $\alpha_3$, is I, $\alpha_4$ is P; $\alpha_5$ is I or R; and $\alpha_6$ is F or G. In some aspects, when $\alpha_3$, is L, $\alpha_4$ is P; $\alpha_5$ is I; and $\alpha_6$ is A or G. In some aspects, when $\alpha_4$, is P, $\alpha_3$ is I or L; $\alpha_5$ is I or R; and $\alpha_6$ is A, F, or G. In some aspects, when $\alpha_5$, is I, $\alpha_3$ is I or L; $\alpha_4$ is P; and $\alpha_6$ is A, F, or G. In some aspects, when $\alpha_6$, is F, $\alpha_3$ is I or is absent; $\alpha_4$ is P or is absent; and $\alpha_5$ is I or G. In some aspects, when $\alpha_6$, is G, $\alpha_3$ is I or L; $\alpha_4$ is P; and as is I or R.

In some aspects, when $\alpha_3$ is L, $\alpha_4$ is P; $\alpha_5$ is I; and $\alpha_6$ is A. In some aspects, when $\alpha_3$ is I, $\alpha_4$ is P; $\alpha_5$ is I; and $\alpha_6$ is F. In some aspects, when $\alpha_3$ is absent, $\alpha_4$ is absent; $\alpha_5$ is G; and $\alpha_6$ is F. In some aspects, when $\alpha_3$ is L, $\alpha_4$ is P; $\alpha_5$ is I; and $\alpha_6$ is G. In some aspects, when $\alpha_3$ is I, $\alpha_4$ is P; $\alpha_5$ is R; and $\alpha_6$ is G.

In some embodiments, the antibody comprises a Chothia CDR-H2 sequence defined by the consensus sequence I-P-$\beta_5$-$\beta_6$-G-$\beta_8$-A (SEQ ID NOS: 56-60), where $\beta_5$ is I, E, S, or T; $\beta_6$ is F, I, or S; and $\beta_8$ is I or T.

In some aspects, when $\beta_5$ is I, $\beta_6$ is F or S and $\beta_8$ is T. In some aspects, when $\beta_6$ is F, $\beta_5$ is E, I, or T and $\beta_8$ is I or T. In some aspects, when $\beta_8$ is T, $\beta_5$ is I, S, or T and $\beta_6$ is F, I, or S.

In some aspects, when $\beta_5$ is I, $\beta_6$ is F and $\beta_8$ is T. In some aspects, when $\beta_5$ is E, $\beta_6$ is F and $\beta_8$ is I. In some aspects, when $\beta_5$ is S, $\beta_6$ is I and $\beta_8$ is T. In some aspects, when $\beta_5$ is I, $\beta_6$ is S and $\beta_8$ is T. In some aspects, when $\beta_5$ is T, $\beta_6$ is S and $\beta_8$ is T.

2.8.3. Chothia CDR-H1 Consensus Sequences

In some embodiments, the antibody comprises a Chothia CDR-H1 sequence defined by the consensus sequence G-Y-T-F-$\Omega_5$-S-Y (SEQ ID NOS: 1-2 and 4-6), where $\Omega_5$ is T, K, Q, F, or V.

In some aspects, $\Omega_5$ is T. In some aspects, $\Omega_5$ is K. In some aspects, $\Omega_5$ is Q. In some aspects, $\Omega_5$ is F. In some aspects, $\Omega_5$ is V.

In some embodiments, the antibody comprises a Chothia CDR-H1 sequence defined by the consensus sequence G-G-T-F-$v_5$-$v_6$-Y (SEQ ID NOS: 17-22 and 24), where $v_5$ is S, G, or E and $v_6$ is S, K, R, or S.

In some aspects, $v_5$ is S when $v_6$ is S or K. In some aspects, $v_6$ is S when $v_5$ is S or E.

In some aspects, $v_5$ is S when $v_6$ is S. In some embodiments, $v_5$ is S when $v_6$ is K. In some aspects, $v_5$ is G when $v_6$ is R. In some aspects $v_5$ is E when $v_6$ is S.

In some embodiments, the antibody comprises a Chothia CDR-H1 sequence defined by the consensus sequence G-G-T-F-$\kappa_5$-$\kappa_6$-$\kappa_7$ (SEQ ID NOS: 7-16), where $\kappa_5$ is S, Q, P, or A; $\kappa_6$ is S, K, H, L, A, or W; and $\kappa_7$ is Y, L, T, N, or M.

In some aspects, when $\kappa_5$ is S, $\kappa_6$ is S, K, H, L, A, or W and $\kappa_7$ is Y, L, T, or M. In some aspects, when $\kappa_6$ is S, $\kappa_5$ is S, Q, P, or A and $\kappa_7$ is Y, L, or N. In some aspects, when $K_7$ is L, $\kappa_5$ is S, Q, or A and $K_6$ is S, K, L, or W.

In some aspects, when $\kappa_5$ is S, $\kappa_6$ is S and $\kappa_7$ is Y. In some aspects, when $\kappa_5$ is S, $\kappa_6$ is S and $\kappa_7$ is L. In some aspects, when $\kappa_5$ is S, $\kappa_6$ is K and $\kappa_7$ is L. In some aspects, when $\kappa_5$ is S, $\kappa_6$ is H and $\kappa_7$ is T. In some aspects, when $\kappa_5$ is S, $\kappa_6$ is L and $\kappa_7$ is L. In some aspects, when $\kappa_5$ is Q, $\kappa_6$ is S and $\kappa_7$ is L. In some aspects, when $\kappa_5$ is P, $\kappa_6$ is S and $\kappa_7$ is N. In some aspects, when $\kappa_5$ is S, $\kappa_6$ is A and $\kappa_7$ is M. In some aspects, when $\kappa_5$ is A, $\kappa_6$ is S and $\kappa_7$ is L. In some aspects, when $\kappa_5$ is S, $\kappa_6$ is W and $\kappa_7$ is L.

2.8.4. Kabat CDR-H2 Consensus Sequences

In some embodiments, the antibody comprises a Kabat CDR-H2 sequence defined by the consensus sequence $\varepsilon_1$-I-N-P-$\varepsilon_5$-$\varepsilon_6$-G-S-T-$\varepsilon_{10}$-Y-A-Q-K-F-Q-G (SEQ ID NOS: 63-66 and 68), where $\varepsilon_1$ is K, S, R, or V; $\varepsilon_5$ is L, R, or S; $\varepsilon_6$ is G or V; and $\varepsilon_{10}$ is S or W.

In some aspects, when $\varepsilon_1$ is V; $\varepsilon_5$ is L or S; $\varepsilon_6$ is G; and $\varepsilon_{10}$ is S. In some aspects, when $\varepsilon_1$ is R; $\varepsilon_5$ is S; $\varepsilon_6$ is V or G; and $\varepsilon_{10}$ is W. In some aspects, when $\varepsilon_5$ is S; $\varepsilon_1$ is R or V; $\varepsilon_6$ is G or V; and $\varepsilon_{10}$ is S or W. In some aspects, when $\varepsilon_6$ is G; $\varepsilon_1$ is R or V; $\varepsilon_5$ is S; and $\varepsilon_{10}$ is S or W. In some aspects, when $\varepsilon_{10}$ is S; $\varepsilon_1$ is V or S; $\varepsilon_5$ is L, R, or S; and $\varepsilon_6$ is G. In some aspects, when $\varepsilon_{10}$ is W; $\varepsilon_1$ is K or R; $\varepsilon_5$ is S; and $\varepsilon_6$ is G or V.

In some aspects, when $\varepsilon_1$ is V; $\varepsilon_5$ is L; $\varepsilon_6$ is G; and $\varepsilon_{10}$ is S. In some aspects, when $\varepsilon_1$ is V; $\varepsilon_5$ is S; $\varepsilon_6$ is G; and $\varepsilon_{10}$ is S. In some aspects, when $\varepsilon_1$ is R; $\varepsilon_5$ is S; $\varepsilon_6$ is V; and $\varepsilon_{10}$ is W. In some aspects, when $\varepsilon_1$ is R; $\varepsilon_5$ is S; $\varepsilon_6$ is G; and $\varepsilon_{10}$ is W. In some aspects, when $\varepsilon_1$ is K; $\varepsilon_5$ is S; $\varepsilon_6$ is G; and $\varepsilon_{10}$ is W. In some aspects, when $\varepsilon_1$ is S; $\varepsilon_5$ is R; $\varepsilon_6$ is G; and $\varepsilon_{10}$ is S.

In some embodiments, the antibody comprises a Kabat CDR-H2 sequence defined by the consensus sequence G-I-$\alpha_3$-$\alpha_4$-$\alpha_5$-$\alpha_6$-G-T-A-N-Y-A-Q-K-F-Q-G (SEQ ID NOS: 69-72), where $\alpha_3$ is I or L or is absent; $\alpha_4$ is P or is absent; and as is I, G, or R; and $\alpha_6$ is A, F, or G.

In some aspects, when $\alpha_3$, is I, $\alpha_4$ is P; $\alpha_5$ is I or R; and $\alpha_6$ is F or G. In some aspects, when $\alpha_3$, is L, $\alpha_4$ is P; $\alpha_5$ is I; and $\alpha_6$ is A or G. In some aspects, when $\alpha_4$, is P, $\alpha_3$ is I or L; $\alpha_5$ is I or R; and $\alpha_6$ is A, F, or G. In some aspects, when $\alpha_5$, is I, $\alpha_3$ is I or L; $\alpha_4$ is P; and $\alpha_6$ is A, F, or G. In some aspects, when $\alpha_6$, is F, $\alpha_3$ is I or is absent; $\alpha_4$ is P or is absent; and $\alpha_5$ is I or G. In some aspects, when $\alpha_6$, is G, $\alpha_3$ is I or L; $\alpha_4$ is P; and $\alpha_5$ is I or R.

In some aspects, when $\alpha_3$ is L, $\alpha_4$ is P; $\alpha_5$ is I; and $\alpha_6$ is A. In some aspects, when $\alpha_3$ is I, $\alpha_4$ is P; $\alpha_5$ is I; and $\alpha_6$ is F. In some aspects, when $\alpha_3$ is absent, $\alpha_4$ is absent; $\alpha_6$ is G; and $\alpha_6$ is F. In some aspects, when $\alpha_3$ is L, $\alpha_4$ is P; $\alpha_5$ is I; and $\alpha_6$ is G. In some aspects, when $\alpha_3$ is I, $\alpha_4$ is P; $\alpha_5$ is R; and $\alpha_6$ is G.

In some embodiments, the antibody comprises a Kabat CDR-H2 sequence defined by the consensus sequence $\beta_1$-I-I-P-$\beta_5$-$\beta_6$-G-$\beta_8$-A-N-Y-A-Q-K-F-G-Q (SEQ ID NOS: 74 and 76-79) where $\beta_1$ is S or G; $\beta_5$ is I, E, S, or T; $\beta_6$ is F, I, or S; and $\beta_8$ is I or T.

In some aspects, when $\beta_1$ is S, $\beta_5$ is E, I, or S; $\beta_6$ is I or F; and $\beta_8$ is I or T. In some aspects, when $\beta_1$ is G, $\beta_5$ is I or T; $\beta_6$ is F or S; and $\beta_8$ is T. In some aspects, when $\beta_5$ is I, $\beta_1$ is G or S; $\beta_6$ is F or S; and $\beta_8$ is T. In some aspects, when $\beta_6$ is F, $\beta_1$ is G or S; $\beta_5$ is E, I, or T; and $\beta_8$ is I or T. In some aspects, when $\beta_8$ is T, $\beta_1$ is G or S; $\beta_5$ is I, S, or T; and $\beta_6$ is F, I, or S.

In some aspects, when $\beta_1$ is S, $\beta_5$ is I; $\beta_5$ is F; and $\beta_8$ is T. In some aspects, when $\beta_1$ is S, $\beta_5$ is E; $\beta_5$ is F; and $\beta_8$ is I. In some aspects, when $\beta_1$ is S, $\beta_5$ is S; $\beta_5$ is I; and $\beta_8$ is T. In some aspects, when $\beta_1$ is G, $\beta_5$ is I; $\beta_5$ is F; and $\beta_8$ is T. In some aspects, when $\beta_1$ is G, $\beta_5$ is I; $\beta_5$ is S; and $\beta_8$ is T. In some aspects, when $\beta_1$ is G, $\beta_5$ is T; $\beta_5$ is F; and $\beta_8$ is T.

2.8.5. Kabat CDR-H1 Consensus Sequences

In some embodiments, the antibody comprises a Kabat CDR-H1 sequence defined by the consensus sequence S-Y-$\Delta_3$-M-$\Delta_5$ (SEQ ID NOS: 25-29 and 44-45), where $\Delta_3$ is E, F, Q, or Y and $\Delta_5$ is H or Y.

In some aspects, when $\Delta_3$ is Y, $\Delta_5$ is H or Y. In some aspects, when $\Delta_5$ is H, $\Delta_3$ is E, F, Q, or Y.

In some aspects, $\Delta_3$ is Y when $\Delta_5$ H. In some aspects, $\Delta_3$ is Y when $\Delta_5$ is Y. In some aspects, $\Delta_3$ is E when $\Delta_5$ is H. In some aspects, $\Delta_3$ is Q when $\Delta_5$ is H. In some aspects, $\Delta_3$ is F when $\Delta_5$ is H.

In some embodiments, the antibody comprises a Kabat CDR-H1 sequence defined by the consensus sequence $\theta_1$-$\theta_2$-$\theta_3$-I-S (SEQ ID NOS: 30-37), where $\theta_1$ is A, H, K, L, S, or W; $\theta_2$ is L, M, N, or T; and $\theta_3$ is A or P.

In some aspects, when $\theta_1$ is S, $\theta_2$ is L or N and $\theta_3$ is A or P. In some aspects, when $\theta_2$ is L, $\theta_1$ is K, L, S, or W and $\theta_3$ is A or P. In some aspects, when $\theta_3$ is A, $\theta_1$ is A, H, K, L, S, or W and $\theta_2$ is L, M, N, or T.

In some aspects, $\theta_1$ is S, when $\theta_2$ is L and $\theta_3$ is A. In some aspects, $\theta_1$ is K, when $\theta_2$ is L and $\theta_3$ is A. In some aspects, $\theta_1$ is H when $\theta_2$ is T and $\theta_3$ is A. In some aspects, $\theta_1$ is S when $\theta_2$ is L and $\theta_3$ is P. In some aspects, $\theta_1$ is L when $\theta_2$ is L and $\theta_3$ is A. In some aspects, $\theta_1$ is S when $\theta_2$ is N and $\theta_3$ is A. In some aspects, $\theta_1$ is A when $\theta_2$ is M and $\theta_3$ is A. In some aspects, $\theta_1$ is W when $\theta_2$ is L and $\theta_3$ is A.

In some embodiments, the antibody comprises a Kabat CDR-H1 sequence defined by the consensus sequence $\eta_1$-Y-$\eta_3$-I-S SEQ ID NOS: 38-41), where $\eta_1$ is S, K, N, or R and $\eta_3$ is A or G.

In some aspects, $\eta_1$ is S where $\eta_3$ is A or G. In some aspects, $\eta_1$ is A where $\eta_1$ is N or S. In some aspects, $\eta_3$ is G where $\eta_1$ is K, R, or S.

In some aspects, when $\eta_1$ is S, $\eta_2$ is A. In some aspects, when $\eta_3$ is S, $\eta_3$ is G. In some aspects, when $\eta_1$ is K, $\eta_3$ is G. In some aspects, when $\eta_1$ is R, $\eta_3$ is G. In some aspects, when $\eta_1$ is N, $\eta_3$ is A.

2.8.6. CDR-L3 Consensus Sequences

In some embodiments, the antibody comprises a CDR-L3 sequence defined by the consensus sequence Q-Q-Y-$\pi_4$-$\pi_5$-$\pi_6$-$\pi_7$-T (SEQ ID NOS: 141-147), where $\pi_4$ is G, H, or Y; $\pi_5$ is S, N, F, G, or R; $\pi_6$ is S, Y, A, G, or R; and $\pi_7$ is P, I, or L.

In some aspects, $\pi_4$ is H when $\pi_5$ is S, N, G, or R; $\pi_6$ is Y, A, G, or R; and $\pi_7$ is I or L. In some aspects, $\pi_5$ is S, when $\pi_4$ is G or H; $\pi_6$ is S, Y, or A; and $\pi_7$ is P, I or L. In some aspects, $\pi_6$ is Y, when $\pi_4$ is H or Y; $\pi_5$ is S or F; and $\pi_7$ is I. In some aspects, $\pi_6$ is A when $\pi_4$ is H; $\pi_5$ is N or S; and $\pi_7$ is I or L. In some aspects, $\pi_7$ is I when $\pi_4$ is H or Y; $\pi_5$ is S, N, F, G, or R; and $\pi_6$ is Y, A, G, or R.

In some aspects, $\pi_4$ is G when $\pi_5$ is S; $\pi_6$ is S; and $\pi_7$ is P. In some aspects, $\pi_4$ is H when $\pi_5$ is S; $\pi_6$ is Y; and $\pi_7$ is I. In some aspects, $\pi_4$ is H when $\pi_5$ is N; $\pi_6$ is I; and $\pi_7$ is A. In some aspects, $\pi_4$ is Y when $\pi_5$ is F; $\pi_6$ is Y; and $\pi_7$ is I. In some aspects, $\pi_4$ is H when $\pi_5$ is S; $\pi_6$ is A; and $\pi_7$ is L. In some aspects, $\pi_4$ is H when $\pi_5$ is G; $\pi_6$ is G; and $\pi_7$ is I. In some aspects, $\pi_4$ is H when $\pi_5$ is R; $\pi_6$ is R; and $\pi_7$ is I.

In some embodiments, the antibody comprises a CDR-L3 sequence defined by consensus sequence Q-Q-$\lambda_3$-$\lambda_4$-$\lambda_5$-$\lambda_6$-P-T (SEQ ID NOS: 148-150), where $\lambda_3$ is R, F, H, S, L, D, Y, or V; $\lambda_4$ is S, V, T, G, L, Y, or N; $\lambda_5$ is N, L, F, K, or V; and $\lambda_6$ is W, F, Y, or L.

In some aspects, $\lambda_3$ is R, when $\lambda_4$ is S or N; $\lambda_5$ is N or F; and $\lambda_6$ is W or Y. In some aspects, $\lambda_3$ is H when $\lambda_4$ is V or T; $\lambda_5$ is N or V; and $\lambda_6$ is F or W. In some aspects, $\lambda_3$ is S when $\lambda_4$ is V or Y; $\lambda_5$ is F; and $\lambda_6$ is W or L. In some aspects, $\lambda_4$ is V when $\lambda_3$ is F, H, S, or D; $\lambda_5$ is L, N, or F; and $\lambda_4$ is W or F. In some aspects, $\lambda_4$ is T when $\lambda_3$ is L or H; $\lambda_5$ is K or V; and $\lambda_6$ is W. In some aspects, $\lambda_5$ is N when $\lambda_3$ is R, H, or V; $\lambda_4$ is S, V, or L; and $\lambda_6$ is W, F, or Y. In some aspects, $\lambda_5$ is L when $\lambda_3$ is F, D, or Y; $\lambda_4$ is V or G; and $\lambda_6$ is W or F. In some aspects, $\lambda_5$ is F when $\lambda_3$ is S or R; $\lambda_4$ is V, Y, or N; and $\lambda_6$ is W, L, or Y. In some aspects, $\lambda_6$ is W when $\lambda_3$ is R, F, S, L, D, or H; is S, V, or T; and $\lambda_5$ is N, L, F, K, or V. In some aspects, $\lambda_6$ is F when $\lambda_3$ is H or Y; $\lambda_4$ is V or G; and $\lambda_5$ is N or L. In some aspects, $\lambda_6$ is Y when $\lambda_3$ is V or R, $\lambda_4$ is L or N; and $\lambda_5$ is N or F.

In some aspects, $\lambda_3$ is R when $\lambda_4$ is S; $\lambda_5$ is N; and $\lambda_6$ is W. In some aspects, $\lambda_3$ is F when $\lambda_4$ is V; $\lambda_5$ is L; and $\lambda_6$ is W. In some aspects, $\lambda_3$ is H when $\lambda_4$ is V; $\lambda_5$ is N; and $\lambda_6$ is F. In some aspects, $\lambda_3$ is S when $\lambda_4$ is V; $\lambda_5$ is F; and $\lambda_6$ is W. In some aspects, $\lambda_3$ is L when $\lambda_4$ is T; $\lambda_5$ is K; and $\lambda_6$ is W. In some aspects, $\lambda_3$ is D when $\lambda_4$ is V; $\lambda_5$ is L; and $\lambda_6$ is W. In some aspects, $\lambda_3$ is Y when $\lambda_4$ is G; $\lambda_5$ is L; and $\lambda_6$ is F. In some aspects, $\lambda_3$ is H when $\lambda_4$ is T; $\lambda_5$ is V; and $\lambda_6$ is W. In some aspects, $\lambda_3$ is V when $\lambda_4$ is L; $\lambda_5$ is N; and $\lambda_6$ is Y. In some aspects, $\lambda_3$ is S when $\lambda_4$ is Y; $\lambda_5$ is F; and $\lambda_6$ is L. In some aspects, $\lambda_3$ is R when $\lambda_4$ is N; $\lambda_5$ is F; and $\lambda_6$ is Y.

In some embodiments, the antibody comprises a CDR-L3 sequence defined by the consensus sequence Q-Q-Y-$\rho_3$-$\rho_4$-W-P-L-T (SEQ ID NOS: 151 and 152), where $\rho_3$ is N or L and $\rho_4$ is N or L.

In some aspects, $\rho_3$ is N when $\rho_4$ is L. In some aspects, $\rho_3$ is L when $\rho_4$ is L.

In some embodiments, the antibody comprises a CDR-L3 sequence defined by the consensus sequence Q-Q-$\omega_3$-$\omega_4$-$\omega_5$-$\omega_6$-P-$\omega_8$-T (SEQ ID NOS: 153-156), where $\omega_3$ is Y or F; $\omega_4$ is Y or W; $\omega_5$ is S, L, T, or F; $\omega_6$ is T, Y, or F; and $\omega_8$ is L or P.

In some aspects, $\omega_3$ is Y when $\omega_4$ is Y or W; $\omega_5$ is S, L, or T; $\omega_6$ is T or Y; and $\omega_8$ is L. In some aspects, $\omega_4$ is Y when $\omega_3$ is Y or F; $\omega_5$ is S, L, or F; $\omega_6$ is T or Y; and $\omega_8$ is L or P. In some aspects, $\omega_6$ is Y when $\omega_3$ is Y; $\omega_4$ is Y or W; $\omega_5$ is L or T; and $\omega_8$ is L. In some aspects, $\omega_8$ is L when $\omega_3$ is Y; $\omega_4$ is Y or W; $\omega_5$ is S, L, or T; and $\omega_6$ is T or Y.

In some aspects, $\omega_3$ is Y when $\omega_4$ is Y; $\omega_5$ is S; $\omega_6$ is T; and $\omega_8$ is L. In some aspects, $\omega_3$ is Y when $\omega_4$ is Y; $\omega_5$ is L; $\omega_6$ is Y; and $\omega_8$ is L. In some aspects, $\omega_3$ is Y when $\omega_4$ is W; $\omega_5$ is T; $\omega_6$ is Y; and $\omega_8$ is L. In some aspects, $\omega_3$ is F when $\omega_4$ is Y; $\omega_5$ is F; $\omega_6$ is F; and $\omega_8$ is P.

2.8.7. CDR-L2 Consensus Sequences

In some embodiments, the antibody comprises a CDR-L2 sequence defined by the consensus sequence $\psi_1$-A-S-$\psi_4$-R-$\psi_6$-$\psi_7$ (SEQ ID NOS: 125-136), where $\psi_1$ is G or Y, $\psi_4$ is S or N; $\psi_6$ is A or H; and $\psi_7$ is T, Y, or N.

In some aspects, $\psi_1$ is G when $\psi_4$ is S or N; $\psi_6$ is A or H; and $\psi_7$ is T or N. In some aspects, $\psi_1$ is Y when is S or N; $\psi_6$ is A; and $\psi_7$ is Y or T. In some aspects, $\psi_4$ is S when $\psi_1$ is G or Y; $\psi_6$ is A; and $\psi_7$ is T, Y, or N. In some aspects, $\psi_4$ is N when $\psi_1$ is G or Y; $\psi_6$ is H or A; and $\psi_7$ is T. In some aspects, $\psi_6$ is A when $\psi_1$ is G or Y; $\psi_4$ is S or N; and $\psi_7$ is T, Y, or N. In some aspects, $\psi_7$ is T when $\psi_1$ is G or Y; $\psi_4$ is S or N; and $\psi_6$ is A or H.

In some aspects, $\psi_1$ is G when $\psi_4$ is S; $\psi_6$ is A; and $\psi_7$ is T. In some aspects, $\psi_1$ is G when $\psi_4$ is N; $\psi_6$ is H; and $\psi_7$ is T. In some aspects, $\psi_1$ is Y when $\psi_4$ is S; $\psi_6$ is A; and $\psi_7$ is Y. In some aspects, $\psi_1$ is G when $\psi_4$ is S; $\psi_6$ is A; and $\psi_7$ is N. In some aspects, $\psi_1$ is Y when $\psi_4$ is N; $\psi_6$ is A; and $\psi_7$ is T.

In some embodiments, the antibody comprises a CDR-L2 sequence defined by the consensus sequence D-A-S-$\chi$4-R-A-T (SEQ ID NOS: 138 and 139), where $\pounds_4$ is N or K.

In some aspects, $\chi_4$ is N. In some aspects, $\chi_4$ is K.

In some embodiments, the antibody comprises a CDR-L2 sequence defined by the consensus sequence W-A-S-T-R-$\sigma_6$-S(SEQ ID NOS: 131 and 133-134), where $\sigma_6$ is A, E, or Q.

In some aspects, $\sigma_6$ is A. In some aspects, $\sigma_6$ is E. In some aspects, $\sigma_6$ is Q.

2.8.8. CDR-L1 Consensus Sequences

In some embodiments, the antibody comprises a CDR-L1 sequence defined by the consensus sequence $\phi_1$-A-S-$\phi_4$-$\phi_5$-V-$\phi_7$-$\phi_8$-$\phi_9$-Y-L-A (SEQ ID NOS: 1101-114), where $\phi_1$ is E, K, or R; $\phi_4$ is Q or E; $\phi_5$ is S or Y; $\phi_7$ is S or A; $\phi_8$ is S or Y; and $\phi_9$ is D or S.

In some aspects, $\phi_1$ is R when $\phi_4$ is Q or E; $\phi_5$ is S or Y; $\phi_7$ is S or A; $\phi_8$ is S or Y; and $\phi_9$ is S or D. In some aspects, $\phi_4$ is E when $\phi_1$ is K or R; $\phi_5$ is S; $\phi_7$ is S; $\phi_8$ is S; and $\phi_9$ is S. In some aspects, $\phi_4$ is Q when $\phi_1$ is E or R; $\phi_5$ is S or Y; $\phi_7$ is S or A; $\phi_8$ is S or Y; and $\phi_9$ is S or D. In some aspects, $\phi_5$ is S when $\phi_1$ is E, K, or R; $\phi_4$ is E or Q; $\phi_7$ is S or A; $\phi_8$ is S or Y; and $\phi_9$ is S or D. In some aspects, $\phi_7$ is S when $\phi_1$ is E, K, or R; $\phi_4$ is E or Q; $\phi_5$ is S or Y; $\phi_8$ is S or Y; and $\phi_9$ is S or D. In some aspects, $\phi_8$ is S when $\phi_1$ is K or R; $\phi_4$ is E or Q; $\phi_5$ is S or 5; $\phi_7$ is A or S; and $\phi_9$ is S or D. In some aspects, $\phi_8$ is R when $\phi_1$ is E or R; $\phi_4$ is Q; $\phi_5$ is S; $\phi_7$ is S; and $\phi_9$ is S. In some aspects, $\phi_9$ is S when $\phi_1$ is E, K, or R; $\phi_4$ is E or Q; $\phi_5$ is S or Y; $\phi_7$ is A or S; and $\phi_8$ is S or Y.

In some aspects, $\phi_1$ is K when $\phi_4$ is E; $\phi_5$ is S; $\phi_7$ is S; $\phi_8$ is S; and $\phi_9$ is S. In some aspects, $\phi_1$ is E, when $\phi_4$ is Q; $\phi_5$ is S; $\phi_7$ is S; $\phi_8$ is Y; and $\phi_9$ is S. In some aspects, $\phi_1$ is R when $\phi_4$ is Q; $\phi_5$ is S; $\phi_7$ is S; $\phi_8$ is S; and $\phi_9$ is D. In some aspects, $\phi_1$ is R when $\phi_4$ is Q; $\phi_5$ is S; $\phi_7$ is S; $\phi_8$ is S; and $\phi_9$ is S. In some aspects, $\phi_1$ is R when $\phi_4$ is Q; $\phi_5$ is S; $\phi_7$ is A; $\phi_8$ is S; and $\phi_9$ is S. In some aspects, $\phi_1$ is R when $\phi_4$ is Q; $\phi_5$ is S; $\phi_7$ is S; $\phi_8$ is Y; and $\phi_9$ is S. In some aspects, $\phi_1$ is R when $\phi_4$ is E; $\phi_5$ is S; $\phi_7$ is S; $\phi_8$ is S; and $\phi_9$ is S. In some aspects, $\phi_1$ is R when $\phi_4$ is Q; $\phi_5$ is Y; $\phi_7$ is S; $\phi_8$ is S; and $\phi_9$ is S.

In some embodiments, the antibody comprises a CDR-L1 sequence defined by the consensus sequence $\sigma_1$-A-S-Q-$\sigma_5$-$\sigma_6$-$\sigma_7$-$\sigma_8$-$\sigma_9$-L-$\sigma_{11}$ (SEQ ID NOS: 118 and 120-123), where $\sigma_1$ is Q or R1; $\sigma_5$ is D or S; $\sigma_6$ is I or V; $\sigma_7$ is G or S; $\sigma_8$ is N, R, or S; $\sigma_9$ is N, Y, or W; and $\sigma_{11}$ is A or N.

In some aspects, when $\sigma_1$ is R, $\sigma_5$ is S; $\sigma_6$ is I or V; $\sigma_7$ is G or S; $\sigma_8$ is R or S; $\sigma_9$ is N, Y, or W; and $\sigma_{11}$ is A. In some aspects, when $\sigma_5$ is S, $\sigma_1$ is R; $\sigma_6$ is I or V; $\sigma_7$ is G or S; $\sigma_8$ is R or S; $\sigma_9$ is N, Y, or W; and $\sigma_{11}$ is A. In some aspects, when $\sigma_6$ is I, $\sigma_1$ is Q or R; $\sigma_5$ is D or S; $\sigma_7$ is S; $\sigma_8$ is N or S; $\sigma_9$ is Y or W; and $\sigma_{11}$ is A or N. In some aspects, when $\sigma_6$ is V, $\sigma_1$ is R; $\sigma_5$ is S; $\sigma_7$ is G or S; $\sigma_8$ is R or S; $\sigma_9$ is N or W; and $\sigma_{11}$ is A. In some aspects, when $\sigma_7$ is S, $\sigma_1$ is Q or R; $\sigma_5$ is D or S; $\sigma_6$ is I or V; $\sigma_8$ is N, S, or R; $\sigma_9$ is Y or W; and $\sigma_{11}$ is A or N. In some aspects, when $\sigma_8$ is S, $\sigma_1$ is R; $\sigma_5$ is S; $\sigma_6$ is I or V; $\sigma_7$ is S; $\sigma_9$ is N, Y, or W; and $\sigma_{11}$ is A. In some aspects, when $\sigma_9$ is Y, $\sigma_1$ is Q or R; $\sigma_5$ is D or S; $\sigma_6$ is I or V; $\sigma_7$ is S; 68 is N, S, or R; and OH is A or N. In some aspects, when OH is A, $\sigma_1$ is R; $\sigma_5$ is S; $\sigma_6$ is I or V; $\sigma_7$ is S or G; $\sigma_8$ is S, or R; and $\sigma_9$ is N, W, or Y.

In some aspects, when $\sigma_1$ is R, $\sigma_5$ is S; $\sigma_6$ is V; $\sigma_7$ is S; $\sigma_8$ is S; $\sigma_9$ is Y; and OH is A. In some aspects, when $\sigma_1$ is Q, $\sigma_5$ is D; $\sigma_6$ is I; $\sigma_7$ is S; $\sigma_8$ is N; $\sigma_9$ is Y; and $\sigma_{11}$ is N. In some aspects, when $\sigma_1$ is R, $\sigma_5$ is S; $\sigma_6$ is V; $\sigma_7$ is S; $\sigma_8$ is R; $\sigma_9$ is Y; and $\sigma_{11}$ is A. In some aspects, when $\sigma_1$ is R, $\sigma_5$ is S; $\sigma_6$ is V; $\sigma_7$ is G; $\sigma_8$ is S; $\sigma_9$ is N; and $\sigma_{11}$ is A. In some aspects, when $\sigma_1$ is R, $\sigma_5$ is S; $\sigma_6$ is I; $\sigma_7$ is S; $\sigma_8$ is S; $\sigma_9$ is W; and $\sigma_{11}$ is A.

In some embodiments, the antibody comprises a CDR-L1 sequence defined by the consensus sequence K-S-S-$\Gamma_4$-S-V-L-$\Gamma_8$-S-$\Gamma_{10}$-N-N-K-N-Y-L-A (SEQ ID NOS: 115-117), where $\Gamma_4$ is Q, R or K; $\Gamma_8$ is F or Y; and $\Gamma_4$ is S or N.

In some aspects, $\Gamma_4$ is Q when $\Gamma_8$ is F or Y and $\Gamma_{10}$ is S. In some aspects, $\Gamma_8$ is F when $\Gamma_4$ is Q or R and $\Gamma_{10}$ is S. In some aspects, $\Gamma_8$ is Y when $\Gamma_4$ is K or Q and $\Gamma_{10}$ is S or N. In some aspects, $\Gamma_{10}$ is S when $\Gamma_4$ is R or Q and $\Gamma_8$ is F or Y.

In some aspects, $\Gamma_4$ is Q when $\Gamma_8$ is Y and $\Gamma_{10}$ is S. In some aspects, $\Gamma_4$ is K when $\Gamma_8$ is Y and $\Gamma_{10}$ is N. In some aspects, $\Gamma_4$ is Q when $\Gamma_8$ is F and $\Gamma_{10}$ is S. In some aspects, $\Gamma_4$ is R when $\Gamma_8$ is F and $\Gamma_{10}$ is S.

3. Germline

In some embodiments, the antibody that specifically binds CD39 is an antibody comprising a variable region that is encoded by a particular germline gene, or a variant thereof. The illustrative antibodies provided herein comprise variable regions that are encoded by the heavy chain variable region germline genes VH1-46, VH1-69, 1-69, and VH1-46, or variants thereof; and the light chain variable region germline genes VK3-20, VK3-11, VK4-01, VK3, and VK3-15, or variants thereof. One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the VH1 or VH3 family, or a variant thereof. In some embodiments, a CDR-L sequence provided herein may be combined with a variable region encoded by a variable region germline gene selected from the Vλ3, Vκ1, Vκ3, and Vκ4 families, or a variant thereof.

4. Affinity

In some embodiments, the affinity of the antibody for CD39, as indicated by KID, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-10}$ M and $10^{-11}$M.

In some embodiments, the affinity of the antibody for human CD39 is between about $4.09 \times 10^{-7}$ M and $7.31 \times 10^{-11}$ M. In some embodiment, the affinity of the antibody for human CD39 is about $1.14 \times 10^{-7}$ M, about $1.31 \times 10^{-7}$ M, about $1.67 \times 10^{-7}$ M, about $1.43 \times 10^{-7}$ M, about $1.30 \times 10^{-8}$ M, about $1.27 \times 10^{-8}$ M, about $1.13 \times 10^{-8}$ M, about $1.60 \times 10^{-8}$ M, about $1.34 \times 10^{-9}$ M, about $1.16 \times 10^{-9}$ M, about $7.31 \times 10^{-11}$ M, about $7.60 \times 10^{-10}$ M, about $2.66 \times 10^{-10}$ M, about $9.22 \times 10^{-10}$ M, about $6.72 \times 10^{-10}$ M, about $9.24 \times 10^{-10}$ M, about $5.58 \times 10^{-10}$ M, about $5.48 \times 10^{-8}$ M, about $3.37 \times 10^{-8}$ M, about $3.11 \times 10^{-8}$ M, about $1.88 \times 10^{-8}$ M, about $1.63 \times 10^{-8}$ M about $1.64 \times 10^{-8}$ M, about $1.01 \times 10^{-8}$ M, about $2.44 \times 10^{-7}$ M, about $4.09 \times 10^{-7}$ M, about $3.35 \times 10^{-}$ M, about $1.91 \times 10^{-8}$ M, about $1.73 \times 10^{-8}$ M, or about $2.39 \times 10^{-8}$ M.

In some embodiments the antibody has a $k_{on}$ when associating with human CD39 of between about $1.93 \times 10^4$ M$^{-1}$ × sec$^{-1}$ and about $1.72 \times 10^6$ M$^{-1}$ × sec$^{-1}$. In some embodiments the antibody has a $k_a$ when associating with human CD39 of about $6.59 \times 10^4$ M$^{-1}$ × sec$^{-1}$, about $1.93 \times 10^4$ × sec$^{-1}$, about $4.44 \times 10^5$ M$^{-1}$ × sec$^{-1}$, about $2.72 \times 10^5$ M$^{-1}$ × about $6.39 \times 10^5$ M$^{-1}$ × sec$^{-1}$, about $8.93 \times 10^5$ M$^{-1}$ × sec$^{-1}$, about $9.55 \times 10^5$ M$^{-1}$ × sec$^{-1}$, about $2.11 \times 10^5$ M$^{-1}$ × sec$^{-1}$, about $1.17 \times 10^5$ M$^{-1}$ × sec$^{-1}$, about $2.02 \times 10^5$ M$^{-1}$ × sec$^{-1}$, about $1.76 \times 10^5$ M$^{-1}$ × sec$^{-1}$, about $1.72 \times 10^5$ M$^{-1}$ × sec$^{-1}$, about $2.73 \times 10^5$ M$^{-1}$ × sec$^{-1}$, about $1.43 \times 10^5$ M$^{-1}$ × sec$^{-1}$, about $9.01 \times 10^5$ M$^{-1}$ × sec$^{-1}$, about $3.13 \times 10^5$ × sec$^{-1}$, about $5.03 \times 10^5$ M$^{-1}$ × sec$^{-1}$, about $3.02 \times 10^5$ M$^{-1}$ × sec$^{-1}$, about $2.73 \times 10^5$ M$^{-1}$ × sec$^{-1}$, about $1.78 \times 10^5$ M$^{-1}$ × sec$^{-1}$, about $2.98 \times 10^5$ M$^{-1}$ × sec$^{-1}$, about $4.31 \times 10^5$ M$^{-1}$ × sec$^{-1}$, about $2.27 \times 10^5$ M$^{-1}$ × sec$^{-1}$, about $3.14 \times 10^5$ M$^{-1}$ × sec$^{-1}$, about $2.81 \times 10^5$ M$^{-1}$ × sec$^{-1}$, about $4.73 \times 10^5$ M$^{-1}$ × sec$^{-1}$, about $3.26 \times 10^5$ M$^{-1}$ × sec$^{-1}$, about $1.73 \times 10^5$ M$^{-1}$ × sec$^{-1}$, about $2.68 \times 10^5$ M$^{-1}$ × sec$^{-1}$, about $2.63 \times 10^5$ M$^{-1}$ × sec$^{-1}$, about $3.82 \times 10^5$ M$^{-1}$ × sec$^{-1}$, about $2.46 \times 10^5$ M$^{-1}$ × sec$^{-1}$, about $3.11 \times 10^5$ M$^{-1}$ × sec$^{-1}$, about $4.53 \times 10^5$ M$^{-1}$ × sec$^{-1}$, about $4.63 \times 10^5$ M$^{-1}$ × sec$^{-1}$, about $9.01 \times 10^5$ M$^{-1}$ × sec$^{-1}$, about $1.03 \times 10^6$ M$^{-1}$ × sec$^{-1}$, about $1.52 \times 10^6$ M$^{-1}$ × sec$^{-1}$, or about $3.53 \times 10^5$ M$^{-1}$ × sec$^{-1}$.

In some embodiments the antibody has a $k_{off}$ of about $7.51 \times 10^{-3}$ sec$^{-1}$ about $6.33 \times 10^{-2}$ sec$^{-1}$, about $4.70 \times 10^{-2}$ sec$^{-1}$, about $7.82 \times 10^{-4}$ sec$^{-1}$, about $4.70 \times 10^{-2}$ sec$^{-1}$, about $1.05 \times 10^{-2}$ sec$^{-1}$, about $3.65 \times 10^{-1}$ sec$^{-1}$, about $1.60 \times 10^{-1}$ sec$^{-1}$, about $7.11 \times 10^{-3}$ sec$^{-1}$, about $6.44 \times 10^{-3}$ sec$^{-1}$, about $3.85 \times 10^{-2}$ sec$^{-1}$, about $2.30 \times 10^{-2}$ sec$^{-1}$, about $5.33 \times 10^{-2}$ sec$^{-1}$, about $9.14 \times 10^{-2}$ sec$^{-1}$, about $1.80 \times 10^{-3}$ sec$^{-1}$, about $8.15 \times 10^{-3}$ sec$^{-1}$, about $3.85 \times 10^{-4}$ sec$^{-1}$, about $1.34 \times 10^{-4}$ sec$^{-1}$, about $2.29 \times 10^{-4}$ sec$^{-1}$, about $4.37 \times 10^{-3}$ sec$^{-1}$, about $3.71 \times 10^{-3}$ sec$^{-1}$, about $4.06 \times 10^{-4}$ sec$^{-1}$, about $6.66 \times 10^{-2}$ sec$^{-1}$, about $2.02 \times 10^{-3}$ sec$^{-1}$, about $2.00 \times 10^{-4}$ sec$^{-1}$, about $5.26 \times 10^{-3}$ sec$^{-1}$, about $1.13 \times 10^{-2}$ sec$^{-1}$, about $3.28 \times 10^{-3}$ sec$^{-1}$, about $2.76 \times 10^{-3}$ sec$^{-1}$, about $2.86 \times 10^{4}$ sec$^{-1}$, about $2.43 \times 10^{-4}$ sec$^{-1}$, about $2.13 \times 10^{-4}$ sec$^{-1}$, about $6.09 \times 10^{-4}$ sec$^{-1}$, about $8.39 \times 10^{-4}$ sec$^{-1}$, about $8.15 \times 10^{-3}$ sec$^{-1}$, about $1.32 \times 10^{-4}$ sec$^{-1}$, about $1.11 \times 10^{-4}$ sec$^{-1}$, about $2.43 \times 10^{4}$ sec$^{-1}$, about $2.13 \times 10^{-4}$ sec$^{-1}$, about $6.09 \times 10^{-4}$ sec$^{-1}$, about $8.15 \times 10^{-3}$ sec$^{-1}$, about $1.32 \times 10^{-4}$ sec$^{-1}$, or about $1.11 \times 10^{-4}$ sec$^{-1}$.

In some aspects, the $K_D$, $k_a$, and $k_d$ are determined at 25° C. In some embodiments, the $K_D$ $k_a$, and $k_d$ are determined by surface plasmon resonance. In some embodiments, the $K_D$, $k_a$, and $k_d$ are determined according to the methods described in the examples.

5. Inhibition of CD39

In some aspects, the antibody decreases affinity of CD39 to its substrate. In some aspects, the antibody inhibits CD39 function on minor cells. In some aspects, the antibody inhibits or impedes the release of ADP or AMP from CD39. In some aspects, the antibody inhibits or impedes CD39 processivity.

In some aspects, the antibody binds CD39 but does not inhibit ATPase. In some aspects, the antibody binds CD39 and inhibits extracellular CD39 activity but not cellular ATPase activity. In some aspects, the antibody binds both the extracellular domain of CD39 and cellular CD39 and can inhibit both the extracellular domain of CD39 and cellular CD39. In some aspects, the antibodies do not compete with A1 and/or others in binding to the extracellular domain.

6. CD39 Assays

In some embodiments, the antibody binds to an epitope of CD39. In some aspects, CD39 has a sequence identical to the amino acid sequence set forth in SEQ ID NO: 249. In some aspects, the epitope has an amino acid sequence that is identical to the amino acid sequence set forth in SEQ ID NO: 249. In some aspects, the epitope is in an extracellular domain of CD39. In some aspects, the extracellular domain corresponds to all or at least a portion of amino acids 38-478 of SEQ ID NO: 249. In some aspects, the epitope has an amino acid sequence that is 60%, 65%, 70%, 75%, 80%, 85%, 90%, or 95% identical to the sequence set forth in SEQ ID NO: 249 or all or a portion of the extracellular domain. In some aspects, the epitope has a sequence that is identical or corresponds to residues 143-158 and/or residues 274-277 of SEQ ID NO: 249. In some aspects, the epitope is in the region of E143 to N158 on the human CD39 polypeptide having the sequence set forth in SEQ ID NO: 249. In some aspects, the epitope has a sequence that has a 60%, 65%, 70%, 75%, 80%, 85%, 90%, or 95% identity to residues 143-158 or 274-277 of the sequence set forth in SEQ ID NO: 249. In some aspects, the epitope has 1, 2, 3, 4, 5, 6, 7, 8, or 9 substitutions from residues 143-158 of the sequence forth in SEQ ID NO: 249. In some aspects, the epitope has 1, 2 or 3 substitutions from residues 274-277 of SEQ ID NO: 249. In some aspects, the antibody makes contact with any of the residues set forth in FIG. 14E, Table 1. In some aspects, the antibody makes contact with any of the residues set forth in FIG. 14E, Table 2. In some aspects, the antibody binds to D150, E153, and/or R154 or to N99 and none, one, two, or three of D150, E153, and R154 or to any of the above alone or in combination.

Figure 14A:
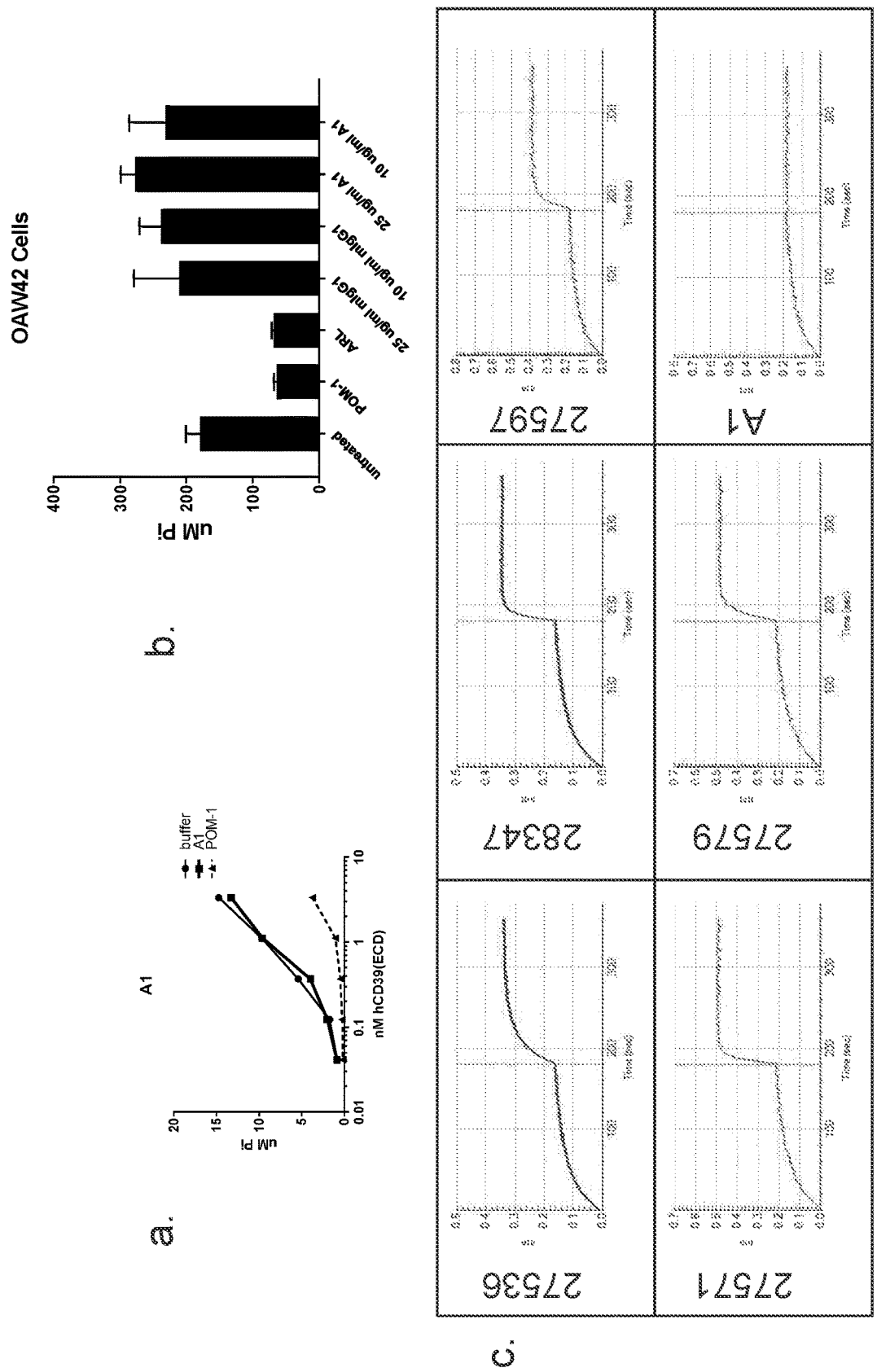
FIG. 14A provides examples of antibodies that bind soluble recombinant CD39 ECD and cellular CD39 but do not inhibit ATPase activity and do not compete with cellular inhibitors for binding to ECD inhibitors.

In some aspects, the antibody competes with 1, 2, 3, 4, or 5 of antibodies 27536, 27571, 28347, 27579, or 27597 as set forth in FIG. 14A. In some aspects, the antibody competes with 1, 2, 3, 4, or 5 antibodies 27536, 27571, 28347, 27579, or 27597 as set forth in FIG. 14A. In some aspects, the antibody competes with 1, 2, or 3 of antibodies 25571, 27536, or 27549 as set forth in FIG. 14C. In some aspects, the antibody competes with 1, 2, or 3 of antibodies 25571, 27536, or 27549 set forth in FIG. 14C.

In some aspects, the antibody inhibits conversion by CD39 of ATP to ADP and/or ADP to AMP. In some aspects, the antibody inhibits platelet aggregation. In some aspects, the antibody decreases or prevents activation of phospho antigen specific T cells selected from MAIT cells and γδ T cells. In some aspects, the antibody inhibits angiogenesis. In some aspects, the antibody decreases levels of phosphate, ADP, AMP, and/or adenosine and/or increasing levels of ATP. In some aspects, the antibody increases T effector cell function. In some aspects, the antibody decreases the number of regulatory T cells in tissues or in circulation. In some aspects, the antibody decreases the regulatory T cells or regulatory T cell activity. In some aspects, the antibody increases B cell function. In some aspects, the antibody increases antigen presenting cell function. In some aspects, the antibody inhibits processing of at least one of phosphoantigen from phosphorylated isoprenoid, phosphorylated vitamin B metabolite, and/or phosphorylated riboflavin.

In some aspects, the antibody has limited ability to limit ATPase of the soluble or extracellular domain. In some aspects, the antibody has limited ability to inhibit ATPase of the cellular and/or extracellular domain of CD39.

7. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In certain embodiments, the antibody is glycosylated. In certain embodiments, the antibody is deglycosylated. Carbohydrates may be removed by standard techniques. In certain embodiments, the antibody is aglycosylated, for instance by expression in a system that does not glycosylate.

8. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, *Ann. Rev. Immunol.*, 1991, 9:457-492.

Non-limiting examples of in vitro assays to assess ADCC activity of a molecule of interest are provided in U.S. Pat. Nos. 5,500,362 and 5,821,337; Hellstrom et al., *Proc. Natl. Acad. Sci. U.S.A.*, 1986, 83:7059-7063; Hellstrom et al., *Proc. Natl. Acad Sci. U.S.A.*, 1985, 82:1499-1502; and Bruggemann et al., *J. Exp. Med*, 1987, 166:1351-1361. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. *Proc. Natl. Acad. Sci. U.S.A.*, 1998, 95:652-656.

C1q binding assays may also be carried out to confirm that the antibody is unable to bind C1q and hence lacks CDC activity. Examples of C1q binding assays include those described in WO 2006/029879 and WO 2005/100402.

Complement activation assays include those described, for example, in Gazzano-Santoro et al., *J. Alumna Methods*, 1996, 202:163-171; Cragg et al., *Blood*, 2003, 101:1045-1052; and Cragg and Glennie, *Blood*, 2004, 103:2738-2743.

FcRn binding and in vivo clearance (half-life determination) can also be measured, for example, using the methods described in Petkova et al., *Intl. Immunol.*, 2006, 18:1759-1769.

9. Preparation of Antibodies

9.1. Antigen Preparation

The CD39 antigen to be used for production of antibodies may be intact CD39 or a fragment of CD39. The intact CD39, or fragment of CD39, may be in the form of an isolated protein or expressed by a cell. Other forms of CD39 useful for generating antibodies will be apparent to those skilled in the art.

9.2. Monoclonal Antibodies

Monoclonal antibodies may be obtained, for example, using the hybridoma method first described by Kohler et al., *Nature*, 1975, 256:495-497, and/or by recombinant DNA methods (see e.g., U.S. Pat. No. 4,816,567). Monoclonal antibodies may also be obtained, for example, using phage or yeast-based libraries. See e.g., U.S. Pat. Nos. 8,258,082 and 8,691,730.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, Calif.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.3. Humanized Antibodies

Humanized antibodies may be generated by replacing most, or all, of the structural portions of a monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat.*

Acad. Sci. U.S.A., 1998, 95:8910-8915; Steinberger et al., J. Biol. Chem., 2000, 275:36073-36078; Queen et al., Proc. Natl. Acad. Sci. USA., 1989, 86:10029-10033; and U.S. Pat. Nos. 5,585,089, 5,693,761, 5,693,762, and 6,180,370.

9.4. Human Antibodies

Human antibodies can be generated by a variety of techniques known in the art, for example by using transgenic animals (e.g., humanized mice). See, e.g., Jakobovits et al., Proc. Natl. Acad. Sci. U.S.A., 1993, 90:2551; Jakobovits et al., Nature, 1993, 362:255-258; Bruggermann et al., Year in Immuno., 1993, 7:33; and U.S. Pat. Nos. 5,591,669, 5,589, 369 and 5,545,807. Human antibodies can also be derived from phage-display libraries (see e.g., Hoogenboom et al., J. Mol. Biol., 1991, 227:381-388; Marks et al., J. Mol. Biol., 1991, 222:581-597; and U.S. Pat. Nos. 5,565,332 and 5,573, 905). Human antibodies may also be generated by in vitro activated B cells (see e.g., U.S. Pat. Nos. 5,567,610 and 5,229,275). Human antibodies may also be derived from yeast-based libraries (see e.g., U.S. Pat. No. 8,691,730).

10. Vectors, Host Cells, and Recombinant Methods

The invention also provides isolated nucleic acids encoding anti-CD39 antibodies, vectors and host cells comprising the nucleic acids, and recombinant techniques for the production of the antibodies.

For recombinant production of the antibody, the nucleic acid encoding it may be isolated and inserted into a replicable vector for further cloning (i.e., amplification of the DNA) or expression. In some aspects, the nucleic acid may be produced by homologous recombination, for example as described in U.S. Pat. No. 5,204,244.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615.

Illustrative examples of suitable host cells are provided below, these host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as Escherichia (E. coli), Enterobacter, Erwinia, Klebsiella, Proteus, Salmonella (S. typhimurium), Serratia (S. marcescans), Shigella, Bacilli (B. subtilis and B. licheniformis), Pseudomonas (P. aeruginosa), and Streptomyces. One useful E. coli cloning host is E. coli 294, although other strains such as E. coli B, E. coli X1776, and E. coli W3110 are suitable.

In addition to prokaryotes, eukaryotic microbes such as filamentous fungi or yeast are also suitable cloning or expression hosts for anti-CD39 antibody-encoding vectors. Saccharomyces cerevisiae, or common baker's yeast, is a commonly used lower eukaryotic host microorganism. However, a number of other genera, species, and strains are available and useful, such as Schizosaccharomyces pombe, Kluyveromyces (K. lactis, K. fragilis, K. bulgaricus K. wickeramii, K. waltii, K. drosophilarum, K. thermotolerans, and K. marxianus), Yarrowia, Pichia pastoris, Candida (C. albicans), Trichoderma reesia, Neurospora crassa, Schwanniomyces (S. occidentalis), and filamentous fungi such as, for example Penicillium, Tolypocladium, and Aspergillus (A. nidulans and A. niger).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-CD39 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., Meth. Enz., 1979, 58:44; Barnes et al., Anal. Biochem., 1980, 102:255; and U.S. Pat. Nos. 4,767,704, 4,657,866, 4,927,762, 4,560,655, and 5,122,469, or WO 90/03430 and WO 87/00195 may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (Bio/Technology, 1992, 10:163-167) describes a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 minutes. Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is E. coli. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J.

*Immunol. Meth.*, 1983, 62:1-13). Protein G is useful for all mouse isotypes and for human γ3 (Guss et al., *EMBO J.*, 1986, 5:1567-1575).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Pharmaceutical Compositions and Methods of Administration

Any of the antibodies provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes. In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

Further encompassed herein are anhydrous pharmaceutical compositions and dosage forms comprising an antibody, since water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

11.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

11.2. Dosage and Unit Dosage Forms

In human therapeutics, the doctor will determine the posology which he considers most appropriate according to a preventive or curative treatment and according to the age, weight, condition and other factors specific to the subject to be treated.

The amount of the antibody or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or for times weekly. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

12. Therapeutic Applications

For therapeutic applications, the antibodies of the invention are administered to a mammal, generally a human, in a pharmaceutically acceptable dosage form such as those known in the art and those discussed above. For example, the antibodies of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies also are suitably administered by peritumoral, intralesional, or perilesional routes, to exert local as well as systemic therapeutic effects. The intraperitoneal route may be particularly useful, for example, in the treatment of ovarian tumors.

The antibodies provided herein may be useful for the treatment of any disease or condition involving CD39, such as cancer, autoimmune disease, and infection.

Any suitable cancer may be treated with the antibodies provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

Any suitable autoimmune disease may be treated with the antibodies provided herein. Illustrative suitable autoimmune diseases, or diseases with an autoimmune component, include, for example, acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal & neuronal neuropathies, Balo disease, Behcet's disease, bullous pemphigoid, cardiomyopathy, Castleman disease, Celiac disease, Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, colitis, congenital heart block, coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibromyalgia, fibrosing alveolitis, giant cell arteritis (temporal arteritis), giant cell myocarditis, glomerulonephritis, Goodpasture's syndrome, granulomatosis with polyangiitis (GPA) (formerly called Wegener's Granulomatosis), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, inflammatory bowel disease. interstitial cystitis, juvenile arthritis, juvenile diabetes (Type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease (chronic), Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, rimary sclerosing cholangitis, psoriasis, psoriatic arthritis, idiopathic pulmonary fibrosis, pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis/giant cell arteritis, thrombotic disease, thrombocytopenic purpura (TTP), Tolosa-Hunt syndrome, transverse myelitis, type 1 diabetes, ulcerative colitis, undifferentiated connective tissue disease (UCTD), uveitis, vasculitis, vesiculobullous dermatosis, vitiligo, and Wegener's granulomatosis (now termed Granulomatosis with Polyangiitis (GPA).

Any suitable infection may be treated with the antibodies provided herein. Illustrative suitable infections include, for example, hepatitis A virus, hepatitis B virus, hepatitis C virus (HCV), human immunodeficiency virus (HIV), and other viral infections.

13. Diagnostic Applications

In some embodiments, the antibodies provided herein are used in diagnostic applications. For example, an ant-CD39 antibody may be useful in assays for CD39 protein. In some aspects, the antibody can be used to detect the expression of CD39 in various cells and tissues. These assays may be useful, for example, evaluating cancer and autoimmune disease.

In some diagnostic applications, the antibody may be labeled with a detectable moiety. Suitable detectable moieties include, but are not limited to radioisotopes, fluorescent labels, and enzyme-substrate labels. In another embodiment of the invention, the anti-CD39 antibody need not be labeled, and the presence thereof can be detected using a labeled antibody which specifically binds to the anti-CD39 antibody.

14. Affinity Purification Reagents

The antibodies of the invention may be used as affinity purification agents. In this process, the antibodies may be immobilized on a solid phase such a resin or filter paper, using methods well known in the art. The immobilized antibody is contacted with a sample containing the CD39 protein (or fragment thereof) to be purified, and thereafter the support is washed with a suitable solvent that will remove substantially all the material in the sample except the CD39 protein, which is bound to the immobilized antibody. Finally, the support is washed with another suitable solvent, such as glycine buffer, pH 5.0, that will release the CD39 protein from the antibody.

15. Kits

In some embodiments, an anti-CD39 antibody provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-CD39 antibody. In some embodiments, the anti-CD39 antibody is provided in the form of a pharmaceutical composition.

EXAMPLES

Example 1: Selection of CD39 Antigen-Binding Proteins

CD39 ABPs were selected from a synthetic library of human antibodies presented on the surface of yeast cells in IgG format, as generally described, e.g., in WO2009036379; WO2010105256; WO2012009568; and Xu et al., Protein Eng. Des. Sel., 2013, 26:663-670 (each incorporated by reference in its entirety), and more specifically as provided below. The sequences and characteristics of the ABPs isolated from the recombinant library are provided in Table S.

Eight naïve human synthetic yeast libraries each of ~10 E+09 diversity were propagated as described in WO2009036379; WO2010105256; WO2012009568; and Xu et al., Protein Eng. Des. Sel., 2013, 26:663-670; each incorporated by reference in its entirety. For the first two rounds of selection, a magnetic bead sorting technique utilizing the Miltenyi MACS® system was performed, as described in Siegel et al., J. Immunol Meth., 2004, 286:141-153. The following rounds of selection were performed using flow cytometry based sorting. For all round of selection, the antigen was biotinylated human CD39 extracellular domain (heretofore "ECD"), and decreasing concentrations of antigen were used in each subsequent round of selection. In addition to selection on antigen, some rounds of selection were employed in order to reduce the number of non-specific binders utilizing soluble membrane proteins from CHO cells (see WO2014179363 and Xu et al., Protein Eng. Des. Sel., 2013, 26:663-670, each incorporated by reference in its entirety). After the final round of sorting, yeast were plated and individual colonies were picked for characterization and for nomination of clones for affinity maturation.

Antibody variable domains of interest were synthesized, with codon optimization to maximize transient expression in host cells. The variable regions were cloned in to expression vectors containing human immunoglobulin constant domains and their sequence confirmed. Antibody heavy and light chain vector pairings were transfected into Expi293 cells using the Expifectamine system (Invitrogen). Transient cultures were harvested on day 4 and clarified cell culture supernatant IgG titer was estimated using Bio-Layer Interferometry (BLI) using Octet (ForteBio) alongside standards. Antibodies were subsequently purified on a Protein A column and eluted using low pH glycine. Purified antibody samples were then buffer-exchanged or dialyzed into downstream assay-compatible buffers.

Antibody purity was assessed by running samples on SDS-PAGE and on an analytical size exclusion chromatography column.

Light Chain Shuffling: Heavy chain plasmids were extracted from naïve outputs (described herein) and transformed into a pre-made naïve light chain library with a diversity of 10E+06. Selections were performed as described above with one round of MACS sorting and three rounds of FACS sorting using decreasing amounts of biotinylated ECD antigen for respective rounds. Selected individual heavy chains from the primary discovery process were also independently transformed into separate pre-made light chain libraries with a diversity of 10E+06 and selections performed as described above with one round of MACS sorting and three rounds of FACS sorting using decreasing amount of biotinylated ECD antigen for respective rounds.

Example 2: Affinity Maturation

Optimization of naïve clones was carried out utilizing three maturation strategies; diversification of CDR-H1 and CDR-H2; diversification of CDR-H3; diversification of CDR-L1, L2 and L3; shuffling of diversified heavy and light chains.

CDR-H1 and CDR-H2 Selection: The CDR-H3s from clones selected from each of the light chain batch diversification, light chain diversification, and naïve discovery efforts were independently recombined into premade libraries with CDR-H1 and CDR-H2 variants of a diversity of >10E+8 and selections were performed using ECD antigen. Affinity pressures were applied by using decreasing concentrations of antigen.

CDR-H3 Selection: Clones obtained from the CDR-H1 and CDR-H2 selection procedure were subject to additional rounds of affinity maturation via walking dimer mutagenesis of the heavy chain. Selections were performed using ECD as antigen generally as described above but with the addition of employing FACS sorting for all selection rounds.

CDR-L1, L2, L3 Selection: Clones obtained from the CDR-H1 and CDR-H2 selection procedure were subject to additional rounds of affinity maturation via mutagenesis of the light chain. The CDR-L1 and CDR-L2 diversity derived from a pre-made library while CDR-L3 diversity derived from walking dimer mutagenesis. Selections were performed using ECD as antigen generally as described above but with the addition of employing FACS sorting for all selection rounds, with one round of MACS followed by three rounds of FACS in the CDR-L1, L2, L3 process described here.

Diversified Heavy Chain and Light Chain Shuffling: Outputs from heavy chain diversification and light diversification described above were recombined and selections were performed using ECD as antigen generally as described above but with the addition of employing FACS sorting for all selection rounds.

Example 3: Monovalent Affinity of Anti-hCD39 Antibodies to Recombinant CD39 Extracellular Domain Binding kinetics were measured using the Octet Red96 system (ForteBio) at 25° C. in running buffer (lx Pall ForteBio Kinetics Buffer diluted into PBS or Tris pH 7.4). In brief, 1.25 mg/ml of unlabeled anti-hCD39 antibodies were immobilized onto anti-human Fc sensors. After a short baseline step in running buffer, the sensors were exposed to varying concentrations (10-300 nM) of rhCD39-ECD-His (R&D Systems) for the association step. Dissociation of the complex was monitored upon exposure of the sensors to running buffer once again. Data was processed using ForteBio Octet software with baseline subtraction, global fit and 1:1 binding model to obtain association and dissociation rates. $K_D$ was calculated from the ratio of $k_d$ to $k_a$.

Data shown in FIG. 1 had $R^2$>0.980. PF=poor fit. The association and dissociation time course data was globally fit with a simple 1:1 Langmuir binding model to yield on-rate (kon) and off-rate (koff) values. The equilibrium dissociation constants ($K_D$) were calculated from the kon and koff values. The kon values ranged from 1.93E+04 to 1.72E+06 $M^{-1}s^{-1}$ and the off rate values ranges from 3.65E-01 to 1.11E-04 $s^{-1}$. The $K_D$ values ranged from 4.09E-07 to 7.31E-011 molar indicating that all of the antibodies bound with moderate or high affinity to human CD39 ECD.

The paralog specificity of the anti-CD39 antibodies was assessed by biolayer interferometry using soluble recombinant human ENTDP2 and soluble recombinant human ENTDP3 (both from R&D Systems). ENTDP2 and ENTDP3 are enzymes with functions similar to CD39. None of the antibodies exhibited detectable binding to ENTDP2 or ENTDP3 (data not shown). Thus all of the antibodies exhibit specific binding to human CD39.

Example 4: Inhibition of Recombinant Human CD39 Extracellular Domain

The inhibition of recombinant human CD39 ECD by anti-CD39 antibodies was measured as follows. Recombinant human CD39/ENTPD1 (4397-EN from R&D systems), (either 5 or 10 nM final concentration) was combined with anti-CD39 IgGs (0.25 or 1 micromolar final concentration) in 25 mM Tris, 5 mM $CaCl_2$), pH 7.5 in a 96-well plate and incubated at room temperature for 2 hrs. ATP (Sigma A1852-1VL) was then added to a final concentration of 500 micromolar and incubated at 37° C. for 60 minutes. The plate was then placed at room temperature and CellTiter-Glo Luminescent Cell Viability Assay solution was added to each well of the assay plate, mixed and read on a microplate reader using "CellTiter-Glo luminescent" preset. Control reactions consisting of negative control IgG, IgG only (no ATP), ATP only (no CD39) were run using the same method. Data values are the average of 2 replicates.

Inhibition of human CD39 ECD enzymatic activity by anti-CD39 antibodies was determined by measuring ATP levels using the CellTiter-Glo assay (FIGS. 2 A-E). The enzymatic catabolism of ATP by CD39 ECD was observed in the presence of an isotype control antibody or no IgG with average RLU values ranging from 38 to 857. All of the anti-CD39 antibodies showed marked inhibition ATP catabolism by CD39, having much higher average RLU values than the isotype control antibody (average RLU values range from 4890 to 20329). In contrast, Benchmark antibody BY40va did not show significant inhibition of CC39 ECD in this assay having RLU values similar to the isotype control antibody (average RLU values 11 and 415).

Example 5: Antibodies Bind to CHO Cells Expressing Human and Cyno CD39

Binding of anti-CD39 IgGs to Chinese Hamster Ovary K1 (CHO) CD39 cells. 100 nanomolar IgGs (each antibody is indicated as a unique clone number in the FIG.) were incubated at 25° C. for 30 minutes on ice in phosphate buffered saline (PBS) with parental CHO cells or CHO cells engineered to express either human or cynomolgus macaque (*Macaca fascicularis*) CD39 (CHO CD39 cells). Cells were then washed with ice cold PBS and incubated with a fluorescently labeled goat-anti-human IgG for 20 minutes on ice. Cells were washed and resuspended in ice cold PBS prior to analysis by flow cytometry. Fold over background binding levels represent the ratio of median fluorescence intensity (MFI) values for anti-CD39 antibodies binding to CHO CD39 to MFI values for anti-CD39 antibodies binding to the parental CHO cells.

The anti-CD39 antibodies bound to CHO cells expressing cellular human CD39 (CHO CD39 cells) and did not exhibit significant binding to parental CHO cells (FIGS. 2F-J). The binding of these antibodies to CHO CD39 cells ranged from 10 to 2033-fold over background. Antibodies 28337 and 27575 did not show significant binding to CHO CD39 cells (only 2 to 4-fold over background) (FIGS. 2F-J) indicating that these antibodies do not have low affinity for the cellular form of human CD39.

The ortholog specificity of the anti-CD39 antibodies was assessed with flow cytometry using CHO cells engineered to express either cynomolgus macaque or mouse CD39. The anti-CD39 antibodies bound to cynomolgus macaque CD39 to a similar extent as human CD39 (FIGS. 2 F-J). None of the anti-CD39 antibodies showed detectable binding to mouse CD39. Thus, the anti-CD39 antibodies are cross reactive to cynomolgus macaque CD39 but not to mouse CD39.

Example 6: Binding of Antibodies to Cell Surface CD39 in MEL-28 or 721 Cells and Antibodies that Inhibit CD39 on MEL-28 Cells a Short Term ATPAse Assay Cells were incubated with serially diluted anti-CD39 antibodies for 30 minutes at 4 degrees C. Cells were washed 3 times in FACS buffer (PS, 2% FBS, and 2 mM EDTA) and next incubated with secondary antibody (goat anti-human IgG Southern Biotech) at 1:100 for 30 minutes at 4 degrees C. Cells were washed, resuspended in FACS buffer, and analyzed for binding by flow cytometry analysis on BD Celesta.

$3.5 \times 10^4$ MEL-28 cells/well were washed with Tris buffer and incubated with serially diluted (100-0.00013 nM) antibody for 30 minutes at 37 degrees C. 50 µM ATP was added to each well and incubated with cells for 15 minutes. The supernatants were collected and analyzed in Malachite Green Assay (R&D) according to manufacturer's protocol. Phosphate released from CD39 processing of ATP was used as a readout of enzyme activity. Palivizumab was used as an isotype control and ARL (Tocris) and POM-1 (Alpha Aesar), non-specific small molecule inhibitors of CD39, were used as positive controls at 100 µm.

All antibodies bound to endogenously expressed CD39 on both cell lines with similar affinity with EC50 ranges from 0.05-0.28 µg/ml on MEL-28 (see FIG. 3 A) and with EC50 ranges of 0.2-7.5 µg/ml on 721.22 cell line (see FIG. 3B). Maximum signal (MFI) differed between antibodies tested even when EC50 values were similar (FIGS. 3A-B).

After confirmation of cellular binding, anti-CD39 antibodies were evaluated for inhibition of ATPase activity on MEL-28 cell in short term 30 minute Malachite Green phosphate readout assay. Isotype control was used to establish maximum possible signal from ATP processing in MEL-28 cells-50 µm ATP addition to cells typically resulted in 55-60 µM phosphate signal in this assay (see FIGS. 4A and B). Anti-CD39 antibodies inhibited ATPase activity in MEL-28 cells by 60-80% at the highest concentration of antibodies tested (100 nM)—this level of inhibition was similar to non-specific ATPase inhibitors ARL and POM1 (see FIG. 4A). IC50 values for anti-CD39 antibodies in MEL-28 malachite green assay were all in sub-nanomolar range (see FIG. 4B).

Example 7: ATP Preservation Quantified when MEL-28 Cells are Treated with CD39 Enzymatic Inhibitors $3.5 \times 10^4$ MEL-28 cells were plated overnight at 37 degrees C. Cells were washed with Tris assay buffer to remove phosphate. 100 nM titrated down to 0.005 pM of monoclonal antibodies were incubated with cells for 30 minutes at 37 degrees C. 50 µM ATP was added and incubated for 15 minutes. Supernates were harvested and frozen. Supernates were thawed and evaluated for ATP using the EnzyLight (EnzyLight ATP Assay Kit, BioAssay Systems). Palivizumab was used as an isotype control and ARL (Tocris) and POM-1 (Alpha Aesar) used at a concentration of 100 µM are non-specific small molecule inhibitors of CD39 as positive controls.

Figure 5:
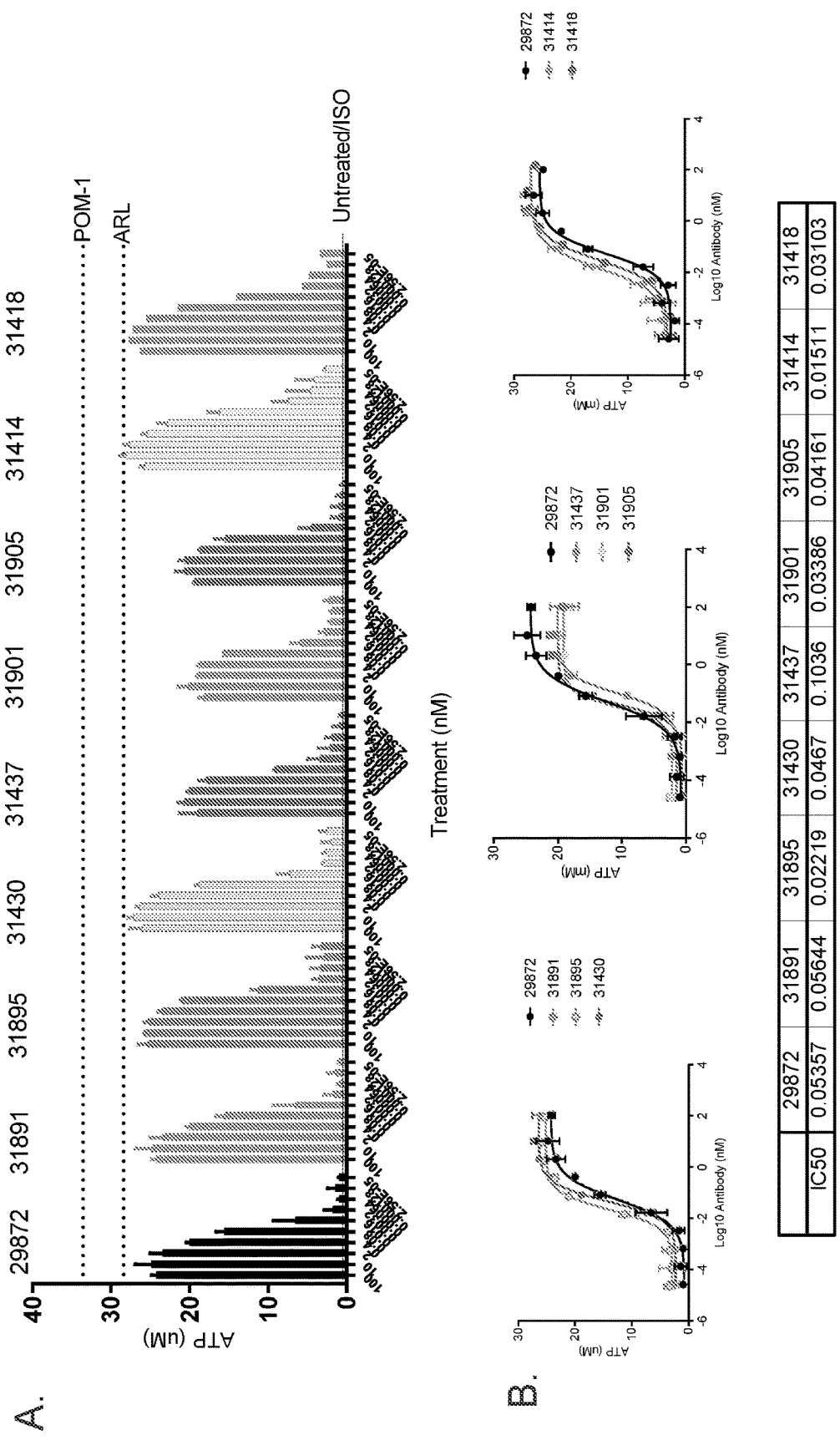
FIG. 5 provides an illustration of quantification when MEL-28 cells are treated with CD39 enzymatic inhibitors.

ATP was almost undetectable after 30 minutes post ATP addition to the cells in untreated and/or isotype treated samples (see FIG. 5 A) while all of the anti-CD39 antibodies tested prevented processing of ATP in dose dependent manner (see FIG. 5 A, B). Most of the anti-CD39 antibodies tested in this assay prevented ATP processing by CD39 to a similar extent as ARL (see FIG. 5A). IC50s of anti-CD39 antibodies in ATP preservation assay ranged from 0.02-0.1 nM. Overall potency of antibodies in this assay was consistent with what was observed in Malachite Green phosphate readout assay.

Example 8: Antibodies Inhibit CD39 Activity on MEL-28 in an Overnight Assay $3.5 \times 10^4$ MEL-28 cells/well were plated and incubated with antibodies overnight at 37 degrees C. Cells were washed to remove FBS. Cells next were pre-treated with antibodies in X-VIVO 15 FBS free media overnight at 37 degrees C. ATP was then spiked in at 50 µM for 15 minutes. Supernatants were collected and analyzed using AMP-Glo kit according to manufacturer's instructions (Promega). Palivizumab was used as an isotype control and POM-1 (Alpha Aesar), a non-specific small molecule inhibitor of CD39, was used as positive control at 100 µM.

Figure 6:
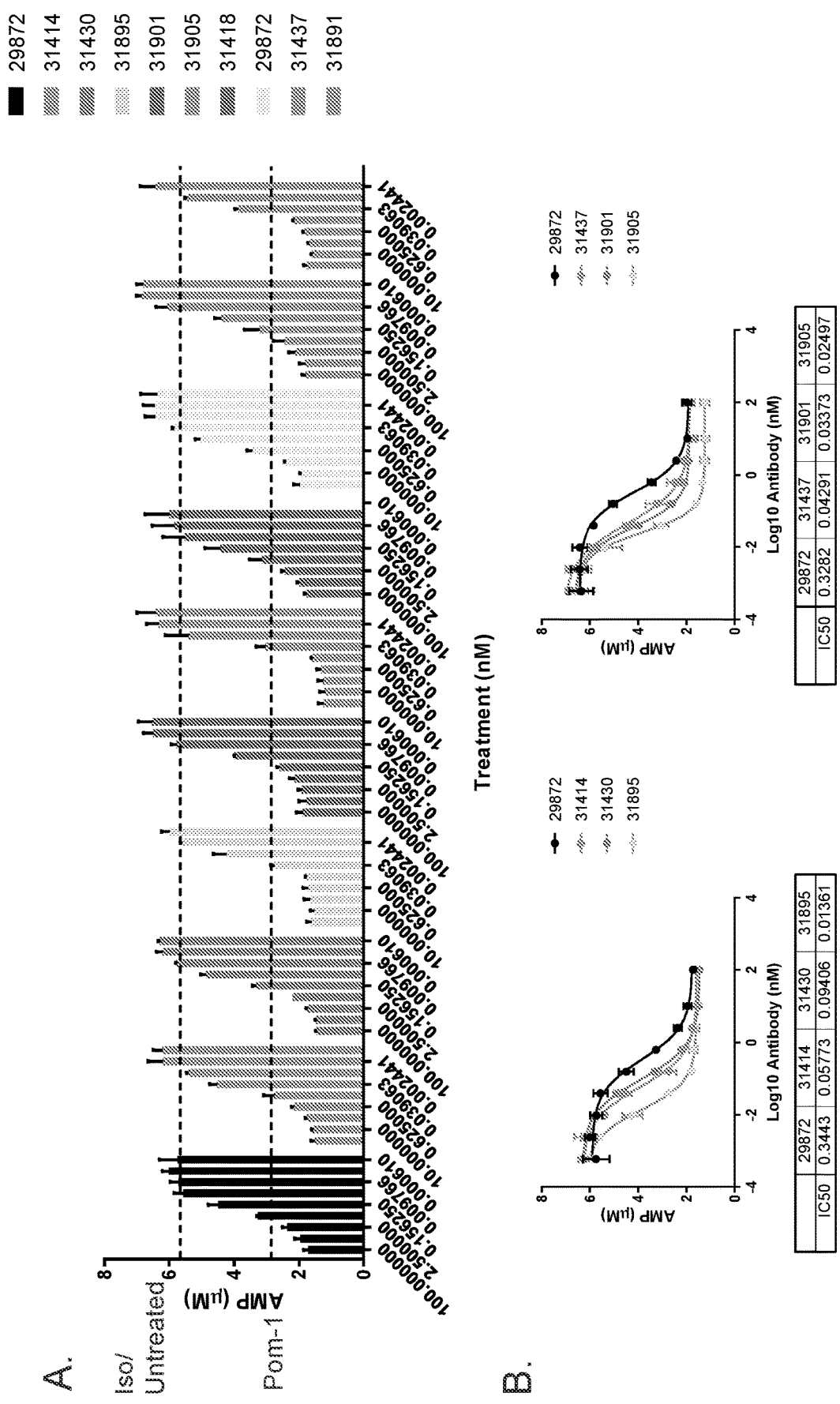
FIG. 6 shows that antibodies were evaluated for inhibiting CD39 enzymatic activity overnight to MEL-28 cells.

Anti-CD39 antibodies tested in overnight AMPGlo assay in MEL-28 cells demonstrated sustained inhibition of ATPase activity as indicated by decreased AMP levels present in the supernatants (see FIG. 6A) Inhibition of CD39 activity by antibodies was equivalent to or more potent compared to POM-1 treatment. The data is consistent with results obtained in CD39 short-term Malachite Green assay in MEL-28 (see FIG. 4). Antibodies tested in an overnight assay had IC50 values in an AMPGlo CD39 inhibition assay ranging from 0.01 to 0.3 nM. (see FIG. 6 B)

Example 9: Anti-CD 39 Antibodies Bind to Primary Human and Cyno B Cells

B cells were isolated from human donor leukopak using EasySep B cell isolation kit (STEMCELL Technologies). Cyno monocytes were purified from fresh cyno blood using NHP CD14 positive selection kit (Miltenyi) and flow through was collected and stained with CD4, CD8, CD20, CD16, and CD3 antibodies (BD). Human B cells or cyno cells were incubated with serially diluted anti-CD39 antibodies (15 µg/ml 7.5 fold serial dilution, 8-point) for 30 minutes at 4 degrees C. Cell were washed 3 times in FACS buffer (PS, 2% FBS, and 2 mM EDTA) and incubated with secondary antibody (mouse anti-human IgG southern biotech) at 1:100 for 30 minutes at 4 degrees C. Cells were washed 2 times in FACS buffer and resuspended in FACS buffer and analyzed on BD Celesta.

Figure 7:
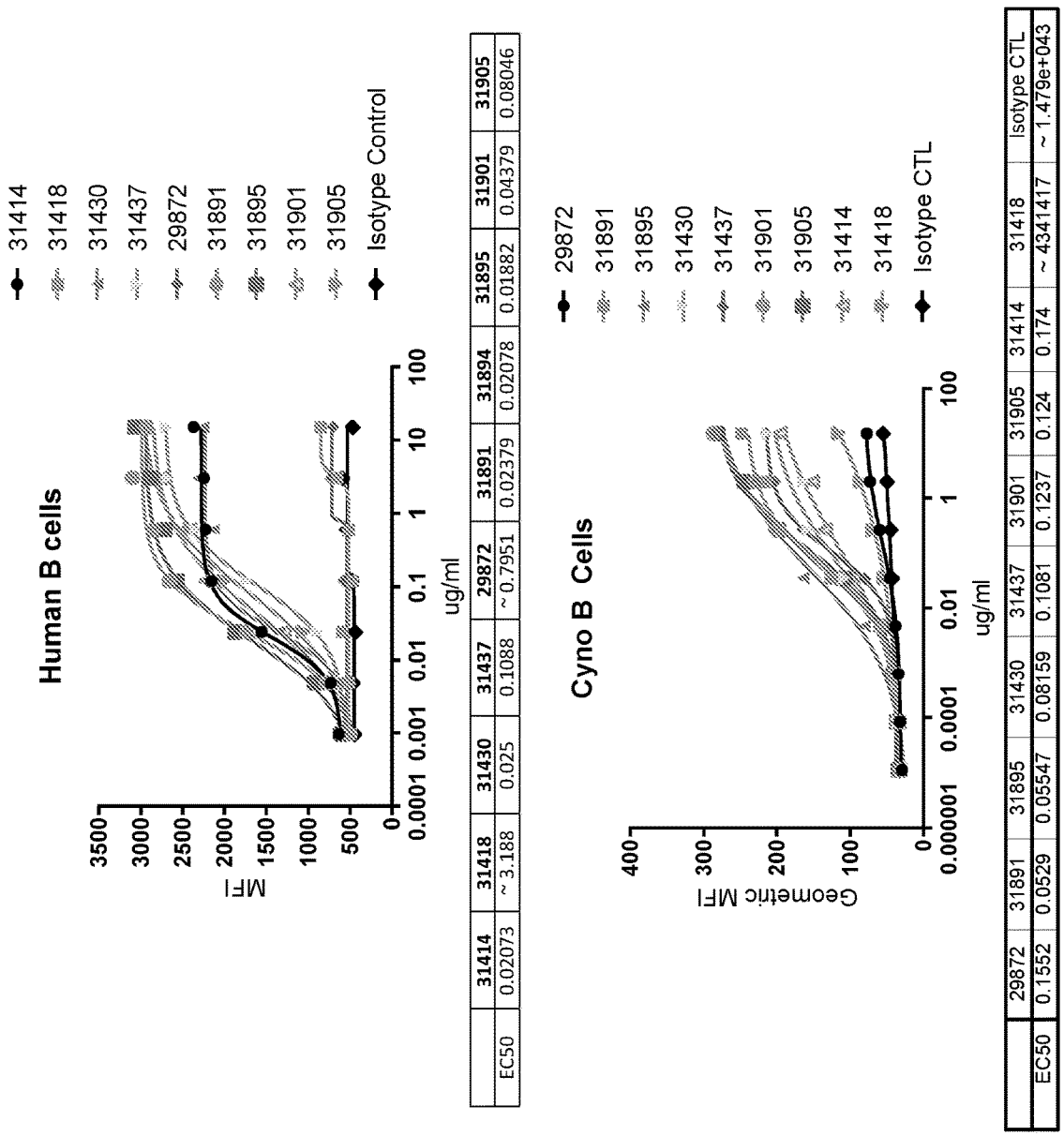
FIG. 7 shows results of testing of antibodies for binding to CD39 on human and cyno primary B cells.

Detection of antibody binding is as described in FIG. 7 where B cells were incubated with serially diluted antibodies and detected using a fluorescently tagged antibody and analyzed by flow cytometry. The results are shown in FIG. 7 and appear to indicate that the antibodies bind specifically to both human and cyno B cells with EC50s that range from 0.02 µg/ml to 3.18 µg/ml (human) and 0.03 µg/ml to 0.17 µg/ml (cyno). Similar binding was observed on human tumor cells lines (FIG. 3) where subset of the antibodies had a low maximal MFI and a subset had a high MFI to both the human and cyno B cells.

Example 10: Antibodies Inhibit CD39 Activity on Human B Cells

B cells were isolated from human leukopak using Easy-Sep B cell isolation kit (STEMCELL Technologies). $5 \times 10^4$ B cells/well were washed with Tris buffer and incubated with serially diluted (100-0.00013 nM) antibodies for 30 minutes at 37 degrees C. 50 µM ATP was added to each well and incubated with cells for 2 hrs. The supernatants were collected and analyzed in Malachite Green Assay (R&D) according to manufacturer's protocol. Phosphate released from CD39 processing of ATP was used as a readout of enzyme activity. Palivizumab was used as an isotype control and ARL (Tocris) and POM-1 (Alpha Aesar), non-specific small molecule inhibitors of CD39, were used as positive controls at 100 µM.

Figure 8:
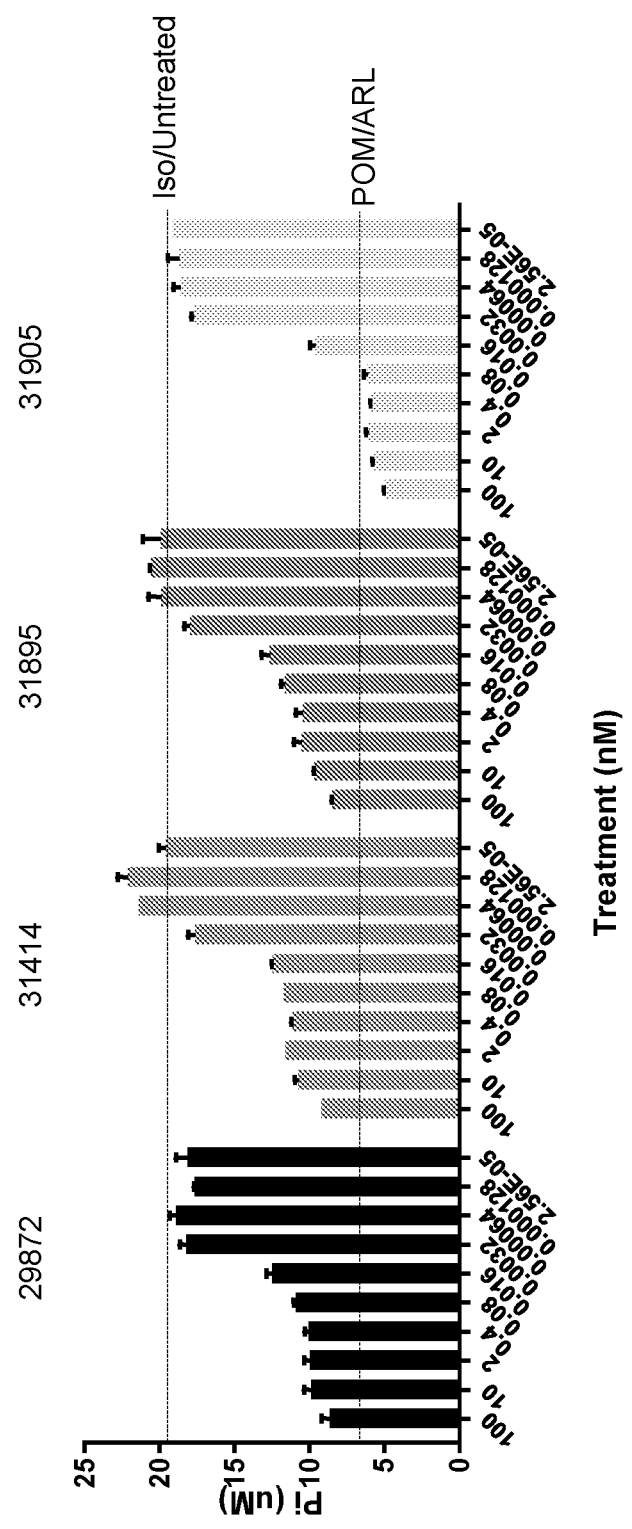
FIG. 8 sets forth antibodies that were evaluated for inhibition of CD39 activity on primary human B cells. Anti-CD39 antibodies (each unique antibody clone number indicated is in the figure) were titrated from 100 to 0.00013 nM.
Figure 9:
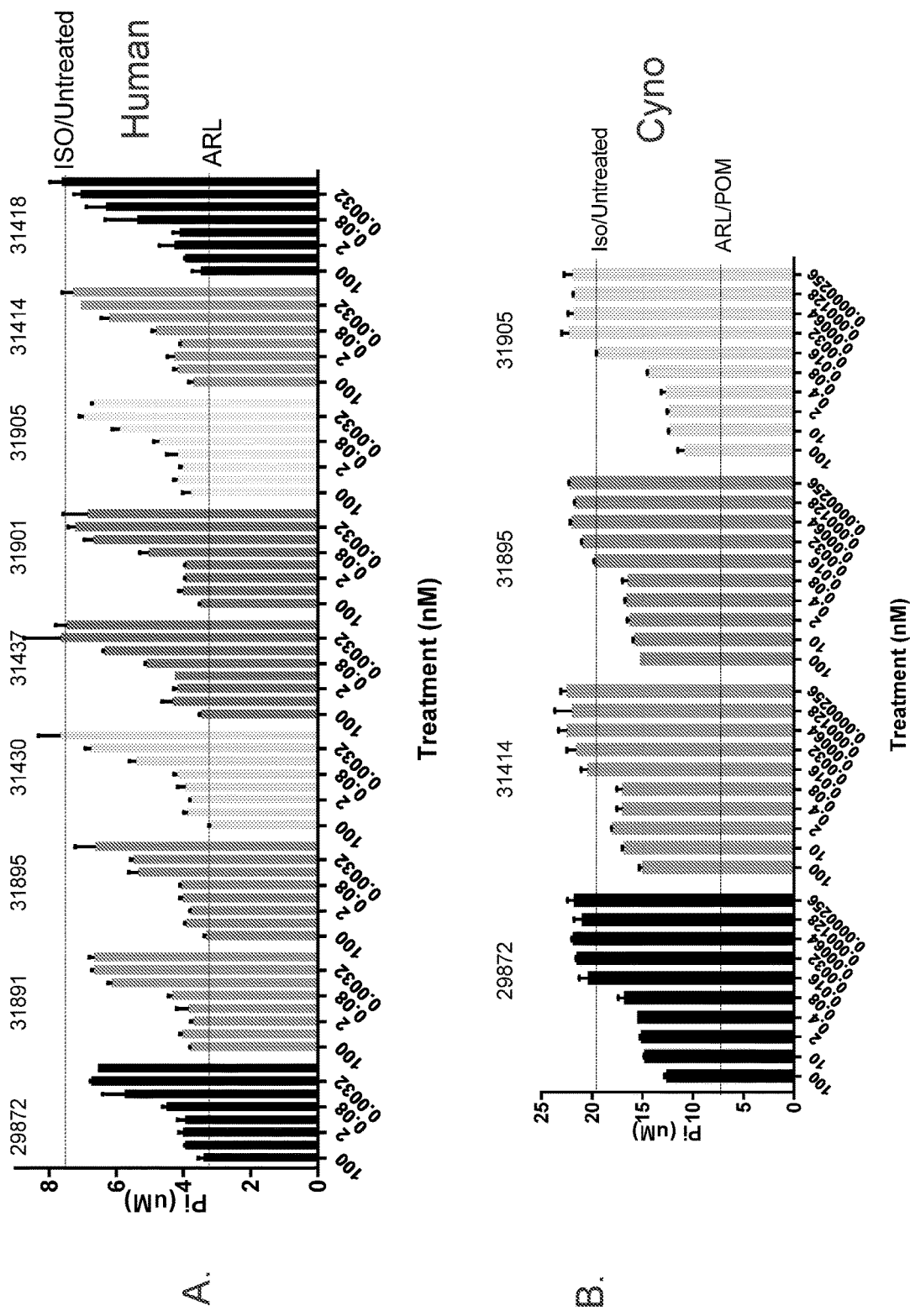
FIG. 9 provides evaluation of inhibition of CD39 activity on primary human (a) and cyno (b) monocytes. Anti-CD39 antibodies (each number represents a unique antibody clone number as indicated in the figure) were titrated from 100 to 0.00013 nM and incubated with monocytes in presence of ATP. Phosphate release by CD39 processing of ATP was quantified using Malachite Green assay.

The antibodies were demonstrated to bind to primary human and cyno B cells (see FIG. 7) and the next step was to evaluate the inhibition of ATP hydrolysis by detection of free phosphate (Pi) using a malachite green assay. The results are shown in FIG. 8 and indicate the anti-CD39 antibodies inhibit the enzymatic inhibition/dephosphorylation of ATP by primary human B cells. The ability of the antibodies to inhibit enzymatic activity was comparable regardless of high vs. low max MFI detected in the binding to human B cells (FIG. 7).

Example 11: Anti-CD39 Antibodies Inhibit ATPAse Activity on Human and Cyano Monocytes Human monocytes were purified from leukopak using EasySep Human monocytes isolation kit (STEMCELL). Cyno monocytes were isolated from whole cyno blood using NHP CD14 positive selection kit (Miltenyi). Monocytes at $5 \times 10^4$ cells/well were washed with Tris buffer and incubated with serially diluted (100-0.00013 nM) anti-CD39 antibodies for 30 minutes at 37 C. 50 µM ATP was added to the cells for 15 minutes at 37 C and supernatants were harvested and analyzed in Malachite Green Assay (R&D) for phosphate levels. Palivizµmab was used as an isotype control and ARL (Tocris) and POM-1 (Alpha Aesar), non-specific small molecule inhibitors of CD39, were used as positive controls at 100 µM.

CD39 expression has been detected on human leukocytes with the highest expression detected on monocytes (Thromb Res. 2007; 121(3):309-17). Because of this information, it was important to evaluate the ability of the anti-CD39 antibodies to inhibit ATPase activity on the cell surface. As demonstrated in FIG. 7, anti-CD39 antibodies bind to both human and cyno B cells. It is appropriate to evaluate the inhibition of enzymatic activity on human and cyno monocytes. The results indicate that all the antibodies are able to inhibit ATPase activity of CD39 on human and cyno monocytes with similar potencies.

Example 12: Anti-CD39 Antibodies Bind to Primary Human TRegs and Inhibit CD39 Enzymatic Activity Treg cells were isolated from human donor leukopak using $CD4^+CD25^+CD127^{dim}$ regulatory T cell isolation kit II (Miltenyi). Human Treg cells were incubated with serially diluted anti-CD39 antibodies (100 nM-0.00064 nM) for 30 minutes at 4 degrees C. Cell were washed 3 times in FACS buffer (PS, 2% FBS, and 2 mM EDTA) and incubated with secondary antibody (mouse anti-human IgG southern biotech) at 1:100 for 30 minutes at 4 degrees C. Cells were washed 2 times in FACS buffer, resuspended in FACS buffer and analyzed on BD Fortessa.

$CD4^+CD25^+CD127^{dim}$ human Treg cells were washed 3× with Tris buffer. Cells were incubated with anti-CD39 antibodies (100 nM-0.00064 nM) for 30 minutes at 37 C. The cells were spiked with 50 µM ATP and supernatants were collected after 15 minutes incubation at 37 C. Supernatants were analyzed for phosphate levels in Malachite Green Assay kit (R&D). Palivizumab was used as an isotype control and ARL (Tocris) and POM-1 (Alpha Aesar), non-specific small molecule inhibitors of CD39, were used as positive controls at 100 µM.

Figure 10:
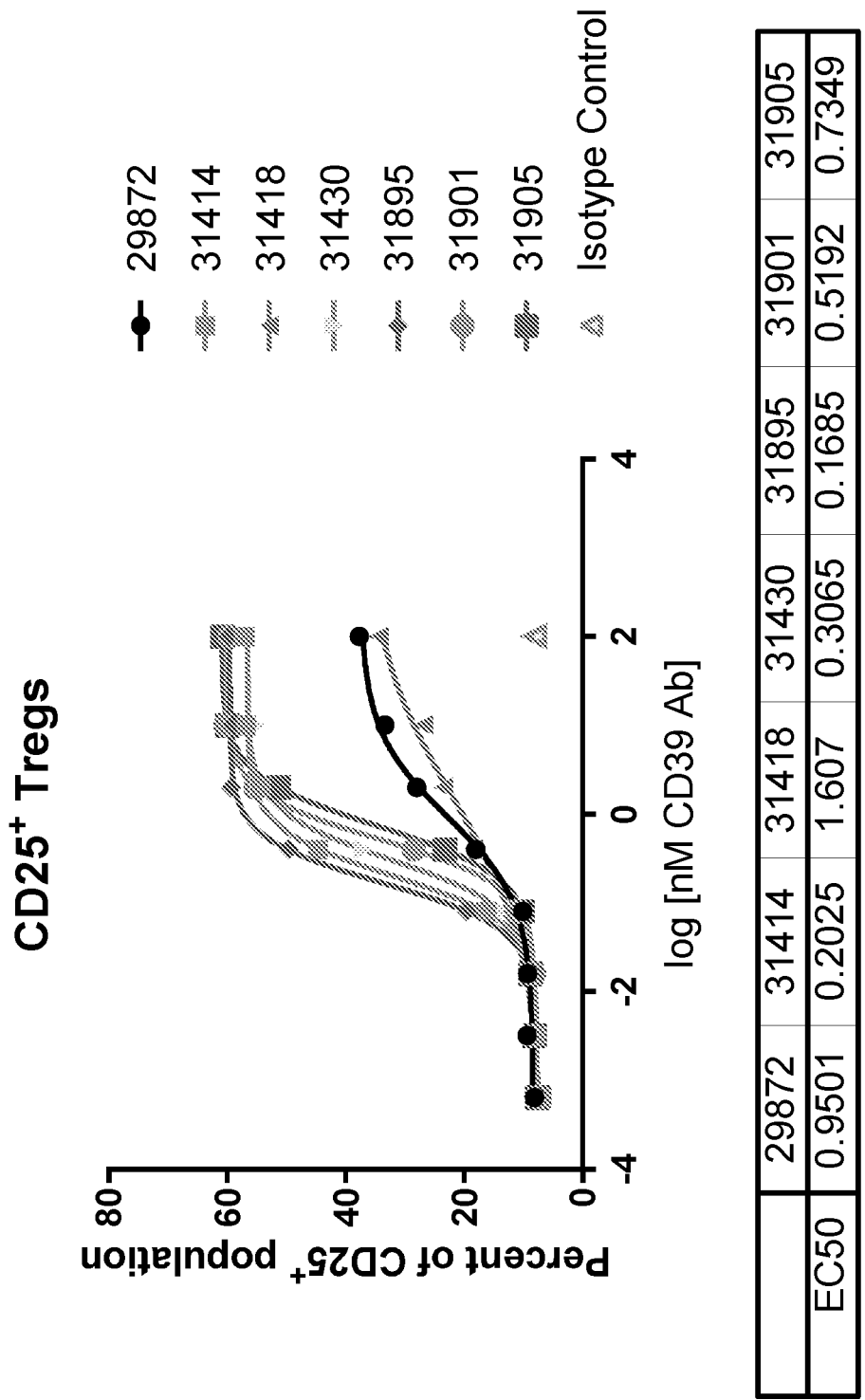
FIG. 10 shows binding of anti-CD39 antibodies on purified human $CD4^+CD25^+CD127^{dim}$ Treg cells by FACS. Anti-CD39 antibodies were titrated on purified Treg from healthy donor and detected with anti-human IgG secondary antibody. $EC_{50}$s were calculated using GraphPad Prism software.
Figure 11:
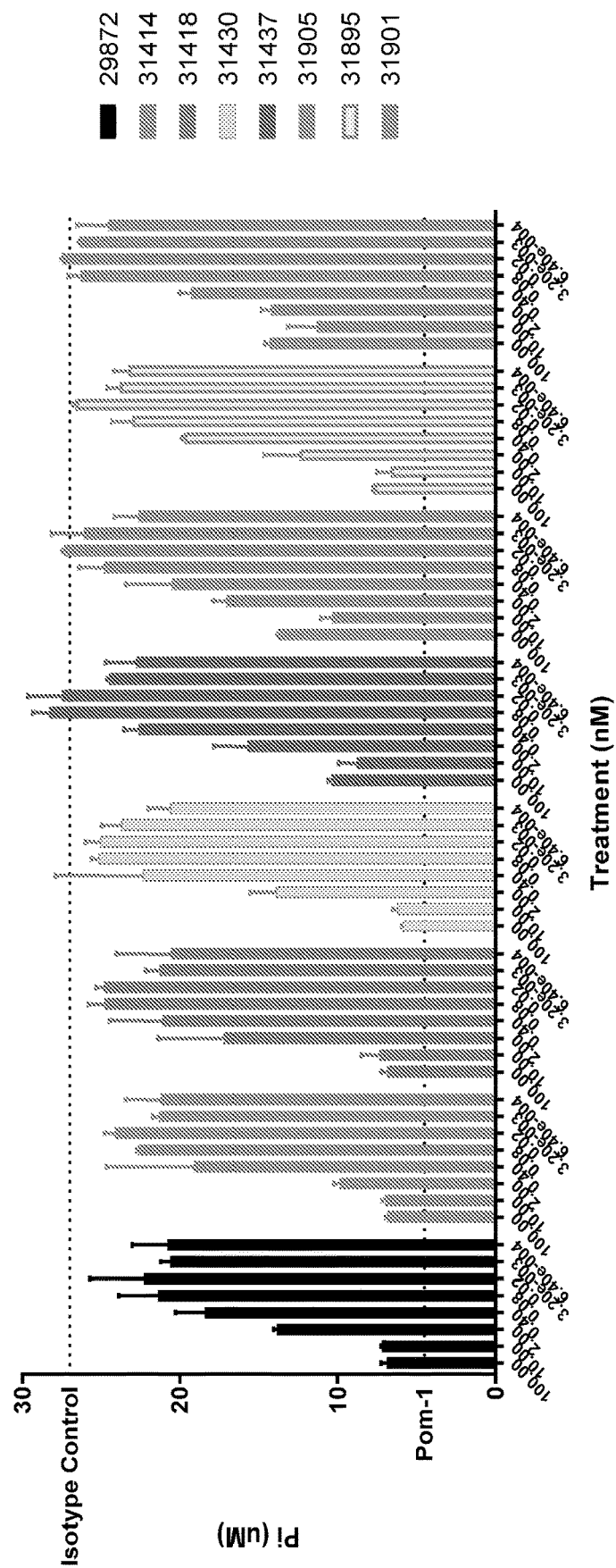
FIG. 11 shows results for antibody ability to inhibit primary Treg CD39 activity. $CD24^+CD25^+CD127^{dim}$ T regulatory cells were incubated with serially diluted anti-CD39 antibodies and tested for ATPase activity after addition of exogenous ATP. Free phosphate (Pi) was used as a readout of CD39 activity.
Figure 12:
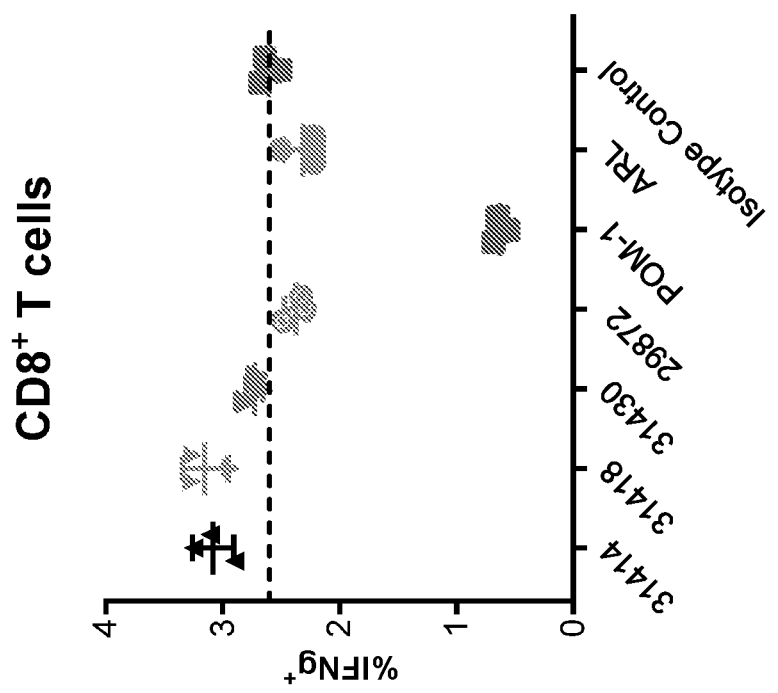
FIG. 12 shows treatment with anti-CD39 antibodies increase the percent of IFN gamma producing $CD8^+$ T cells that respond to CMV peptides in an antigen recall response assay.
Figure 13:
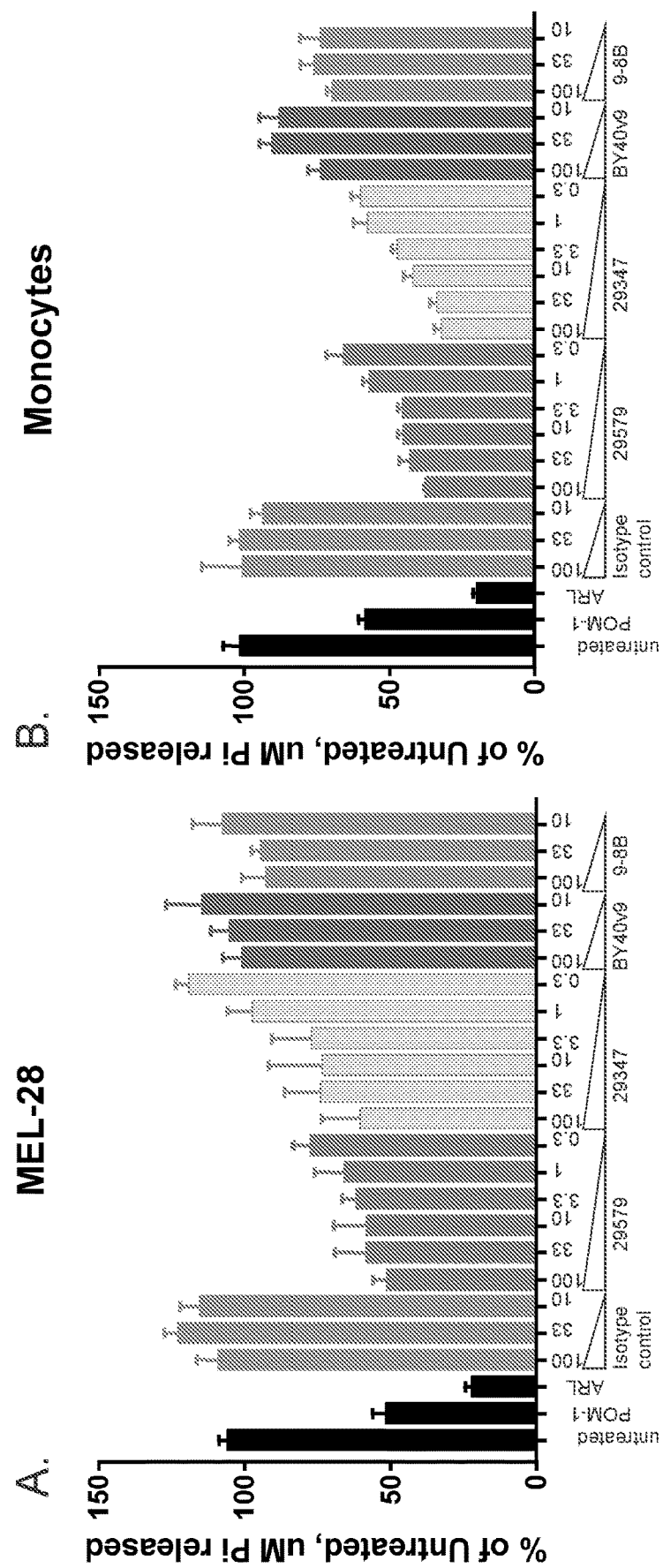
FIG. 13 shows evaluation of antibodies for inhibition of CD39 activity on MEL-28 (FIG. 13A.) and human monocytes (FIG. 13B.) as compared to the anti-CD39 antibodies generated based on Innate/Orega (BY-40v9) and Igenica (9-8B) and variants thereof. Anti-CD39 antibodies were titrated as indicated and incubated in presence of ATP. Phosphate release by CD39 processing of ATP was quantified using Malachite Green assay.

CD39 had been shown to be expressed on human regulatory T cells (Treg) and important for their suppressive function by hydrolysis of ATP to immune suppressive adenosine. (Blood. 2007 Aug. 15; 110(4):1225-32, *Cellular & Molecular Immunology* (2017) 14, 521-528; doi:10.1038/cmi.2016.30). In order to determine whether the anti-CD39 antibodies were capable of inhibiting CD39 enzymatic activity, it was important to evaluate the binding to human Tregs. Tregs were isolated from human PBMCs and the Tregs were purified and the anti-bodies were evaluated for binding by flow cytometry. The result indicate that the anti-CD39 antibodies bind to human Tregs (FIG. 10). Of note, both the high maximum MFI and low MFI profiles were observed similar to the human B cell staining (see FIG. 8). The ability of the antibodies to inhibit the ATPase activity on human Tregs was also evaluated. All the antibodies inhibit Treg CD39 enzymatic activity (see FIG. 11) equally well regardless of the maximal MFI staining observed.

Example 13: Anti-CD39 Antibodies Increase $CD8^+$ T Cell Response in a CMV Recall Response Assay Frozen PBMCs are thawed and resuspended at $3 \times 10^6$/ml and cultured in presence of CMV peptides (Miltenyi, Pept-Tivator CMV pp65) for 3 days in complete (10% FBS) media at 37 degrees C. T cells were then purified (STEMCELL, EasyStep) and rested for 24 hours at 37 degrees C. APCs were generated by depleting CD2 positive cells (STEMCELL, Easystep) from PBMCs from the same donor and plated at $5 \times 10^4$/well overnight at 37 degreesC. The following day $5 \times 10^4$ rested T cells were added to the APCs. Antibodies were added at 25 µg/ml plus 100 µM ATP+1 µM EHNA and Golgi plug/stop with CMV peptides and incubated at 37 degrees C. for 5 hours. T cells were stained and analyzed for intracellular IFN gamma on a Fortessa (Becton Dickinson) flow cytometer.

Adenosine has been shown to inhibit T cell activation. (Int J Oncol. 2008 March; 32(3):527-35). As the rate-limiting enzyme in ATP/ADP-AMP-adenosine pathway, inhibiting CD39 would diminish the levels of immune suppressive adenosine and increase immune activating ATP resulting in enhanced T cell activity. In order to evaluate the role of anti-CD39 antibodies inhibiting ATP/ADP-AMP hydrolysis, preventing the generation of adenosine which could result in an increased T cell response, a CMV recall assay was used. PBMCs were cultured in the presence of a pool of CMV peptides for 3 days and then the T cells were purified cultured with autologous PBMC plus CMV peptides and ATP+EHNA. After 5 hours the T cells were evaluated for the production of IFN gamma. The results indicate that some of the anti-CD39 antibodies were able to increase $cD8^+$ T cells activity in a CMV recall responses assay. This demonstrates that inhibiting the enzymatic activity of CD39 prevents the generation of adenosine and preserves ATP levels and allowing for a robust T cell response to a peptide:MHC complex. In addition, not all antibodies that bind to CD39 and inhibit cell surface enzymatic activity are capable of increasing T cell response and the specific interaction of the antibody to CD39 is important.

Example 14: Evaluation of Antibodies for Inhibition of CD39 Activity on Mel-28 and Human Monocytes $3.5 \times 10^4$ MEL-28 cells/well were incubated with 100 nM down to 0.32 pM of monoclonal antibodies for 30 minutes. 50 µM ATP was added and incubated for 15 minutes. Supernate was evaluated for free phosphate (Pi) using the Malachite Green Phosphate Detection Kit (R&D Systems cat #DY996). Palivizumab was used as an isotype control and ARL (Tocris) and POM-1 (Alpha Aesar) used at a concentration of 100 µM as non-specific small molecule inhibitors of CD39 as positive controls. Cyno monocytes were isolated from whole cyno blood using NHP CD14 positive selection kit (Miltenyi). Monocytes at $5 \times 10^4$ cells/well were washed with Tris buffer and incubated as described above.

When comparing anti-CD39 antibodies for enzymatic inhibition in short term assays, differences were observed. Some were able to block the release of free phosphate (Pi) measured in a malachite green assay and others demonstrated very little activity. For example, BY40v9 and 9-8B have little to no enzymatic inhibition at concentrations of 100 nM using both the MEL-28 cell or primary human monocyte compared to other anti-CD39 antibodies (e.g., 29579 and 28347) that are able to inhibit ATPase activity at low nM concentrations.

9-8B was produced as described in US 2017/0335007 A1, using SEQ ID Nos. 22 and 23, as hIgG4. BY40v9 is an engineered variant of the antibody BY40 described in WO 2009/095478 A1 SEQ ID Nos. 1 and 5. We tried to express BY40 as described as a human IgG4 but repeated attempts failed. The VH described in SEQ No. 1 appears to be missing several N-terminal residues compared to germline VH's, so we engineered in the missing residues with closest germline sequence from IMGT (http://imgt.org/), resulting in BY40-v9, which expressed and was determined to specifically bind rhCD39-ECD and cellular ECD.

Example 15: Design of Chimera and Region of Distinct Binding (a) Examples of Antibodies that Bind Soluble Recombinant CD39 ECD and Cellular CD39 but do not Inhibit ATPase Activity and do not Compete with Cellular Inhibitors for Binding to ECD Inhibitors 0.04-3.3 nM rhCD39-ECD (R&D Systems) was incubated with buffer, 50 µg/ml antibody or 100 µM POM-1 (Alpha Aesar) for 1 hr at 37° C. in assay buffer (25 mM Tris pH 7.5, 5 mM $CaCl_2$)) at which point ATP (Sigma) was spiked in to a final concentration of 10 µM, and the reaction further incubated for 30 min 37° C. Production of free phosphate (Pi) was subsequently measured using Malachite Green Phosphate Detection kit (R&D Systems).

Indicated cells were incubated in assay buffer with 10-25 µg/ml antibody, 100 µM POM-1 or 100 µM ARL for 30 min at 37° C. 5% $CO_2$. ATP was added to a final concentration of 50 µM and the incubation continued for 15 min. Supernatant was evaluated for free phosphate (Pi) using the Malachite Green Phosphate Detection kit. Palivizumab is used as an isotype control and POM-1 and ARL are non-specific small molecule inhibitors of CD39.

A1 antibody was immobilized onto an Anti-Mouse IgG Fc Capture (AMC) biosensor (ForteBio). Association of hCD39-ECD was then monitored for 180 seconds via Bio-Layer Interferometry (BLI) using the Octet system (ForteBio), at which point the biosensor was dipped into competitor antibody and monitored for another 180 seconds. Association of the second antibody was recorded as an upward shift in the interference pattern and indicates that the antibodies bind to different epitopes on CD39. No change in the interference pattern indicated that A1 blocks the second antibody from binding to CD39.

Although A1 does bind hCD39 ECD (FIG. 1), it does not inhibit its ATPase activity. Although A1 does bind cellular CD39 (FIG. 2), it does not appreciably directly inhibit the ATPase activity of CD39 expressed on OAW42. Capture of hCD39 ECD by A1 blocks subsequent binding by A1 (FIG. 14A, bottom right hand sensorgram), but does not block binding of inhibitory antibodies such as 27536, 27571, 27579, 27597, or 38347.

The commercially available A1 antibody represents a group of anti-human CD39 monoclonal antibodies that do not directly inhibit the ATPase activity of CD39 and do not bin with any of the other anti-CD39 antibodies described here. More than 30 antibodies were discovered that do not inhibit ECD ATPase activity, do not inhibit cellular CD39 ATPase activity, but do compete with A1 for binding to ECD. These antibodies may be considered to bin with anti-hCD39 antibody A1.

(b) Example of Antibodies that have Limited Ability to Inhibit the ATPase Activity of Both Soluble Recombinant and Cellular CD39 and Bin Separately from Other Cellular CD39 Inhibitors The methods are the same as set forth above except that instead of A1, the representative antibody was immobilized using anti-human IgG Fc Capture (AHC) biosensor.

Anti-hCD39 antibodies exemplified by 27536 and 28337 represent a group of antibodies that bind both soluble ECD and cellular CD39 and have the ability to inhibit their ATPase activity yet do not compete with other inhibitors for CD39 binding. Both 27536 and 28337 are able to inhibit the hydrolysis of ATP by hCD39 ECD compared to isotype or buffer controls as shown by µM Pi, as described herein (top left panel). 27536 and 28337 inhibit the hydrolysis of CD39 expressed on MEL-28 and OAW42 cells, as shown, compared to isotype control. Antibodies 27536 and 28337 represent a distinct bin group of anti-hCD39 inhibitory antibodies since they are blocked from binding CD39 ECD by another bin member that does not block other inhibitory antibodies such as 27571, 27579, 27597, or 38347 (see insert (c) at the bottom of FIG. 14B).

(c) Example of Antibodies that Inhibit the ATPase Activity of Soluble Recombinant CD39ECD but do not Inhibit Cellular CD39 and Bin Separately from Other CD39 ECD Inibitors The methods are as provided above, with the addition of experimental design where inhibition of 0.37 nM CD39 by 50 µg/ml antibody was challenged by ATP concentrations of 3-100 µM. Also, an 18 hour incubation was used with the antibody or isotype control. Finally, an additional 30 second baseline dip in buffer between antigen capture and dipping into a second competitor antibody for 300 seconds was used.

Figure 14C:
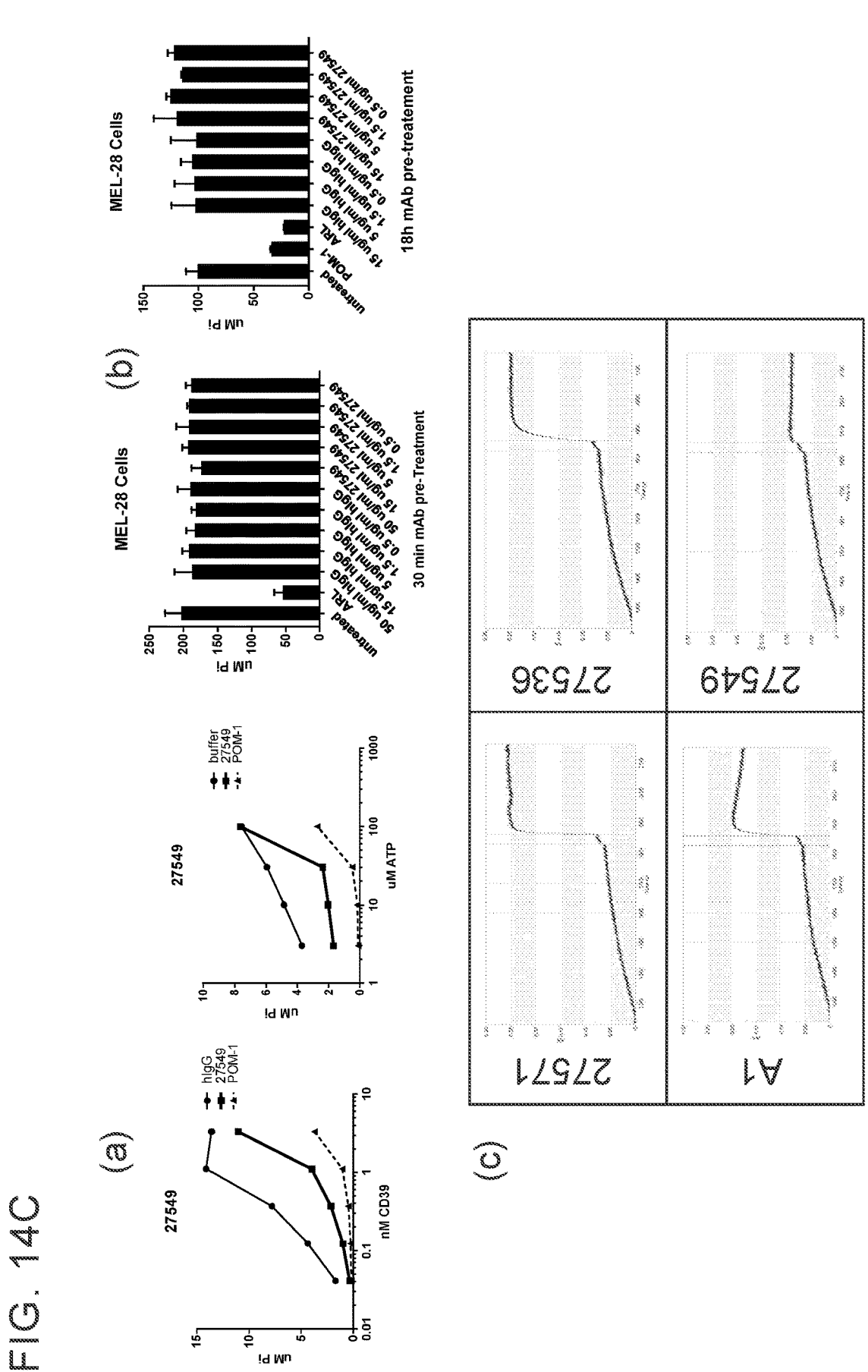
FIG. 14C provides example of antibodies that inhibit the ATPase activity of soluble recombinant CD39 ECD but do not inhibit cellular CD39 and bin separately from other CD39 ECD inhibitors.

Anti-hCD39 antibodies exemplified by 27549 represent a group of antibodies that can bind ECD and cellular CD39 but can only inhibit ECD ATPase activity and not cellular CD39 ATPase activity. As can be seen in FIG. 14C (top left), 27549 is able to inhibit the hydrolysis of ATP by hCD39 ECD compared to isotype or buffer controls. Also from FIG. 14C (top right), 27549 is unable to inhibit the hydrolysis of CD39 expressed on MEL-28 cells compared to isotype control. Antibodies 27536 and 28337 represent a distinct bin group of anti-hCD39 inhibitory antibodies since they are blocked from binding CD39 ECD by another bin member that does not block other inhibitory antibodies such as 27571, 27579, 27597, or 38347 (see FIG. 14C, bottom).

Antibody 27549 represents a group of anti-human CD39 monoclonal antibodies that directly inhibit the ATPase activity of sol CD39 ECD yet does inhibit cellular CD39 despite being able to bind to CD39 expressed on cells (FIG. 2). It does not compete with A1 or with any of the other inhibitory anti-CD39 antibodies described here for binding to ECD, so 27549 represents another bin of anti-hCD39 antibodies (see FIG. 14C).

(d) Example of Antibodies that Inhibit the ATPase Activity of ECD and Cellular CD39 and Bin Separately from Other CD39 ECD and/or Cellular Inhibitors The methods are as provided above.

Figure 14D:
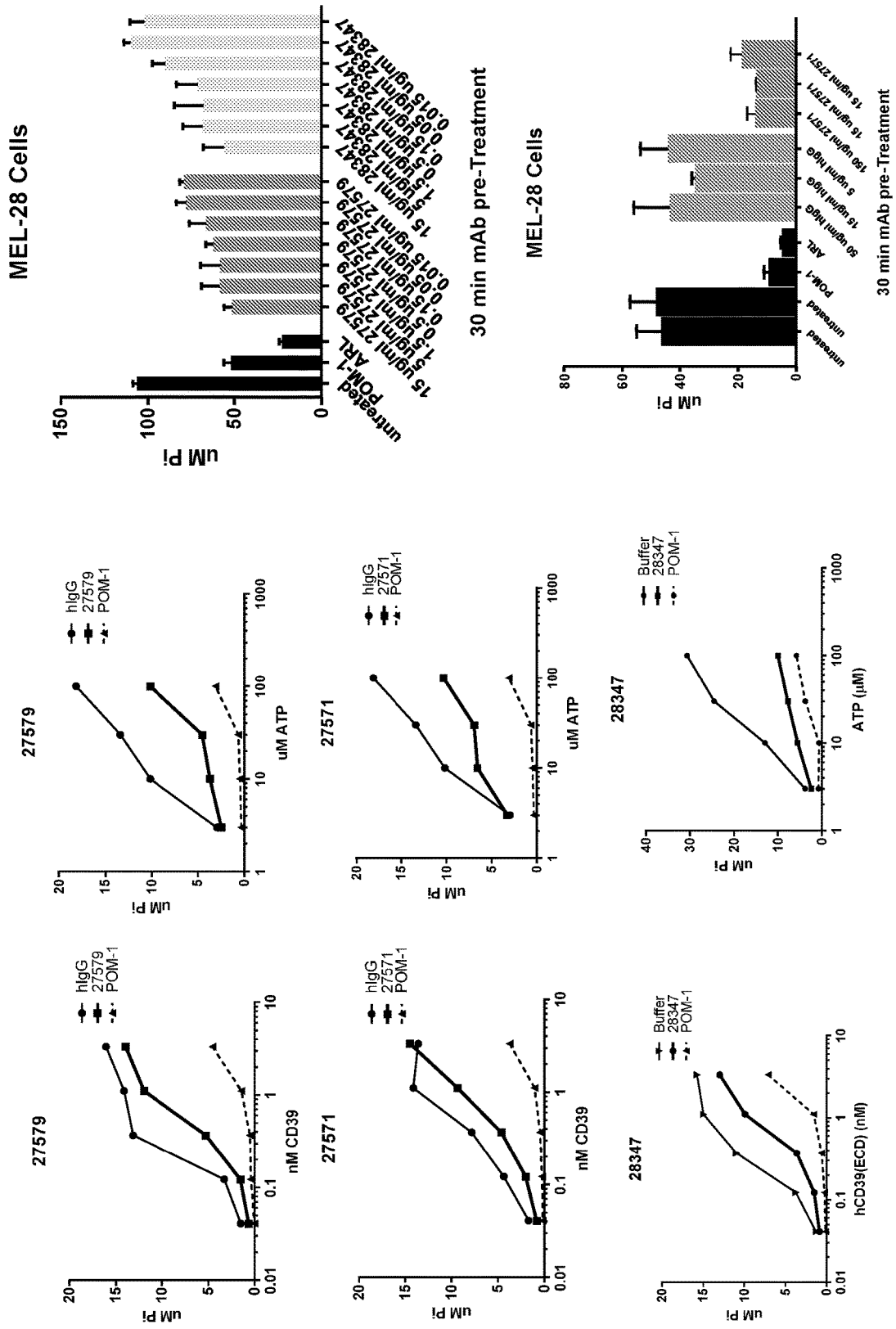
FIG. 14D provides examples of antibodies that inhibit the ATPase activity of ECD and cellular CD39 and bin separately from other CD39 ECD and/or cellular inhibitors.

Antibodies 27571, 27579 and 28347 represent a group of anti-human CD39 antibodies that directly inhibit the ATPase activity of soluble CD39 ECD and inhibit cellular CD39 and yet do not compete with A1, cellular inhibitors 27536 or 28337, or ECD inhibitor 27549 (FIGS. 14A-C) for binding to ECD. 27571, 27579, and 28347 are able to inhibit the hydrolysis of ATP by hCD39 ECD compared to isotype or buffer controls (see FIG. 14D, left). 27571, 27579, and 28347 also inhibit the hydrolysis of CD39 expressed on MEL-28 cells compared to isotype control (see FIG. 14D, right). These cellular inhibitors represent another bin of anti-hCD39 antibodies (see FIG. 14D).

(e) Examples of Inhibitory Antibodies that Make Distinct Contacts with CD39

Chimeras were generated by replacing human CD39 with mouse CD39 sequence in mammalian expression vectors. The chimeras were expressed in CHO cells and the ability of anti-human CD39 antibodies to bind the chimeras tested via FACS. In brief, cells were washed and blocked in FACS buffer (PBS/2% FBS) for 30 min on ice. They were then incubated with 15 µg/ml anti-human CD39 antibodies diluted in FACS buffer×1 h on ice. After 2 washes, cells were incubated with fluorescently labeled anti-human Fc antibodies, anti-mouse Fc antibodies, or anti-mCD39 antibody (R&D Systems 495826) diluted in FACS buffer per manufacturers' instructions×30 min on ice. After 2 washes, cells were resuspended in FACS buffer and analyzed on BD Fortessa. Data was processed with FlowJo. Positive binding was scored as "yes" and lack of binding was scored as "NO" and examples of FACS plots used to generate this table are in FIGS. 14.F and 14.G.

Chimeras formed between human and mouse CD39 distinguish regions critical for antibody contact that are unique to inhibitory antibodies such as 31414, 31895, 31873, 31901, 31905, reference antibodies such as BY40v9 and 9-8B, and commercial antibodies such as A1 and 498403. Columns 1 and 3 describe the human CD39 sequences flanking the mouse CD39 sequence described in column 2 Column 4 lists the exact mouse amino sequence in the chimera.

The antibodies described thus far have no/minimal cross-reactivity to mouse CD39, which shares 78% percent identity with human CD39 in the extracellular domain. Chimeras were therefore made between human and mouse CD39 in order to identify those region(s) critical to antibody recognition and binding. To that end, 8 chimeras were generated with the sequence swaps chosen based on sequence diversity between human and mouse CD39 and potential for surface exposure based on rat ENTPD1 and rat ENTPD2 crystal structures. Thus, these 8 chimeras do not comprehensively interrogate all potential contact residues. All tested antibodies were able to bind Chimeras #1,3,5,6,7, and 8, suggesting that these chimeras maintained overall global structural integrity. A1 and 498403 lost the ability to bind Chimera #4, indicating that residues critical to their contact with human CD39 had been lost. A1, 498403, BY40v9 and 9-8B were able to bind Chimera #2, suggesting that this chimera maintained overall global structural integrity. In contrast, inhibitory antibodies 31414, 31895, 31901, 31905, and 31873 were able to bind all chimeras but Chimera #2. Thus, Chimera #2 has lost residues critical to making contacts with these antibodies and therefore E143-N158 constitute part or all of the human CD39 epitope for these antibodies. Notably, these antibodies belong to the bin group exemplified by 27571, 27579 and 28347 in FIG. 14D, i.e. they do not bin with anti-CD39 antibody bin groups represented by antibodies A1, 27536, or 27549.

Chimeras were generated by mutagenesis of Chimera #2 or WT hCD39 expression vectors. Residues for mutagenesis were chosen based on divergence between human and mouse CD39. The chimeras were expressed in CHO cells and the ability of anti-human CD39 antibodies to bind the chimeras tested via FACS, as described in FIG. 14E. Table 2. Positive binding was scored as "Yes" and lack of binding was scored as "No" and examples of FACS plots used to generate this table are in FIGS. 14.F and 14.G.

Figure 14F:
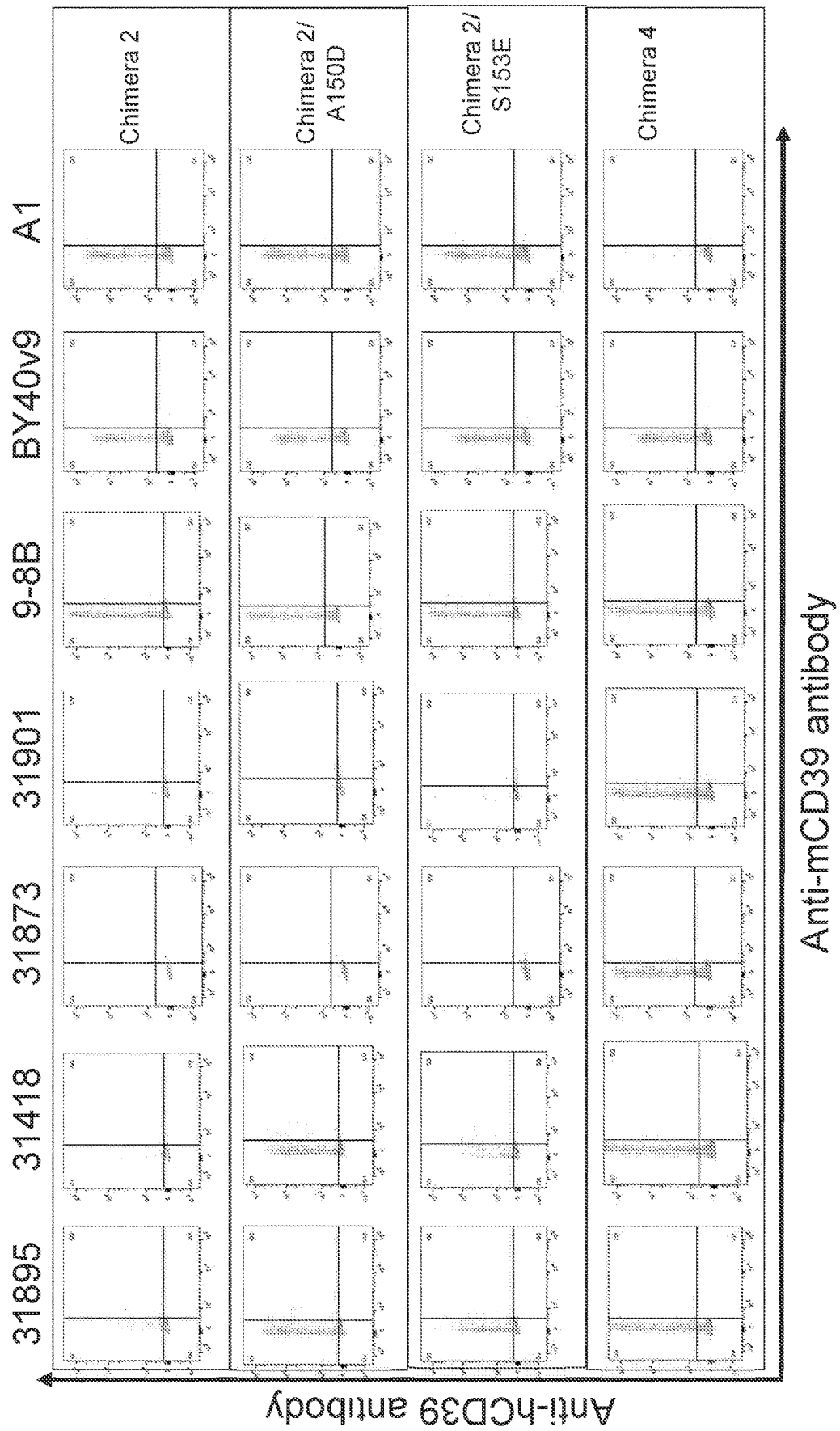
FIG. 14F and FIG. 14G provide FACS plotting highlighting the importance of certain human CD39 residues.
Figure 14G:
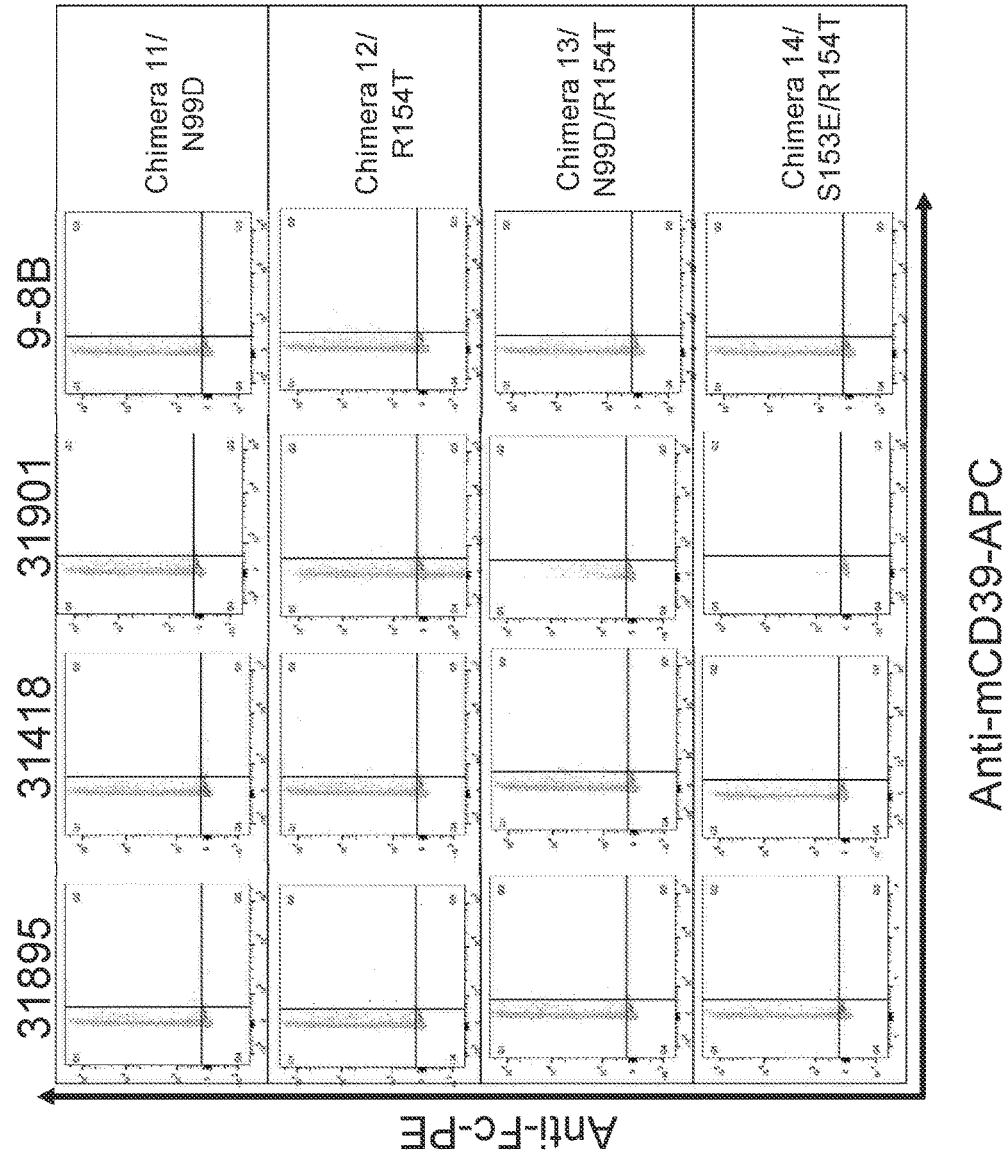

Specific residues critical for antibody contact can distinguish inhibitory antibodies 31414, 31418, and 31895 from 31901, 31905, and 31873. Individual amino acids in the mouse sequence of human-mouse Chimera #2, when reverted back to the respective human residue (resulting in Chimera #9,10), restore the ability of antibodies 31895, 31414, 31418 to bind to CD39 but not the ability of 31901, 31905, or 31873 to bind CD39. Mutation of individual residues in the context of otherwise fully human CD39 (Chimeras #11,12) did not impair the binding ability of any of the tested antibodies. Co-mutation of two human residues to the cognate mouse residues (Chimeras #13,14) did not impair binding by antibodies 31414, 31418 or 31895. In stark contrast, antibodies 31901, 31905, and 31873 completely lost their ability to bind Chimeras #13 and 14. The ability of indicated antibodies to bind a given chimera was determined by FACS. In particular, FIG. 14F and FIG. 14G show representative FACS plots used to populate this table and FIG. 14G shows the importance of human CD39 residues N99, R154, and/or 5153 in recognition by antibodies represented by 31901, 31905, and 31873.

As demonstrated in FIG. 14E, Table 1, inhibitory antibodies 31414, 31418, 31895, 31901, 31905 and 31873 can be distinguished from other monoclonal anti-CD39 antibodies based on their inability to recognize Chimera #2. In Table 2, these antibodies are further distinguished by the gain or loss of the ability to bind specific point mutants of hCD39 or Chimera #2. Thus, these antibodies, while binding the same general region of human CD39, form distinct contacts with different critical residues in hCD39. Since these antibodies share the requirement for residues E143-N158, they may share some common contact residues yet can be differentiated based on the demonstrated unique points of contact.

(f) FACS Plots Highlighting the Importance of Human CD39 Residue D150 and/or E153 in Recognition of Antibodies Represented by 31414, 31418, and 31895 and FACS Plots Highlighting the Importance of Human CD39 Residues N99, R154, and/or E153 in Recognition by Antibodies Represented by 31901, 31905, and 31873

The methods are as provided above for the examples of inhibitory antibodies that make distinct contacts with CD39.

The ability of indicated antibodies to bind to a given chimera was determined by FACS.

While antibodies 31414, 31418, 31895, 31873, 31901, and 31905 all share a common requirement for human CD39 residues E143-N158, these antibodies make different critical contacts with residues within and outside of this region. Thus, antibodies, which belong to the bin group represented, by antibodies 27571, 27579, and 28347 (FIG. 14.D) can be further distinguished into at least two more groups based on sensitivity to distinct residues. There are at least 5 bin groups: (1) A1-like antibodies that compete each other for ECD binding yet do not inhibit ECD activity, but do not compete with antibodies in bin groups 2,3,4, or 5 for ECD binding and make critical contacts with N275-I277 as evidenced by loss of binding to Chimera #4; (2) 27536/28337-like antibodies that compete each other for ECD binding and can inhibit both ECD and cellular CD39 ATPase activity, but do not compete with antibodies in bin groups 1,3,4 or 5 for ECD binding; (3) 27549-like antibodies that compete each other for ECD binding and can inhibit CD39 ECD but not cellular CD39, and do not compete with antibodies in bin groups 1,2,4 or 5 for ECD binding; (4) 31414/31418/31895-like antibodies that make critical contacts with E143-N158 in cellular CD39 including (but not limited to) D150 and E153, inhibit the ATPase activity of both ECD and cellular CD39, compete with each other for ECD binding, but do not compete with antibodies in bins 1, 2 or 3 for ECD binding; and (5) 31873/31901/31905-like antibodies that make critical contacts with E143-N158 in cellular CD39 including (but not limited to) E153 and R154, as well as a sensitivity to residue N99, inhibit the ATPase activity of both ECD and cellular CD39, compete with each other for ECD binding, but do not compete with antibodies in bins 1, 2, or 3 for ECD binding. Thus, there are anti-human CD39 antibodies that can be distinguished based on their affinity for ECD, affinity for cells, ability to inhibit ECD ATPase activity, ability to inhibit cellular ATPase activity, and points of contact with CD39. For example, 27549 binds both ECD (FIG. 1) and cells well (FIG. 2) yet can only inhibit ECD ATPase activity. 27579 binds ECD weakly but is a potent cellular CD39 inhibitor.

Example 16: Anti-CD39 Antibodies are Reversible Allosteric, not Competitive, Inhibitors Due to $V_{max}$ Suppression of $V_{max}$ Anti-CD39 antibodies or isotype control antibody (100 nanomolar final concentration) were incubated with MEL-28 cells (35,000 MEL-28 cells/well) endogenously expressing human CD39 at 37° C. for 20 minutes in the presence of EnzChek reagents (PNP & MESG) Immediately following the addition of ATP (final concentrations ranging from 0-450 micromolar), the rate of ATP hydrolysis to free phosphate (Pi) by CD39 was monitored over time at Abs360 nm using SpectraMax i3x plate reader. The initial enzyme velocity, v0, was determined from the linear region of Pi vs. time curve for each ATP concentration. The plot of v0 vs. [ATP] was curve fit using non-linear regression of the Michaelis-Menten kinetic model.

Figure 15:
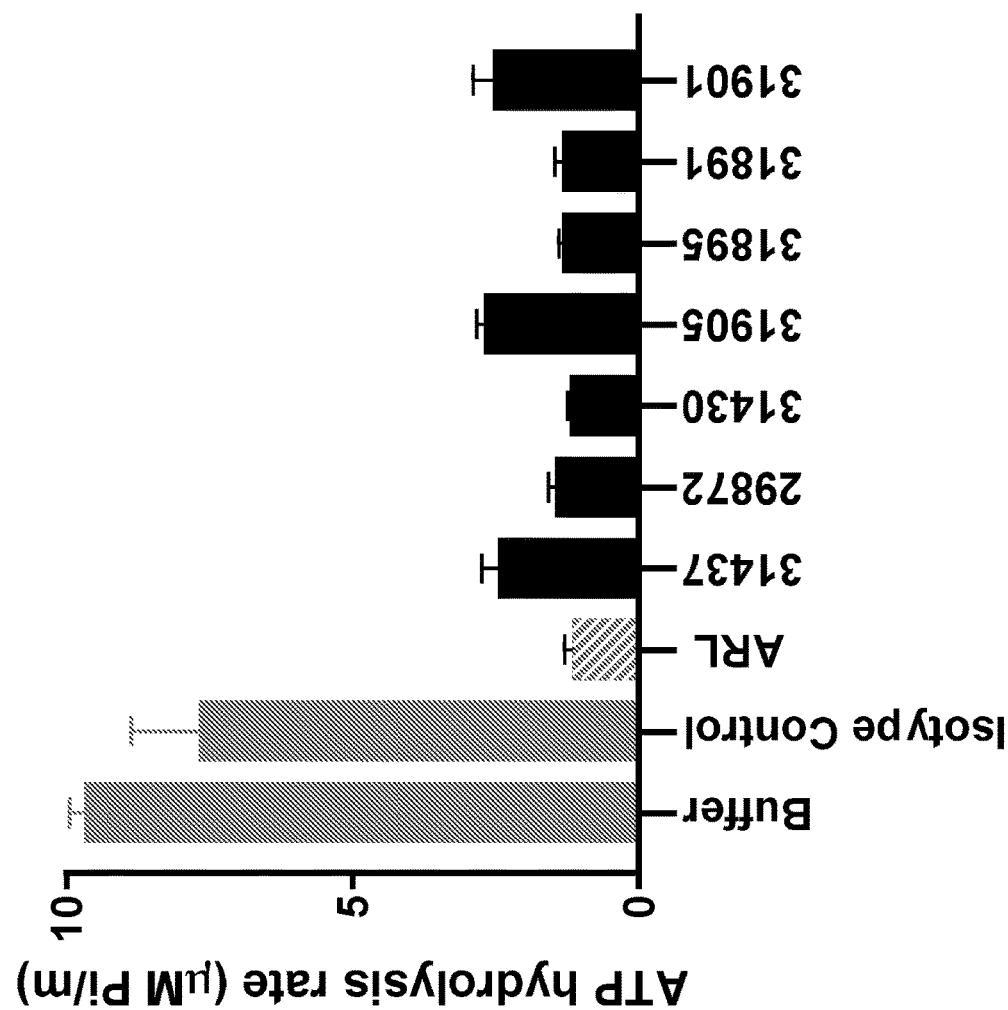
FIG. 15 shows that anti-CD39 antibodies inhibit CD39 by 75-90%. Anti-CD39 antibodies (100 nanomolar), isotype control antibody (100 nanomolar), or ARL (200 micromolar) were incubated with MEL-28 cells endogenously expressing human CD39 for 2 hours. ATP was then added and the rate of ATP hydrolysis to Pi by CD39 was monitored using the EnzChek kinetic Pi detection assay. The initial enzyme velocity, v0, was determined from the linear region of Pi vs. time curve over the first 15 minutes post-ATP addition. Each value is the mean of 3 replicates.

The ATP hydrolysis rate by CD39 expressed on MEL-28 cells can be markedly reduced by the anti-CD39 antibodies (see FIG. 15). The ATP hydrolysis rate in the presence of the anti-CD39 antibodies ranges from 1.2 to 2.7 micromolar Pi per minute, which is much less than the ATP hydrolysis rate observed in the presence of an isotype control antibody (7.7 micromolar Pi per minute) and similar in magnitude to the pan ATPase inhibitor ARL (1.2 micromolar Pi per minute).

Figure 16A:
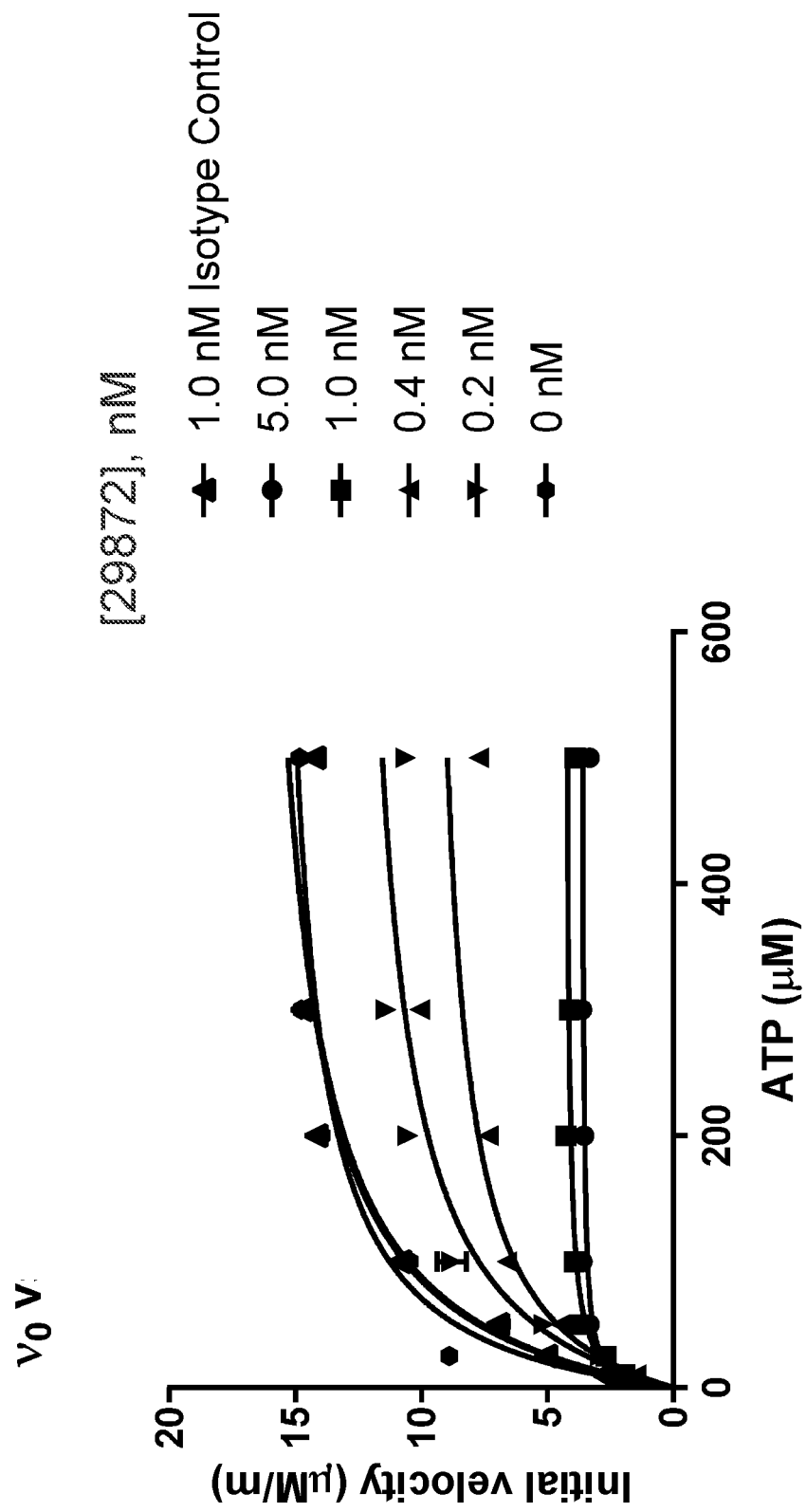
FIGS. 16A-B shows that the CD39 inhibitor 29872 is not a competitive inhibitor due to suppression of $V_{max}$ suppression.
Figure 16B:
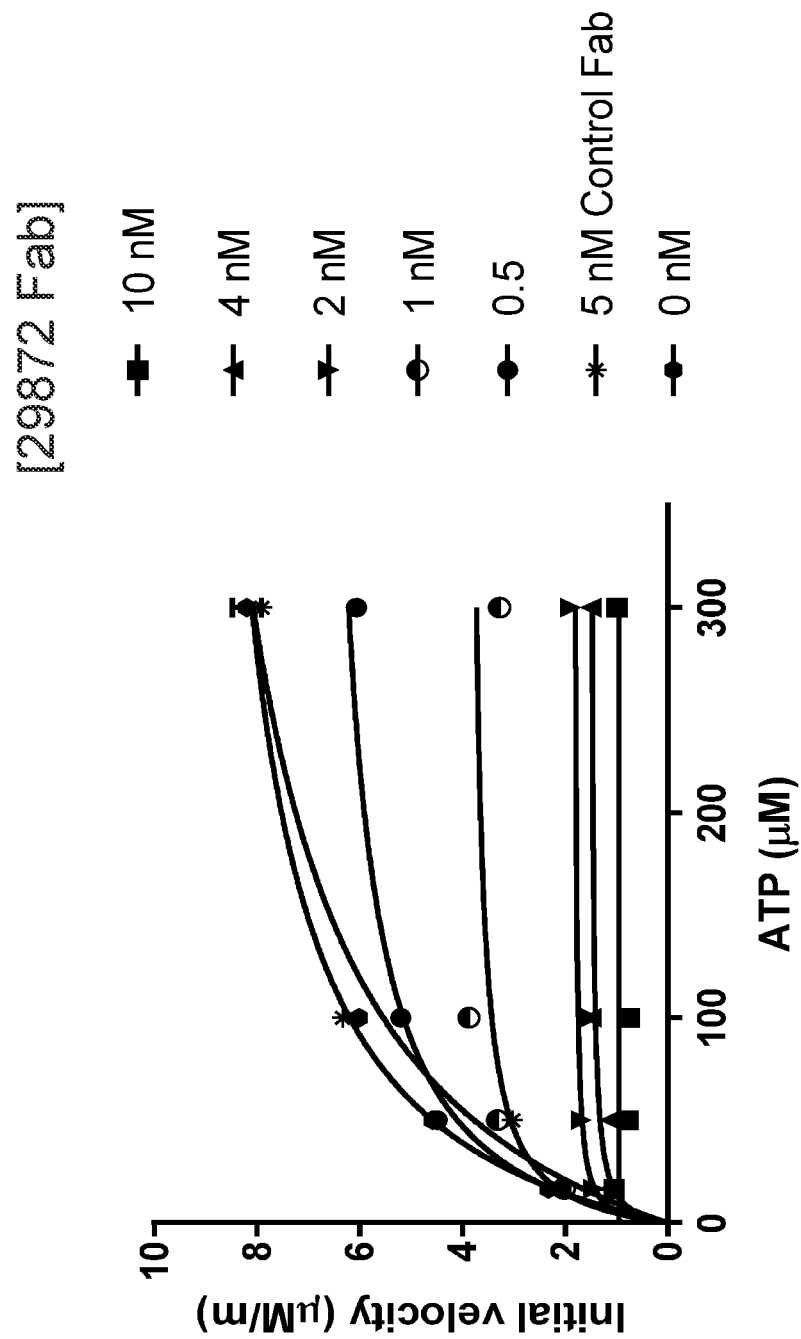

The plot of initial velocity versus ATP concentration for multiple concentrations of the anti-CD39 antibody 29872 indicates that the mechanism of inhibition of this IgG antibody is not competitive (see FIG. 16 A.). The reduction in initial velocity is constant for ATP concentrations above 100 micromolar (100, 200, 300 and 500 micromolar) in the presence of 5 nanomolar 29872. 29872 could be a non-competitive inhibitor, an un-competitive inhibitor, or a mixed inhibitor of CD39 (having properties of both non-competitive and un-competitive inhibition). The monovalent Fab form of anti-CD39 antibody 29872 showed a very similar inhibition profile (see FIG. 16 B.), indicating that the CD39 inhibition activity of 29872 is not dependent on the bivalent structure of the IgG and the potential properties that could result from IgG bivalency such as CD39 crosslinking.

Many of the other anti-CD39 antibodies tested in this assay showed a similar profile for CD39 enzymatic inhibition (data not shown), indicating that they also may be non-competitive inhibitors, un-competitive inhibitors, or mixed inhibitors of CD39. The mechanism of enzymatic inhibition of these antibodies suggests that they retain their full inhibition of CD39 enzymatic inhibition at high ATP concentrations. The anti-CD39 antibodies appear to be reversible inhibitors.

Example 17: Anti-CD39 can Induce Internalization of CD39 on Cyno Monocytes

Figure 17:
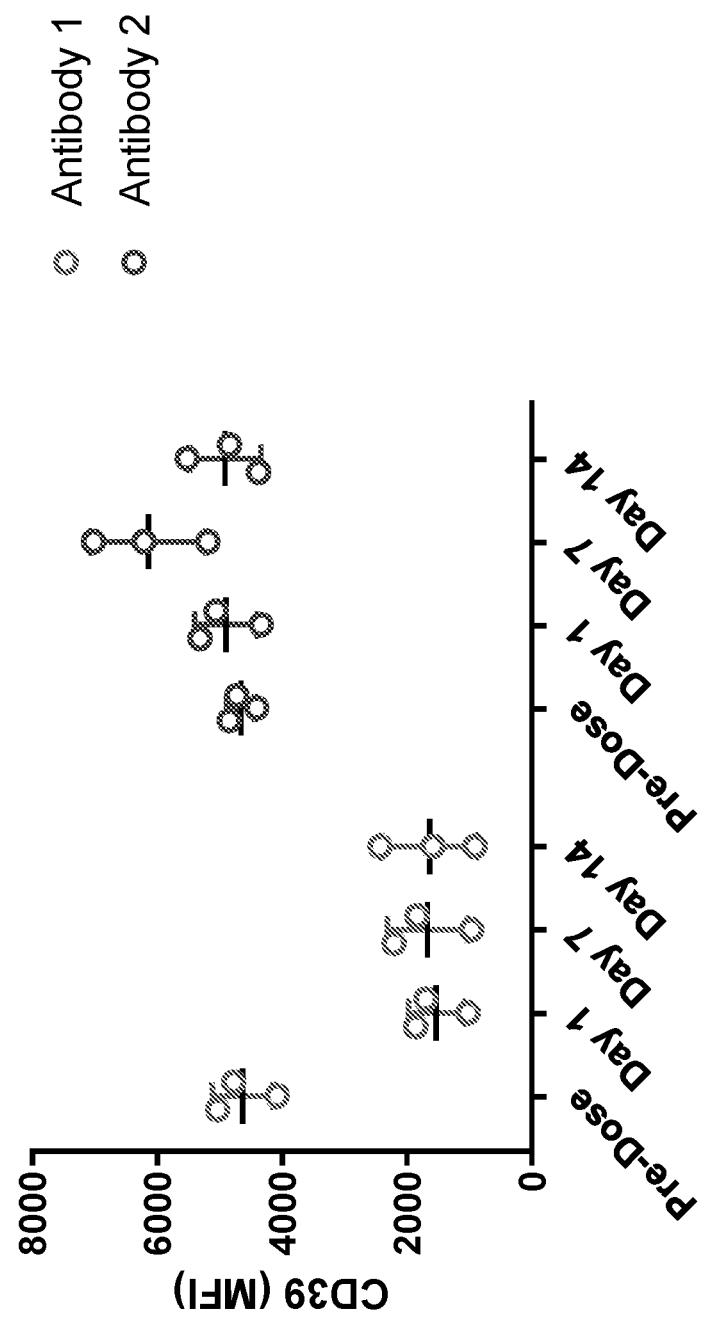
FIG. 17 shows that anti-CD39 antibodies can induce internalization of CD39 on cyno monocytes.
Figure 18:
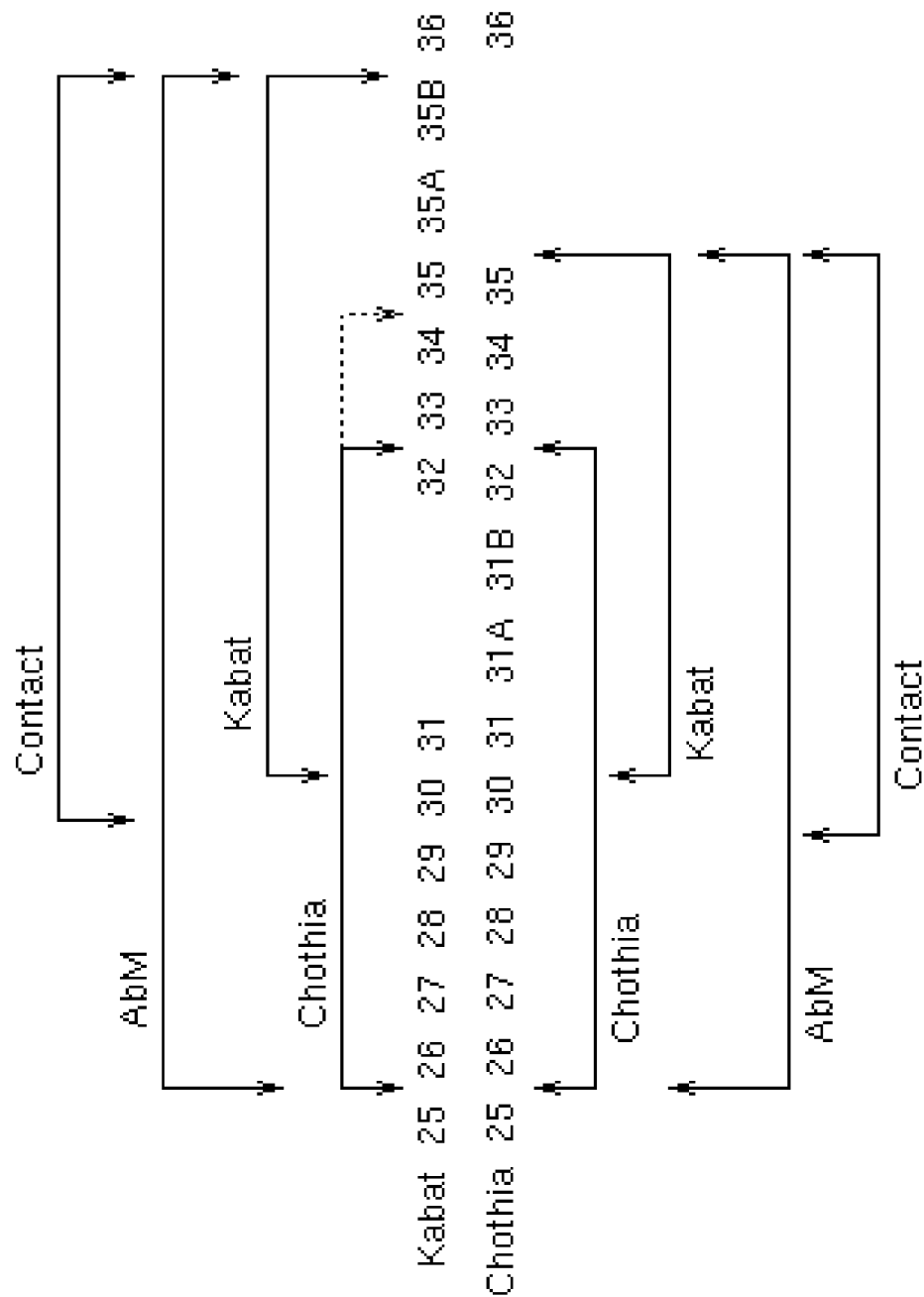
FIG. 18 provides a comparison of the Kabat and Chothia numbering systems for CDR-H1. Adapted from Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.

Anti-CD39 antibodies were injected into cynomolgus monkeys to test for ability to downregulate CD39 on cell surface of cyno monocytes. CD39 internalization was assessed by FACS of whole blood samples collected pre-dose, Day 1, Day 7, and Day 14 after antibody treatment. Non-competing anti-CD39-PE antibody (clone A1) was used to measure CD39 levels on CD14+ gated monocytes. Data is shown as MFI of A1-PE on gated cyno monocytes in FIG. 17.

Cynomolgus monkeys were injected with anti-CD39 antibodies at 10 mg/kg. Blood samples were collected prior to injection and on Day 1, Day 7, and Day 14 after treatment. For each time-point, 50 uL of cynomolgus whole blood was incubated with 30 uL of staining buffer (PBS, 2% FBS, 2 mM EDTA, 3% mouse serum, 5% goat serum) containing CD14 and CD20 antibodies (eBioscience) and an Fc blocking reagent (BD) for 30 minutes at 4 C. CD39 antibody (clone eBioAl, eBioscience) was added to the sample and incubated for an additional 40 minutes at 4 degrees C. Following incubation, the samples were treated with ACK lysis buffer (ThermoFisher) for 10 minutes at room temperature to lyse red blood cells. Samples were washed several times with staining buffer and fixed with 1% PFA (Sigma) before acquisition on a BD Fortessa X-20 flow cytometer. Total CD39 receptor expression on CD14 positive monocytes was determined by mean fluorescence intensity.

CD39 was highly expressed on cyno monocytes prior to antibody treatment in all blood samples tested (pre-dose). Anti-CD39 antibodies tested in vivo had distinct internalization profiles where antibody 1 treatment led to downregulation of CD39 on cell surface of monocytes and antibody 2 had no effect on overall CD39 levels. Apparent decrease of CD39 levels after antibody 1 treatment was not due to A1 antibody competing with antibody 1 for binding to CD39 as the epitopes for A1 and antibody 1 are distinct from each other.

Example 18: Anti-CD39 Antibody Increases Stimulated Human CD4+ and CD8+ T Cell in the Presence of Exogenous ATP Anti-CD3+anti-CD28 stimulated PBMCs were treated with anti-CD39 antibody 31895 or isotype control in the presence of 50 µM ATP for 96 hours. Proliferation of CD4+ and CD8+ T cells was measured by Cell Trace Violet by flow cytometry.

Figure 19:
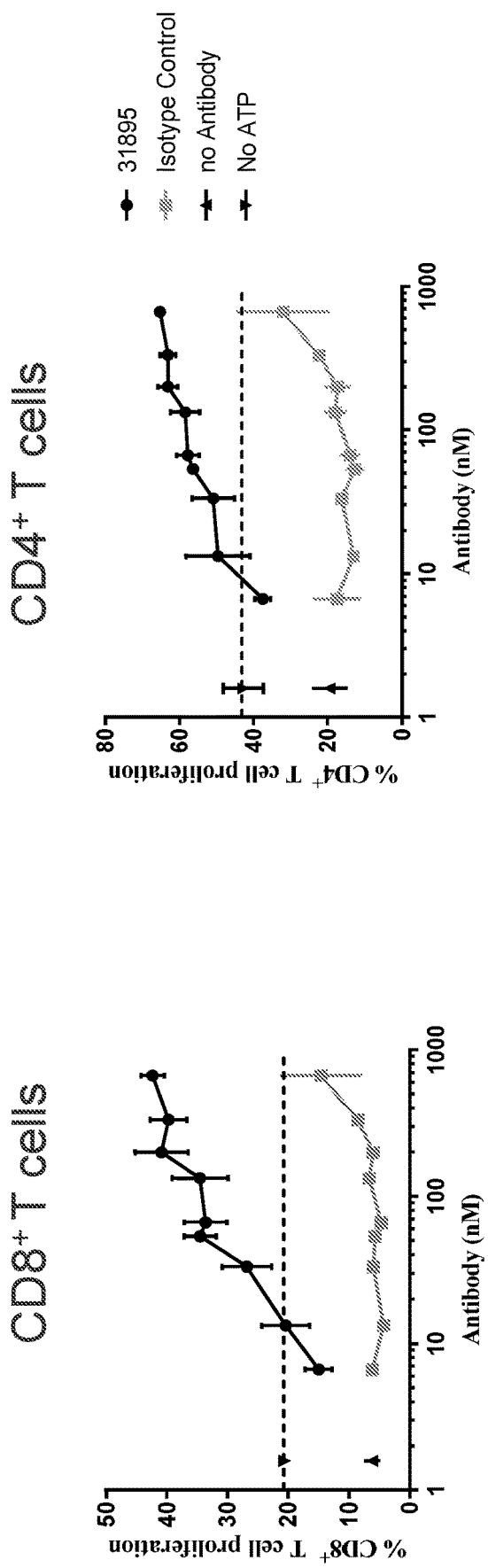
FIG. 19 shows an anti-CD39 antibody increases proliferation of stimulated CD4$^+$ and CD8$^+$ T cells.

FIG. 19 shows that anti-CD39 antibody increases proliferation of stimulated human CD4+ and CD8+ T cell in the presence of exogenous ATP. The left side shows CD8+ T cells, with the x-axis showing antibody (nM) and the y-axis showing % CD8+ T cell proliferation. The right side shows CD4+ T cells, with the x-axis showing antibody (nM) and the y-axis showing % CD4+ T cell proliferation. The inset to the right shows symbols for the respective antibodies and controls.

Example 19: Anti-CD39 Antibody Increase Stimulated PBMC Secretion of INF-γ, TNF-α and IL-2

Human PBMCs were treated with anti-CD3+anti-CD28 and incubated with anti-CD39 antibody 31895 or isotype control in presence (B) or absence (A) of exogenous ATP (5004). Supernatants were harvested after 96 hours and cytokines were measured using a Meso Scale Discovery human cytokine kit.

FIG. 20 shows anti-CD39 antibody 31895 increases cytokine secretion by anti-CD3+anti-CD28 activated PBMC in absence (A) or presence (B) of exogenous ATP in a dose dependent manner. The top row shows results with exogenous ATP added and the bottom row shows results with no exogeonous ATP added. The x-axis shows antibody (nM) and the y-axis shows secretion of INF-γ, TNF-α and IL-2, respectively.

Example 20: Anti-CD39 Antibody Increases Stimulated PBMC Secretion of INF-γ, TNF-α, IL-2 and IL-1β

Human PBMCs were stimulated with anti-CD3+anti-CD28 and incubated with anti-CD39 antibodies 31895, HAO-391 (See, SEQ ID 10/SEQ ID 11 from WO 2017/089334), HAO mAb4 (See SEQ ID 12/SEQ ID 13 from WO2017157948) or isotype control at a fixed concentration of 50 µg/ml in presence of ATP. Supernatants were harvested after 96 hours and analyzed by Meso Scale Discovery human cytokine kit.

Figure 21:
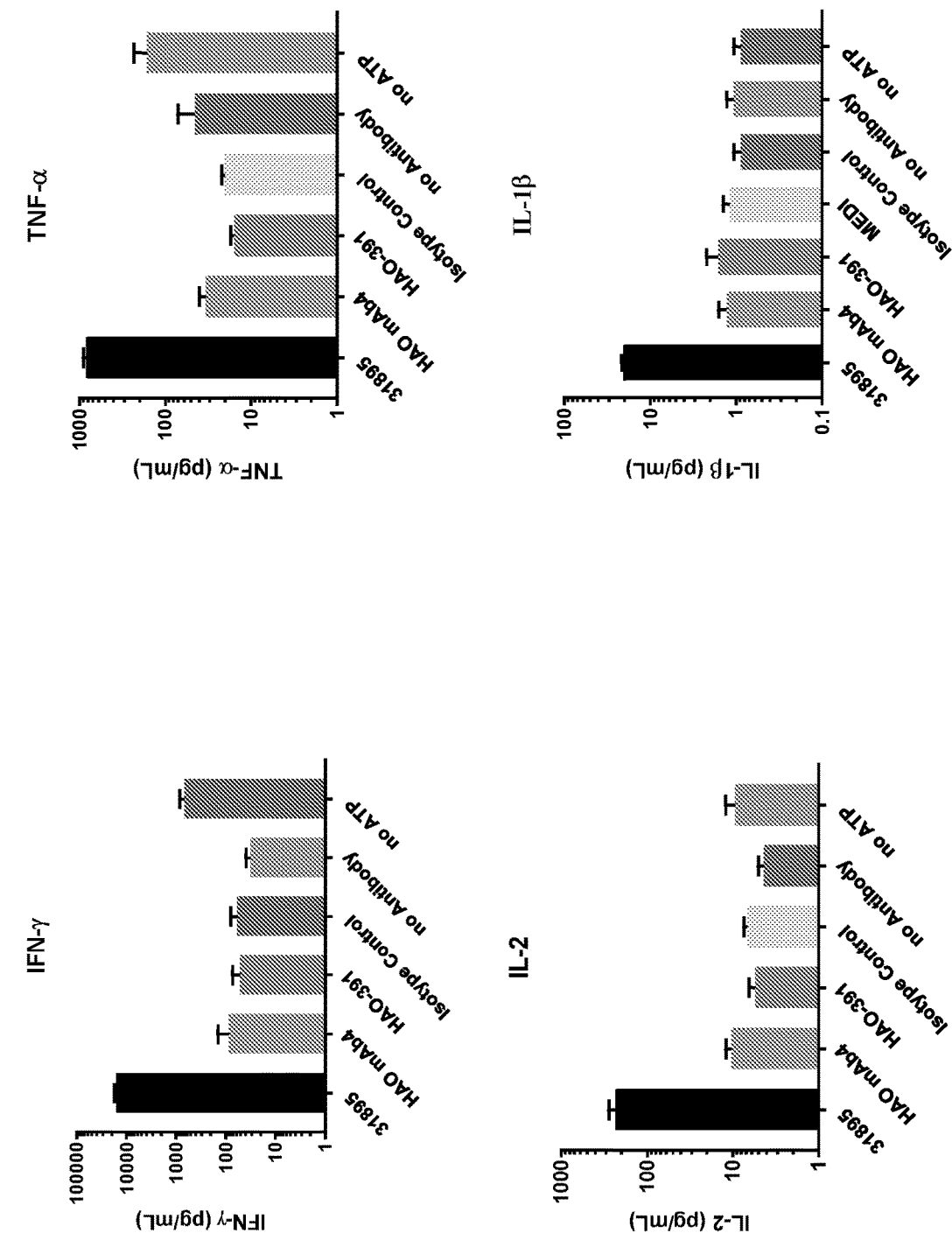
FIG. 21 shows anti-CD39 antibody increases stimulated PBMC secretion of INF-γ, TNF-α, IL-2 and IL-1β.

FIG. 21 shows anti-CD39 antibody 31895 increased cytokine release by activated PBMCs to a higher degree compared to anti-CD39 antibodies HAO-391 (VL SEQ ID No. 10; VH SEQ ID No. 11 from WO 2017/089334) and HAO mAb4 (VL SEQ ID No. 12; VH SEQ ID No. 13 from WO2017157948). The x-axis indicates the andtibody and/or conditions and the y-axis shows INF-γ, TNF-α, IL-2 and IL-10, respectively.

Example 21: Anti-39 Antibody 31895 Increase Extracellular ATP Accumulation and Reduces Adenosine Generation by $CD39^+CD73^+$SK-MEL-28 Cells SK-MEL-28 cells were treated with 31895, isotype control, or small molecule inhibitors (EHNA, ARL, or POM-1) for 1 hour and 50 µM ATP was added for 15 min prior to harvesting of the supernatants. The supernatants were analyzed for ATP levels using AmpGlo Kit (A) and for adenosine levels using LC/MS analysis (B). % Adenosine levels were normalized to isotype control (100%) and SK-MEL-28 CD39 KO cells (0%).

The results are shown in FIG. 22. The left graph shows ATP accumulation and the right graph shows adenosine generation (LC/MC). The x-axis for each graph shows conditions. The y-axis for the left graph shows ATP (µM) and the y-axis for the right graph shows % of adenosine levels.

Example S: Sequences

Table S provides sequences referred to herein.

TABLE S

| SEQ ID NO: | Region | Scheme/Clone | Sequence |
|---|---|---|---|
| 1 | CDR-H1 | Chothia | GYTFTSY |
| 2 | CDR-H1 | Chothia | GYTFKSY |
| 3 | CDR-H1 | Chothia | GYIFKSY |
| 4 | CDR-H1 | Chothia | GYTFQSY |
| 5 | CDR-H1 | Chothia | GYTFFSY |
| 6 | CDR-H1 | Chothia | GYTFVSY |
| 7 | CDR-H1 | Chothia | GGTFSSLAIS |
| 8 | CDR-H1 | Chothia | GGTFSKLAIS |
| 9 | CDR-H1 | Chothia | GGTFSHT |
| 10 | CDR-H1 | Chothia | GGTFSSL |
| 11 | CDR-H1 | Chothia | GGTFSLL |
| 12 | CDR-H1 | Chothia | GGTFQSL |
| 13 | CDR-H1 | Chothia | GGTFPSN |
| 14 | CDR-H1 | Chothia | GGTFSAM |
| 15 | CDR-H1 | Chothia | GGTFASL |
| 16 | CDR-H1 | Chothia | GGTFSWL |
| 17 | CDR-H1 | Chothia | GGTFSSY |
| 18 | CDR-H1 | Chothia | GGTFGSY |

TABLE S-continued

Sequences.

| SEQ ID NO: | Region | Scheme/Clone | Sequence |
|---|---|---|---|
| 19 | CDR-H1 | Chothia | GGTFSKY |
| 20 | CDR-H1 | Chothia | GGTFGRY |
| 21 | CDR-H1 | Chothia | GGTFESY |
| 22 | CDR-H1 | Chothia | GGTFSNY |
| 23 | CDR-H1 | Chothia | GGAFSSY |
| 24 | CDR-H1 | Chothia | GFTFSSY |
| 25 | CDR-H1 | Kabat | SYYMH |
| 26 | CDR-H1 | Kabat | SYEMH |
| 27 | CDR-H1 | Kabat | SYQMH |
| 28 | CDR-H1 | Kabat | SYYMY |
| 29 | CDR-H1 | Kabat | SYFMH |
| 30 | CDR-H1 | Kabat | SLAIS |
| 31 | CDR-H1 | Kabat | KLAIS |
| 32 | CDR-H1 | Kabat | HTAIS |
| 33 | CDR-H1 | Kabat | SLPIS |
| 34 | CDR-H1 | Kabat | LLAIS |
| 35 | CDR-H1 | Kabat | SNAIS |
| 36 | CDR-H1 | Kabat | AMAIS |
| 37 | CDR-H1 | Kabat | WLAIS |
| 38 | CDR-H1 | Kabat | SYAIS |
| 39 | CDR-H1 | Kabat | SYGIS |
| 40 | CDR-H1 | Kabat | KYGIS |
| 41 | CDR-H1 | Kabat | NYAIS |
| 42 | CDR-H1 | Kabat | SYATS |
| 43 | CDR-H1 | Kabat | SYAIG |
| 44 | CDR-H1 | Kabat | SYSMN |
| 45 | CDR-H1 | Kabat | SYGMN |
| 46 | CDR-H2 | Chothia | NPSGGST |
| 47 | CDR-H2 | Chothia | NPSVGS |
| 48 | CDR-H2 | Chothia | NPSGGS |
| 49 | CDR-H2 | Chothia | NPLGGG |
| 50 | CDR-H2 | Chothia | NPRGGS |
| 51 | CDR-H2 | Chothia | IPIFGT |
| 52 | CDR-H2 | Chothia | GFGT |
| 53 | CDR-H2 | Chothia | LPIGGT |
| 54 | CDR-H2 | Chothia | LPIAGT |
| 55 | CDR-H2 | Chothia | LPIFGE |

TABLE S-continued

Sequences.

| SEQ ID NO: | Region | Scheme/Clone | Sequence |
|---|---|---|---|
| 56 | CDR-H2 | Chothia | IPRGGT |
| 57 | CDR-H2 | Chothia | IPEFGI |
| 58 | CDR-H2 | Chothia | IPSIGT |
| 59 | CDR-H2 | Chothia | IPISGT |
| 60 | CDR-H2 | Chothia | IPTFGT |
| 61 | CDR-H2 | Chothia | SSSSSY |
| 62 | CDR-H2 | Chothia | WYDGSN |
| 63 | CDR-H2 | Kabat | VINPSGGSTSYAQKFQG |
| 64 | CDR-H2 | Kabat | RINPSVGSTWYAQKFQG |
| 65 | CDR-H2 | Kabat | RINPSGGSTWYAQKFQG |
| 66 | CDR-H2 | Kabat | KINPSGGSTWYAQKFQG |
| 67 | CDR-H2 | Kabat | VINPLGGTSYAQKFQG |
| 68 | CDR-H2 | Kabat | SINPRGGSTSYAQKFQG |
| 69 | CDR-H2 | Kabat | GIIPIFGTANYAQKFQG |
| 70 | CDR-H2 | Kabat | GI--GFGTANYAQKFQG |
| 71 | CDR-H2 | Kabat | GILPIGGTANYAQKFQG |
| 72 | CDR-H2 | Kabat | GILPIAGTANYAQKFQG |
| 73 | CDR-H2 | Kabat | GILPIFGEANYAQKFQG |
| 74 | CDR-H2 | Kabat | GIIPRGGTANYAQKFQG |
| 75 | CDR-H2 | Kabat | SIIPIFGTANYAQKFRG |
| 76 | CDR-H2 | Kabat | SIIPEFGIANYAQKFQG |
| 77 | CDR-H2 | Kabat | SIIPIFGTANYAQKFQG |
| 78 | CDR-H2 | Kabat | GIIPISGTANYAQEFQG |
| 79 | CDR-H2 | Kabat | GIIPTFGTANYAQKFQG |
| 80 | CDR-H2 | Kabat | SISSSSSYIYYADSVKG |
| 81 | CDR-H2 | Kabat | VIWYDGSNKYYADSVKG |
| 82 | CDR-H3 | | GKREGGTEYLRH |
| 83 | CDR-H3 | | GKREGGTEYLRK |
| 84 | CDR-H3 | | GKREGGTEYLRS |
| 85 | CDR-H3 | | GKREGGTEYLRN |
| 86 | CDR-H3 | | GKREGGTEYLRV |
| 87 | CDR-H3 | | GGAKYASTYGMDV |
| 88 | CDR-H3 | | GGAKYASTHGMDV |
| 89 | CDR-H3 | | GGAKYASQLGMDV |
| 90 | CDR-H3 | | GGAKYASKWGMDV |
| 91 | CDR-H3 | | GGAKYAVGYGMDV |
| 92 | CDR-H3 | | GGAKYAGRYGMDV |
| 93 | CDR-H3 | | GGAKYARTYGMDV |

TABLE S-continued

Sequences.

| SEQ ID NO: | Region | Scheme/Clone Sequence |
|---|---|---|
| 94 | CDR-H3 | ESGGYRDHRLDV |
| 95 | CDR-H3 | ESGTYRDHRLDV |
| 96 | CDR-H3 | ESGGYRDHRLGV |
| 97 | CDR-H3 | DFTDYSSGYSSGWTY |
| 98 | CDR-H3 | DTLYSSGAYYGYNV |
| 99 | CDR-H3 | AKRGYDSYGGVYFDY |
| 100 | CDR-H3 | GPTVTATTSIGTHNWFDP |
| 101 | CDR-H3 | EGRGYDSSRYYKFWFDPWGQGTLVTVSS |
| 102 | CDR-H3 | DGGGYRHHYFDL |
| 103 | CDR-H3 | ESGGYRDHKLDV |
| 104 | CDR-H3 | DGGGYQHHYFDL |
| 105 | CDR-H3 | DSGYHRHYSDY |
| 106 | CDR-H3 | DPLGIRKHWFDP |
| 107 | CDR-H3 | DTPRWRYHYFDY |
| 108 | CDR-H3 | ERRGSLALGMDV |
| 109 | CDR-H3 | DLGGYSYGEPYYYYYGMDV |
| 110 | CDR-L1 | RASQSVSSSYLA |
| 111 | CDR-L1 | RASQSVASSYLA |
| 112 | CDR-L1 | EASQSVSYSYLA |
| 113 | CDR-L1 | KASESVSSSYLA |
| 114 | CDR-L1 | RASQYVSSSYLA |
| 115 | CDR-L1 | KSSQSVLFSSNNKNYLA |
| 116 | CDR-L1 | KSSRSVLFSSNNKNYLA |
| 117 | CDR-L1 | KSSKSVLYSNNNKNYLA |
| 118 | CDR-L1 | RASQSVGSNLA |
| 119 | CDR-L1 | KSSQSVLYSSNNKNYLA |
| 120 | CDR-L1 | QASQDISNYLN |
| 121 | CDR-L1 | RASQSVSSYLA |
| 122 | CDR-L1 | RASQSVSRYLA |
| 123 | CDR-L1 | RASQSISSWLA |
| 124 | CDR-L1 | RASQSVSSDYLA |
| 125 | CDR-L2 | GASSRAT |
| 126 | CDR-L2 | GASNRHT |
| 127 | CDR-L2 | YASSRAY |
| 128 | CDR-L2 | GASSRAN |
| 129 | CDR-L2 | YASSRAT |
| 130 | CDR-L2 | YASNRAT |

TABLE S-continued

Sequences.

| SEQ ID NO: | Region | Scheme/Clone | Sequence |
|---|---|---|---|
| 131 | CDR-L2 | | WASTRES |
| 132 | CDR-L2 | | WASSRES |
| 133 | CDR-L2 | | WASTRQS |
| 134 | CDR-L2 | | WASTRAS |
| 135 | CDR-L2 | | GASTRAT |
| 136 | CDR-L2 | | GASTRAS |
| 137 | CDR-L2 | | DASNLET |
| 138 | CDR-L2 | | DASNRAT |
| 139 | CDR-L2 | | DASKRAT |
| 140 | CDR-L2 | | KASSLES |
| 141 | CDR-L3 | | QQYHSYIT |
| 142 | CDR-L3 | | QQYHNAIT |
| 143 | CDR-L3 | | QQYYFYIT |
| 144 | CDR-L3 | | QQYHSALT |
| 145 | CDR-L3 | | QQYHGGIT |
| 146 | CDR-L3 | | QQYHRRIT |
| 147 | CDR-L3 | | QQYHSGIT |
| 148 | CDR-L3 | | QQYYLYPLT |
| 149 | CDR-L3 | | QQYWTYPLT |
| 150 | CDR-L3 | | QQYLLYPLT |
| 151 | CDR-L3 | | QQYLIWPLT |
| 152 | CDR-L3 | | QQYLLWPLT |
| 153 | CDR-L3 | | QQFYFFPPT |
| 154 | CDR-L3 | | QQAYTFPPT |
| 155 | CDR-L3 | | QQYYIFPPT |
| 156 | CDR-L3 | | QQRNFYPPT |
| 157 | CDR-L3 | | QQFVLWPRT |
| 158 | CDR-L3 | | QQHVNFPLT |
| 159 | CDR-L3 | | QQSVFWPIT |
| 160 | CDR-L3 | | QQLTKWPLT |
| 161 | CDR-L3 | | QQDVLWPLT |
| 162 | CDR-L3 | | QQYGLFPIT |
| 163 | CDR-L3 | | QQHTVWPIT |
| 164 | CDR-L3 | | QQVLNYPLT |
| 165 | CDR-L3 | | QQSYFLPPT |
| 166 | CDR-L3 | | QQAHSSPYT |
| 167 | Leader for scFV, scFv-Fc | Leader | MKYLLPTAAAGLLLLAAQPAMA |

TABLE S-continued

Sequences.

| SEQ ID NO: | Region | Scheme/Clone | Sequence |
|---|---|---|---|
| 168 | Linker for scFV, scFV-FC | Linker | GGGGSGGGGSGGGGS |
| 169 | C-Term Tag for scFV, scFV-FC | C-Term Tag | GPGGQHHHHHH |
| 170 | C-Term Tag for scFv, scFV-FC | C-Term Tag | PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV YTLPPSREEMTKNQVSLTCLVKGFYPSDIAVEW ESNGQPENNYKTTPPVLDSDGSFFLYSKLTVDK SRWQQGNVFSCSVMHEALHNHYTQKSLSLSPGK |
| 171 | scFv | 29872 | MKYLLPTAAAGLLLLAAQPAMAQVQLVQSGAEV KEPGASVKVSCKAPGYTFTSYYMHWVRQAPGQG LEWMGVINPSGGSTSYAQKFQGRVTMTRDTSTS TVYMELSSLRSEDTAVYYCARGKREGGTEYLRH WGQGTLVTVSSGGGGSGGGGSGGGGSEIVLTQS PGTLSLSPGERATLSCRSQSVSSSYLAWYQQK PGQAPRLLIYGASSRATGIPDRFSGSGSGTDFT LTISRLEPEDFAVYYCQQYHSYITFGGGTKVEI KGPGGQHHHHHH |
| 172 | scFv | 31895 | MKYLLPTAAAGLLLLAAQPAMAQVQLVQSGAEV KKPGASVKVSCKASGYTFKSYEMHWVRQAPGQG LEWMGRINPSVGSTWYAQKFQGRVTMTRDTSTS TVYMELSSLRSEDTAVYYCARGKREGGTEYLRK WGQGTLVTVSSGGGGSGGGGSGGGGSEIVLTQS PGTLSLSPGERATLSCRSQSVASSYLAWYQQK PGQAPRLLIYGASNRHTGIPDRFSGSGSGTDFT LTISRLEPEDFAVYYCQQYHNAITFGGGTKVEI KGPGGQHHHHHH |
| 173 | scFv | 31414 | MKYLLPTAAAGLLLLAAQPAMAQVQLVQSGAEV KKPGASVKVSCKASGYTFKSYEMHWVRQAPGQG LEWMGRINPSVGSTWYAQKFQGRVTMTRDTSTS TVYMELSSLRSEDTAVYYCARGKREGGTEYLRN WGQGTLVTVSSGGGGSGGGGSGGGGSEIVLTQS PGTLSLSPGERATLSCRASQSVSSSYLAWYQQK PGQAPRLLIYGASSRATGIPDRFSGSGSGTDFT LTISRLEPEDFAVYYCQQYHSYITFGGGTKVEI KGPGGQHHHHHH |
| 174 | scFv | 31905 | MKYLLPTAAAGLLLLAAQPAMAQVQLVQSGAEV KKPGSSVKVSCKASGGTFPSNAISWVRQAPGQG LEWMGGIGFGTANYAQKFQGRVTITADESTSTA YMELSSLRSEDTAVYYCARGGAKYARTYGMDVW GQGTTVTVSSGGGGSGGGGSGGGGSDIVMTQSP DSLAVSLGERATINCKSSKSVLYSNNNKNYLAW YQQKPGQPPKLLIYWASTRQSGVPDRFSGSGSG TDFTLTISSLQAEDVAVYYCQQYLLYPLTFGGG TKVEIKGPGGQHHHHHH |
| 175 | scFv-Fc | 29872 | MKYLLPTAAAGLLLLAAQPAMAQVQLVQSGAEV KEPGASVKVSCKAPGYTFTSYYMHWVRQAPGQG LEWMGVINPSGGSTSYAQKFQGRVTMTRDTSTS TVYMELSSLRSEDTAVYYCARGKREGGTEYLRH WGQGTLVTVSSGGGGSGGGGSGGGGSEIVLTQS PGTLSLSPGERATLSCRSQSVSSSYLAWYQQK PGQAPRLLIYGASSRATGIPDRFSGSGSGTDFT LTISRLEPEDFAVYYCQQYHSYITFGGGTKVEI KPKSCDKTHTCPPCPAPELLGGPSVFLFPPKPK DTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTVD KSRWQQGNVFSCSVMHEALHNHYTQKSLSLSPG K |
| 176 | scFv-Fc | 31895 | MKYLLPTAAAGLLLLAAQPAMAQVQLVQSGAEV KKPGASVKVSCHASGYTFKSYEMHWVRQAPGQG LEWMGRINPSVGSTWYAQKFQGRVTMTRDTSTS TVYMELSSLRSEDTAVYYCARGKREGGTEYLRK |

TABLE S-continued

Sequences.

| SEQ ID NO: | Region | Scheme/Clone | Sequence |
|---|---|---|---|
| | | | WGQGTLVTVSSGGGGSGGGGSGGGGSEIVLTQS PGTLSLSPGERATLSCRSQSVASSYLAWYQQK PGQAPRLLIYGASNRHTGIPDRFSGSGSGTDFT LTISRLEPEDFAVYYCQQYHNAITFGGGTKVEI KPKSCDKTHTCPPCPAPELLGGPSVFLFPPKPK DTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTVD KSRWQQGNVFSCSVMHEALHNHYTQKSLSLSPG K |
| 177 | scFv-Fc | 31414 | MKYLLPTAAAGLLLLAAQPAMAQVQLVQSGAEV KKPGASVKVSCKASGYTFKSYEMHWVRQAPGQG LEWMGRINPSVGSTWYAQKFQGRVTMTRDTSTS TVYMELSSLRSEDTAVYYCARGKREGGTEYLRN WGQGTLVTVSSGGGGSGGGGSGGGGSEIVLTQS PGTLSLSPGERATLSCRSQSVSSSYLAWYQQK PGQAPRLLIYGASSRATGIPDRFSGSGSGTDFT LTISRLEPEDFAVYYCQQYHSYITFGGGTKVEI KPKSCDKTHTCPPCPAPELLGGPSVFLFPPKPK DTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQ VYTLPPSREEMTKNQVSLTCLVKGFYPSDIAVE WESNGQPENNYKTTPPVLDSDGSFFLYSKLTVD KSRWQQGNVFSCSVMHEALHNHYTQKSLSLSPG K |
| 178 | scFv-Fc | 31905 | MKYLLPTAAAGLLLLAAQPAMAQVQLVQSGAEV KKPGSSVKVSCKASGGTFPSNAISWVRQAPGQG LEWMGGIGFGTANYAQKFQGRVTITADESTSTA YMELSSLRSEDTAVYYCARGGAKYARTYGMDVW GQGTTVTVSSGGGGSGGGGSGGGGSDIVMTQSP DSLAVSLGERATINCKSSKSVLYSNNNKNYLAW YQQKPGQPPKLLIYWASTRQSGVPDRFSGSGSG TDFTLTISSLQAEDVAVYYCQQYLLYPLTFGGG TKVEIKPKSCDKTHTCPPCPAPELLGGPSVFLF PPKPKDTLMISRTPEVTCVVVDVSHEDPEVKFN WYVDGVEVHNAKTKPREEQYNSTYRVVSVLTVL HQDWLNGKEYKCKVSNKALPAPIEKTISKAKGQ PREPQVYTLPPSREEMTKNQVSLTCLVKGFYPS DIAVEWESNGQPENNYKTTPPVLDSDGSFFLYS KLTVDKSRWQQGNVFSCSVMHEALHNHYTQKSL SLSPGK |
| 179 | VH | 27579 | QVQLVQSGAEVKEPGASVKVSCKAPGYTFTSYY MHWVRQAPGQGLEWMGVINPSGGSTSYAQKFQG RVTMTRDTSTSTVYMELSSLRSEDTAVYYCARG KREGGTEYLRHWGQGTLVTVSS |
| 180 | VH | 31895 | QVQLVQSGAEVKKPGASVKVSCKASGYTFKSYE MHWVRQAPGQGLEWMGRINPSVGSTWYAQKFQG RVTMTRDTSTSTVYMELSSLRSEDTAVYYCARG KREGGTEYLRKWGQGTLVTVSS |
| 181 | VH | 31415 | QVQLVQSGAEVKKPGASVKVSCKASGYTFTSYQ MHWVRQAPGQGLEWMGRINPSGGSTWYAQKFQG RVTMTRDTSTSTVYMELSSLRSEDTAVYYCARG KREGGTEYLRSWGQGTLVTVSS |
| 182 | VH | 31414 | QVQLVQSGAEVKKPGASVKVSCKASGYTFKSYE MHWVRQAPGQGLEWMGRINPSVGSTWYAQKFQG RVTMTRDTSTSTVYMELSSLRSEDTAVYYCARG KREGGTEYLRNWGQGTLVTVSS |
| 183 | VH | 31891 | QVQLVQSGAEVKKPGASVKVSCKASGYIFKSYE MHWVRQAPGQGLEWMGRINPSVGSTWYAQKFQG RVTMTRDTSTSTVYMELSSLRSEDTAVYYCARG KREGGTEYLRVWGQGTLVTVSS |

TABLE S-continued

Sequences.

| SEQ ID NO: | Region | Scheme/Clone | Sequence |
|---|---|---|---|
| 184 | VH | 29871 | QVQLVQSGAEVKKPGASVKVSCKASGYTFQSYYMHWVRQAPGQGLEWMGKINPSGGSTWYAQKFQGRVTMTRDTSTSTVYMELSSLRSEDTAVYYCARGKREGGTEYLRHWGQGTLVTVSS |
| 185 | VH | 31418 | QVQLVQSGAEVKKPGASVKVSCKASGYTFKSYEMHWVRQAPGQGLEWMGRINPSGGSTWYAQKFQGRVTMTRDTSTSTVYMELSSLRSEDTAVYYCARGKREGGTEYLRHWGQGTLVTVSS |
| 186 | VH | 31431 | QVQLVQSGAEVKKPGASVKVSCKASGYTFTSYQMHWVRQAPGQGLEWMGRINPSGGSTWYAQKFQGRVTMTRDTSTSTVYMELSSLRSEDTAVYYCARGKREGGTEYLRHWGQGTLVTVSS |
| 187 | VH | 31421 | QVQLVQSGAEVKKPGASVKVSCKASCYTFFSYYMYWVRQAPGQGLEWMGVINPLGGGTSYAQKFQGRVTMTRDTSTSTVYMELSSLRSEDTAVYYCARGKREGGTEYLRHWGQGTLVTVSS |
| 188 | VH | 31429 | QVQLVQSGAEVKKPGASVKVSCKASGYTFVSYFMHWVRQAPGQGLEWMGSINPRGGSTSYAQKFQGRVTMTRDTSTSTVYMELSSLRSEDTAVYYCARGKREGGTEYLRHWGQGTLVTVSS |
| 189 | VH | 29872 | QVQLVQSGAEVKKPGASVKVSCKASGYTFKSYEMHWVRQAPGQGLEWMGRINPSVGSTWYAQKFQGRVTMTRDTSTSTVYMELSSLRSEDTAVYYCARGKREGGTEYLRHWGQGTLVTVSS |
| 190 | VH | 28347 | QVQLVQSGAEVKKPGSSVKVSCKASGGTFSSLAISWVRQAPGQGLEWMGGIIPIFGTANYAQKFQGRVTITADESTNTAYMELSSLRSEDTAVYYCARGGAKYASTYGMDVWGQGTTVTVSS |
| 191 | VH | 31896 | QVQLVQSGAEVKKPGSSVKVSCKASGGTFSKLAISWVRQAPGQGLEWMGGIGFGTANYAQKFQGRVTITADESASTAYMELSSLRSEDTAVYYCARGGAKYASTHGMDVWGQGTTVTVSS |
| 192 | VH | 31432 | QVQLVQSGAEVKKPGSSVKVSCKASGGTFSHTAISWVRQAPGQGLEWMGGILPIGGTANYAQKFQGRVTITADESTSTAYMELSSLRSEDTAVYYCARGGAKYASQLGMDVWGQGTTVTVSS |
| 193 | VH | 31915 | QVQLVQSGAEVKKPGSSVKVSCKASGGTFSSLPISWVRQAPGQGLEWMGGIGFGTANYAQKFQGRVTITADESTSTAYMELSSLRSEDTAVYYCARGGAKYASKWGMDVWGQGTTVTVSS |
| 194 | VH | 31436 | QVQLVQSGAEVKKRGSSVKVSCKASGGTFSLLAISWVRQAPGQGLEWMGGILPIAGTANYAQKFQGRVTITADESTSTAYMELSSLRSEDTAVYYCARGGAKYAVGYGMDVWGQGTTVTVSS |
| 195 | VH | 31437 | QVQLVQSGAEVKKPGASVKVSCKASGGTFQSLAISWVRQAPGQGLEWMGGILPIGGTANYAQKFQGRVTITADESTSTAYMELSSLRSEDTAVYYCARGGAKYAGRYGMDVWGQGTTVTVSS |
| 196 | VH | 31905 | QVQLVQSGAEVKKRGSSVKVSCKASGGTFRSNAISWVRQAPGQGLEWMGGIGFGTANYAQKFQGRVTITADESTSTAYMELSSLRSEDTAVYYCARGGAKYARTYGMDVWGQGTTVTVSS |
| 197 | VH | 31901 | QVQLVQSGAEVKKPGSSVKVSCKASGGTFSSLPISWVRQAPGQGLEWMGGIGFGTANYAQKFQGRVTITADESTSTAYMELSSLRSEDTAVYYCARGGAKYAGRYGMDVWGQGTTVTVSS |
| 198 | VH | 29852 | QVQLVQSGAEVKKPGSSVKVSCKASGGTFSAMAISWVRQAPGQGLEWMGGILPIAGTANYAQKFQGRVTITADESTSTAYMELSSLRSEDTAVYYCARGGAKYASTYGMDVWGQGTTVTVSS |

TABLE S-continued

Sequences.

| SEQ ID NO: | Region | Scheme/Clone | Sequence |
|---|---|---|---|
| 199 | VH | 29851 | QVQLVQSGAEVKKRGSSVKVSCKASGGTFASLA ISWVRQAPGQGLEWMGGILPIFGEANYAQKFQG RVTITADESTSTAYMELSSLRSEDTAVYYCARG GAKYASTYGMDVWGQGTTVTVSS |
| 200 | VH | 29857 | QVQLVQSGAEVKKPGSSVKVSCKASGGTFSWLA ISWVRQAPGQGLEWMGGIIPRGGTANYAQKFQG RVTITADESTSTAYMELSSLRSEDTAVYYCARG GAKYASTYGMDVWGQGTTVTVSS |
| 201 | VH | 27571 | QVQLVQSGAEVKKRGSSVKASCKASGGTFSSYA ISWVRQAPGQGLEWMGSIIPIFGTANYAQKFRG RVTITADESTSTTYMELSSLRSEDTAVYYCARE SGGYRDHRLDVWGQGTMVTVSS |
| 202 | VH | 31861 | QVQLVQSGAEVKKPGSSVKVSCKASGGTFGSYG ISWVRQAPGQGLEWMGSIIPEFGTANYAQKFQG RVTITADESTSTAYMELSSLRSEDTAVYYCARE SGTYRDHRLDVWGQGTMVTVSS |
| 203 | VH | 31873 | QVQLVQSGAEVKKPGSSVKVSCKASGGTFSKYG ISWVRQAPGQGLEWMGSIIPEFGTANYAQKFQG RVTITADESTSTAYMELSSLRSEDTAVYYCARE SGGYRDHRLGVWGQGTMVTVSS |
| 204 | VH | 31393 | QVQLVQSGAEVKKPGSSVKVSCKASGGTFESYG ISWVRQAPGQGLEWMGSIIPEFGTANYAQKFQG RVTITADESTSTTYMELSSLRSEDTAVYYCARE SGGYRDHRLDVWGQGTMVTVSS |
| 205 | VH | 27534 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD FTDYSSGYSSGWTYWGQGTLVTVSS |
| 206 | VH | 27536 | QVQLVQSGAEVKKPGSSVKVSCKASGGTFSNYA ISWVRQAPGQGLEWMGGIIPIFGTANYAQKFQG RVTITADESTSTAYMELSSLRSEDTAVYYCARD TLYSSGAYYGYNVWGQGTMVTVSS |
| 207 | VH | 27588 | QVQLVQSGAEVKKPGSSVKVSCKASGGTFSNYA ISWVRQAPGQGLEWMGGIIPIFGTANYAQKFQG RVTITADESTSTAYMELSSLRSEDTAVYYCARA KRGYDSYGGVYFDYWGQGTLVTVSS |
| 208 | VH | 27590 | QVQLVQSGAEVKKPGSSVKVSCKASGGTFSNYA ISWVRQAPGQGLEWMGGIIPIFGTANYAQKFQG RVTITADESTSTAYMELSSLRSEDTAVYYCARG PTVTATTSIGTHNWFDPWGQGTLVTVSS |
| 209 | VH | 27597 | QVQLVQSGAEVNKPGSSVKVSCKASGGTFSSYA ISWVRQAPGQGLEWMGSIIPIFGTANYAQKFQG RVTITADESTSTAYMELSSLRSEDTAVYYCARE GRGYDSSRYYKFWFDPWGQGTLVTVSS |
| 210 | VH | 27575 | QVQLVQSGAEVKEPGSSVKVSCKASGGTFSSYA TSWVRQAPGQGLEWMGGIIPISGTANYAQEFQG RVTITADESTSTAYMELSSLRSEDTAVYYCARD GGGYRHHYFDLWGRGTLVTVSS |
| 211 | VH | 27568 | QVQLVQSGAEVKKPGSSVKVPCKASGGTFSSYA ISWVRQAPEQGLEWMGSIIPIFGTANYAQKFQG RVTITADESTSTAYMELSSLRSEDTAVYYCAGE SGGYRDHKLDVWGQGTVVTVSS |
| 212 | VH | 27577 | QVQLVQSGAEVKKPGSSVKVSCKASGGAFSSYA IGWVRQAPGQGLEWMGGIIPTFGTANYAQKFQG RVTITADESTSTAYMELSSLRSEDTAVYYCARD GGGYQHHYFDLWGRGTLVTVSS |
| 213 | VH | 27587 | QVQLVQSGAEVKKPGSSVKVSCKASGGTFSSYA ISWVRQAPGQGLEWMGSIIPIFGTANYAQKFQG RVTITADESTSTAYMELSSLRSEDTAVYYCARE SGGYRDHKLDVWGQGTMVTVSS |

TABLE S-continued

Sequences.

| SEQ ID NO: | Region | Scheme/Clone | Sequence |
|---|---|---|---|
| 214 | VH | 27589 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD SGYHRHYSDYWGQGTLVTVSS |
| 215 | VH | 27596 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD PLGIRKHWFDPWGQGTLVTVSS |
| 216 | VH | 27535 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD TPRWRYHYFDYWGQGTLVTVSS |
| 217 | VH | 27550 | EVQLVESGGGLVKPGGSLRLSCAASGFTFSSYS MNWVRQAPGKGLEWVSSISSSSSYIYYADSVKG RFTISRDNAKNSLYLQMNSLRAEDTAVYYCARE RRGSLALGMDVWGQGTLVTVSS |
| 218 | VH | 27549 | QVQLVESGGGVVQPGRSLRLSCAASGFTFSSYG MNWVRQAPGKGLEWVAVIWYDGSNKYYADSVKG RFTISRDNSKNTLYLQMNSLRAEDTAVYYCARD LGGYSYGEPYYYYGMDVWGQGTTVTVSS |
| 219 | VL | 27579 | EIVLTQSPGTLSLSPGERATLSCRASQSVSSSY LAWYQQKPGQAPRLLIYGASSRATGIPDRFSGS GSGTDFTLTISRLEPEDFAVYYCQQYHSYITFG GGTKVEIK |
| 220 | VL | 31895 | EIVLTQSPGTLSLSPGERATLSCRASQSVASSY LAWYQQKPGQAPRLLIYGASNRHTGIPDRFSGS GSGTDFTLTISRLEPEDFAVYYCQQYHNAITFG GGTKVEIK |
| 221 | VL | 31891 | EIVLTQSPGTLSLSPGERATLSCRASQSVSSSY LAWYQQKPGQAPRLLIYYASSRAYGIPDRFSGS GSGTDFTLTISRLEPEDFAVYYCQQYHNAITFG GGTKVEIK |
| 222 | VL | 31418 | EIVLTQSPGTLSLSPGERATLSCRASQSVSSSY LAWYQQKPGQAPRLLIYGASSRATGIPDRFSGS GSGTDFTLTISRLEPEDFAVYYCQQYYFYITFG GGTKVEIK |
| 223 | VL | 31430 | EIVLTQSPGTLSLSPGERATLSCEASQSVSYSY LAWYQQKPGQAPRLLIYGASSRANGIPDRFSGS GSGTDFTLTISRLEPEDFAVYYCQQYHSALTFG GGTKVEIK |
| 224 | VL | 31431 | EIVLTQSPGTLSLSPGERATLSCRASQSVASSY LAWYQQKPGQAPRLLIYGASNRHTGIPDRESGS GSGTDFTLTISRLEPEDFAVYYCQQYHGGITFG GGTKVEIK |
| 225 | VL | 31421 | EIVLTQSPGTLSLSPGERATLSCKASESVSSSY LAWYQQKPGQAPRLLIYYASSRATGIPDRFSGS GSGTDFTLTISRLEPEDFAVYYCQQYHRRITFG GGTKVEIK |
| 226 | VL | 31429 | EIVLTQSPGTLSLSPGERATLSCRASQYVSSSY LAWYQQKPGQAPRLLIYYASNRATGIPDRFSGS GSGTDFTLTISRLEPEDFAVYYCQQYHSGITFG GGTKVEIK |
| 227 | VL | 28347 | DIVMTQSPDSLAVSLGERATINCKSSQSVLFSS NNKNYLAWYQQKPGQPPKLLIYWASTRESGVPD RFSGSGSGTDFTLTISSLQAEDVAVYYCQQYYL YPLTFGGGTKVEIK |
| 228 | VL | 31896 | DIVMTQSPDSLAVSLGERATINCKSSRSVLFSS NNKNYLAWYQQKPGQPPKLLIYWASTRESGVPD RFSGSGSGTDFTLTISSLQAEDVAVYYCQQYWT YPLTFGGGTKVEIK |

TABLE S-continued

Sequences.

| SEQ ID NO: | Region | Scheme/Clone | Sequence |
|---|---|---|---|
| 229 | VL | 31915 | DIVMTQSPDSLAVSLGERATINCKSSQSVLFSSNNKNYLAWYQQKPGQPPKLLIYWASSRESGVPDRFSGSGSGTDFTLTISSLQAEDVAVYYCQQYWTYPLTFGGGTKVEIK |
| 230 | VL | 31905 | DIVMTQSPDSLAVSLGERATINCKSSKSVLYSNNNKNYLAWYQQKPGQPPKLLIYWASTRQSGVPDRFSGSGSGTDFTLTISSLQAEDVAVYYCQQYLLYPLTFGGGTKVEIK |
| 231 | VL | 31901 | GIVMTQSPDSLAVSLGERATINCKSSQSVLFSSNNKNYLAWYQQKPGQPPKLLIYWASTRASGVPDRFSGSGSGTDFTLTISSLQAEDVAVYYCQQYYLYPLTFGGGTKVEIK |
| 232 | VL | 27571 | EIVMTQSPATLSVSPGERATLSCRASQSVGSNLAWYQQKPGQAPRLLIYGASTRATGIPARFSGSGSGTEFTLTISSLQSEDFAVYYCQQYLIWPLTFGGGTKVEIK |
| 233 | VL | 31861 | EIVMTQSPATLSVSPGERATLSCRASQSVGSNLAWYQQKPGQAPRLLIYGASTRATGIPARFSGSGSGTEFTLTISSLQSEDFAVYYCQQYLLWPLTFGGGTKVEIK |
| 234 | VL | 31873 | EIVMTQSPATLSVSPGERATLSCRASQSVGSNLAWYQQKPGQAPRLLIYGASTRASGIPARFSGSGSGTEFTLTISSLQSEDFAVYYCQQYLLWPLTFGGGTKVEIK |
| 235 | VL | 28337 | DIVMTQSPDSLAVSLGERATINCKSSQSVLFSSNNKNYLAWYQQKPGQPPKLLIYWASTRESGVPDRFSGSGSGTDFTLTISSLQAEDVAVYYCQQFYFYPPTFGGGTKVEIK |
| 236 | VL | 27536 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQAYTFPPTFGGGTKVEIK |
| 237 | VL | 27588 | DIQMTQSPSSLSASVGDRVTITCQASQDISNYLNWYQQKPGKAPKLLIYDASNLETGVPSRFSGSGSGTDFTFTISSLQPEDIATYYCQQYYIFPPTFGGGTKVEIK |
| 238 | VL | 27590 | EIVLTQSPATLSLSPGERATLSCRASQSVSSYLAWYQQKPGQAPRLLIYDASNRATGIPARFSGSGSGTDFTLTISSLEPEDFAVYYCQQRNFYPPTFGGGTKVEIK |
| 239 | VL | 27597 | EIVLTQSPATLSLSPGERATLSCRASQSVSSYLAWYQQKPGQAPRLLIYDASNRATGIPARFSGSGSGTDFTLTISSLEPEDFAVYYCQQFVLWPRTFGGGTKVEIK |
| 240 | VL | 27575 | EIVLTQSPATLSLSPGERATLSCRASQSVSRYLAWYQQKPGQAPRLLIYDASNRATGIPARFSGSGSGTDFTLTISSLEPEDFAVYYCQQHVNFPLTFGGGTKVEIK |
| 241 | VL | 27568 | EIVLTQSPATLSLSPGERATLSCRASQSVSSYLAWYQQKPGQAPRLLIYDASNRATGIPARFSGSGSGTDFTLTISSLEPEDFAVYYCQQSVFWPITFGGGTKVEIK |
| 242 | VL | 27577 | EIVMTQSPATLSVSPGERATLSCRASQSVGSNLAWYQQKPGQAPRLLIYGASTRATGIPARFSGSGSGTEFTLTISSLQSEDFAVYYCQQLTKWPLTFGGGTKVEIK |
| 243 | VL | 27587 | EIVLTQSPATLSLSPGERATLSCRASQSVSSYLAWYQQKPGQAPRLLIYDASKRATGIPARFSGSGSGTDFTLTISSLEPEDFAVYYCQQDVLWPLTFGGGTKVEIK |

TABLE S-continued

Sequences.

| SEQ ID NO: | Region | Scheme/Clone | Sequence |
|---|---|---|---|
| 244 | VL | 27589 | DIQMTQSPSTLSASVGDRVTITCRASQSISSWL AWYQQKPGKAPKLLIYKASSLESGVPSRFSGSG SGTEFTLTISSLQPDDFATYYCQQYGLFPITFG GGTKVEIK |
| 245 | VL | 27596 | EIVMTQSPATLSLSPGERATLSCRASQSVSSYL AWYQQKPGQAPRLLIYDASNRATGIPARFSGSG SGTDFTLTISSLEPEDFAVYYCQQHTVWPITFG GGTKVEIK |
| 246 | VL | 27535 | EIVLTQSPATLSLSPGERATLSCRASQSVSSYL AWYQQKPGQAPRLLIYDASKRATGIPARFSGSG SGTDFTLTISSLEPEDFAVYYCQQVLNYPLTFG GGTKVEIK |
| 247 | VL | 27550 | DIQMTQSPSSLSASVGDRVTITCQASQDISNYL NWYQQKPGKAPKLLIYDASNLETGVPSRFSGSG SGTDFTFTISSLQPEDIATYYCQQSYFLPPTFG GGTKVEIK |
| 248 | VL | 27549 | EIVLTQSPGTLSLSPGERATLSCRASQSVSSDY LAWYQQKPGQAPRLLIYGASSRATGIPDRFSGS GSGTDFTLTISRLEPEDFAVYYCQQAHSSPYTF GGGTKVEIK |
| 249 | | hCD39 | MEDTKESNVKTFCSKNILAILGFSSIIAVIALL AVGLTQNKALPENVKYGIVLDAGSSHTSLYIYK WPAEKENDTGVVHQVEECRVKGPGISKFVQKVN EIGIYLTDCMERAREVIPRSQHQETPVYLGATA GMRLLRMESEELADRVLDVVERSLSNYPFDFQG ARIITGQEEGAYGWITINYLLGKFSQKTRWFSI VPYETNNQETFGALDLGGASTQVTFVPQNQTIE SPDNALQFRLYGKDYNVYTHSFLCYGKDQALWQ KLAKDIQVASNEILRDPCFHPGYKKVVNVSDLY KTPCTKRFEMTLPFQQFEIQGIGNYQQCHQSIL ELFNTSYCPYSQCAFNGIFLPPLQGDFGAFSAF YFVMKFLNLTSEKVSQEKVIEMMKKFCAQPWEE IKTSYAGVKEKYLSEYCFSGTYILSLLLQGYHF TADSWEHIHFGKIQGSDAGWTLGYMLNLTNMI PAEQPLSTPLSHSTYVFLMVLFSLVLFTVAIIG LLIFHKPSYFWKDMV |
| 250 | | mCD39 | MEDIKDSKVKRFCSKNILIILGFTSILAVIALI AVGLTQNKPLPENVKYGIVLDAGSSHTNLYIYK WPAEKENDTGVVQQLEECQVKGPGISKYAQKTD EIGAYLAECMELSTELIPTSKHHQTPVYLGATA GMRLLRMESEQSADEVLAAVSTSLKSYPFDFQG AKIITGQEEGAYGWITINYLLGRFTQEQSWLSL ISDSQKQETFGALDLGGASTQITFVPQNSTIES PENSLQFRLYGEDYTVYTHSFLCYGKDQALWQK LAKDIQVSSGGVLKDPCFNPGYEKVVNVSELYG TPCTKRFEKKLPFDQFRIQGTGDYEQCHQSILE LFNNSHCPYSQCAFNGVFLPPLHGSFGAFSAFY FVMDFFKKVAKNSVISQEKMTEITKNFCSKSWE ETKTSYPSVKEKYLSEYCFSGAYILSLLQGYNF TDSSWEQIHFMGKIKDSNAGWTLGYMLNLTNMI PAEQPLSPPLPHSTYIGLMVLFSLLLVAVAITG LFIYSKPSYFWKEAV |
| 251 | | *Macaca fascicularis* cCD39 | MLFDSILSTVGLSKLVSVVSSPAAALSKSNVKT FCSKNILAILGFSSIIAVIALLAVGLTQNKALP ENIKYGIVLDAGSSHTSLYIYKWPAEKENDTGV VHQVEECRVKGPGISKYVQKVNEIGIYLTDCME RAREVIPRSQHQETPVYLGATAGMRLLRMESEE LADRVLDVVERSLSNYPFDFQGARIITGQEEGA YGWITINYLLGKFSQKTRWFSIVPYETNNQETF GALDLGGASTQITFVPQNQTTESPDNALQFRLY GKDYNVYTHSFLCYGKDQALWQKLAKDIQVASN EILRDPCFHPGYKKVVNVSDLYKTPCTKRFEMT LPFQQFEIQGIGNYQQCHQSVLELFNTSYCPYS QCAFNGIFLPPLQGDFGAFSAFYFVMNFLNLTS |

TABLE S-continued

Sequences.

| SEQ ID NO: | Region | Scheme/Clone | Sequence |
|---|---|---|---|
| | | | EKVSQEKVTEMMKKFCSQPWEEIKTSYAGVKEK YLSEYCFSGTYILSLLLQGYHFTADSWEHIHFI GKIQGSDAGWTLGYMLNLTNMIPAEQPLSTPLS HSTYVFLMVLFSLVLVIVAIIGLLIFHKPSYFW KDMV |
| 252 | | hCD39 ECD | TQNKALPENVKYGIVLDAGSSHTSLYIYKWPAE KENDTGVVHQVEECRVKGPGISKFVQKVNEIGI YLTDCMERAREVIPRSQHQETPVYLGATAGMRL LRMESEELADRVLDVVERSLSNYPFDFQGARII TGQEEGAYGWITINYLLGKFSQKTRWFSIVPYE TNNQETFGALDLGGASTQVTFVPQNQTIESPDN ALQFRLYGKDYNVYTHSFLCYGKDQALWQKLAK DIQVASNEILRDPCFHPGYKKVVNVSDLYKTPC TKRFEMTLPFQQFEIQGIGNYQQCHQSILELFN TSYCPYSQCAFNGIFLPPLQGDFGAFSAFYFVM KFLNLTSEKVSQEKVTEMMKKFCAQPWEEIKTS YAGVKEKYLSEYCFSGTYILSLLLQGYHFTADS WEHIHFIGKIQGSDAGWTLGYMLNLTNMIPAEQ PLSTPLSHSTYVFLMVLFSLVLFTVAIIGLLIF HKPSYFWKDMV |
| 253 | | mCD39 ECD | TQNKPLPENVKYGIVLDAGSSHTNLYIYKWPAE KENDTGVVQQLEECQVKGPGISKYAQKTDEIGA YLAECMELSTELIPTSKHHQTPVYLGATAGMRL LRMESEQSADEVLAAVSTSLKSYPFDFQGAKII TGQEEGAYGWITINYLLGRFTQEQSWLSLISDS QKQETFGALDLGGASTQITFVPQNSTIESPENS LQFRLYGEDYTVYTHSFLCYGKDQALWQKLAKD IQVSSGGVLKDPCFNPGYEKVVNVSELYGTPCT KRFEKKLPFDQFRIQGTGDYEQCHQSILELFNN SHCPYSQCAFNGVFLPPLHGSFGAFSAFYFVMD FFKKVAKNSVISQEKMTEITKNFCSKSWEETKT SYPSVKEKYLSEYCFSGAYILSLLQGYNFTDSS WEQIHFMGKIKDSNAGWTLGYMLNLTNMIPAEQ PLSPPLPHSTYIGLMVLFSLLLVAVAITGLFIY SKPSYFWKEAV |
| 254 | | cCD39 ECD | TQNKALPENIKYGIVLDAGSSHTSLYIYKWPAE KENDTGVVHQVEECRVKGPGISKYVQKVNEIGI YLTDCMERAREVIPRSQHQETPVYLGATAGMRL LRMESEELADRVLDVVERSLSNYPFDFQGARII TGQEEGAYGWITINYLLGKFSQKTRWFSIVPYE TNNQETFGALDLGGASTQITFVPQNQTTESPDN ALQFRLYGKDYNVYTHSFLCYGKDQALWQKLAK DIQVASNEILRDPCFHPGYKKVVNVSDLYKTPC TKRFEMTLPFQQFEIQGIGNYQQCHQSVLELFN TSYCPYSQCAFNGIFLPPLQGDFGAFSAFYFVM NFLNLTSEKVSQEKVTEMMKKFCSQPWEEIKTS YAGVKEKYLSEYCFSGTYILSLLLQGYHFTADS WEHIHFIGKIQGSDAGWTLGYMLNLTNMIPAEQ PLSTPLSHSTYVFLMVLFSLVLVIVAIIGLLIF HKPSYFWKDMV |
| 255 | HC | 31895 | QVQLVQSGAEVKKPGASVKVSCKASGYTFKSYE MHWVRQAPGQGLEWMGRINPSVGSTWYAQKFQG RVTMTRDTSTSTVYMELSSLRSEDTAVYYCARG KREGGTEYLRKWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDILMISRTPEVTCVT VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |

TABLE S-continued

Sequences.

| SEQ ID NO: | Region | Scheme/Clone | Sequence |
|---|---|---|---|
| 256 | LC | 31895 | EIVLTQSPGTLSLSPGERATLSCRASQSVASSY LAWYQQKPGQAPRLLIYGASNRHTGIPDRFSGS GSGTDFTLTISRLEPEDFAVYYCQQYHNAITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 257 | HC | 31415 | QVQLVQSGAEVKKPGASVKVSCKASGYTFTSYQ MHWVRQAPGQGLEWMGRINPSGGSTWYAQKFQG RVTMTRDTSTSTVYMELSSLRSEDTAVYYCARG KREGGTEYLRSWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 258 | LC | 31415 | EIVLTQSPGTLSLSPGERATLSCRASQSVSSSY LAWYQQKPGQAPRLLIYGASSRATGIPDRFSGS GSGTDFTLTISRLEPEDFAVYYCQQYHSYITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 259 | HC | 31891 | QVQLVQSGAEVKKPGASVKVSCKASGYIFKSYE MHWVRQAPGQGLEWMGRINPSVGSTWYAQKFQG RVTMTRDTSTSTVYMELSSLRSEDTAVYYCARG KREGGTEYLRVWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 260 | LC | 31891 | EIVLTQSPGTLSLSPGERATLSCRASQSVSSSY LAWYQQKPGQAPRLLIYYASSRAYGIPDRFSGS GSGTDFTLTISRLEPEDFAVYYCQQYHNAITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 261 | HC | 31418 | QVQLVQSGAEVKKPGASVKVSCKASGYTFKSYE MHWVRQAPGQGLEWMGRINPSGGSTWYAQKFQG RVTMTRDTSTSTVYMELSSLRSEDTAVYYCARG KREGGTEYLRHWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |

TABLE S-continued

Sequences.

| SEQ ID NO: | Region | Scheme/Clone | Sequence |
|---|---|---|---|
| 262 | LC | 31418 | EIVLTQSPGTLSLSPGERATLSCRASQSVSSSY LAWYQQKPGQAPRLLIYGASSRATGIPDRFSGS GSGTDFTLTISRLEPEDFAVYYCQQYYFYITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 263 | HC | 31430 | QVQLVQSGAEVKKPGASVKVSCKASGYTFKSYE MHWVRQAPGQGLEWMGRINPSGGSTWYAQKFQG RVTMTRDTSTSTVYMELSSLRSEDTAVYYCARG KREGGTEYLRHWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 264 | LC | 31430 | EIVLTQSPGTLSLSPGERATLSCEASQSVSYSY LAWYQQKPGQAPRLLIYGASSRANGIPDRFSGS GSGTDFTLTISRLEPEDFAVYYCQQYHSALTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 265 | HC | 31915 | QVQLVQSGAEVKKPGSSVKVSCKASGGTFSSLP ISWVRQAPGQGLEWMGGIGFGTANYAQKFQGRV TITADESTSTAYMELSSLRSEDTAVYYCARGGA KYASKWGMDVWGQGTTVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLGK |
| 266 | LC | 31915 | DIVMTQSPDSLAVSLGERATINCKSSQSVLFSS NNKNYLAWYQQKPGQPPKLLIYWASSRESGVPD RFSGSGSGTDFTLTISSLQAEDVAVYYCQQYWT YPLTFGGGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| 267 | HC | 31905 | QVQLVQSGAEVKKPGSSVKVSCKASGGTFPSNA ISWVRQAPGQGLEWMGGIGFGTANYAQKFQGRV TITADESTSTAYMELSSLRSEDTAVYYCARGGA KYARTYGMDVWGQGTTVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLGK |

TABLE S-continued

Sequences.

| SEQ ID NO: | Region | Scheme/Clone | Sequence |
|---|---|---|---|
| 268 | LC | 31905 | DIVMTQSPDSLAVSLGERATINCKSSKSVLYSN NNKNYLAWYQQKPGQPPKLLIYWASTRQSGVPD RFSGSGSGTDFTLTISSLQAEDVAVYYCQQYLL YPLTFGGGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| 269 | HC | 31901 | QVQLVQSGAEVKKPGSSVKVSCKASGGTFSSLP ISWVRQAPGQGLEWMGGIGFGTANYAQKFQGRV TITADESTSTAYMELSSLRSEDTAVYYCARGGA KYAGRYGMDVWGQGTTVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLGK |
| 270 | LC | 31901 | GIVMTQSPDSLAVSLGERATINCKSSQSVLFSS NNKNYLAWYQQKPGQPPKLLIYWASTRASGVPD RFSGSGSGTDFTLTISSLQAEDVAVYYCQQYYL YPLTFGGGTKVEIKRTVAAPSVFIFPPSDEQLK SGTASVVCLLNNFYPREAKVQWKVDNALQSGNS QESVTEQDSKDSTYSLSSTLTLSKADYEKHKVY ACEVTHQGLSSPVTKSFNRGEC |
| 271 | HC | 31861 | QVQLVQSGAEVKKPGSSVKVSCKASGGTFGSYG ISWVRQAPGQGLEWMGSIIPEFGIANYAQKFQG RVTITADESTSTAYMELSSLRSEDTAVYYCARE SGTYRDHRLDVWGQGTMVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 272 | LC | 31861 | EIVMTQSPATLSVSPGERATLSCRASQSVGSNL AWYQQKPGQAPRLLIYGASTRATGIPARFSGSG SGTEFTLTISSLQSEDFAVYYCQQYLLWPLTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 273 | HC | 31873 | QVQLVQSGAEVKKPGSSVKVSCKASGGTFSKYG ISWVRQAPGQGLEWMGSIIPEFGIANYAQKFQG RVTITADESTSTAYMELSSLRSEDTAVYYCARE SGGYRDHRLGVWGQGTMVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDILMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |

TABLE S-continued

Sequences.

| SEQ ID NO: | Region | Scheme/Clone | Sequence |
|---|---|---|---|
| 274 | LC | 31873 | EIVMTQSPATLSVSPGERATLSCRASQSVGSNLAWYQQKPGQAPRLLIYGASTRASGIPARFSGSGSGTEFTLTISSLQSEDFAVYYCQQYLLWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 275 | HC | 31393 | QVQLVQSGAEVKKPGSSVKVSCKASGGTFESYGISWVRQAPGQGLEWMGSIIPEFGIANYAQKFQGRVTITADESTSTTYMELSSLRSEDTAVYYCARESGGYRDHRLDVWGQGTMVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDILMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 276 | LC | 31393 | EIVMTQSPATLSVSPGERATLSCRASQSVGSNLAWYQQKPGQAPRLLIYGASTRATGIPARFSGSGSGTEFTLTISSLQSEDFAVYYCQQYLLWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 277 | HC | 27597 | QVQLVQSGAEVKKPGSSVKVSCKASGGTFSSYAISWVRQAPGQGLEWMGSIIPIFGTANYAQKFQGRVTITADESTSTAYMELSSLRSEDTAVYYCAREGRGYDSSRYYKFWFDPWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 278 | LC | 27597 | EIVLTQSPATLSLSPGERATLSCRASQSVSSYLAWYQQKPGQAPRLLIYDASNRATGIPARFSGSGSGTDFTLTISSLEPEDFAVYYCQQFVLWPRTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 279 | HC | 27575 | QVQLVQSGAEVKEPGSSVKVSCKASGGTFSSYATSWVRQAPGQGLEWMGGIIPISGTANYAQEFQGRVTITADESTSTAYMELSSLRSEDTAVYYCARDGGGYRHHYFDLWGRGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |

TABLE S-continued

Sequences.

| SEQ ID NO: | Region | Scheme/Clone | Sequence |
|---|---|---|---|
| 280 | LC | 27575 | EIVLTQSPATLSLSPGERATLSCRASQSVSRYLAWYQQKPGQAPRLLIYDASNRATGIPARFSGSGSGTDFTLTISSLEPEDFAVYYCQQHVNFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 281 | HC | 27568 | QVQLVQSGAEVKKPGSSVKVPCKASGGTFSSYAISWVRQAPEQGLEWMGSIIPIFGTANYAQKFQGRVTITADESTSTAYMELSSLRSEDTAVYYCAGESGGYRDHKLDVWGQGTVVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDILMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 282 | LC | 27568 | EIVLTQSPATLSLSPGERATLSCRASQSVSSYLAWYQQKPGQAPRLLIYDASNRATGIPARFSGSGSGTDFTLTISSLEPEDFAVYYCQQSVFWPITFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 283 | HC | 27577 | QVQLVQSGAEVKKPGSSVKVSCKASGGAFSSYAIGWVRQAPGQGLEWMGGIIPTFGTANYAQKFQGRVTITADESTSTAYMELSSLRSEDTAVYYCARDGGGYQHHYFDLWGRGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 284 | LC | 27577 | EIVMTQSPATLSVSPGERATLSCRASQSVGSNLAWYQQKPGQAPRLLIYGASTRATGIPARFSGSGSGTEFTLTISSLQSEDFAVYYCQQLTKWPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 285 | HC | 27587 | QVQLVQSGAEVKKPGSSVKVSCKASGGTFSSYAISWVRQAPGQGLEWMGSIIPIFGTANYAQKFQGRVTITADESTSTAYMELSSLRSEDTAVYYCARESGGYRDHKLDVWGQGTMVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |

TABLE S-continued

Sequences.

| SEQ ID NO: | Region | Scheme/Clone | Sequence |
|---|---|---|---|
| 286 | LC | 27587 | EIVLTQSPATLSLSPGERATLSCRASQSVSSYL AWYQQKPGQAPRLLIYDASKRATGIPARFSGSG SGTDFTLTISSLEPEDFAVYYCQQDVLWPLTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 287 | HC | 27589 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD SGYHRHYSDYWGQGTLVTVSSASTKGPSVFPLA PCSRSTSESTAALGCLVKDYFPEPVTVSWNSGA LTSGVHTFPAVLQSSGLYSLSSVVTVPSSSLGT KTYTCNVDHKPSNTKVDKRVESKYGPPCPPCPA PEFLGGPSVFLFPPKPKDTLMISRTPEVTCVVV DVSQEDPEVQFNWYVDGVEVHNAKTKPREEQFN STYRVVSVLTVLHQDWLNGKEYKCKVSNKGLPS SIEKTISKAKGQPREPQVYTLPPSQEEMTKNQV SLTCLVKGFYPSDIAVEWESNGQPENNYKTTPP VLDSDGSFFLYSRLTVDKSRWQEGNVFSCSVMH EALHNHYTQKSLSLSLGK |
| 288 | LC | 27589 | DIQMTQSPSTLSASVGDRVTITCRASQSISSWL AWYQQKPGKAPKLLIYKASSLESGVPSRFSGSG SGTEFTLTISSLQPDDFATYYCQQYGLEPITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 289 | HC | 27596 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD PLGIRKHWFDPWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 290 | LC | 27596 | EIVMTQSPATLSLSPGERATLSCRASQSVSSYL AWYQQKPGQAPRLLIYDASNRATGIPARFSGSG SGTDFTLTISSLEPEDFAVYYCQQHTVWPITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 291 | HC | 27535 | QVQLVQSGAEVKKPGSSVKVSCKASGGTFSSYA ISWVRQAPGQGLEWMGGIIPIFGTANYAQKFQG RVTITADESTSTAYMELSSLRSEDTAVYYCARD TPRWRYHYFDYWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |

TABLE S-continued

Sequences.

| SEQ ID NO: | Region | Scheme/Clone | Sequence |
|---|---|---|---|
| 292 | LC | 27535 | EIVLTQSPATLSLSPGERATLSCRASQSVSSYL AWYQQKPGQAPRLLIYDASKRATGIPARFSGSG SGTDFTLTISSLEPEDFAVYYCQQVLNYPLTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 293 | HC | 27550 | EVQLVESGGGLVKPGGSLRLSCAASGFTFSSYS MNWVRQAPGKGLEWVSSISSSSSYIYYADSVKG RFTISRDNAKNSLYLQMNSLRAEDTAVYYCARE RRGSLALGMDVWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTTP PVLDSDGSFFLYSRLTVDKSRWQEGNVFSCSVM HEALHNHYTQKSLSLSLGK |
| 294 | LC | 27550 | DIQMTQSPSSLSASVGDRVTITCQASQDISNYL NWYQQKPGKAPKLLIYDASNLETGVPSRFSGSG SGTDFTFTISSLQPEDIATYYCQQSYFLPPTFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |
| 295 | HC | 27549 | QVQLVESGGGVVQPGRSLRLSCAASGFTFSSYG MNWVRQAPGKGLEWVAVIWYDGSNKYYADSVKG RFTISRDNSKNTLYLQMNSLRAEDTAVYYCARD LGGYSYGEPYYYYYGMDVWGQGTTVTVSSASTK GPSVFPLAPCSRSTSESTAALGCLVKDYFPEPV TVSWNSGALTSGVHTFPAVLQSSGLYSLSSVVT VPSSSLGTKTYTCNVDHKPSNTKVDKRVESKYG PPCPPCPAPEFLGGPSVFLFPPKPKDTLMISRT PEVTCVVVDVSQEDPEVQFNWYVDGVEVHNAKT KPREEQFNSTYRVVSVLTVLHQDWLNGKEYKCK VSNKGLPSSIEKTISKAKGQPREPQVYTLPPSQ EEMTKNQVSLTCLVKGFYPSDIAVEWESNGQPE NNYKTTPPVLDSDGSFFLYSRLTVDKSRWQEGN VFSCSVMHEALHNHYTQKSLSLSLGK |
| 296 | LC | 27549 | EIVLTQSPGTLSLSPGERATLSCRASQSVSSDY LAWYQQKPGQAPRLLIYGASSRATGIPDRFSGS GSGTDFTLTISRLEPEDFAVYYCQQAHSSPYTF GGGTKVEIKRTVAAPSVFIFPPSDEQLKSGTAS VVCLLNNFYPREAKVQWKVDNALQSGNSQESVT EQDSKDSTYSLSSTLTLSKADYEKHKVYACEVT HQGLSSPVTKSFNRGEC |
| 297 | HC | 31414 | QVQLVQSGAEVKKPGASVKVSCKASGYTFKSYE MHWVRQAPGQGLEWMGRINPSVGSTWYAQKFQG RVTMTRDTSTSTVYMELSSLRSEDTAVYYCARG KREGGTEYLRNWGQGTLVTVSSASTKGPSVFPL APCSRSTSESTAALGCLVKDYFPEPVTVSWNSG ALTSGVHTFPAVLQSSGLYSLSSVVTVPSSSLG TKTYTCNVDHKPSNTKVDKRVESKYGPPCPPCP APEFLGGPSVFLFPPKPKDTLMISRTPEVTCVV VDVSQEDPEVQFNWYVDGVEVHNAKTKPREEQF NSTYRVVSVLTVLHQDWLNGKEYKCKVSNKGLP SSIEKTISKAKGQPREPQVYTLPPSQEEMTKNQ VSLTCLVKGFYPSDIAVEWESNGQPENNYKTIP PVLDSDGSFFLYSRLTVDKSRWQEGNVFSCSVM HEALHNHYTQKSLSLSLGK |

TABLE S-continued

Sequences.

| SEQ ID NO: | Region | Scheme/Clone | Sequence |
|---|---|---|---|
| 298 | LC | 31414 | EIVLTQSPGTLSLSPGERATLSCRASQSVSSSY LAWYQQKPGQAPRLLIYGASSRATGIPDRFSGS GSGTDFTLTISRLEPEDFAVYYCQQYHSYITFG GGTKVEIKRTVAAPSVFIFPPSDEQLKSGTASV VCLLNNFYPREAKVQWKVDNALQSGNSQESVTE QDSKDSTYSLSSTLTLSKADYEKHKVYACEVTH QGLSSPVTKSFNRGEC |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. An isolated antibody molecule capable of binding to human CD39 (hCD39), comprising a heavy chain variable region (VH) and a light chain variable region (VL),
the VH comprising,
   a) a VHCDR1 having a sequence set forth in SEQ ID NO: 2 or SEQ ID NO: 26,
   b) a VHCDR2 having a sequence set forth in SEQ ID NO: 47 or SEQ ID NO: 64, and
   c) a VHCDR3 having a sequence set forth in SEQ ID NO: 83; and the VL comprising,
   a) a VLCDR1 having a sequence set forth in SEQ ID NO: 111,
   b) a VLCDR2 having a sequence set forth in SEQ ID NO: 126, and
   c) a VLCDR3 having a sequence set forth in SEQ ID NO: 142.

2. The isolated antibody molecule capable of binding to human CD39 (hCD39) comprising a heavy chain variable region (VH) and a light chain variable region (VL) according to claim 1, wherein the VH comprises a VH having the sequence set forth in SEQ ID NO: 180 and the VL comprises a VL having the sequence set forth in SEQ ID NO: 220.

3. An isolated nucleic acid encoding the isolated antibody molecule according to claim 1.

4. An expression vector comprising the nucleic acid according to claim 3.

5. A prokaryotic or eukaryotic host cell comprising the vector of claim 4.

6. A method for the production of an isolated antibody molecule comprising the steps of expressing a nucleic acid according to claim 3 in a prokaryotic or eukaryotic host cell and recovering the antibody molecule from the cell or the cell culture supernatant.

7. An isolated antibody molecule capable of binding to human CD39 (hCD39), comprising a heavy chain and a light chain, the heavy chain comprising a molecule having a sequence consisting of SEQ ID NO: 255 and the light chain comprising a molecule having a sequence consisting of SEQ ID NO: 256.

* * * * *

SEQUENCE LISTING

```
<160> NUMBER OF SEQ ID NOS: 298

<210> SEQ ID NO 1
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 1

Gly Tyr Thr Phe Thr Ser Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 2

Gly Tyr Thr Phe Lys Ser Tyr
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 3

Gly Tyr Ile Phe Lys Ser Tyr
1               5

<210> SEQ ID NO 4
<211> LENGTH: 7
<212> TYPE: PRT
<213> ORGANISM: Artificial Sequence
<220> FEATURE:
```

```
<223> OTHER INFORMATION: Synthetic: CDR-H1, Chothia

<400> SEQUENCE: 4

Gly Tyr Thr Phe Gln Ser Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 5

Gly Tyr Thr Phe Phe Ser Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 6

Gly Tyr Thr Phe Val Ser Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic: CDR-H1, Chothia

<400> SEQUENCE: 7

Gly Gly Thr Phe Ser Ser Leu Ala Ile Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic: CDR-H1, Chothia

<400> SEQUENCE: 8

Gly Gly Thr Phe Ser Lys Leu Ala Ile Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 9

Gly Gly Thr Phe Ser His Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic: CDR-H1, Chothia
```

<400> SEQUENCE: 10

Gly Gly Thr Phe Ser Ser Leu
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 11

Gly Gly Thr Phe Ser Leu Leu
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 12

Gly Gly Thr Phe Gln Ser Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 13

Gly Gly Thr Phe Pro Ser Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 14

Gly Gly Thr Phe Ser Ala Met
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 15

Gly Gly Thr Phe Ala Ser Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic: CDR-H1, Chothia

```
<400> SEQUENCE: 16

Gly Gly Thr Phe Ser Trp Leu
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 17

Gly Gly Thr Phe Ser Ser Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 18

Gly Gly Thr Phe Gly Ser Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 19

Gly Gly Thr Phe Ser Lys Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 20

Gly Gly Thr Phe Gly Arg Tyr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 21

Gly Gly Thr Phe Glu Ser Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 22
```

```
Gly Gly Thr Phe Ser Asn Tyr
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 23

Gly Gly Ala Phe Ser Ser Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: CDR-H1, Chothia

<400> SEQUENCE: 24

Gly Phe Thr Phe Ser Ser Tyr
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 25

Ser Tyr Tyr Met His
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 26

Ser Tyr Glu Met His
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 27

Ser Tyr Gln Met His
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 28
```

```
Ser Tyr Tyr Met Tyr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 29

Ser Tyr Phe Met His
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 30

Ser Leu Ala Ile Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 31

Lys Leu Ala Ile Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 32

His Thr Ala Ile Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 33

Ser Leu Pro Ile Ser
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 34

Leu Leu Ala Ile Ser
```

```
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 35

Ser Asn Ala Ile Ser
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 36

Ala Met Ala Ile Ser
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 37

Trp Leu Ala Ile Ser
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 38

Ser Tyr Ala Ile Ser
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 39

Ser Tyr Gly Ile Ser
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 40

Lys Tyr Gly Ile Ser
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 41

Asn Tyr Ala Ile Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 42

Ser Tyr Ala Thr Ser
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 43

Ser Tyr Ala Ile Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 44

Ser Tyr Ser Met Asn
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic: CDR-H1, Kabat

<400> SEQUENCE: 45

Ser Tyr Gly Met Asn
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic: CDR-H2, Chothia

<400> SEQUENCE: 46

Asn Pro Ser Gly Gly Ser Thr
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 47

Asn Pro Ser Val Gly Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 48

Asn Pro Ser Gly Gly Ser
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 49

Asn Pro Leu Gly Gly Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 50

Asn Pro Arg Gly Gly Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 51

Ile Pro Ile Phe Gly Thr
1               5

<210> SEQ ID NO 52
<211> LENGTH: 4
<212> TYPE: PRT
<213> ORGANISM: Artificial Sequence
<220> FEATURE:
<223> OTHER INFORMATION: Synthetic: CDR-H2, Chothia

<400> SEQUENCE: 52

Gly Phe Gly Thr
1
```

```
<210> SEQ ID NO 53
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 53

Leu Pro Ile Gly Gly Thr
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 54

Leu Pro Ile Ala Gly Thr
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 55

Leu Pro Ile Phe Gly Glu
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 56

Ile Pro Arg Gly Gly Thr
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 57

Ile Pro Glu Phe Gly Ile
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 58

Ile Pro Ser Ile Gly Thr
1               5

<210> SEQ ID NO 59
```

-continued

```
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 59

Ile Pro Ile Ser Gly Thr
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 60

Ile Pro Thr Phe Gly Thr
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 61

Ser Ser Ser Ser Ser Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic: CDR-H2, Chothia

<400> SEQUENCE: 62

Trp Tyr Asp Gly Ser Asn
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 63

Val Ile Asn Pro Ser Gly Gly Ser Thr Ser Tyr Ala Gln Lys Phe Gln
1               5                   10                  15

Gly

<210> SEQ ID NO 64
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 64

Arg Ile Asn Pro Ser Val Gly Ser Thr Trp Tyr Ala Gln Lys Phe Gln
1               5                   10                  15

Gly
```

<210> SEQ ID NO 65
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 65

Arg Ile Asn Pro Ser Gly Gly Ser Thr Trp Tyr Ala Gln Lys Phe Gln
1               5                   10                  15

Gly

<210> SEQ ID NO 66
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 66

Lys Ile Asn Pro Ser Gly Gly Ser Thr Trp Tyr Ala Gln Lys Phe Gln
1               5                   10                  15

Gly

<210> SEQ ID NO 67
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 67

Val Ile Asn Pro Leu Gly Gly Thr Ser Tyr Ala Gln Lys Phe Gln
1               5                   10                  15

Gly

<210> SEQ ID NO 68
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 68

Ser Ile Asn Pro Arg Gly Gly Ser Thr Ser Tyr Ala Gln Lys Phe Gln
1               5                   10                  15

Gly

<210> SEQ ID NO 69
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 69

Gly Ile Ile Pro Ile Phe Gly Thr Ala Asn Tyr Ala Gln Lys Phe Gln
1               5                   10                  15

Gly

<210> SEQ ID NO 70
<211> LENGTH: 15

```
<212> TYPE: PRT
<213> ORGANISM: Artificial Sequence
<220> FEATURE:
<223> OTHER INFORMATION: Synthetic: CDR-H2, Kabat

<400> SEQUENCE: 70

Gly Ile Gly Phe Gly Thr Ala Asn Tyr Ala Gln Lys Phe Gln Gly
1               5                   10                  15

<210> SEQ ID NO 71
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 71

Gly Ile Leu Pro Ile Gly Gly Thr Ala Asn Tyr Ala Gln Lys Phe Gln
1               5                   10                  15

Gly

<210> SEQ ID NO 72
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 72

Gly Ile Leu Pro Ile Ala Gly Thr Ala Asn Tyr Ala Gln Lys Phe Gln
1               5                   10                  15

Gly

<210> SEQ ID NO 73
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 73

Gly Ile Leu Pro Ile Phe Gly Glu Ala Asn Tyr Ala Gln Lys Phe Gln
1               5                   10                  15

Gly

<210> SEQ ID NO 74
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 74

Gly Ile Ile Pro Arg Gly Gly Thr Ala Asn Tyr Ala Gln Lys Phe Gln
1               5                   10                  15

Gly

<210> SEQ ID NO 75
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 75
```

Ser Ile Ile Pro Ile Phe Gly Thr Ala Asn Tyr Ala Gln Lys Phe Arg
1               5                   10                  15

Gly

<210> SEQ ID NO 76
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 76

Ser Ile Ile Pro Glu Phe Gly Ile Ala Asn Tyr Ala Gln Lys Phe Gln
1               5                   10                  15

Gly

<210> SEQ ID NO 77
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 77

Ser Ile Ile Pro Ile Phe Gly Thr Ala Asn Tyr Ala Gln Lys Phe Gln
1               5                   10                  15

Gly

<210> SEQ ID NO 78
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 78

Gly Ile Ile Pro Ile Ser Gly Thr Ala Asn Tyr Ala Gln Glu Phe Gln
1               5                   10                  15

Gly

<210> SEQ ID NO 79
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 79

Gly Ile Ile Pro Thr Phe Gly Thr Ala Asn Tyr Ala Gln Lys Phe Gln
1               5                   10                  15

Gly

<210> SEQ ID NO 80
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 80

Ser Ile Ser Ser Ser Ser Ser Tyr Ile Tyr Tyr Ala Asp Ser Val Lys
1               5                   10                  15

Gly

<210> SEQ ID NO 81
<211> LENGTH: 17
<212> TYPE: PRT
<213> ORGANISM: Artificial Sequence
<220> FEATURE:
<223> OTHER INFORMATION: Synthetic: CDR-H2, Kabat

<400> SEQUENCE: 81

Val Ile Trp Tyr Asp Gly Ser Asn Lys Tyr Tyr Ala Asp Ser Val Lys
1               5                   10                  15

Gly

<210> SEQ ID NO 82
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 82

Gly Lys Arg Glu Gly Gly Thr Glu Tyr Leu Arg His
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 83

Gly Lys Arg Glu Gly Gly Thr Glu Tyr Leu Arg Lys
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 84

Gly Lys Arg Glu Gly Gly Thr Glu Tyr Leu Arg Ser
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 85

Gly Lys Arg Glu Gly Gly Thr Glu Tyr Leu Arg Asn
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 86

```
Gly Lys Arg Glu Gly Gly Thr Glu Tyr Leu Arg Val
1               5                   10
```

<210> SEQ ID NO 87
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 87

```
Gly Gly Ala Lys Tyr Ala Ser Thr Tyr Gly Met Asp Val
1               5                   10
```

<210> SEQ ID NO 88
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 88

```
Gly Gly Ala Lys Tyr Ala Ser Thr His Gly Met Asp Val
1               5                   10
```

<210> SEQ ID NO 89
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 89

```
Gly Gly Ala Lys Tyr Ala Ser Gln Leu Gly Met Asp Val
1               5                   10
```

<210> SEQ ID NO 90
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 90

```
Gly Gly Ala Lys Tyr Ala Ser Lys Trp Gly Met Asp Val
1               5                   10
```

<210> SEQ ID NO 91
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 91

```
Gly Gly Ala Lys Tyr Ala Val Gly Tyr Gly Met Asp Val
1               5                   10
```

<210> SEQ ID NO 92
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 92

```
Gly Gly Ala Lys Tyr Ala Gly Arg Tyr Gly Met Asp Val
```

```
1               5                  10
```

<210> SEQ ID NO 93
<211> LENGTH: 13
<212> TYPE: PRT
<213> ORGANISM: Artificial Sequence
<220> FEATURE:
<223> OTHER INFORMATION: Synthetic: CDR-H3

<400> SEQUENCE: 93

```
Gly Gly Ala Lys Tyr Ala Arg Thr Tyr Gly Met Asp Val
1               5                  10
```

<210> SEQ ID NO 94
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 94

```
Glu Ser Gly Gly Tyr Arg Asp His Arg Leu Asp Val
1               5                  10
```

<210> SEQ ID NO 95
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 95

```
Glu Ser Gly Thr Tyr Arg Asp His Arg Leu Asp Val
1               5                  10
```

<210> SEQ ID NO 96
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 96

```
Glu Ser Gly Gly Tyr Arg Asp His Arg Leu Gly Val
1               5                  10
```

<210> SEQ ID NO 97
<211> LENGTH: 15
<212> TYPE: PRT
<213> ORGANISM: Artificial Sequence
<220> FEATURE:
<223> OTHER INFORMATION: Synthetic: CDR-H3

<400> SEQUENCE: 97

```
Asp Phe Thr Asp Tyr Ser Ser Gly Tyr Ser Ser Gly Trp Thr Tyr
1               5                  10                 15
```

<210> SEQ ID NO 98
<211> LENGTH: 14
<212> TYPE: PRT
<213> ORGANISM: Artificial Sequence
<220> FEATURE:
<223> OTHER INFORMATION: Synthetic: CDR-H3

<400> SEQUENCE: 98

```
Asp Thr Leu Tyr Ser Ser Gly Ala Tyr Tyr Gly Tyr Asn Val
1               5                  10
```

<210> SEQ ID NO 99
<211> LENGTH: 15
<212> TYPE: PRT
<213> ORGANISM: Artificial Sequence
<220> FEATURE:
<223> OTHER INFORMATION: Synthetic: CDR-H3

<400> SEQUENCE: 99

Ala Lys Arg Gly Tyr Asp Ser Tyr Gly Gly Val Tyr Phe Asp Tyr
1               5                   10                  15

<210> SEQ ID NO 100
<211> LENGTH: 18
<212> TYPE: PRT
<213> ORGANISM: Artificial Sequence
<220> FEATURE:
<223> OTHER INFORMATION: Synthetic: CDR-H3

<400> SEQUENCE: 100

Gly Pro Thr Val Thr Ala Thr Thr Ser Ile Gly Thr His Asn Trp Phe
1               5                   10                  15

Asp Pro

<210> SEQ ID NO 101
<211> LENGTH: 28
<212> TYPE: PRT
<213> ORGANISM: Artificial Sequence
<220> FEATURE:
<223> OTHER INFORMATION: Synthetic: CDR-H3

<400> SEQUENCE: 101

Glu Gly Arg Gly Tyr Asp Ser Ser Arg Tyr Tyr Lys Phe Trp Phe Asp
1               5                   10                  15

Pro Trp Gly Gln Gly Thr Leu Val Thr Val Ser Ser
            20                  25

<210> SEQ ID NO 102
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 102

Asp Gly Gly Gly Tyr Arg His His Tyr Phe Asp Leu
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 103

Glu Ser Gly Gly Tyr Arg Asp His Lys Leu Asp Val
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic: CDR-H3

```
<400> SEQUENCE: 104

Asp Gly Gly Gly Tyr Gln His His Tyr Phe Asp Leu
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic: CDR-H3

<400> SEQUENCE: 105

Asp Ser Gly Tyr His Arg His Tyr Ser Asp Tyr
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 106

Asp Pro Leu Gly Ile Arg Lys His Trp Phe Asp Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 107

Asp Thr Pro Arg Trp Arg Tyr His Tyr Phe Asp Tyr
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Synthetic: CDR-H3

<400> SEQUENCE: 108

Glu Arg Arg Gly Ser Leu Ala Leu Gly Met Asp Val
1               5                   10

<210> SEQ ID NO 109
<211> LENGTH: 19
<212> TYPE: PRT
<213> ORGANISM: Artificial Sequence
<220> FEATURE:
<223> OTHER INFORMATION: Synthetic: CDR-H3

<400> SEQUENCE: 109

Asp Leu Gly Gly Tyr Ser Tyr Gly Glu Pro Tyr Tyr Tyr Tyr Gly
1               5                   10                  15

Met Asp Val

<210> SEQ ID NO 110
<211> LENGTH: 12
<212> TYPE: PRT
<213> ORGANISM: Artificial Sequence
<220> FEATURE:
<223> OTHER INFORMATION: Synthetic: CDR-L1
```

```
<400> SEQUENCE: 110

Arg Ala Ser Gln Ser Val Ser Ser Ser Tyr Leu Ala
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Synthetic: CDR-L1

<400> SEQUENCE: 111

Arg Ala Ser Gln Ser Val Ala Ser Ser Tyr Leu Ala
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Synthetic: CDR-L1

<400> SEQUENCE: 112

Glu Ala Ser Gln Ser Val Ser Tyr Ser Tyr Leu Ala
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Synthetic: CDR-L1

<400> SEQUENCE: 113

Lys Ala Ser Glu Ser Val Ser Ser Ser Tyr Leu Ala
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Synthetic: CDR-L1

<400> SEQUENCE: 114

Arg Ala Ser Gln Tyr Val Ser Ser Ser Tyr Leu Ala
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Synthetic: CDR-L1

<400> SEQUENCE: 115

Lys Ser Ser Gln Ser Val Leu Phe Ser Ser Asn Asn Lys Asn Tyr Leu
1               5                   10                  15

Ala

<210> SEQ ID NO 116
<211> LENGTH: 17
<212> TYPE: PRT
<213> ORGANISM: Artificial Sequence
<220> FEATURE:
```

<223> OTHER INFORMATION: Synthetic: CDR-L1

<400> SEQUENCE: 116

Lys Ser Ser Arg Ser Val Leu Phe Ser Ser Asn Asn Lys Asn Tyr Leu
1               5                   10                  15
Ala

<210> SEQ ID NO 117
<211> LENGTH: 17
<212> TYPE: PRT
<213> ORGANISM: Artificial Sequence
<220> FEATURE:
<223> OTHER INFORMATION: Synthetic: CDR-L1

<400> SEQUENCE: 117

Lys Ser Ser Lys Ser Val Leu Tyr Ser Asn Asn Lys Asn Tyr Leu
1               5                   10                  15
Ala

<210> SEQ ID NO 118
<211> LENGTH: 11
<212> TYPE: PRT
<213> ORGANISM: Artificial Sequence
<220> FEATURE:
<223> OTHER INFORMATION: Synthetic: CDR-L1

<400> SEQUENCE: 118

Arg Ala Ser Gln Ser Val Gly Ser Asn Leu Ala
1               5                   10

<210> SEQ ID NO 119
<211> LENGTH: 17
<212> TYPE: PRT
<213> ORGANISM: Artificial Sequence
<220> FEATURE:
<223> OTHER INFORMATION: Synthetic: CDR-L1

<400> SEQUENCE: 119

Lys Ser Ser Gln Ser Val Leu Tyr Ser Ser Asn Asn Lys Asn Tyr Leu
1               5                   10                  15
Ala

<210> SEQ ID NO 120
<211> LENGTH: 11
<212> TYPE: PRT
<213> ORGANISM: Artificial Sequence
<220> FEATURE:
<223> OTHER INFORMATION: Synthetic: CDR-L1

<400> SEQUENCE: 120

Gln Ala Ser Gln Asp Ile Ser Asn Tyr Leu Asn
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic: CDR-L1

<400> SEQUENCE: 121

Arg Ala Ser Gln Ser Val Ser Ser Tyr Leu Ala
1               5                   10

```
<210> SEQ ID NO 122
<211> LENGTH: 11
<212> TYPE: PRT
<213> ORGANISM: Artificial Sequence
<220> FEATURE:
<223> OTHER INFORMATION: Synthetic: CDR-L1

<400> SEQUENCE: 122

Arg Ala Ser Gln Ser Val Ser Arg Tyr Leu Ala
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic: CDR-L1

<400> SEQUENCE: 123

Arg Ala Ser Gln Ser Ile Ser Ser Trp Leu Ala
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Synthetic: CDR-L1

<400> SEQUENCE: 124

Arg Ala Ser Gln Ser Val Ser Ser Asp Tyr Leu Ala
1               5                   10

<210> SEQ ID NO 125
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 125

Gly Ala Ser Ser Arg Ala Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 126

Gly Ala Ser Asn Arg His Thr
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 127

Tyr Ala Ser Ser Arg Ala Tyr
1               5

<210> SEQ ID NO 128
```

```
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 128

Gly Ala Ser Ser Arg Ala Asn
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 129

Tyr Ala Ser Ser Arg Ala Thr
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 130

Tyr Ala Ser Asn Arg Ala Thr
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 131

Trp Ala Ser Thr Arg Glu Ser
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 132

Trp Ala Ser Ser Arg Glu Ser
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 133

Trp Ala Ser Thr Arg Gln Ser
1               5

<210> SEQ ID NO 134
<211> LENGTH: 7
```

```
<212> TYPE: PRT
<213> ORGANISM: Artificial Sequence
<220> FEATURE:
<223> OTHER INFORMATION: Synthetic: CDR-L2

<400> SEQUENCE: 134

Trp Ala Ser Thr Arg Ala Ser
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 135

Gly Ala Ser Thr Arg Ala Thr
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 136

Gly Ala Ser Thr Arg Ala Ser
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 137

Asp Ala Ser Asn Leu Glu Thr
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 138

Asp Ala Ser Asn Arg Ala Thr
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic: CDR-L2

<400> SEQUENCE: 139

Asp Ala Ser Lys Arg Ala Thr
1               5

<210> SEQ ID NO 140
<211> LENGTH: 7
<212> TYPE: PRT
```

<213> ORGANISM: Artificial Sequence
<220> FEATURE:
<223> OTHER INFORMATION: Synthetic: CDR-L2

<400> SEQUENCE: 140

Lys Ala Ser Ser Leu Glu Ser
1               5

<210> SEQ ID NO 141
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 141

Gln Gln Tyr His Ser Tyr Ile Thr
1               5

<210> SEQ ID NO 142
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 142

Gln Gln Tyr His Asn Ala Ile Thr
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 143

Gln Gln Tyr Tyr Phe Tyr Ile Thr
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 144

Gln Gln Tyr His Ser Ala Leu Thr
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 145

Gln Gln Tyr His Gly Gly Ile Thr
1               5

<210> SEQ ID NO 146
<211> LENGTH: 8
<212> TYPE: PRT
<213> ORGANISM: Artificial Sequence

```
<220> FEATURE:
<223> OTHER INFORMATION: Synthetic: CDR-L3

<400> SEQUENCE: 146

Gln Gln Tyr His Arg Arg Ile Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic: CDR-L3

<400> SEQUENCE: 147

Gln Gln Tyr His Ser Gly Ile Thr
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 148

Gln Gln Tyr Tyr Leu Tyr Pro Leu Thr
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 149

Gln Gln Tyr Trp Thr Tyr Pro Leu Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 150

Gln Gln Tyr Leu Leu Tyr Pro Leu Thr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 151

Gln Gln Tyr Leu Ile Trp Pro Leu Thr
1               5

<210> SEQ ID NO 152
<211> LENGTH: 9
<212> TYPE: PRT
<213> ORGANISM: Artificial Sequence
<220> FEATURE:
```

<223> OTHER INFORMATION: Synthetic: CDR-L3

<400> SEQUENCE: 152

Gln Gln Tyr Leu Leu Trp Pro Leu Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 153

Gln Gln Phe Tyr Phe Phe Pro Pro Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 154

Gln Gln Ala Tyr Thr Phe Pro Pro Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 155

Gln Gln Tyr Tyr Ile Phe Pro Pro Thr
1               5

<210> SEQ ID NO 156
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 156

Gln Gln Arg Asn Phe Tyr Pro Pro Thr
1               5

<210> SEQ ID NO 157
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 157

Gln Gln Phe Val Leu Trp Pro Arg Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 158

Gln Gln His Val Asn Phe Pro Leu Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 159

Gln Gln Ser Val Phe Trp Pro Ile Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 160

Gln Gln Leu Thr Lys Trp Pro Leu Thr
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 161

Gln Gln Asp Val Leu Trp Pro Leu Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 162

Gln Gln Tyr Gly Leu Phe Pro Ile Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 163

Gln Gln His Thr Val Trp Pro Ile Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic: CDR-L3

```
<400> SEQUENCE: 164

Gln Gln Val Leu Asn Tyr Pro Leu Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 165

Gln Gln Ser Tyr Phe Leu Pro Pro Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic: CDR-L3

<400> SEQUENCE: 166

Gln Gln Ala His Ser Ser Pro Tyr Thr
1               5

<210> SEQ ID NO 167
<211> LENGTH: 22
<212> TYPE: PRT
<213> ORGANISM: Artificial Sequence
<220> FEATURE:
<223> OTHER INFORMATION: Synthetic: Leader for scFV, scFv-Fc, Leader

<400> SEQUENCE: 167

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 168
<211> LENGTH: 15
<212> TYPE: PRT
<213> ORGANISM: Artificial Sequence
<220> FEATURE:
<223> OTHER INFORMATION: Synthetic: Linker for scFV, scFV-FC, Linker

<400> SEQUENCE: 168

Gly Gly Gly Gly Ser Gly Gly Gly Gly Ser Gly Gly Gly Gly Ser
1               5                   10                  15

<210> SEQ ID NO 169
<211> LENGTH: 11
<212> TYPE: PRT
<213> ORGANISM: Artificial Sequence
<220> FEATURE:
<223> OTHER INFORMATION: Synthetic: C-Term Tag for scFV, scFV-FC, C-Term
      Tag

<400> SEQUENCE: 169

Gly Pro Gly Gly Gln His His His His His
1               5                   10

<210> SEQ ID NO 170
<211> LENGTH: 231
<212> TYPE: PRT
<213> ORGANISM: Artificial Sequence
```

<220> FEATURE:
<223> OTHER INFORMATION: Synthetic: C-Term Tag for scFv, scFV-FC, C-Term
    Tag

<400> SEQUENCE: 170

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 171
<211> LENGTH: 276
<212> TYPE: PRT
<213> ORGANISM: Artificial Sequence
<220> FEATURE:
<223> OTHER INFORMATION: Synthetic: scFv, 29872

<400> SEQUENCE: 171

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
            20                  25                  30

Val Lys Glu Pro Gly Ala Ser Val Lys Val Ser Cys Lys Ala Pro Gly
        35                  40                  45

Tyr Thr Phe Thr Ser Tyr Tyr Met His Trp Val Arg Gln Ala Pro Gly
    50                  55                  60

Gln Gly Leu Glu Trp Met Gly Val Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

```
Ser Thr Ser Thr Val Tyr Met Glu Leu Ser Ser Leu Arg Ser Glu Asp
            100                 105                 110

Thr Ala Val Tyr Tyr Cys Ala Arg Gly Lys Arg Glu Gly Gly Thr Glu
            115                 120                 125

Tyr Leu Arg His Trp Gly Gln Gly Thr Leu Val Thr Val Ser Ser Gly
        130                 135                 140

Gly Gly Gly Ser Gly Gly Gly Gly Ser Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Val Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Ser Arg Ala Thr Gly Ile Pro Asp Arg Phe Ser Gly Ser
        210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Ser Tyr Ile Thr Phe
            245                 250                 255

Gly Gly Gly Thr Lys Val Glu Ile Lys Gly Pro Gly Gly Gln His His
            260                 265                 270

His His His His
        275

<210> SEQ ID NO 172
<211> LENGTH: 276
<212> TYPE: PRT
<213> ORGANISM: Artificial Sequence
<220> FEATURE:
<223> OTHER INFORMATION: Synthetic: scFv, 31895

<400> SEQUENCE: 172

Met Lys Tyr Leu Leu Pro Thr Ala Ala Ala Gly Leu Leu Leu Ala
1               5                   10                  15

Ala Gln Pro Ala Met Ala Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Lys Ser Tyr Glu Met His Trp Val Arg Gln Ala Pro Gly
    50                  55                  60

Gln Gly Leu Glu Trp Met Gly Arg Ile Asn Pro Ser Val Gly Ser Thr
65                  70                  75                  80

Trp Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Gly Lys Arg Glu Gly Gly Thr Glu
            115                 120                 125

Tyr Leu Arg Lys Trp Gly Gln Gly Thr Leu Val Thr Val Ser Ser Gly
        130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
                165                 170                 175
```

```
Ala Thr Leu Ser Cys Arg Ala Ser Gln Ser Val Ala Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Asn Arg His Thr Gly Ile Pro Asp Arg Phe Ser Gly Ser
        210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Asn Ala Ile Thr Phe
                245                 250                 255

Gly Gly Gly Thr Lys Val Glu Ile Lys Gly Pro Gly Gly Gln His His
                260                 265                 270

His His His His
        275

<210> SEQ ID NO 173
<211> LENGTH: 276
<212> TYPE: PRT
<213> ORGANISM: Artificial Sequence
<220> FEATURE:
<223> OTHER INFORMATION: Synthetic: scFv, 31414

<400> SEQUENCE: 173

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Lys Ser Tyr Glu Met His Trp Val Arg Gln Ala Pro Gly
        50                  55                  60

Gln Gly Leu Glu Trp Met Gly Arg Ile Asn Pro Ser Val Gly Ser Thr
65                  70                  75                  80

Trp Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Gly Lys Arg Glu Gly Gly Thr Glu
        115                 120                 125

Tyr Leu Arg Asn Trp Gly Gln Gly Thr Leu Val Thr Val Ser Ser Gly
    130                 135                 140

Gly Gly Gly Ser Gly Gly Gly Ser Gly Gly Gly Gly Ser Gly Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Val Ser Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Ser Arg Ala Thr Gly Ile Pro Asp Arg Phe Ser Gly Ser
    210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Ser Tyr Ile Thr Phe
                245                 250                 255
```

Gly Gly Gly Thr Lys Val Glu Ile Lys Gly Pro Gly Gln His His
            260                 265                 270
His His His His
        275

<210> SEQ ID NO 174
<211> LENGTH: 281
<212> TYPE: PRT
<213> ORGANISM: Artificial Sequence
<220> FEATURE:
<223> OTHER INFORMATION: Synthetic: scFv, 31905

<400> SEQUENCE: 174

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Pro Ser Asn Ala Ile Ser Trp Val Arg Gln Ala Pro Gly
    50                  55                  60

Gln Gly Leu Glu Trp Met Gly Gly Ile Gly Phe Gly Thr Ala Asn Tyr
65                  70                  75                  80

Ala Gln Lys Phe Gln Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg Gly Gly Ala Lys Tyr Ala Arg Thr Tyr Gly
        115                 120                 125

Met Asp Val Trp Gly Gln Gly Thr Thr Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Asp Ser Leu Ala Val Ser Leu Gly Glu Arg Ala
                165                 170                 175

Thr Ile Asn Cys Lys Ser Ser Lys Ser Val Leu Tyr Ser Asn Asn Asn
            180                 185                 190

Lys Asn Tyr Leu Ala Trp Tyr Gln Gln Lys Pro Gly Gln Pro Pro Lys
        195                 200                 205

Leu Leu Ile Tyr Trp Ala Ser Thr Arg Gln Ser Gly Val Pro Asp Arg
    210                 215                 220

Phe Ser Gly Ser Gly Ser Gly Thr Asp Phe Thr Leu Thr Ile Ser Ser
225                 230                 235                 240

Leu Gln Ala Glu Asp Val Ala Val Tyr Tyr Cys Gln Gln Tyr Leu Leu
                245                 250                 255

Tyr Pro Leu Thr Phe Gly Gly Gly Thr Lys Val Glu Ile Lys Gly Pro
            260                 265                 270

Gly Gly Gln His His His His His His
        275                 280

<210> SEQ ID NO 175
<211> LENGTH: 496
<212> TYPE: PRT
<213> ORGANISM: Artificial Sequence
<220> FEATURE:
<223> OTHER INFORMATION: Synthetic: scFv-Fc, 29872

<400> SEQUENCE: 175

```
Met Lys Tyr Leu Leu Pro Thr Ala Ala Ala Gly Leu Leu Leu Ala
1               5                   10                  15

Ala Gln Pro Ala Met Ala Gln Val Gln Leu Val Gln Ser Gly Ala Glu
            20                  25                  30

Val Lys Glu Pro Gly Ala Ser Val Lys Val Ser Cys Lys Ala Pro Gly
            35                  40                  45

Tyr Thr Phe Thr Ser Tyr Tyr Met His Trp Val Arg Gln Ala Pro Gly
            50                  55                  60

Gln Gly Leu Glu Trp Met Gly Val Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
                100                 105                 110

Thr Ala Val Tyr Tyr Cys Ala Arg Gly Lys Arg Glu Gly Gly Thr Glu
            115                 120                 125

Tyr Leu Arg His Trp Gly Gln Gly Thr Leu Val Thr Val Ser Ser Gly
            130                 135                 140

Gly Gly Gly Ser Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
            165                 170                 175

Ala Thr Leu Ser Cys Arg Ala Ser Gln Ser Val Ser Ser Ser Tyr Leu
            180                 185                 190

Ala Trp Tyr Gln Gln Lys Pro Gly Gln Ala Pro Arg Leu Leu Ile Tyr
            195                 200                 205

Gly Ala Ser Ser Arg Ala Thr Gly Ile Pro Asp Arg Phe Ser Gly Ser
            210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Ser Tyr Ile Thr Phe
            245                 250                 255

Gly Gly Gly Thr Lys Val Glu Ile Lys Pro Lys Ser Cys Asp Lys Thr
            260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
            290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
                405                 410                 415
```

```
Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
                435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 176
<211> LENGTH: 496
<212> TYPE: PRT
<213> ORGANISM: Artificial Sequence
<220> FEATURE:
<223> OTHER INFORMATION: Synthetic: scFv-Fc, 31895

<400> SEQUENCE: 176

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Lys Ser Tyr Glu Met His Trp Val Arg Gln Ala Pro Gly
        50                  55                  60

Gln Gly Leu Glu Trp Met Gly Arg Ile Asn Pro Ser Val Gly Ser Thr
65                  70                  75                  80

Trp Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
                100                 105                 110

Thr Ala Val Tyr Tyr Cys Ala Arg Gly Lys Arg Glu Gly Gly Thr Glu
            115                 120                 125

Tyr Leu Arg Lys Trp Gly Gln Gly Thr Leu Val Thr Val Ser Ser Gly
        130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Gln Ser Val Ala Ser Ser Tyr Leu
            180                 185                 190

Ala Trp Tyr Gln Gln Lys Pro Gly Gln Ala Pro Arg Leu Leu Ile Tyr
        195                 200                 205

Gly Ala Ser Asn Arg His Thr Gly Ile Pro Asp Arg Phe Ser Gly Ser
    210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Asn Ala Ile Thr Phe
                245                 250                 255

Gly Gly Gly Thr Lys Val Glu Ile Lys Pro Lys Ser Cys Asp Lys Thr
            260                 265                 270

His Thr Cys Pro Pro Cys Pro Ala Pro Glu Leu Leu Gly Gly Pro Ser
        275                 280                 285
```

```
Val Phe Leu Phe Pro Pro Lys Pro Lys Asp Thr Leu Met Ile Ser Arg
    290                 295                 300
Thr Pro Glu Val Thr Cys Val Val Val Asp Val Ser His Glu Asp Pro
305                 310                 315                 320
Glu Val Lys Phe Asn Trp Tyr Val Asp Gly Val Glu Val His Asn Ala
                325                 330                 335
Lys Thr Lys Pro Arg Glu Glu Gln Tyr Asn Ser Thr Tyr Arg Val Val
            340                 345                 350
Ser Val Leu Thr Val Leu His Gln Asp Trp Leu Asn Gly Lys Glu Tyr
        355                 360                 365
Lys Cys Lys Val Ser Asn Lys Ala Leu Pro Ala Pro Ile Glu Lys Thr
    370                 375                 380
Ile Ser Lys Ala Lys Gly Gln Pro Arg Glu Pro Gln Val Tyr Thr Leu
385                 390                 395                 400
Pro Pro Ser Arg Glu Glu Met Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495

<210> SEQ ID NO 177
<211> LENGTH: 496
<212> TYPE: PRT
<213> ORGANISM: Artificial Sequence
<220> FEATURE:
<223> OTHER INFORMATION: Synthetic: scFv-Fc, 31414

<400> SEQUENCE: 177

Met Lys Tyr Leu Leu Pro Thr Ala Ala Ala Gly Leu Leu Leu Leu Ala
1               5                   10                  15
Ala Gln Pro Ala Met Ala Gln Val Gln Leu Val Gln Ser Gly Ala Glu
            20                  25                  30
Val Lys Lys Pro Gly Ala Ser Val Lys Val Ser Cys Lys Ala Ser Gly
        35                  40                  45
Tyr Thr Phe Lys Ser Tyr Glu Met His Trp Val Arg Gln Ala Pro Gly
    50                  55                  60
Gln Gly Leu Glu Trp Met Gly Arg Ile Asn Pro Ser Val Gly Ser Thr
65                  70                  75                  80
Trp Tyr Ala Gln Lys Phe Gln Gly Arg Val Thr Met Thr Arg Asp Thr
                85                  90                  95
Ser Thr Ser Thr Val Tyr Met Glu Leu Ser Ser Leu Arg Ser Glu Asp
            100                 105                 110
Thr Ala Val Tyr Tyr Cys Ala Arg Gly Lys Arg Glu Gly Gly Thr Glu
        115                 120                 125
Tyr Leu Arg Asn Trp Gly Gln Gly Thr Leu Val Thr Val Ser Ser Gly
    130                 135                 140
Gly Gly Gly Ser Gly Gly Gly Gly Ser Gly Gly Gly Gly Ser Glu Ile
145                 150                 155                 160
```

Val Leu Thr Gln Ser Pro Gly Thr Leu Ser Leu Ser Pro Gly Glu Arg
            165                 170                 175

Ala Thr Leu Ser Cys Arg Ala Ser Gln Ser Val Ser Ser Tyr Leu
        180                 185                 190

Ala Trp Tyr Gln Gln Lys Pro Gly Gln Ala Pro Arg Leu Leu Ile Tyr
        195                 200                 205

Gly Ala Ser Ser Arg Ala Thr Gly Ile Pro Asp Arg Phe Ser Gly Ser
        210                 215                 220

Gly Ser Gly Thr Asp Phe Thr Leu Thr Ile Ser Arg Leu Glu Pro Glu
225                 230                 235                 240

Asp Phe Ala Val Tyr Tyr Cys Gln Gln Tyr His Ser Tyr Ile Thr Phe
                245                 250                 255

Gly Gly Gly Thr Lys Val Glu Ile Lys Pro Lys Ser Cys Asp Lys Thr
                260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
                340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
        370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
                405                 410                 415

Leu Val Lys Gly Phe Tyr Pro Ser Asp Ile Ala Val Glu Trp Glu Ser
                420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
        450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 178
<211> LENGTH: 501
<212> TYPE: PRT
<213> ORGANISM: Artificial Sequence
<220> FEATURE:
<223> OTHER INFORMATION: Synthetic: scFv-Fc, 31905

<400> SEQUENCE: 178

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
            20                  25                  30

-continued

Val Lys Lys Pro Gly Ser Ser Val Lys Val Ser Cys Lys Ala Ser Gly
            35                  40                  45

Gly Thr Phe Pro Ser Asn Ala Ile Ser Trp Val Arg Gln Ala Pro Gly
 50                  55                  60

Gln Gly Leu Glu Trp Met Gly Gly Ile Gly Phe Gly Thr Ala Asn Tyr
 65                  70                  75                  80

Ala Gln Lys Phe Gln Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
                100                 105                 110

Val Tyr Tyr Cys Ala Arg Gly Gly Ala Lys Tyr Ala Arg Thr Tyr Gly
            115                 120                 125

Met Asp Val Trp Gly Gln Gly Thr Thr Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Asp Ser Leu Ala Val Ser Leu Gly Glu Arg Ala
                165                 170                 175

Thr Ile Asn Cys Lys Ser Ser Lys Ser Val Leu Tyr Ser Asn Asn Asn
            180                 185                 190

Lys Asn Tyr Leu Ala Trp Tyr Gln Gln Lys Pro Gly Gln Pro Pro Lys
        195                 200                 205

Leu Leu Ile Tyr Trp Ala Ser Thr Arg Gln Ser Gly Val Pro Asp Arg
    210                 215                 220

Phe Ser Gly Ser Gly Ser Gly Thr Asp Phe Thr Leu Thr Ile Ser Ser
225                 230                 235                 240

Leu Gln Ala Glu Asp Val Ala Val Tyr Tyr Cys Gln Gln Tyr Leu Leu
                245                 250                 255

Tyr Pro Leu Thr Phe Gly Gly Gly Thr Lys Val Glu Ile Lys Pro Lys
            260                 265                 270

Ser Cys Asp Lys Thr His Thr Cys Pro Pro Cys Pro Ala Pro Glu Leu
        275                 280                 285

Leu Gly Gly Pro Ser Val Phe Leu Phe Pro Pro Lys Pro Lys Asp Thr
    290                 295                 300

Leu Met Ile Ser Arg Thr Pro Glu Val Thr Cys Val Val Val Asp Val
305                 310                 315                 320

Ser His Glu Asp Pro Glu Val Lys Phe Asn Trp Tyr Val Asp Gly Val
                325                 330                 335

Glu Val His Asn Ala Lys Thr Lys Pro Arg Glu Glu Gln Tyr Asn Ser
            340                 345                 350

Thr Tyr Arg Val Val Ser Val Leu Thr Val Leu His Gln Asp Trp Leu
        355                 360                 365

Asn Gly Lys Glu Tyr Lys Cys Lys Val Ser Asn Lys Ala Leu Pro Ala
    370                 375                 380

Pro Ile Glu Lys Thr Ile Ser Lys Ala Lys Gly Gln Pro Arg Glu Pro
385                 390                 395                 400

Gln Val Tyr Thr Leu Pro Pro Ser Arg Glu Glu Met Thr Lys Asn Gln
                405                 410                 415

Val Ser Leu Thr Cys Leu Val Lys Gly Phe Tyr Pro Ser Asp Ile Ala
            420                 425                 430

Val Glu Trp Glu Ser Asn Gly Gln Pro Glu Asn Asn Tyr Lys Thr Thr
        435                 440                 445

Pro Pro Val Leu Asp Ser Asp Gly Ser Phe Phe Leu Tyr Ser Lys Leu

```
                450             455             460
Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
                    485                 490                 495

Leu Ser Pro Gly Lys
            500

<210> SEQ ID NO 179
<211> LENGTH: 121
<212> TYPE: PRT
<213> ORGANISM: Artificial Sequence
<220> FEATURE:
<223> OTHER INFORMATION: Synthetic: VH, 27579

<400> SEQUENCE: 179

Gln Val Gln Leu Val Gln Ser Gly Ala Glu Val Lys Glu Pro Gly Ala
1               5                   10                  15

Ser Val Lys Val Ser Cys Lys Ala Pro Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Val Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg His Trp Gly
                100                 105                 110

Gln Gly Thr Leu Val Thr Val Ser Ser
            115                 120

<210> SEQ ID NO 180
<211> LENGTH: 121
<212> TYPE: PRT
<213> ORGANISM: Artificial Sequence
<220> FEATURE:
<223> OTHER INFORMATION: Synthetic: VH, 31895

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
                20                  25                  30

Glu Met His Trp Val Arg Gln Ala Pro Gly Gln Gly Leu Glu Trp Met
            35                  40                  45

Gly Arg Ile Asn Pro Ser Val Gly Ser Thr Trp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Lys Trp Gly
                100                 105                 110

Gln Gly Thr Leu Val Thr Val Ser Ser
            115                 120
```

<210> SEQ ID NO 181
<211> LENGTH: 121
<212> TYPE: PRT
<213> ORGANISM: Artificial Sequence
<220> FEATURE:
<223> OTHER INFORMATION: Synthetic: VH, 31415

<400> SEQUENCE: 181

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gln Met His Trp Val Arg Gln Ala Pro Gly Gln Gly Leu Glu Trp Met
        35                  40                  45

Gly Arg Ile Asn Pro Ser Gly Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Ser Trp Gly
            100                 105                 110

Gln Gly Thr Leu Val Thr Val Ser Ser
        115                 120
```

<210> SEQ ID NO 182
<211> LENGTH: 121
<212> TYPE: PRT
<213> ORGANISM: Artificial Sequence
<220> FEATURE:
<223> OTHER INFORMATION: Synthetic: VH, 31414

<400> SEQUENCE: 182

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Asn Trp Gly
            100                 105                 110

Gln Gly Thr Leu Val Thr Val Ser Ser
        115                 120
```

<210> SEQ ID NO 183
<211> LENGTH: 121
<212> TYPE: PRT
<213> ORGANISM: Artificial Sequence
<220> FEATURE:
<223> OTHER INFORMATION: Synthetic: VH, 31891

<400> SEQUENCE: 183

```
Gln Val Gln Leu Val Gln Ser Gly Ala Glu Val Lys Lys Pro Gly Ala
```

-continued

```
1               5                   10                  15
Ser Val Lys Val Ser Cys Lys Ala Ser Gly Tyr Ile Phe Lys Ser Tyr
            20                  25                  30

Glu Met His Trp Val Arg Gln Ala Pro Gly Gln Gly Leu Glu Trp Met
            35                  40                  45

Gly Arg Ile Asn Pro Ser Val Gly Ser Thr Trp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Val Trp Gly
            100                 105                 110

Gln Gly Thr Leu Val Thr Val Ser Ser
            115                 120
```

<210> SEQ ID NO 184
<211> LENGTH: 121
<212> TYPE: PRT
<213> ORGANISM: Artificial Sequence
<220> FEATURE:
<223> OTHER INFORMATION: Synthetic: VH, 29871

<400> SEQUENCE: 184

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gln Ser Tyr
            20                  25                  30

Tyr Met His Trp Val Arg Gln Ala Pro Gly Gln Gly Leu Glu Trp Met
            35                  40                  45

Gly Lys Ile Asn Pro Ser Gly Gly Ser Thr Trp Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
            115                 120
```

<210> SEQ ID NO 185
<211> LENGTH: 121
<212> TYPE: PRT
<213> ORGANISM: Artificial Sequence
<220> FEATURE:
<223> OTHER INFORMATION: Synthetic: VH, 31418

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
            35                  40                  45

Gly Arg Ile Asn Pro Ser Gly Gly Ser Thr Trp Tyr Ala Gln Lys Phe
        50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
        115                 120
```

<210> SEQ ID NO 186
<211> LENGTH: 121
<212> TYPE: PRT
<213> ORGANISM: Artificial Sequence
<220> FEATURE:
<223> OTHER INFORMATION: Synthetic: VH, 31431

<400> SEQUENCE: 186

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gln Met His Trp Val Arg Gln Ala Pro Gly Gln Gly Leu Glu Trp Met
            35                  40                  45

Gly Arg Ile Asn Pro Ser Gly Gly Ser Thr Trp Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
        115                 120
```

<210> SEQ ID NO 187
<211> LENGTH: 121
<212> TYPE: PRT
<213> ORGANISM: Artificial Sequence
<220> FEATURE:
<223> OTHER INFORMATION: Synthetic: VH, 31421

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Phe Ser Tyr
                20                  25                  30

Tyr Met Tyr Trp Val Arg Gln Ala Pro Gly Gln Gly Leu Glu Trp Met
            35                  40                  45

Gly Val Ile Asn Pro Leu Gly Gly Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
        115                 120
```

<210> SEQ ID NO 188
<211> LENGTH: 121
<212> TYPE: PRT
<213> ORGANISM: Artificial Sequence
<220> FEATURE:
<223> OTHER INFORMATION: Synthetic: VH, 31429

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Ser Tyr
            20                  25                  30

Phe Met His Trp Val Arg Gln Ala Pro Gly Gln Gly Leu Glu Trp Met
        35                  40                  45

Gly Ser Ile Asn Pro Arg Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
        115                 120

<210> SEQ ID NO 189
<211> LENGTH: 121
<212> TYPE: PRT
<213> ORGANISM: Artificial Sequence
<220> FEATURE:
<223> OTHER INFORMATION: Synthetic: VH, 29872

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg His Trp Gly
            100                 105                 110

Gln Gly Thr Leu Val Thr Val Ser Ser
        115                 120

<210> SEQ ID NO 190
<211> LENGTH: 122
<212> TYPE: PRT
<213> ORGANISM: Artificial Sequence
<220> FEATURE:
<223> OTHER INFORMATION: Synthetic: VH, 28347

<400> SEQUENCE: 190

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Leu
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Lys Tyr Ala Ser Thr Tyr Gly Met Asp Val Trp
            100                 105                 110

Gly Gln Gly Thr Thr Val Thr Val Ser Ser
            115                 120
```

<210> SEQ ID NO 191
<211> LENGTH: 120
<212> TYPE: PRT
<213> ORGANISM: Artificial Sequence
<220> FEATURE:
<223> OTHER INFORMATION: Synthetic: VH, 31896

<400> SEQUENCE: 191

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Lys Leu
            20                  25                  30

Ala Ile Ser Trp Val Arg Gln Ala Pro Gly Gln Gly Leu Glu Trp Met
            35                  40                  45

Gly Gly Ile Gly Phe Gly Thr Ala Asn Tyr Ala Gln Lys Phe Gln Gly
        50                  55                  60

Arg Val Thr Ile Thr Ala Asp Glu Ser Ala Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Ser Thr His Gly Met Asp Val Trp Gly Gln
            100                 105                 110

Gly Thr Thr Val Thr Val Ser Ser
            115                 120
```

<210> SEQ ID NO 192
<211> LENGTH: 122
<212> TYPE: PRT
<213> ORGANISM: Artificial Sequence
<220> FEATURE:
<223> OTHER INFORMATION: Synthetic: VH, 31432

<400> SEQUENCE: 192

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser His Thr
            20                  25                  30

Ala Ile Ser Trp Val Arg Gln Ala Pro Gly Gln Gly Leu Glu Trp Met
            35                  40                  45

Gly Gly Ile Leu Pro Ile Gly Gly Thr Ala Asn Tyr Ala Gln Lys Phe
        50                  55                  60
```

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Lys Tyr Ala Ser Gln Leu Gly Met Asp Val Trp
                100                 105                 110

Gly Gln Gly Thr Thr Val Thr Val Ser Ser
            115                 120
```

<210> SEQ ID NO 193
<211> LENGTH: 120
<212> TYPE: PRT
<213> ORGANISM: Artificial Sequence
<220> FEATURE:
<223> OTHER INFORMATION: Synthetic: VH, 31915

<400> SEQUENCE: 193

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Leu
                20                  25                  30

Pro Ile Ser Trp Val Arg Gln Ala Pro Gly Gln Gly Leu Glu Trp Met
            35                  40                  45

Gly Gly Ile Gly Phe Gly Thr Ala Asn Tyr Ala Gln Lys Phe Gln Gly
        50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Ser Lys Trp Gly Met Asp Val Trp Gly Gln
                100                 105                 110

Gly Thr Thr Val Thr Val Ser Ser
            115                 120
```

<210> SEQ ID NO 194
<211> LENGTH: 122
<212> TYPE: PRT
<213> ORGANISM: Artificial Sequence
<220> FEATURE:
<223> OTHER INFORMATION: Synthetic: VH, 31436

<400> SEQUENCE: 194

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Leu Leu
                20                  25                  30

Ala Ile Ser Trp Val Arg Gln Ala Pro Gly Gln Gly Leu Glu Trp Met
            35                  40                  45

Gly Gly Ile Leu Pro Ile Ala Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Lys Tyr Ala Val Gly Tyr Gly Met Asp Val Trp
                100                 105                 110

Gly Gln Gly Thr Thr Val Thr Val Ser Ser
```

115             120

<210> SEQ ID NO 195
<211> LENGTH: 122
<212> TYPE: PRT
<213> ORGANISM: Artificial Sequence
<220> FEATURE:
<223> OTHER INFORMATION: Synthetic: VH, 31437

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Gln Ser Leu
            20                  25                  30

Ala Ile Ser Trp Val Arg Gln Ala Pro Gly Gln Gly Leu Glu Trp Met
        35                  40                  45

Gly Gly Ile Leu Pro Ile Gly Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Lys Tyr Ala Gly Arg Tyr Gly Met Asp Val Trp
            100                 105                 110

Gly Gln Gly Thr Thr Val Thr Val Ser Ser
        115                 120

<210> SEQ ID NO 196
<211> LENGTH: 120
<212> TYPE: PRT
<213> ORGANISM: Artificial Sequence
<220> FEATURE:
<223> OTHER INFORMATION: Synthetic: VH, 31905

<400> SEQUENCE: 196

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Pro Ser Asn
            20                  25                  30

Ala Ile Ser Trp Val Arg Gln Ala Pro Gly Gln Gly Leu Glu Trp Met
        35                  40                  45

Gly Gly Ile Gly Phe Gly Thr Ala Asn Tyr Ala Gln Lys Phe Gln Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Arg Thr Tyr Gly Met Asp Val Trp Gly Gln
            100                 105                 110

Gly Thr Thr Val Thr Val Ser Ser
        115                 120

<210> SEQ ID NO 197
<211> LENGTH: 120
<212> TYPE: PRT
<213> ORGANISM: Artificial Sequence
<220> FEATURE:
<223> OTHER INFORMATION: Synthetic: VH, 31901

<400> SEQUENCE: 197

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Leu
            20                  25                  30

Pro Ile Ser Trp Val Arg Gln Ala Pro Gly Gln Gly Leu Glu Trp Met
        35                  40                  45

Gly Gly Ile Gly Phe Gly Thr Ala Asn Tyr Ala Gln Lys Phe Gln Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Gly Arg Tyr Gly Met Asp Val Trp Gly Gln
            100                 105                 110

Gly Thr Thr Val Thr Val Ser Ser
        115                 120
```

<210> SEQ ID NO 198
<211> LENGTH: 122
<212> TYPE: PRT
<213> ORGANISM: Artificial Sequence
<220> FEATURE:
<223> OTHER INFORMATION: Synthetic: VH, 29852

<400> SEQUENCE: 198

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ala Met
            20                  25                  30

Ala Ile Ser Trp Val Arg Gln Ala Pro Gly Gln Gly Leu Glu Trp Met
        35                  40                  45

Gly Gly Ile Leu Pro Ile Ala Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ala Lys Tyr Ala Ser Thr Tyr Gly Met Asp Val Trp
            100                 105                 110

Gly Gln Gly Thr Thr Val Thr Val Ser Ser
        115                 120
```

<210> SEQ ID NO 199
<211> LENGTH: 122
<212> TYPE: PRT
<213> ORGANISM: Artificial Sequence
<220> FEATURE:
<223> OTHER INFORMATION: Synthetic: VH, 29851

<400> SEQUENCE: 199

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ala Ser Leu
            20                  25                  30

Ala Ile Ser Trp Val Arg Gln Ala Pro Gly Gln Gly Leu Glu Trp Met
        35                  40                  45

Gly Gly Ile Leu Pro Ile Phe Gly Glu Ala Asn Tyr Ala Gln Lys Phe
```

```
                50                  55                  60
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ala Lys Tyr Ala Ser Thr Tyr Gly Met Asp Val Trp
                100                 105                 110

Gly Gln Gly Thr Thr Val Thr Val Ser Ser
            115                 120

<210> SEQ ID NO 200
<211> LENGTH: 122
<212> TYPE: PRT
<213> ORGANISM: Artificial Sequence
<220> FEATURE:
<223> OTHER INFORMATION: Synthetic: VH, 29857

<400> SEQUENCE: 200

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Trp Leu
                 20                  25                  30

Ala Ile Ser Trp Val Arg Gln Ala Pro Gly Gln Gly Leu Glu Trp Met
             35                  40                  45

Gly Gly Ile Ile Pro Arg Gly Gly Thr Ala Asn Tyr Ala Gln Lys Phe
         50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Ala Lys Tyr Ala Ser Thr Tyr Gly Met Asp Val Trp
                100                 105                 110

Gly Gln Gly Thr Thr Val Thr Val Ser Ser
            115                 120

<210> SEQ ID NO 201
<211> LENGTH: 121
<212> TYPE: PRT
<213> ORGANISM: Artificial Sequence
<220> FEATURE:
<223> OTHER INFORMATION: Synthetic: VH, 27571

<400> SEQUENCE: 201

Gln Val Gln Leu Val Gln Ser Gly Ala Glu Val Lys Lys Pro Gly Ser
 1               5                  10                  15

Ser Val Lys Ala Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Ser Ile Ile Pro Ile Phe Gly Thr Ala Asn Tyr Ala Gln Lys Phe
         50                  55                  60

Arg Gly Arg Val Thr Ile Thr Ala Asp Glu Ser Thr Ser Thr Thr Tyr
 65                  70                  75                  80

Met Glu Leu Ser Ser Leu Arg Ser Glu Asp Thr Ala Val Tyr Tyr Cys
                 85                  90                  95

Ala Arg Glu Ser Gly Gly Tyr Arg Asp His Arg Leu Asp Val Trp Gly
                100                 105                 110
```

Gln Gly Thr Met Val Thr Val Ser Ser
        115                 120

<210> SEQ ID NO 202
<211> LENGTH: 121
<212> TYPE: PRT
<213> ORGANISM: Artificial Sequence
<220> FEATURE:
<223> OTHER INFORMATION: Synthetic: VH, 31861

<400> SEQUENCE: 202

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Gly Ile Ser Trp Val Arg Gln Ala Pro Gly Gln Gly Leu Glu Trp Met
        35                  40                  45

Gly Ser Ile Ile Pro Glu Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Thr Tyr Arg Asp His Arg Leu Asp Val Trp Gly
            100                 105                 110

Gln Gly Thr Met Val Thr Val Ser Ser
        115                 120

<210> SEQ ID NO 203
<211> LENGTH: 121
<212> TYPE: PRT
<213> ORGANISM: Artificial Sequence
<220> FEATURE:
<223> OTHER INFORMATION: Synthetic: VH, 31873

<400> SEQUENCE: 203

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Lys Tyr
            20                  25                  30

Gly Ile Ser Trp Val Arg Gln Ala Pro Gly Gln Gly Leu Glu Trp Met
        35                  40                  45

Gly Ser Ile Ile Pro Glu Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Gly Tyr Arg Asp His Arg Leu Gly Val Trp Gly
            100                 105                 110

Gln Gly Thr Met Val Thr Val Ser Ser
        115                 120

<210> SEQ ID NO 204
<211> LENGTH: 121
<212> TYPE: PRT
<213> ORGANISM: Artificial Sequence
<220> FEATURE:
<223> OTHER INFORMATION: Synthetic: VH, 31393

-continued

<400> SEQUENCE: 204

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu Ser Tyr
            20                  25                  30

Gly Ile Ser Trp Val Arg Gln Ala Pro Gly Gln Gly Leu Glu Trp Met
        35                  40                  45

Gly Ser Ile Ile Pro Glu Phe Gly Ile Ala Asn Tyr Ala Gln Lys Phe
    50                  55                  60

Gln Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Gly Tyr Arg Asp His Arg Leu Asp Val Trp Gly
            100                 105                 110

Gln Gly Thr Met Val Thr Val Ser Ser
        115                 120

<210> SEQ ID NO 205
<211> LENGTH: 124
<212> TYPE: PRT
<213> ORGANISM: Artificial Sequence
<220> FEATURE:
<223> OTHER INFORMATION: Synthetic: VH, 27534

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Phe Thr Asp Tyr Ser Ser Gly Tyr Ser Ser Gly Trp Thr
            100                 105                 110

Tyr Trp Gly Gln Gly Thr Leu Val Thr Val Ser Ser
        115                 120

<210> SEQ ID NO 206
<211> LENGTH: 123
<212> TYPE: PRT
<213> ORGANISM: Artificial Sequence
<220> FEATURE:
<223> OTHER INFORMATION: Synthetic: VH, 27536

<400> SEQUENCE: 206

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
            50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Thr Leu Tyr Ser Ser Gly Ala Tyr Tyr Gly Tyr Asn Val
            100                 105                 110

Trp Gly Gln Gly Thr Met Val Thr Val Ser Ser
            115                 120

<210> SEQ ID NO 207
<211> LENGTH: 124
<212> TYPE: PRT
<213> ORGANISM: Artificial Sequence
<220> FEATURE:
<223> OTHER INFORMATION: Synthetic: VH, 27588

<400> SEQUENCE: 207

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Lys Arg Gly Tyr Asp Ser Tyr Gly Gly Val Tyr Phe Asp
            100                 105                 110

Tyr Trp Gly Gln Gly Thr Leu Val Thr Val Ser Ser
        115                 120

<210> SEQ ID NO 208
<211> LENGTH: 127
<212> TYPE: PRT
<213> ORGANISM: Artificial Sequence
<220> FEATURE:
<223> OTHER INFORMATION: Synthetic: VH, 27590

<400> SEQUENCE: 208

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Pro Thr Val Thr Ala Thr Thr Ser Ile Gly Thr His Asn
            100                 105                 110

```
Trp Phe Asp Pro Trp Gly Gln Gly Thr Leu Val Thr Val Ser Ser
        115                 120                 125

<210> SEQ ID NO 209
<211> LENGTH: 126
<212> TYPE: PRT
<213> ORGANISM: Artificial Sequence
<220> FEATURE:
<223> OTHER INFORMATION: Synthetic: VH, 27597

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Arg Gly Tyr Asp Ser Ser Arg Tyr Tyr Lys Phe Trp
            100                 105                 110

Phe Asp Pro Trp Gly Gln Gly Thr Leu Val Thr Val Ser Ser
        115                 120                 125

<210> SEQ ID NO 210
<211> LENGTH: 121
<212> TYPE: PRT
<213> ORGANISM: Artificial Sequence
<220> FEATURE:
<223> OTHER INFORMATION: Synthetic: VH, 27575

<400> SEQUENCE: 210

Gln Val Gln Leu Val Gln Ser Gly Ala Glu Val Lys Glu Pro Gly Ser
1               5                   10                  15

Ser Val Lys Val Ser Cys Lys Ala Ser Gly Gly Thr Phe Ser Ser Tyr
            20                  25                  30

Ala Thr Ser Trp Val Arg Gln Ala Pro Gly Gln Gly Leu Glu Trp Met
        35                  40                  45

Gly Gly Ile Ile Pro Ile Ser Gly Thr Ala Asn Tyr Ala Gln Glu Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Tyr Arg His His Tyr Phe Asp Leu Trp Gly
            100                 105                 110

Arg Gly Thr Leu Val Thr Val Ser Ser
        115                 120

<210> SEQ ID NO 211
<211> LENGTH: 121
<212> TYPE: PRT
<213> ORGANISM: Artificial Sequence
<220> FEATURE:
<223> OTHER INFORMATION: Synthetic: VH, 27568
```

<400> SEQUENCE: 211

Gln Val Gln Leu Val Gln Ser Gly Ala Glu Val Lys Lys Pro Gly Ser
1               5                   10                  15

Ser Val Lys Val Pro Cys Lys Ala Ser Gly Gly Thr Phe Ser Ser Tyr
            20                  25                  30

Ala Ile Ser Trp Val Arg Gln Ala Pro Glu Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Ser Gly Gly Tyr Arg Asp His Lys Leu Asp Val Trp Gly
            100                 105                 110

Gln Gly Thr Val Val Thr Val Ser Ser
        115                 120

<210> SEQ ID NO 212
<211> LENGTH: 121
<212> TYPE: PRT
<213> ORGANISM: Artificial Sequence
<220> FEATURE:
<223> OTHER INFORMATION: Synthetic: VH, 27577

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Ser Tyr
            20                  25                  30

Ala Ile Gly Trp Val Arg Gln Ala Pro Gly Gln Gly Leu Glu Trp Met
        35                  40                  45

Gly Gly Ile Ile Pro Thr Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Gly Tyr Gln His His Tyr Phe Asp Leu Trp Gly
            100                 105                 110

Arg Gly Thr Leu Val Thr Val Ser Ser
        115                 120

<210> SEQ ID NO 213
<211> LENGTH: 121
<212> TYPE: PRT
<213> ORGANISM: Artificial Sequence
<220> FEATURE:
<223> OTHER INFORMATION: Synthetic: VH, 27587

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Gly Tyr Arg Asp His Lys Leu Asp Val Trp Gly
            100                 105                 110

Gln Gly Thr Met Val Thr Val Ser Ser
            115                 120

<210> SEQ ID NO 214
<211> LENGTH: 120
<212> TYPE: PRT
<213> ORGANISM: Artificial Sequence
<220> FEATURE:
<223> OTHER INFORMATION: Synthetic: VH, 27589

<400> SEQUENCE: 214

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Gly Tyr His Arg His Tyr Ser Asp Tyr Trp Gly Gln
            100                 105                 110

Gly Thr Leu Val Thr Val Ser Ser
            115                 120

<210> SEQ ID NO 215
<211> LENGTH: 121
<212> TYPE: PRT
<213> ORGANISM: Artificial Sequence
<220> FEATURE:
<223> OTHER INFORMATION: Synthetic: VH, 27596

<400> SEQUENCE: 215

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Leu Gly Ile Arg Lys His Trp Phe Asp Pro Trp Gly

```
                100               105               110
Gln Gly Thr Leu Val Thr Val Ser Ser
        115                 120

<210> SEQ ID NO 216
<211> LENGTH: 121
<212> TYPE: PRT
<213> ORGANISM: Artificial Sequence
<220> FEATURE:
<223> OTHER INFORMATION: Synthetic: VH, 27535

<400> SEQUENCE: 216

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Arg Trp Arg Tyr His Tyr Phe Asp Tyr Trp Gly
            100                 105                 110

Gln Gly Thr Leu Val Thr Val Ser Ser
        115                 120

<210> SEQ ID NO 217
<211> LENGTH: 121
<212> TYPE: PRT
<213> ORGANISM: Artificial Sequence
<220> FEATURE:
<223> OTHER INFORMATION: Synthetic: VH, 27550

<400> SEQUENCE: 217

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Arg Gly Ser Leu Ala Leu Gly Met Asp Val Trp Gly
            100                 105                 110

Gln Gly Thr Leu Val Thr Val Ser Ser
        115                 120

<210> SEQ ID NO 218
<211> LENGTH: 128
<212> TYPE: PRT
<213> ORGANISM: Artificial Sequence
<220> FEATURE:
```

<223> OTHER INFORMATION: Synthetic: VH, 27549

<400> SEQUENCE: 218

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Tyr Ser Tyr Gly Glu Pro Tyr Tyr Tyr
            100                 105                 110

Tyr Gly Met Asp Val Trp Gly Gln Gly Thr Thr Val Thr Val Ser Ser
            115                 120                 125

<210> SEQ ID NO 219
<211> LENGTH: 107
<212> TYPE: PRT
<213> ORGANISM: Artificial Sequence
<220> FEATURE:
<223> OTHER INFORMATION: Synthetic: VL, 27579

<400> SEQUENCE: 219

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Ser Tyr Ile
                85                  90                  95

Thr Phe Gly Gly Gly Thr Lys Val Glu Ile Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: Synthetic: VL, 31895

<400> SEQUENCE: 220

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg His Thr Gly Ile Pro Asp Arg Phe Ser

```
                50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr His Asn Ala Ile
                 85                  90                  95

Thr Phe Gly Gly Gly Thr Lys Val Glu Ile Lys
                100                 105

<210> SEQ ID NO 221
<211> LENGTH: 107
<212> TYPE: PRT
<213> ORGANISM: Artificial Sequence
<220> FEATURE:
<223> OTHER INFORMATION: Synthetic: VL, 31891

<400> SEQUENCE: 221

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Tyr Ala Ser Ser Arg Ala Tyr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr His Asn Ala Ile
                 85                  90                  95

Thr Phe Gly Gly Gly Thr Lys Val Glu Ile Lys
                100                 105

<210> SEQ ID NO 222
<211> LENGTH: 107
<212> TYPE: PRT
<213> ORGANISM: Artificial Sequence
<220> FEATURE:
<223> OTHER INFORMATION: Synthetic: VL, 31418

<400> SEQUENCE: 222

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Tyr Phe Tyr Ile
                 85                  90                  95

Thr Phe Gly Gly Gly Thr Lys Val Glu Ile Lys
                100                 105

<210> SEQ ID NO 223
<211> LENGTH: 107
<212> TYPE: PRT
<213> ORGANISM: Artificial Sequence
<220> FEATURE:
```

<223> OTHER INFORMATION: Synthetic: VL, 31430

<400> SEQUENCE: 223

Glu Ile Val Leu Thr Gln Ser Pro Gly Thr Leu Ser Leu Ser Pro Gly
1               5                   10                  15

Glu Arg Ala Thr Leu Ser Cys Glu Ala Ser Gln Ser Val Ser Tyr Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Asn Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Ser Ala Leu
                85                  90                  95

Thr Phe Gly Gly Gly Thr Lys Val Glu Ile Lys
            100                 105

<210> SEQ ID NO 224
<211> LENGTH: 107
<212> TYPE: PRT
<213> ORGANISM: Artificial Sequence
<220> FEATURE:
<223> OTHER INFORMATION: Synthetic: VL, 31431

<400> SEQUENCE: 224

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg His Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Gly Gly Ile
                85                  90                  95

Thr Phe Gly Gly Gly Thr Lys Val Glu Ile Lys
            100                 105

<210> SEQ ID NO 225
<211> LENGTH: 107
<212> TYPE: PRT
<213> ORGANISM: Artificial Sequence
<220> FEATURE:
<223> OTHER INFORMATION: Synthetic: VL, 31421

<400> SEQUENCE: 225

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Glu Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr His Arg Arg Ile
                    85                  90                  95

Thr Phe Gly Gly Gly Thr Lys Val Glu Ile Lys
                100                 105

<210> SEQ ID NO 226
<211> LENGTH: 107
<212> TYPE: PRT
<213> ORGANISM: Artificial Sequence
<220> FEATURE:
<223> OTHER INFORMATION: Synthetic: VL, 31429

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Val Ser Ser Ser
                20                  25                  30

Tyr Leu Ala Trp Tyr Gln Gln Lys Pro Gly Gln Ala Pro Arg Leu Leu
            35                  40                  45

Ile Tyr Tyr Ala Ser Asn Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Ser Gly Ile
                    85                  90                  95

Thr Phe Gly Gly Gly Thr Lys Val Glu Ile Lys
                100                 105

<210> SEQ ID NO 227
<211> LENGTH: 113
<212> TYPE: PRT
<213> ORGANISM: Artificial Sequence
<220> FEATURE:
<223> OTHER INFORMATION: Synthetic: VL, 28347

<400> SEQUENCE: 227

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                    85                  90                  95

Tyr Tyr Leu Tyr Pro Leu Thr Phe Gly Gly Gly Thr Lys Val Glu Ile
                100                 105                 110

Lys

<210> SEQ ID NO 228
<211> LENGTH: 113
<212> TYPE: PRT
<213> ORGANISM: Artificial Sequence
<220> FEATURE:
<223> OTHER INFORMATION: Synthetic: VL, 31896
```

<400> SEQUENCE: 228

Asp Ile Val Met Thr Gln Ser Pro Asp Ser Leu Ala Val Ser Leu Gly
1               5                   10                  15

Glu Arg Ala Thr Ile Asn Cys Lys Ser Ser Arg Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Trp Thr Tyr Pro Leu Thr Phe Gly Gly Thr Lys Val Glu Ile
            100                 105                 110

Lys

<210> SEQ ID NO 229
<211> LENGTH: 113
<212> TYPE: PRT
<213> ORGANISM: Artificial Sequence
<220> FEATURE:
<223> OTHER INFORMATION: Synthetic: VL, 31915

<400> SEQUENCE: 229

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Trp Thr Tyr Pro Leu Thr Phe Gly Gly Thr Lys Val Glu Ile
            100                 105                 110

Lys

<210> SEQ ID NO 230
<211> LENGTH: 113
<212> TYPE: PRT
<213> ORGANISM: Artificial Sequence
<220> FEATURE:
<223> OTHER INFORMATION: Synthetic: VL, 31905

<400> SEQUENCE: 230

Asp Ile Val Met Thr Gln Ser Pro Asp Ser Leu Ala Val Ser Leu Gly
1               5                   10                  15

Glu Arg Ala Thr Ile Asn Cys Lys Ser Ser Lys Ser Val Leu Tyr Ser
            20                  25                  30

Asn Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val

```
                    50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Leu Leu Tyr Pro Leu Thr Phe Gly Gly Gly Thr Lys Val Glu Ile
                100                 105                 110

Lys

<210> SEQ ID NO 231
<211> LENGTH: 113
<212> TYPE: PRT
<213> ORGANISM: Artificial Sequence
<220> FEATURE:
<223> OTHER INFORMATION: Synthetic: VL, 31901

<400> SEQUENCE: 231

Gly Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Phe Ser
                 20                  25                  30

Ser Asn Asn Lys Asn Tyr Leu Ala Trp Tyr Gln Gln Lys Pro Gly Gln
                 35                  40                  45

Pro Pro Lys Leu Leu Ile Tyr Trp Ala Ser Thr Arg Ala Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Leu Tyr Pro Leu Thr Phe Gly Gly Gly Thr Lys Val Glu Ile
                100                 105                 110

Lys

<210> SEQ ID NO 232
<211> LENGTH: 107
<212> TYPE: PRT
<213> ORGANISM: Artificial Sequence
<220> FEATURE:
<223> OTHER INFORMATION: Synthetic: VL, 27571

<400> SEQUENCE: 232

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Gly Ser Asn
                 20                  25                  30

Leu Ala Trp Tyr Gln Gln Lys Pro Gly Gln Ala Pro Arg Leu Leu Ile
                 35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Leu Ile Trp Pro Leu
                 85                  90                  95

Thr Phe Gly Gly Gly Thr Lys Val Glu Ile Lys
                100                 105

<210> SEQ ID NO 233
```

```
<211> LENGTH: 107
<212> TYPE: PRT
<213> ORGANISM: Artificial Sequence
<220> FEATURE:
<223> OTHER INFORMATION: Synthetic: VL, 31861

<400> SEQUENCE: 233

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Leu Leu Trp Pro Leu
                85                  90                  95

Thr Phe Gly Gly Gly Thr Lys Val Glu Ile Lys
            100                 105

<210> SEQ ID NO 234
<211> LENGTH: 107
<212> TYPE: PRT
<213> ORGANISM: Artificial Sequence
<220> FEATURE:
<223> OTHER INFORMATION: Synthetic: VL, 31873

<400> SEQUENCE: 234

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Leu Leu Trp Pro Leu
                85                  90                  95

Thr Phe Gly Gly Gly Thr Lys Val Glu Ile Lys
            100                 105

<210> SEQ ID NO 235
<211> LENGTH: 113
<212> TYPE: PRT
<213> ORGANISM: Artificial Sequence
<220> FEATURE:
<223> OTHER INFORMATION: Synthetic: VL, 28337

<400> SEQUENCE: 235

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45
```

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Phe Tyr Phe Tyr Pro Pro Thr Phe Gly Gly Gly Thr Lys Val Glu Ile
              100                 105                 110

Lys

<210> SEQ ID NO 236
<211> LENGTH: 113
<212> TYPE: PRT
<213> ORGANISM: Artificial Sequence
<220> FEATURE:
<223> OTHER INFORMATION: Synthetic: VL, 27536

<400> SEQUENCE: 236

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ala Tyr Thr Phe Pro Pro Thr Phe Gly Gly Gly Thr Lys Val Glu Ile
              100                 105                 110

Lys

<210> SEQ ID NO 237
<211> LENGTH: 107
<212> TYPE: PRT
<213> ORGANISM: Artificial Sequence
<220> FEATURE:
<223> OTHER INFORMATION: Synthetic: VL, 27588

<400> SEQUENCE: 237

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Tyr Ile Phe Pro Pro
                85                  90                  95

Thr Phe Gly Gly Gly Thr Lys Val Glu Ile Lys
              100                 105

-continued

```
<210> SEQ ID NO 238
<211> LENGTH: 107
<212> TYPE: PRT
<213> ORGANISM: Artificial Sequence
<220> FEATURE:
<223> OTHER INFORMATION: Synthetic: VL, 27590

<400> SEQUENCE: 238

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Phe Tyr Pro Pro
                85                  90                  95

Thr Phe Gly Gly Gly Thr Lys Val Glu Ile Lys
            100                 105

<210> SEQ ID NO 239
<211> LENGTH: 107
<212> TYPE: PRT
<213> ORGANISM: Artificial Sequence
<220> FEATURE:
<223> OTHER INFORMATION: Synthetic: VL, 27597

<400> SEQUENCE: 239

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Val Leu Trp Pro Arg
                85                  90                  95

Thr Phe Gly Gly Gly Thr Lys Val Glu Ile Lys
            100                 105

<210> SEQ ID NO 240
<211> LENGTH: 107
<212> TYPE: PRT
<213> ORGANISM: Artificial Sequence
<220> FEATURE:
<223> OTHER INFORMATION: Synthetic: VL, 27575

<400> SEQUENCE: 240

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45
```

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln His Val Asn Phe Pro Leu
                 85                  90                  95

Thr Phe Gly Gly Gly Thr Lys Val Glu Ile Lys
            100                 105

<210> SEQ ID NO 241
<211> LENGTH: 107
<212> TYPE: PRT
<213> ORGANISM: Artificial Sequence
<220> FEATURE:
<223> OTHER INFORMATION: Synthetic: VL, 27568

<400> SEQUENCE: 241

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Val Phe Trp Pro Ile
                 85                  90                  95

Thr Phe Gly Gly Gly Thr Lys Val Glu Ile Lys
            100                 105

<210> SEQ ID NO 242
<211> LENGTH: 107
<212> TYPE: PRT
<213> ORGANISM: Artificial Sequence
<220> FEATURE:
<223> OTHER INFORMATION: Synthetic: VL, 27577

<400> SEQUENCE: 242

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Gly Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Leu Thr Lys Trp Pro Leu
                 85                  90                  95

Thr Phe Gly Gly Gly Thr Lys Val Glu Ile Lys
            100                 105

<210> SEQ ID NO 243
<211> LENGTH: 107
<212> TYPE: PRT

```
<213> ORGANISM: Artificial Sequence
<220> FEATURE:
<223> OTHER INFORMATION: Synthetic: VL, 27587

<400> SEQUENCE: 243

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp Val Leu Trp Pro Leu
                85                  90                  95

Thr Phe Gly Gly Gly Thr Lys Val Glu Ile Lys
            100                 105

<210> SEQ ID NO 244
<211> LENGTH: 107
<212> TYPE: PRT
<213> ORGANISM: Artificial Sequence
<220> FEATURE:
<223> OTHER INFORMATION: Synthetic: VL, 27589

<400> SEQUENCE: 244

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Leu Phe Pro Ile
                85                  90                  95

Thr Phe Gly Gly Gly Thr Lys Val Glu Ile Lys
            100                 105

<210> SEQ ID NO 245
<211> LENGTH: 107
<212> TYPE: PRT
<213> ORGANISM: Artificial Sequence
<220> FEATURE:
<223> OTHER INFORMATION: Synthetic: VL, 27596

<400> SEQUENCE: 245

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln His Thr Val Trp Pro Ile
                 85                  90                  95

Thr Phe Gly Gly Gly Thr Lys Val Glu Ile Lys
            100                 105
```

<210> SEQ ID NO 246
<211> LENGTH: 107
<212> TYPE: PRT
<213> ORGANISM: Artificial Sequence
<220> FEATURE:
<223> OTHER INFORMATION: Synthetic: VL, 27535

<400> SEQUENCE: 246

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Lys Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Val Leu Asn Tyr Pro Leu
                 85                  90                  95

Thr Phe Gly Gly Gly Thr Lys Val Glu Ile Lys
            100                 105
```

<210> SEQ ID NO 247
<211> LENGTH: 107
<212> TYPE: PRT
<213> ORGANISM: Artificial Sequence
<220> FEATURE:
<223> OTHER INFORMATION: Synthetic: VL, 27550

<400> SEQUENCE: 247

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Tyr Phe Leu Pro Pro
                 85                  90                  95

Thr Phe Gly Gly Gly Thr Lys Val Glu Ile Lys
            100                 105
```

<210> SEQ ID NO 248
<211> LENGTH: 108
<212> TYPE: PRT
<213> ORGANISM: Artificial Sequence
<220> FEATURE:
<223> OTHER INFORMATION: Synthetic: VL, 27549

<400> SEQUENCE: 248

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala His Ser Ser Pro
                85                  90                  95

Tyr Thr Phe Gly Gly Gly Thr Lys Val Glu Ile Lys
            100                 105

<210> SEQ ID NO 249
<211> LENGTH: 510
<212> TYPE: PRT
<213> ORGANISM: Artificial Sequence
<220> FEATURE:
<223> OTHER INFORMATION: Synthetic: hCD39

<400> SEQUENCE: 249

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

-continued

Leu Tyr Gly Lys Asp Tyr Asn Val Tyr Thr His Ser Phe Leu Cys Tyr
            245                 250                 255

Gly Lys Asp Gln Ala Leu Trp Gln Lys Leu Ala Lys Asp Ile Gln Val
        260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
        290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
        370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
        450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
            500                 505                 510

<210> SEQ ID NO 250
<211> LENGTH: 510
<212> TYPE: PRT
<213> ORGANISM: Artificial Sequence
<220> FEATURE:
<223> OTHER INFORMATION: Synthetic: mCD39

<400> SEQUENCE: 250

Met Glu Asp Ile Lys Asp Ser Lys Val Lys Arg Phe Cys Ser Lys Asn
1               5                   10                  15

Ile Leu Ile Ile Leu Gly Phe Thr Ser Ile Leu Ala Val Ile Ala Leu
            20                  25                  30

Ile Ala Val Gly Leu Thr Gln Asn Lys Pro Leu Pro Glu Asn Val Lys
        35                  40                  45

Tyr Gly Ile Val Leu Asp Ala Gly Ser Ser His Thr Asn Leu Tyr Ile
    50                  55                  60

Tyr Lys Trp Pro Ala Glu Lys Glu Asn Asp Thr Gly Val Val Gln Gln
65                  70                  75                  80

Leu Glu Glu Cys Gln Val Lys Gly Pro Gly Ile Ser Lys Tyr Ala Gln
                85                  90                  95

```
Lys Thr Asp Glu Ile Gly Ala Tyr Leu Ala Glu Cys Met Glu Leu Ser
            100                 105                 110

Thr Glu Leu Ile Pro Thr Ser Lys His His Gln Thr Pro Val Tyr Leu
            115                 120                 125

Gly Ala Thr Ala Gly Met Arg Leu Leu Arg Met Glu Ser Glu Gln Ser
        130                 135                 140

Ala Asp Glu Val Leu Ala Val Ser Thr Ser Leu Lys Ser Tyr Pro
145                 150                 155                 160

Phe Asp Phe Gln Gly Ala Lys Ile Ile Thr Gly Gln Glu Glu Gly Ala
                    165                 170                 175

Tyr Gly Trp Ile Thr Ile Asn Tyr Leu Leu Gly Arg Phe Thr Gln Glu
                180                 185                 190

Gln Ser Trp Leu Ser Leu Ile Ser Asp Ser Gln Lys Gln Glu Thr Phe
            195                 200                 205

Gly Ala Leu Asp Leu Gly Gly Ala Ser Thr Gln Ile Thr Phe Val Pro
            210                 215                 220

Gln Asn Ser Thr Ile Glu Ser Pro Glu Asn Ser Leu Gln Phe Arg Leu
225                 230                 235                 240

Tyr Gly Glu Asp Tyr Thr Val Tyr Thr His Ser Phe Leu Cys Tyr Gly
                    245                 250                 255

Lys Asp Gln Ala Leu Trp Gln Lys Leu Ala Lys Asp Ile Gln Val Ser
                260                 265                 270

Ser Gly Gly Val Leu Lys Asp Pro Cys Phe Asn Pro Gly Tyr Glu Lys
            275                 280                 285

Val Val Asn Val Ser Glu Leu Tyr Gly Thr Pro Cys Thr Lys Arg Phe
290                 295                 300

Glu Lys Lys Leu Pro Phe Asp Gln Phe Arg Ile Gln Gly Thr Gly Asp
305                 310                 315                 320

Tyr Glu Gln Cys His Gln Ser Ile Leu Glu Leu Phe Asn Asn Ser His
                    325                 330                 335

Cys Pro Tyr Ser Gln Cys Ala Phe Asn Gly Val Phe Leu Pro Pro Leu
                340                 345                 350

His Gly Ser Phe Gly Ala Phe Ser Ala Phe Tyr Phe Val Met Asp Phe
            355                 360                 365

Phe Lys Lys Val Ala Lys Asn Ser Val Ile Ser Gln Glu Lys Met Thr
370                 375                 380

Glu Ile Thr Lys Asn Phe Cys Ser Lys Ser Trp Glu Glu Thr Lys Thr
385                 390                 395                 400

Ser Tyr Pro Ser Val Lys Glu Lys Tyr Leu Ser Glu Tyr Cys Phe Ser
                405                 410                 415

Gly Ala Tyr Ile Leu Ser Leu Leu Gln Gly Tyr Asn Phe Thr Asp Ser
            420                 425                 430

Ser Trp Glu Gln Ile His Phe Met Gly Lys Ile Lys Asp Ser Asn Ala
            435                 440                 445

Gly Trp Thr Leu Gly Tyr Met Leu Asn Leu Thr Asn Met Ile Pro Ala
        450                 455                 460

Glu Gln Pro Leu Ser Pro Pro Leu Pro His Ser Thr Tyr Ile Gly Leu
465                 470                 475                 480

Met Val Leu Phe Ser Leu Leu Leu Val Ala Val Ala Ile Thr Gly Leu
                485                 490                 495

Phe Ile Tyr Ser Lys Pro Ser Tyr Phe Trp Lys Glu Ala Val
                500                 505                 510
```

```
<210> SEQ ID NO 251
<211> LENGTH: 532
<212> TYPE: PRT
<213> ORGANISM: Macaca fascicularis
<220> FEATURE:
<221> NAME/KEY: misc_feature
<222> LOCATION: (1)..(532)
<223> OTHER INFORMATION: Macaca fascicularis cCD39

<400> SEQUENCE: 251

Met Leu Phe Asp Ser Ile Leu Ser Thr Val Gly Leu Ser Lys Leu Val
1               5                   10                  15

Ser Val Val Ser Ser Pro Ala Ala Leu Ser Lys Ser Asn Val Lys
            20                  25                  30

Thr Phe Cys Ser Lys Asn Ile Leu Ala Ile Leu Gly Phe Ser Ser Ile
        35                  40                  45

Ile Ala Val Ile Ala Leu Leu Ala Val Gly Leu Thr Gln Asn Lys Ala
    50                  55                  60

Leu Pro Glu Asn Ile Lys Tyr Gly Ile Val Leu Asp Ala Gly Ser Ser
65                  70                  75                  80

His Thr Ser Leu Tyr Ile Tyr Lys Trp Pro Ala Glu Lys Glu Asn Asp
                85                  90                  95

Thr Gly Val Val His Gln Val Glu Glu Cys Arg Val Lys Gly Pro Gly
            100                 105                 110

Ile Ser Lys Tyr Val Gln Lys Val Asn Glu Ile Gly Ile Tyr Leu Thr
        115                 120                 125

Asp Cys Met Glu Arg Ala Arg Glu Val Ile Pro Arg Ser Gln His Gln
    130                 135                 140

Glu Thr Pro Val Tyr Leu Gly Ala Thr Ala Gly Met Arg Leu Leu Arg
145                 150                 155                 160

Met Glu Ser Glu Glu Leu Ala Asp Arg Val Leu Asp Val Val Glu Arg
                165                 170                 175

Ser Leu Ser Asn Tyr Pro Phe Asp Phe Gln Gly Ala Arg Ile Ile Thr
            180                 185                 190

Gly Gln Glu Glu Gly Ala Tyr Gly Trp Ile Thr Ile Asn Tyr Leu Leu
        195                 200                 205

Gly Lys Phe Ser Gln Lys Thr Arg Trp Phe Ser Ile Val Pro Tyr Glu
    210                 215                 220

Thr Asn Asn Gln Glu Thr Phe Gly Ala Leu Asp Leu Gly Gly Ala Ser
225                 230                 235                 240

Thr Gln Ile Thr Phe Val Pro Gln Asn Gln Thr Thr Glu Ser Pro Asp
                245                 250                 255

Asn Ala Leu Gln Phe Arg Leu Tyr Gly Lys Asp Tyr Asn Val Tyr Thr
            260                 265                 270

His Ser Phe Leu Cys Tyr Gly Lys Asp Gln Ala Leu Trp Gln Lys Leu
        275                 280                 285

Ala Lys Asp Ile Gln Val Ala Ser Asn Glu Ile Leu Arg Asp Pro Cys
    290                 295                 300

Phe His Pro Gly Tyr Lys Lys Val Val Asn Val Ser Asp Leu Tyr Lys
305                 310                 315                 320

Thr Pro Cys Thr Lys Arg Phe Glu Met Thr Leu Pro Phe Gln Gln Phe
                325                 330                 335

Glu Ile Gln Gly Ile Gly Asn Tyr Gln Gln Cys His Gln Ser Val Leu
            340                 345                 350

Glu Leu Phe Asn Thr Ser Tyr Cys Pro Tyr Ser Gln Cys Ala Phe Asn
        355                 360                 365
```

```
Gly Ile Phe Leu Pro Pro Leu Gln Gly Asp Phe Gly Ala Phe Ser Ala
    370                 375                 380
Phe Tyr Phe Val Met Asn Phe Leu Asn Leu Thr Ser Glu Lys Val Ser
385                 390                 395                 400
Gln Glu Lys Val Thr Glu Met Met Lys Lys Phe Cys Ser Gln Pro Trp
                405                 410                 415
Glu Glu Ile Lys Thr Ser Tyr Ala Gly Val Lys Glu Lys Tyr Leu Ser
            420                 425                 430
Glu Tyr Cys Phe Ser Gly Thr Tyr Ile Leu Ser Leu Leu Leu Gln Gly
        435                 440                 445
Tyr His Phe Thr Ala Asp Ser Trp Glu His Ile His Phe Ile Gly Lys
    450                 455                 460
Ile Gln Gly Ser Asp Ala Gly Trp Thr Leu Gly Tyr Met Leu Asn Leu
465                 470                 475                 480
Thr Asn Met Ile Pro Ala Glu Gln Pro Leu Ser Thr Pro Leu Ser His
                485                 490                 495
Ser Thr Tyr Val Phe Leu Met Val Leu Phe Ser Leu Val Leu Val Ile
            500                 505                 510
Val Ala Ile Ile Gly Leu Leu Ile Phe His Lys Pro Ser Tyr Phe Trp
        515                 520                 525
Lys Asp Met Val
    530

<210> SEQ ID NO 252
<211> LENGTH: 473
<212> TYPE: PRT
<213> ORGANISM: Artificial Sequence
<220> FEATURE:
<223> OTHER INFORMATION: Synthetic: hCD39 ECD

<400> SEQUENCE: 252

Thr Gln Asn Lys Ala Leu Pro Glu Asn Val Lys Tyr Gly Ile Val Leu
1               5                   10                  15
Asp Ala Gly Ser Ser His Thr Ser Leu Tyr Ile Tyr Lys Trp Pro Ala
            20                  25                  30
Glu Lys Glu Asn Asp Thr Gly Val Val His Gln Val Glu Glu Cys Arg
        35                  40                  45
Val Lys Gly Pro Gly Ile Ser Lys Phe Val Gln Lys Val Asn Glu Ile
    50                  55                  60
Gly Ile Tyr Leu Thr Asp Cys Met Glu Arg Ala Arg Glu Val Ile Pro
65                  70                  75                  80
Arg Ser Gln His Gln Glu Thr Pro Val Tyr Leu Gly Ala Thr Ala Gly
                85                  90                  95
Met Arg Leu Leu Arg Met Glu Ser Glu Glu Leu Ala Asp Arg Val Leu
            100                 105                 110
Asp Val Val Glu Arg Ser Leu Ser Asn Tyr Pro Phe Asp Phe Gln Gly
        115                 120                 125
Ala Arg Ile Ile Thr Gly Gln Glu Glu Gly Ala Tyr Gly Trp Ile Thr
    130                 135                 140
Ile Asn Tyr Leu Leu Gly Lys Phe Ser Gln Lys Thr Arg Trp Phe Ser
145                 150                 155                 160
Ile Val Pro Tyr Glu Thr Asn Asn Gln Glu Thr Phe Gly Ala Leu Asp
                165                 170                 175
Leu Gly Gly Ala Ser Thr Gln Val Thr Phe Val Pro Gln Asn Gln Thr
            180                 185                 190
```

Ile Glu Ser Pro Asp Asn Ala Leu Gln Phe Arg Leu Tyr Gly Lys Asp
            195                 200                 205

Tyr Asn Val Tyr Thr His Ser Phe Leu Cys Tyr Gly Lys Asp Gln Ala
        210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285

His Gln Ser Ile Leu Glu Leu Phe Asn Thr Ser Tyr Cys Pro Tyr Ser
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
            340                 345                 350

Cys Ala Gln Pro Trp Glu Glu Ile Lys Thr Ser Tyr Ala Gly Val Lys
        355                 360                 365

Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
            420                 425                 430

Thr Pro Leu Ser His Ser Thr Tyr Val Phe Leu Met Val Leu Phe Ser
        435                 440                 445

Leu Val Leu Phe Thr Val Ala Ile Ile Gly Leu Leu Ile Phe His Lys
    450                 455                 460

Pro Ser Tyr Phe Trp Lys Asp Met Val
465                 470

<210> SEQ ID NO 253
<211> LENGTH: 473
<212> TYPE: PRT
<213> ORGANISM: Artificial Sequence
<220> FEATURE:
<223> OTHER INFORMATION: Synthetic: mCD39 ECD

<400> SEQUENCE: 253

Thr Gln Asn Lys Pro Leu Pro Glu Asn Val Lys Tyr Gly Ile Val Leu
1               5                   10                  15

Asp Ala Gly Ser Ser His Thr Asn Leu Tyr Ile Tyr Lys Trp Pro Ala
            20                  25                  30

Glu Lys Glu Asn Asp Thr Gly Val Val Gln Leu Glu Glu Cys Gln
        35                  40                  45

Val Lys Gly Pro Gly Ile Ser Lys Tyr Ala Gln Lys Thr Asp Glu Ile
    50                  55                  60

Gly Ala Tyr Leu Ala Glu Cys Met Glu Leu Ser Thr Glu Leu Ile Pro
65                  70                  75                  80

```
Thr Ser Lys His His Gln Thr Pro Val Tyr Leu Gly Ala Thr Ala Gly
            85                  90                  95

Met Arg Leu Leu Arg Met Glu Ser Glu Gln Ser Ala Asp Glu Val Leu
            100                 105                 110

Ala Ala Val Ser Thr Ser Leu Lys Ser Tyr Pro Phe Asp Phe Gln Gly
            115                 120                 125

Ala Lys Ile Ile Thr Gly Gln Glu Gly Ala Tyr Gly Trp Ile Thr
130                 135                 140

Ile Asn Tyr Leu Leu Gly Arg Phe Thr Gln Glu Gln Ser Trp Leu Ser
145                 150                 155                 160

Leu Ile Ser Asp Ser Gln Lys Gln Glu Thr Phe Gly Ala Leu Asp Leu
                165                 170                 175

Gly Gly Ala Ser Thr Gln Ile Thr Phe Val Pro Gln Asn Ser Thr Ile
                180                 185                 190

Glu Ser Pro Glu Asn Ser Leu Gln Phe Arg Leu Tyr Gly Glu Asp Tyr
            195                 200                 205

Thr Val Tyr Thr His Ser Phe Leu Cys Tyr Gly Lys Asp Gln Ala Leu
            210                 215                 220

Trp Gln Lys Leu Ala Lys Asp Ile Gln Val Ser Ser Gly Gly Val Leu
225                 230                 235                 240

Lys Asp Pro Cys Phe Asn Pro Gly Tyr Glu Lys Val Val Asn Val Ser
                245                 250                 255

Glu Leu Tyr Gly Thr Pro Cys Thr Lys Arg Phe Glu Lys Lys Leu Pro
                260                 265                 270

Phe Asp Gln Phe Arg Ile Gln Gly Thr Gly Asp Tyr Glu Gln Cys His
                275                 280                 285

Gln Ser Ile Leu Glu Leu Phe Asn Asn Ser His Cys Pro Tyr Ser Gln
290                 295                 300

Cys Ala Phe Asn Gly Val Phe Leu Pro Pro Leu His Gly Ser Phe Gly
305                 310                 315                 320

Ala Phe Ser Ala Phe Tyr Phe Val Met Asp Phe Lys Lys Val Ala
                325                 330                 335

Lys Asn Ser Val Ile Ser Gln Glu Lys Met Thr Glu Ile Thr Lys Asn
                340                 345                 350

Phe Cys Ser Lys Ser Trp Glu Glu Thr Lys Thr Ser Tyr Pro Ser Val
                355                 360                 365

Lys Glu Lys Tyr Leu Ser Glu Tyr Cys Phe Ser Gly Ala Tyr Ile Leu
            370                 375                 380

Ser Leu Leu Gln Gly Tyr Asn Phe Thr Asp Ser Ser Trp Glu Gln Ile
385                 390                 395                 400

His Phe Met Gly Lys Ile Lys Asp Ser Asn Ala Gly Trp Thr Leu Gly
                405                 410                 415

Tyr Met Leu Asn Leu Thr Asn Met Ile Pro Ala Glu Gln Pro Leu Ser
                420                 425                 430

Pro Pro Leu Pro His Ser Thr Tyr Ile Gly Leu Met Val Leu Phe Ser
                435                 440                 445

Leu Leu Leu Val Ala Val Ala Ile Thr Gly Leu Phe Ile Tyr Ser Lys
450                 455                 460

Pro Ser Tyr Phe Trp Lys Glu Ala Val
465                 470

<210> SEQ ID NO 254
<211> LENGTH: 473
```

```
<212> TYPE: PRT
<213> ORGANISM: Artificial Sequence
<220> FEATURE:
<223> OTHER INFORMATION: Synthetic: cCD39 ECD

<400> SEQUENCE: 254
```

Thr Gln Asn Lys Ala Leu Pro Glu Asn Ile Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Tyr Val Gln Lys Val Asn Glu Ile
50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
            85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
            165                 170                 175

Leu Gly Gly Ala Ser Thr Gln Ile Thr Phe Val Pro Gln Asn Gln Thr
            180                 185                 190

Thr Glu Ser Pro Asp Asn Ala Leu Gln Phe Arg Leu Tyr Gly Lys Asp
            195                 200                 205

Tyr Asn Val Tyr Thr His Ser Phe Leu Cys Tyr Gly Lys Asp Gln Ala
210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
            245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
            275                 280                 285

His Gln Ser Val Leu Glu Leu Phe Asn Thr Ser Tyr Cys Pro Tyr Ser
            290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Phe Val Met Asn Phe Leu Asn Leu Thr
            325                 330                 335

Ser Glu Lys Val Ser Gln Glu Lys Val Thr Glu Met Met Lys Lys Phe
            340                 345                 350

Cys Ser Gln Pro Trp Glu Glu Ile Lys Thr Ser Tyr Ala Gly Val Lys
            355                 360                 365

Glu Lys Tyr Leu Ser Glu Tyr Cys Phe Ser Gly Thr Tyr Ile Leu Ser
370                 375                 380

```
Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
            405                 410                 415

Tyr Met Leu Asn Leu Thr Asn Met Ile Pro Ala Glu Gln Pro Leu Ser
        420                 425                 430

Thr Pro Leu Ser His Ser Thr Tyr Val Phe Leu Met Val Leu Phe Ser
        435                 440                 445

Leu Val Leu Val Ile Val Ala Ile Ile Gly Leu Leu Ile Phe His Lys
        450                 455                 460

Pro Ser Tyr Phe Trp Lys Asp Met Val
465                 470

<210> SEQ ID NO 255
<211> LENGTH: 448
<212> TYPE: PRT
<213> ORGANISM: Artificial Sequence
<220> FEATURE:
<223> OTHER INFORMATION: Synthetic: HC, 31895

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Lys Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270
```

```
Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 256
<211> LENGTH: 214
<212> TYPE: PRT
<213> ORGANISM: Artificial Sequence
<220> FEATURE:
<223> OTHER INFORMATION: Synthetic: LC, 31895

<400> SEQUENCE: 256

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ala Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg His Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Asn Ala Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
             195                 200                 205

Phe Asn Arg Gly Glu Cys
    210

<210> SEQ ID NO 257
<211> LENGTH: 448
<212> TYPE: PRT
<213> ORGANISM: Artificial Sequence
<220> FEATURE:
<223> OTHER INFORMATION: Synthetic: HC, 31415

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gln Met His Trp Val Arg Gln Ala Pro Gly Gln Gly Leu Glu Trp Met
        35                  40                  45

Gly Arg Ile Asn Pro Ser Gly Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Ser Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 258
<211> LENGTH: 214
<212> TYPE: PRT
<213> ORGANISM: Artificial Sequence
<220> FEATURE:
<223> OTHER INFORMATION: Synthetic: LC, 31415

<400> SEQUENCE: 258

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Ser Tyr Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 259
<211> LENGTH: 448
<212> TYPE: PRT
<213> ORGANISM: Artificial Sequence
<220> FEATURE:

<223> OTHER INFORMATION: Synthetic: HC, 31891

<400> SEQUENCE: 259

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

-continued

```
Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 260
<211> LENGTH: 214
<212> TYPE: PRT
<213> ORGANISM: Artificial Sequence
<220> FEATURE:
<223> OTHER INFORMATION: Synthetic: LC, 31891

<400> SEQUENCE: 260

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Tyr Ala Ser Ser Arg Ala Tyr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Asn Ala Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 261
<211> LENGTH: 448
<212> TYPE: PRT
<213> ORGANISM: Artificial Sequence
<220> FEATURE:
<223> OTHER INFORMATION: Synthetic: HC, 31418

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45
```

Gly Arg Ile Asn Pro Ser Gly Ser Thr Trp Tyr Ala Gln Lys Phe
 50                 55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Lys Arg Glu Gly Gly Thr Glu Tyr Leu Arg His Trp Gly
                 100                 105                 110

Gln Gly Thr Leu Val Thr Val Ser Ser Ala Ser Thr Lys Gly Pro Ser
             115                 120                 125

Val Phe Pro Leu Ala Pro Cys Ser Arg Ser Thr Ser Glu Ser Thr Ala
 130                 135                 140

Ala Leu Gly Cys Leu Val Lys Asp Tyr Phe Pro Glu Pro Val Thr Val
 145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
                 180                 185                 190

Pro Ser Ser Ser Leu Gly Thr Lys Thr Tyr Thr Cys Asn Val Asp His
                 195                 200                 205

Lys Pro Ser Asn Thr Lys Val Asp Lys Arg Val Glu Ser Lys Tyr Gly
 210                 215                 220

Pro Pro Cys Pro Pro Cys Pro Ala Pro Glu Phe Leu Gly Gly Pro Ser
 225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser Gln Glu Asp Pro
                 260                 265                 270

Glu Val Gln Phe Asn Trp Tyr Val Asp Gly Val Glu Val His Asn Ala
             275                 280                 285

Lys Thr Lys Pro Arg Glu Glu Gln Phe Asn Ser Thr Tyr Arg Val Val
 290                 295                 300

Ser Val Leu Thr Val Leu His Gln Asp Trp Leu Asn Gly Lys Glu Tyr
 305                 310                 315                 320

Lys Cys Lys Val Ser Asn Lys Gly Leu Pro Ser Ser Ile Glu Lys Thr
                 325                 330                 335

Ile Ser Lys Ala Lys Gly Gln Pro Arg Glu Pro Gln Val Tyr Thr Leu
                 340                 345                 350

Pro Pro Ser Gln Glu Glu Met Thr Lys Asn Gln Val Ser Leu Thr Cys
             355                 360                 365

Leu Val Lys Gly Phe Tyr Pro Ser Asp Ile Ala Val Glu Trp Glu Ser
 370                 375                 380

Asn Gly Gln Pro Glu Asn Asn Tyr Lys Thr Thr Pro Pro Val Leu Asp
 385                 390                 395                 400

Ser Asp Gly Ser Phe Phe Leu Tyr Ser Arg Leu Thr Val Asp Lys Ser
                 405                 410                 415

Arg Trp Gln Glu Gly Asn Val Phe Ser Cys Ser Val Met His Glu Ala
                 420                 425                 430

Leu His Asn His Tyr Thr Gln Lys Ser Leu Ser Leu Ser Leu Gly Lys
             435                 440                 445

<210> SEQ ID NO 262
<211> LENGTH: 214

```
<212> TYPE: PRT
<213> ORGANISM: Artificial Sequence
<220> FEATURE:
<223> OTHER INFORMATION: Synthetic: LC, 31418

<400> SEQUENCE: 262

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Tyr Phe Tyr Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 263
<211> LENGTH: 448
<212> TYPE: PRT
<213> ORGANISM: Artificial Sequence
<220> FEATURE:
<223> OTHER INFORMATION: Synthetic: HC, 31430

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Gly Gly Ser Thr Trp Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg His Trp Gly
            100                 105                 110
```

```
Gln Gly Thr Leu Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Lys Thr Tyr Thr Cys Asn Val Asp His
        195                 200                 205
Lys Pro Ser Asn Thr Lys Val Asp Lys Arg Val Glu Ser Lys Tyr Gly
210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
        275                 280                 285
Lys Thr Lys Pro Arg Glu Glu Gln Phe Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
        435                 440                 445

<210> SEQ ID NO 264
<211> LENGTH: 214
<212> TYPE: PRT
<213> ORGANISM: Artificial Sequence
<220> FEATURE:
<223> OTHER INFORMATION: Synthetic: LC, 31430

<400> SEQUENCE: 264

Glu Ile Val Leu Thr Gln Ser Pro Gly Thr Leu Ser Leu Ser Pro Gly
1               5                   10                  15
Glu Arg Ala Thr Leu Ser Cys Glu Ala Ser Gln Ser Val Ser Tyr Ser
            20                  25                  30
```

```
Tyr Leu Ala Trp Tyr Gln Gln Lys Pro Gly Gln Ala Pro Arg Leu Leu
         35                  40                  45

Ile Tyr Gly Ala Ser Ser Arg Ala Asn Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr His Ser Ala Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 265
<211> LENGTH: 447
<212> TYPE: PRT
<213> ORGANISM: Artificial Sequence
<220> FEATURE:
<223> OTHER INFORMATION: Synthetic: HC, 31915

<400> SEQUENCE: 265

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Leu
                20                  25                  30

Pro Ile Ser Trp Val Arg Gln Ala Pro Gly Gln Gly Leu Glu Trp Met
         35                  40                  45

Gly Gly Ile Gly Phe Gly Thr Ala Asn Tyr Ala Gln Lys Phe Gln Gly
 50                  55                  60

Arg Val Thr Ile Thr Ala Asp Glu Ser Thr Ser Thr Ala Tyr Met Glu
 65                  70                  75                  80

Leu Ser Ser Leu Arg Ser Glu Asp Thr Ala Val Tyr Tyr Cys Ala Arg
                 85                  90                  95

Gly Gly Ala Lys Tyr Ala Ser Lys Trp Gly Met Asp Val Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 266
<211> LENGTH: 220
<212> TYPE: PRT
<213> ORGANISM: Artificial Sequence
<220> FEATURE:
<223> OTHER INFORMATION: Synthetic: LC, 31915

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

```
Tyr Trp Thr Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 267
<211> LENGTH: 447
<212> TYPE: PRT
<213> ORGANISM: Artificial Sequence
<220> FEATURE:
<223> OTHER INFORMATION: Synthetic: HC, 31905

<400> SEQUENCE: 267

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Pro Ser Asn
            20                  25                  30

Ala Ile Ser Trp Val Arg Gln Ala Pro Gly Gln Gly Leu Glu Trp Met
        35                  40                  45

Gly Gly Ile Gly Phe Gly Thr Ala Asn Tyr Ala Gln Lys Phe Gln Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Arg Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240
```

-continued

```
Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 268
<211> LENGTH: 220
<212> TYPE: PRT
<213> ORGANISM: Artificial Sequence
<220> FEATURE:
<223> OTHER INFORMATION: Synthetic: LC, 31905

<400> SEQUENCE: 268

Asp Ile Val Met Thr Gln Ser Pro Asp Ser Leu Ala Val Ser Leu Gly
1               5                   10                  15

Glu Arg Ala Thr Ile Asn Cys Lys Ser Ser Lys Ser Val Leu Tyr Ser
            20                  25                  30

Asn Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Leu Leu Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 269
<211> LENGTH: 447
<212> TYPE: PRT
<213> ORGANISM: Artificial Sequence
<220> FEATURE:
<223> OTHER INFORMATION: Synthetic: HC, 31901

<400> SEQUENCE: 269

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Leu
            20                  25                  30

Pro Ile Ser Trp Val Arg Gln Ala Pro Gly Gln Gly Leu Glu Trp Met
        35                  40                  45

Gly Gly Ile Gly Phe Gly Thr Ala Asn Tyr Ala Gln Lys Phe Gln Gly
    50                  55                  60

Arg Val Thr Ile Thr Ala Asp Glu Ser Thr Ser Thr Ala Tyr Met Glu
65                  70                  75                  80

Leu Ser Ser Leu Arg Ser Glu Asp Thr Ala Val Tyr Tyr Cys Ala Arg
                85                  90                  95

Gly Gly Ala Lys Tyr Ala Gly Arg Tyr Gly Met Asp Val Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 270
<211> LENGTH: 220
<212> TYPE: PRT
<213> ORGANISM: Artificial Sequence
<220> FEATURE:
<223> OTHER INFORMATION: Synthetic: LC, 31901

<400> SEQUENCE: 270

Gly Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Leu Tyr Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 271
<211> LENGTH: 448
<212> TYPE: PRT
<213> ORGANISM: Artificial Sequence
<220> FEATURE:
<223> OTHER INFORMATION: Synthetic: HC, 31861

<400> SEQUENCE: 271

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Gly Ser Tyr
            20                  25                  30

Gly Ile Ser Trp Val Arg Gln Ala Pro Gly Gln Gly Leu Glu Trp Met
        35                  40                  45

Gly Ser Ile Ile Pro Glu Phe Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Gly Thr Tyr Arg Asp His Arg Leu Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 272
<211> LENGTH: 214
<212> TYPE: PRT
<213> ORGANISM: Artificial Sequence
<220> FEATURE:
<223> OTHER INFORMATION: Synthetic: LC, 31861

<400> SEQUENCE: 272

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Leu Leu Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 273
<211> LENGTH: 448
<212> TYPE: PRT
<213> ORGANISM: Artificial Sequence
<220> FEATURE:
<223> OTHER INFORMATION: Synthetic: HC, 31873

<400> SEQUENCE: 273

Gln Val Gln Leu Val Gln Ser Gly Ala Glu Val Lys Lys Pro Gly Ser

-continued

```
1               5                   10                  15
Ser Val Lys Val Ser Cys Lys Ala Ser Gly Gly Thr Phe Ser Lys Tyr
                20                  25                  30
Gly Ile Ser Trp Val Arg Gln Ala Pro Gly Gln Gly Leu Glu Trp Met
                35                  40                  45
Gly Ser Ile Ile Pro Glu Phe Gly Ile Ala Asn Tyr Ala Gln Lys Phe
            50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Ser Gly Gly Tyr Arg Asp His Arg Leu Gly Val Trp Gly
                100                 105                 110
Gln Gly Thr Met Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Gln Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
```

-continued

Leu His Asn His Tyr Thr Gln Lys Ser Leu Ser Leu Ser Leu Gly Lys
            435                 440                 445

<210> SEQ ID NO 274
<211> LENGTH: 214
<212> TYPE: PRT
<213> ORGANISM: Artificial Sequence
<220> FEATURE:
<223> OTHER INFORMATION: Synthetic: LC, 31873

<400> SEQUENCE: 274

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Leu Leu Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 275
<211> LENGTH: 448
<212> TYPE: PRT
<213> ORGANISM: Artificial Sequence
<220> FEATURE:
<223> OTHER INFORMATION: Synthetic: HC, 31393

<400> SEQUENCE: 275

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Glu Ser Tyr
            20                  25                  30

Gly Ile Ser Trp Val Arg Gln Ala Pro Gly Gln Gly Leu Glu Trp Met
        35                  40                  45

Gly Ser Ile Ile Pro Glu Phe Gly Ile Ala Asn Tyr Ala Gln Lys Phe
    50                  55                  60

Gln Gly Arg Val Thr Ile Thr Ala Asp Glu Ser Thr Ser Thr Thr Tyr

```
                65                  70                  75                  80
            Met Glu Leu Ser Ser Leu Arg Ser Glu Asp Thr Ala Val Tyr Tyr Cys
                                85                  90                  95

Ala Arg Glu Ser Gly Gly Tyr Arg Asp His Arg Leu Asp Val Trp Gly
                            100                 105                 110

Gln Gly Thr Met Val Thr Val Ser Ala Ser Thr Lys Gly Pro Ser
                        115                 120                 125

Val Phe Pro Leu Ala Pro Cys Ser Arg Ser Thr Ser Glu Ser Thr Ala
                130                 135                 140

Ala Leu Gly Cys Leu Val Lys Asp Tyr Phe Pro Glu Pro Val Thr Val
            145                 150                 155                 160

Ser Trp Asn Ser Gly Ala Leu Thr Ser Gly Val His Thr Phe Pro Ala
                                165                 170                 175

Val Leu Gln Ser Ser Gly Leu Tyr Ser Leu Ser Ser Val Val Thr Val
                            180                 185                 190

Pro Ser Ser Ser Leu Gly Thr Lys Thr Tyr Thr Cys Asn Val Asp His
                        195                 200                 205

Lys Pro Ser Asn Thr Lys Val Asp Lys Arg Val Glu Ser Lys Tyr Gly
                210                 215                 220

Pro Pro Cys Pro Pro Cys Pro Ala Pro Glu Phe Leu Gly Gly Pro Ser
            225                 230                 235                 240

Val Phe Leu Phe Pro Pro Lys Pro Lys Asp Thr Leu Met Ile Ser Arg
                                245                 250                 255

Thr Pro Glu Val Thr Cys Val Val Val Asp Val Ser Gln Glu Asp Pro
                            260                 265                 270

Glu Val Gln Phe Asn Trp Tyr Val Asp Gly Val Glu Val His Asn Ala
                        275                 280                 285

Lys Thr Lys Pro Arg Glu Glu Gln Phe Asn Ser Thr Tyr Arg Val Val
                290                 295                 300

Ser Val Leu Thr Val Leu His Gln Asp Trp Leu Asn Gly Lys Glu Tyr
            305                 310                 315                 320

Lys Cys Lys Val Ser Asn Lys Gly Leu Pro Ser Ser Ile Glu Lys Thr
                                325                 330                 335

Ile Ser Lys Ala Lys Gly Gln Pro Arg Glu Pro Gln Val Tyr Thr Leu
                            340                 345                 350

Pro Pro Ser Gln Glu Glu Met Thr Lys Asn Gln Val Ser Leu Thr Cys
                        355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
            385                 390                 395                 400

Ser Asp Gly Ser Phe Phe Leu Tyr Ser Arg Leu Thr Val Asp Lys Ser
                                405                 410                 415

Arg Trp Gln Glu Gly Asn Val Phe Ser Cys Ser Val Met His Glu Ala
                            420                 425                 430

Leu His Asn His Tyr Thr Gln Lys Ser Leu Ser Leu Ser Leu Gly Lys
                        435                 440                 445

<210> SEQ ID NO 276
<211> LENGTH: 214
<212> TYPE: PRT
<213> ORGANISM: Artificial Sequence
<220> FEATURE:
<223> OTHER INFORMATION: Synthetic: LC, 31393
```

<400> SEQUENCE: 276

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Leu Leu Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 277
<211> LENGTH: 453
<212> TYPE: PRT
<213> ORGANISM: Artificial Sequence
<220> FEATURE:
<223> OTHER INFORMATION: Synthetic: HC, 27597

<400> SEQUENCE: 277

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Arg Gly Tyr Asp Ser Ser Arg Tyr Tyr Lys Phe Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr

```
            130                 135                 140
Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Leu Gly Thr Lys Thr Tyr Thr
                195                 200                 205

Cys Asn Val Asp His Lys Pro Ser Asn Thr Lys Val Asp Lys Arg Val
            210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser Gln Glu Asp Pro Glu Val Gln Phe Asn Trp Tyr Val Asp Gly Val
            275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
                340                 345                 350

Gln Val Tyr Thr Leu Pro Pro Ser Gln Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
            435                 440                 445

Leu Ser Leu Gly Lys
        450

<210> SEQ ID NO 278
<211> LENGTH: 214
<212> TYPE: PRT
<213> ORGANISM: Artificial Sequence
<220> FEATURE:
<223> OTHER INFORMATION: Synthetic: LC, 27597

<400> SEQUENCE: 278

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
```

```
                35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Phe Val Leu Trp Pro Arg
                 85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 279
<211> LENGTH: 448
<212> TYPE: PRT
<213> ORGANISM: Artificial Sequence
<220> FEATURE:
<223> OTHER INFORMATION: Synthetic: HC, 27575

<400> SEQUENCE: 279

Gln Val Gln Leu Val Gln Ser Gly Ala Glu Val Lys Glu Pro Gly Ser
 1               5                  10                  15
Ser Val Lys Val Ser Cys Lys Ala Ser Gly Gly Thr Phe Ser Ser Tyr
             20                  25                  30
Ala Thr Ser Trp Val Arg Gln Ala Pro Gly Gln Gly Leu Glu Trp Met
         35                  40                  45
Gly Gly Ile Ile Pro Ile Ser Gly Thr Ala Asn Tyr Ala Gln Glu Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Gly Gly Tyr Arg His His Tyr Phe Asp Leu Trp Gly
            100                 105                 110
Arg Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
```

```
            180                 185                 190
Pro Ser Ser Ser Leu Gly Thr Lys Thr Tyr Thr Cys Asn Val Asp His
            195                 200                 205
Lys Pro Ser Asn Thr Lys Val Asp Lys Arg Val Glu Ser Lys Tyr Gly
            210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser Gln Glu Asp Pro
            260                 265                 270
Glu Val Gln Phe Asn Trp Tyr Val Asp Gly Val Glu Val His Asn Ala
            275                 280                 285
Lys Thr Lys Pro Arg Glu Glu Gln Phe Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Gln Glu Glu Met Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
            405                 410                 415
Arg Trp Gln Glu Gly Asn Val Phe Ser Cys Ser Val Met His Glu Ala
            420                 425                 430
Leu His Asn His Tyr Thr Gln Lys Ser Leu Ser Leu Ser Leu Gly Lys
            435                 440                 445

<210> SEQ ID NO 280
<211> LENGTH: 214
<212> TYPE: PRT
<213> ORGANISM: Artificial Sequence
<220> FEATURE:
<223> OTHER INFORMATION: Synthetic: LC, 27575

<400> SEQUENCE: 280

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Arg Tyr
            20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
            50                  55                  60
Ser Gly Ser Gly Thr Asp Phe Thr Leu Thr Ile Ser Ser Leu Glu Pro
65              70                  75                  80
Glu Asp Phe Ala Val Tyr Tyr Cys Gln Gln His Val Asn Phe Pro Leu
            85                  90                  95
Thr Phe Gly Gly Gly Thr Lys Val Glu Ile Lys Arg Thr Val Ala Ala
```

```
            100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 281
<211> LENGTH: 448
<212> TYPE: PRT
<213> ORGANISM: Artificial Sequence
<220> FEATURE:
<223> OTHER INFORMATION: Synthetic: HC, 27568

<400> SEQUENCE: 281

Gln Val Gln Leu Val Gln Ser Gly Ala Glu Val Lys Lys Pro Gly Ser
1               5                   10                  15

Ser Val Lys Val Pro Cys Lys Ala Ser Gly Gly Thr Phe Ser Ser Tyr
            20                  25                  30

Ala Ile Ser Trp Val Arg Gln Ala Pro Glu Gln Gly Leu Glu Trp Met
        35                  40                  45

Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Ser Gly Gly Tyr Arg Asp His Lys Leu Asp Val Trp Gly
            100                 105                 110

Gln Gly Thr Val Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
```

```
                245                 250                 255
Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 282
<211> LENGTH: 214
<212> TYPE: PRT
<213> ORGANISM: Artificial Sequence
<220> FEATURE:
<223> OTHER INFORMATION: Synthetic: LC, 27568

<400> SEQUENCE: 282

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Val Phe Trp Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                    165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 283
<211> LENGTH: 448
<212> TYPE: PRT
<213> ORGANISM: Artificial Sequence
<220> FEATURE:
<223> OTHER INFORMATION: Synthetic: HC, 27577

<400> SEQUENCE: 283

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Ser Tyr
            20                  25                  30

Ala Ile Gly Trp Val Arg Gln Ala Pro Gly Gln Gly Leu Glu Trp Met
        35                  40                  45

Gly Gly Ile Ile Pro Thr Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Gly Tyr Gln His His Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
```

```
                305                 310                 315                 320
Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 284
<211> LENGTH: 214
<212> TYPE: PRT
<213> ORGANISM: Artificial Sequence
<220> FEATURE:
<223> OTHER INFORMATION: Synthetic: LC, 27577

<400> SEQUENCE: 284

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Leu Thr Lys Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 285
<211> LENGTH: 448
<212> TYPE: PRT
<213> ORGANISM: Artificial Sequence
<220> FEATURE:
<223> OTHER INFORMATION: Synthetic: HC, 27587

<400> SEQUENCE: 285
```

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Thr | Phe | Ser | Ser | Tyr | |
| | | | 20 | | | | | 25 | | | | | 30 | | |
| Ala | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Ser | Ile | Ile | Pro | Ile | Phe | Gly | Thr | Ala | Asn | Tyr | Ala | Gln | Lys | Phe |
| 50 | | | | | 55 | | | | | 60 | | | | | |
| Gln | Gly | Arg | Val | Thr | Ile | Thr | Ala | Asp | Glu | Ser | Thr | Ser | Thr | Ala | Tyr |
| 65 | | | | 70 | | | | | 75 | | | | | 80 | |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Glu | Ser | Gly | Gly | Tyr | Arg | Asp | His | Lys | Leu | Asp | Val | Trp | Gly |
| | | | 100 | | | | | 105 | | | | | 110 | | |
| Gln | Gly | Thr | Met | Val | Thr | Val | Ser | Ser | Ala | Ser | Thr | Lys | Gly | Pro | Ser |
| | | 115 | | | | | 120 | | | | | 125 | | | |
| Val | Phe | Pro | Leu | Ala | Pro | Cys | Ser | Arg | Ser | Thr | Ser | Glu | Ser | Thr | Ala |
| 130 | | | | | 135 | | | | | 140 | | | | | |
| Ala | Leu | Gly | Cys | Leu | Val | Lys | Asp | Tyr | Phe | Pro | Glu | Pro | Val | Thr | Val |
| 145 | | | | 150 | | | | | 155 | | | | | 160 | |
| Ser | Trp | Asn | Ser | Gly | Ala | Leu | Thr | Ser | Gly | Val | His | Thr | Phe | Pro | Ala |
| | | | | 165 | | | | | 170 | | | | | 175 | |
| Val | Leu | Gln | Ser | Ser | Gly | Leu | Tyr | Ser | Leu | Ser | Ser | Val | Val | Thr | Val |
| | | | 180 | | | | | 185 | | | | | 190 | | |
| Pro | Ser | Ser | Ser | Leu | Gly | Thr | Lys | Thr | Tyr | Thr | Cys | Asn | Val | Asp | His |
| | | 195 | | | | | 200 | | | | | 205 | | | |
| Lys | Pro | Ser | Asn | Thr | Lys | Val | Asp | Lys | Arg | Val | Glu | Ser | Lys | Tyr | Gly |
| 210 | | | | | 215 | | | | | 220 | | | | | |
| Pro | Pro | Cys | Pro | Pro | Cys | Pro | Ala | Pro | Glu | Phe | Leu | Gly | Gly | Pro | Ser |
| 225 | | | | 230 | | | | | 235 | | | | | 240 | |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | Gln | Glu | Asp | Pro |
| | | | 260 | | | | | 265 | | | | | 270 | | |
| Glu | Val | Gln | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Phe | Asn | Ser | Thr | Tyr | Arg | Val | Val |
| 290 | | | | | 295 | | | | | 300 | | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Gly | Leu | Pro | Ser | Ser | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Gln | Glu | Glu | Met | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |

```
                370              375              380
Asn Gly Gln Pro Glu Asn Asn Tyr Lys Thr Thr Pro Pro Val Leu Asp
385                  390              395              400

Ser Asp Gly Ser Phe Phe Leu Tyr Ser Arg Leu Thr Val Asp Lys Ser
            405              410              415

Arg Trp Gln Glu Gly Asn Val Phe Ser Cys Ser Val Met His Glu Ala
        420              425              430

Leu His Asn His Tyr Thr Gln Lys Ser Leu Ser Leu Ser Leu Gly Lys
        435              440              445
```

<210> SEQ ID NO 286
<211> LENGTH: 214
<212> TYPE: PRT
<213> ORGANISM: Artificial Sequence
<220> FEATURE:
<223> OTHER INFORMATION: Synthetic: LC, 27587

<400> SEQUENCE: 286

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp Val Leu Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 287
<211> LENGTH: 447
<212> TYPE: PRT
<213> ORGANISM: Artificial Sequence
<220> FEATURE:
<223> OTHER INFORMATION: Synthetic: HC, 27589

<400> SEQUENCE: 287

```
Gln Val Gln Leu Val Gln Ser Gly Ala Glu Val Lys Lys Pro Gly Ser
1               5                   10                  15
```

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Asp Ser Gly Tyr His Arg His Tyr Ser Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys

<210> SEQ ID NO 288
<211> LENGTH: 214
<212> TYPE: PRT
<213> ORGANISM: Artificial Sequence
<220> FEATURE:
<223> OTHER INFORMATION: Synthetic: LC, 27589

<400> SEQUENCE: 288

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Leu Phe Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 289
<211> LENGTH: 448
<212> TYPE: PRT
<213> ORGANISM: Artificial Sequence
<220> FEATURE:
<223> OTHER INFORMATION: Synthetic: HC, 27596

<400> SEQUENCE: 289

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Asp Pro Leu Gly Ile Arg Lys His Trp Phe Asp Pro Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 290
<211> LENGTH: 214
<212> TYPE: PRT
<213> ORGANISM: Artificial Sequence
<220> FEATURE:
<223> OTHER INFORMATION: Synthetic: LC, 27596

<400> SEQUENCE: 290

-continued

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Thr Val Trp Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 291
<211> LENGTH: 448
<212> TYPE: PRT
<213> ORGANISM: Artificial Sequence
<220> FEATURE:
<223> OTHER INFORMATION: Synthetic: HC, 27535

<400> SEQUENCE: 291

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Thr Pro Arg Trp Arg Tyr His Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 292
<211> LENGTH: 214
<212> TYPE: PRT
<213> ORGANISM: Artificial Sequence
<220> FEATURE:
<223> OTHER INFORMATION: Synthetic: LC, 27535

<400> SEQUENCE: 292

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
    50                  55                  60

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Val Leu Asn Tyr Pro Leu
                 85                  90                  95

Thr Phe Gly Gly Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 293
<211> LENGTH: 448
<212> TYPE: PRT
<213> ORGANISM: Artificial Sequence
<220> FEATURE:
<223> OTHER INFORMATION: Synthetic: HC, 27550

<400> SEQUENCE: 293

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Arg Gly Ser Leu Ala Leu Gly Met Asp Val Trp Gly
             100                 105                 110

Gln Gly Thr Leu Val Thr Val Ser Ser Ala Ser Thr Lys Gly Pro Ser
         115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205
```

-continued

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
    435                 440                 445

<210> SEQ ID NO 294
<211> LENGTH: 214
<212> TYPE: PRT
<213> ORGANISM: Artificial Sequence
<220> FEATURE:
<223> OTHER INFORMATION: Synthetic: LC, 27550

<400> SEQUENCE: 294

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Tyr Phe Leu Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 295
<211> LENGTH: 455
<212> TYPE: PRT
<213> ORGANISM: Artificial Sequence
<220> FEATURE:
<223> OTHER INFORMATION: Synthetic: HC, 27549

<400> SEQUENCE: 295

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Tyr Ser Tyr Gly Glu Pro Tyr Tyr Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270
```

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455

<210> SEQ ID NO 296
<211> LENGTH: 215
<212> TYPE: PRT
<213> ORGANISM: Artificial Sequence
<220> FEATURE:
<223> OTHER INFORMATION: Synthetic: LC, 27549

<400> SEQUENCE: 296

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala His Ser Ser Pro
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 297
<211> LENGTH: 448
<212> TYPE: PRT
<213> ORGANISM: Artificial Sequence
<220> FEATURE:
<223> OTHER INFORMATION: Synthetic: HC, 31414

<400> SEQUENCE: 297

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Ser Tyr
            20                  25                  30

Glu Met His Trp Val Arg Gln Ala Pro Gly Gln Gly Leu Glu Trp Met
        35                  40                  45

Gly Arg Ile Asn Pro Ser Val Gly Ser Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Lys Arg Glu Gly Gly Thr Glu Tyr Leu Arg Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 298
<211> LENGTH: 214
<212> TYPE: PRT
<213> ORGANISM: Artificial Sequence
<220> FEATURE:
<223> OTHER INFORMATION: Synthetic: LC, 31414

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr His Ser Tyr Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```